United States Patent
Schmidt et al.

(10) Patent No.: US 9,056,853 B2
(45) Date of Patent: *Jun. 16, 2015

(54) N-THIO-ANTHRANILAMID COMPOUNDS AND THEIR USE AS PESTICIDES

(71) Applicant: BASF SE, Ludwigshafen (DE)

(72) Inventors: Thomas Schmidt, Neustadt (DE);
Michael Puhl, Lamperthelm (DE);
Joachim Dickhaut, Heidelberg (DE);
Henricus Maria Martinus Bastiaans, Usingen (DE); Michael Rack, Eppelheim (DE); Deborah L. Culbertson, Fuquay Varina, NC (US);
Douglas D. Anspaugh, Apex, NC (US);
Franz-Josef Braun, Durham, NC (US);
Toni Bucci, Fuquay Varina, NC (US);
Henry Van Tuyl Cotter, Raleigh, NC (US); David G. Kuhn, Apex, NC (US);
Hassan Oloumi-Sadeghi, Raleigh, NC (US)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/293,288

(22) Filed: Jun. 2, 2014

(65) Prior Publication Data
US 2014/0378458 A1 Dec. 25, 2014

Related U.S. Application Data

(63) Continuation of application No. 13/682,246, filed on Nov. 20, 2012, now Pat. No. 8,772,289, which is a continuation of application No. 13/400,752, filed on Feb. 21, 2012, now Pat. No. 8,338,419, which is a continuation of application No. 11/994,812, filed as application No. PCT/EP2006/063761 on Jun. 30, 2006, now Pat. No. 8,143,292.

(60) Provisional application No. 60/697,166, filed on Jul. 7, 2005.

(51) Int. Cl.
C07D 401/04 (2006.01)
C07D 409/14 (2006.01)
A01N 43/84 (2006.01)
C07D 413/14 (2006.01)
A01N 43/56 (2006.01)
C07D 401/14 (2006.01)

(52) U.S. Cl.
CPC ............ *C07D 401/04* (2013.01); *C07D 401/14* (2013.01); *C07D 409/14* (2013.01); *C07D 413/14* (2013.01); *A01N 43/56* (2013.01); *A01N 43/84* (2013.01)

(58) Field of Classification Search
USPC ............ 514/341, 236.5, 318, 333; 546/275.4, 546/194, 256; 544/131
See application file for complete search history.

(56) References Cited

U.S. PATENT DOCUMENTS

| | | | |
|---|---|---|---|
| 6,136,983 A | 10/2000 | Lowder et al. | |
| 7,232,926 B2 | 6/2007 | Hamprecht et al. | |
| 8,143,292 B2 | 3/2012 | Schmidt et al. | |
| 8,338,419 B2 * | 12/2012 | Schmidt et al. | 514/236.5 |
| 8,772,289 B2 * | 7/2014 | Schmidt et al. | 514/236.5 |
| 2002/0032328 A1 | 3/2002 | Shermolovich et al. | |
| 2005/0159622 A1 | 7/2005 | Hamprecht et al. | |

(Continued)

FOREIGN PATENT DOCUMENTS

| | | |
|---|---|---|
| EP | 0 580 374 | 1/1994 |
| EP | 2 281 810 | 2/2011 |

(Continued)

OTHER PUBLICATIONS

International Search Report for International Application No. PCT/EP2006/063761, Internationally filed on Jun. 30, 2006.

(Continued)

*Primary Examiner* — Kristin Vajda
(74) *Attorney, Agent, or Firm* — Brinks Gilson & Lione

(57) ABSTRACT

N-Thio-anthranilamid compounds of formula (I)

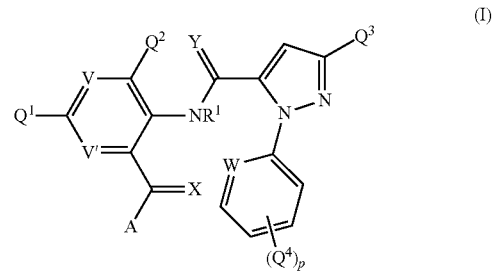

wherein A is $A^1$

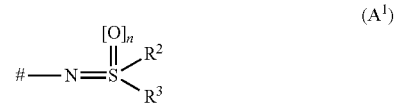

wherein the variables and the indices are as defined per the description, processes for preparing the compounds I, pesticidal compositions comprising compounds I, use of compounds I for the control of insects, acarids or nematodes, and methods for treating, controlling, preventing or protecting animals against infestation or infection by parasites by use of compounds of formula I.

25 Claims, No Drawings

(56) References Cited

U.S. PATENT DOCUMENTS

2014/0155264 A1* 6/2014 Kaiser et al. .......... 504/100
2014/0179519 A1* 6/2014 Kaiser et al. .......... 504/100

FOREIGN PATENT DOCUMENTS

| JP | 6 321903 | 11/1994 |
|----|----------|---------|
| JP | 2002/284608 | 10/2002 |
| JP | 2003 528081 | 9/2003 |
| JP | 2005-89730 | 4/2005 |
| NL | 9202078 | 6/1994 |
| WO | WO 01/70671 | 9/2001 |
| WO | WO 02070483 | 9/2002 |
| WO | WO 02/089579 | 11/2002 |
| WO | WO 02/090320 | 11/2002 |
| WO | WO 02/090321 | 11/2002 |
| WO | WO 03/015518 | 2/2003 |
| WO | WO 03/015519 | 2/2003 |
| WO | WO 03/016284 | 2/2003 |
| WO | WO 03/016300 | 2/2003 |
| WO | WO 03/024222 | 3/2003 |
| WO | WO 03/097589 | 11/2003 |
| WO | WO 2004/006677 | 1/2004 |
| WO | WO 2004/011447 | 2/2004 |
| WO | WO 2004/020399 | 3/2004 |
| WO | WO 2004033468 | 4/2004 |
| WO | WO 2004/046129 | 6/2004 |
| WO | WO 2005/085234 | 9/2005 |
| WO | WO 2006/000336 | 1/2006 |
| WO | WO 2006/040113 | 4/2006 |
| WO | WO 2006/068669 | 6/2006 |
| WO | WO 2007/024833 | 3/2007 |
| WO | WO 2007/043677 | 4/2007 |
| WO | WO 2008/130021 | 10/2008 |
| WO | WO 2011117806 | 9/2011 |
| WO | WO 2012034960 | 3/2012 |
| WO | WO 2012034961 | 3/2012 |
| WO | WO 2013/024003 | 2/2013 |
| WO | WO 2013/024004 | 2/2013 |
| WO | WO 2013/024005 | 2/2013 |
| WO | WO 2013/024006 | 2/2013 |
| WO | WO 2013/024007 | 2/2013 |
| WO | WO 2013/024009 | 2/2013 |
| WO | WO 2013024008 | 2/2013 |
| WO | WO 2013024010 | 2/2013 |

OTHER PUBLICATIONS

International Preliminary Report on Patentability with Annexes for International Application No. PCT/EP2006/063761, Internationally filed on Jun. 30, 2006.

Coppola, The chemistry of 4$H$-3,1-benzoxazin-4-ones. J. Hetercyclic Chemistry, 36, 563-588 (1999).

Haake, M., "S,S-Diorgano-sulfoximide", in Methoden der organischen Chemie [Methods of Organic Chemistry], Houben-Weyl, E11, 1299-1320, (1985).

Jakobsen et al., "Inhibitors of the tissue factor/factor viia-induced coagulation: Synthesis and in vitro evaluation of novel specific 2-aryl substituted 4$H$-3,1-benzoxazin-4-Ones", Bioorganic and Medicinal Chemistry, 8, 2095-2103 (2000).

Larock,R., "Interconversion of nitriles, carboxylic acids and derivatives" in a Guide to Functional Group Preparations, Comprehensive organic Transformations, VCH Publishers, p. 965-966 and 978 (1989).

Mar., J., "Classifications of reactions", in Reactions, Mechanisms, and Structure, Advanced organic chemistry, 4$^{th}$ Ed., p. 1297 (1992).

Tamura et al., "Synthesis and some properties of n-unsubstituted sulfilimines", Tetrahedron, 31, 3035-3040 (1975).

* cited by examiner

N-THIO-ANTHRANILAMID COMPOUNDS AND THEIR USE AS PESTICIDES

CROSS REFERENCE TO RELATED APPLICATIONS

This application is a continuation of U.S. application Ser. No. 13/682,246, filed Nov. 20, 2012, now U.S. Pat. No. 8,772,289 the entire contents of which is hereby incorporated by reference. U.S. application Ser. No. 13/682,246 is a continuation of U.S. application Ser. No. 13/400,752, filed Feb. 21, 2012, now U.S. Pat. No. 8,338,419, which is a continuation of U.S. application Ser. No. 11/994,812, filed Jan. 4, 2008, now U.S. Pat. No. 8,143,292, the entire contents of each are hereby incorporated by reference. U.S. application Ser. No. 11/994,812, is a National Stage application of International Application No. PCT/EP2006/063761, filed Jun. 30, 2006, which claims the benefit of U.S. Provisional Application No. 60/697,166, filed Jul. 7, 2005, the entire contents of which are hereby incorporated herein by reference.

The present invention relates to N-Thio-anthranilamid compounds of formula (I)

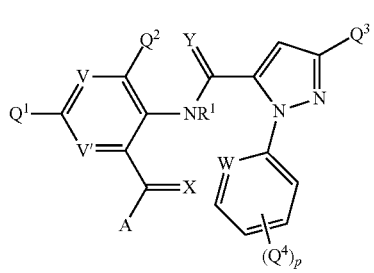

wherein $R^1$ is hydrogen; or $C_1$-$C_{10}$-alkyl, $C_2$-$C_{10}$-alkenyl, $C_2$-$C_{10}$-alkynyl, or $C_3$-$C_8$-cycloalkyl, each of which is unsubstituted or substituted with 1 to 5 groups independently selected from halogen, cyano, nitro, hydroxy, $C_1$-$C_{10}$-alkoxy, $C_1$-$C_{10}$-alkylthio, $C_1$-$C_{10}$-alkylsulfinyl, $C_1$-$C_{10}$-alkylsulfonyl, $C_2$-$C_{10}$-alkoxycarbonyl, $C_1$-$C_{10}$-alkylamino, di($C_1$-$C_{10}$-alkyl)amino and $C_3$-$C_8$-cycloalkylamino; or $C_1$-$C_{10}$-alkylcarbonyl, $C_1$-$C_{10}$-alkoxycarbonyl $C_1$-$C_{10}$-alkylaminocarbonyl, di($C_1$-$C_{10}$-alkyl)aminocarbonyl;

A is a group selected from $A^1$ and $A^2$

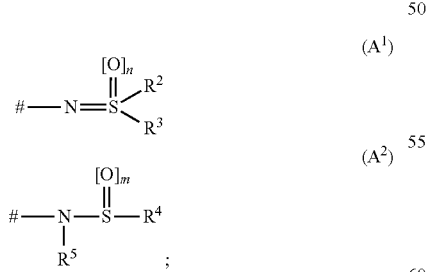

wherein

\# denotes the binding site;

$R^2$ and $R^3$ each independently are $R^6$, —C(=G)$R^7$, —C(=NOR$^7$)$R^7$, —C(=NNR$^7{}_2$)$R^7$, —C(=G)OR$^7$, —C(=G)NR$^7{}_2$, —OC(=G)$R^7$, —OC(=G)OR$^7$, —NR$^7$C(=G)$R^7$, —N[C(=G)R$^7$]$_2$, —NR$^7$C(=G)OR$^7$, —C(=G)NR$^7$—NR$^7{}_2$, —C(=G)NR$^7$—NR$^7$[C(=G)R$^7$], —NR$^7$—C(=G)NR$^7{}_2$, —NR$^7$—NR$^7$C(=G)R$^7$, —NR$^7$—N[C(=G)R$^7$]$_2$, —N[(C=G)R$^7$]-NR$^7{}_2$, —NR$^7$—NR$^7$[(C=G)GR$^7$], —NR$^7$[(C=G)NR$^7{}_2$, —NR$^7$[C=NR$^7$]R$^7$, —NR$^7$(C=NR$^7$)NR$^7{}_2$, —O—NR$^7{}_2$, —O—NR$^7$(C=G)R$^7$, —SO$_2$NR$^7{}_2$, —NR$^7$SO$_2$R$^7$, —SO$_2$OR$^7$, —OSO2R$^7$, —NR$^7{}_2$, —SR$^7$, —SiR$^7{}_3$, —PR$^7{}_2$, —P(=G)R$^7$, —SOR$^7$, —SO$_2$R$^7$, —PG$_2$R$^7{}_2$, or —PG$_3$R$^7{}_2$; or $R^2$ and $R^3$ together with the sulfur atom to which they are attached form a saturated, partially unsaturated or unsaturated 3- to 8-membered ring which contains 1 to 4 heteroatoms selected from oxygen, nitrogen, sulfur, which ring can be fused with one or two saturated, partially unsaturated or unsaturated 5- to 6-membered rings which may contain 1 to 4 heteroatoms selected from oxygen, nitrogen, sulfur, wherein all of the above rings are unsubstituted or substituted by any combination of 1 to 6 groups $R^8$;

G is oxygen or sulfur;

$R^6$ is $C_1$-$C_{20}$-alkyl, $C_2$-$C_{20}$-alkenyl, $C_2$-$C_{20}$-alkynyl, $C_3$-$C_8$-cycloalkyl, $C_3$-$C_8$-cycloalkenyl, $C_3$-$C_8$-cycloalkynyl, phenyl, naphthyl, biphenyl, or a saturated, partially unsaturated or unsaturated 3- to 8-membered ring system which contains 1 to 4 heteroatoms selected from oxygen, nitrogen, sulfur, wherein all of these groups are unsubstituted or substituted by any combination of 1 to 6 groups $R^8$;

$R^7$ is hydrogen or $R^6$;

$R^8$ is $R^9$; or two groups $R^8$ together with the atoms to which they are attached form a saturated, partially unsaturated or unsaturated 3- to 8-membered ring system which may contain 1 to 4 heteroatoms/heterogroups selected from oxygen, nitrogen, sulfur, SO and SO$_2$, and which ring system is unsubstituted or substituted with any combination of 1 to 6 groups $R^9$.

$R^9$ is $R^{10}$, $R^{11}$, —C(=G)$R^{10}$, —C(=NOR$^{10}$)$R^{10}$, —C(=NNR$^{10}{}_2$)$R^{10}$, —C(=G)OR$^{10}$, —C(=G)NR$^{10}{}_2$, —OC(=G)R$^{10}$, —OC(=G)OR$^{10}$, —NR$^{10}$C(=G)R$^{10}$, —N[C(=G)R$^{10}$]$_2$, —NR$^{10}$C(=G)OR$^{10}$, —C(=G)NR$^{10}$—NR$^{10}{}_2$, —C(=G)NR$^{10}$—NR$^{10}$[C(=G)R$^{10}$], —NR$^{10}$—C(=G)NR$^{10}{}_2$, —NR$^{10}$—NR$^{10}$C(=G)R$^{10}$, —NR$^{10}$—N[C(=G)R$^{10}$]$_2$, —N[(C=G)R$^{10}$]—NR$^{10}{}_2$, —NR$^{10}$—NR$^{10}$[(C=G)GR$^{10}$], —NR$^{10}$[(C=G)NR$^{10}{}_2$, —NR$^{10}$[C=NR$^{10}$]R$^{10}$, —NR$^{10}$(C=NR$^{10}$)NR$^{10}{}_2$, —O—NR$^{10}{}_2$, —O—NR$^{10}$(C=G)R$^{10}$, —SO$_2$NR$^{10}{}_2$, —NR$^{10}$SO$_2$R$^{10}$, —SO$_2$OR$^{10}$, —OSO2R$^{10}$, —OR$^{10}$, —NR$^{10}{}_2$, —SR$^{10}$, —SiR$^{10}{}_3$, —PR$^{10}{}_2$, —P(=G)R$^{10}$, —SOR$^{10}$, —SO$_2$R$^{10}$, —PG$_2$R$^{10}{}_2$, —PG$_3$R$^{10}{}_2$, or two groups $R^9$ together are (=G), (=N—R$^{10}$), (=CR$^{10}{}_2$), (=CHR$^{10}$), or (=CH$_2$);

$R^{10}$ is $C_1$-$C_{10}$-alkyl, $C_2$-$C_{10}$-alkenyl, $C_2$-$C_{10}$-alkynyl, $C_3$-$C_8$-cycloalkyl, $C_4$-$C_8$-cycloalkenyl, $C_3$-$C_8$-cycloalkyl-$C_1$-$C_4$-alkyl, $C_4$-$C_8$-cycloalkenyl-$C_1$-$C_4$-alkyl, $C_3$-$C_8$-cycloalkyl-$C_2$-$C_4$-alkenyl, $C_4$-$C_8$-cycloalkenyl-$C_2$-$C_4$-alkenyl, $C_1$-$C_{10}$-alkyl-$C_3$-$C_8$-cycloalkyl, $C_2$-$C_{10}$-alkenyl-$C_3$-$C_8$-cycloalkyl, $C_2$-$C_{10}$-alkynyl-$C_3$-$C_8$-cycloalkyl, $C_1$-$C_{10}$-alkyl-$C_4$-$C_8$-cycloalkenyl, $C_2$-$C_{10}$-alkenyl-$C_4$-$C_8$-cycloalkenyl, $C_2$-$C_{10}$-alkynyl-$C_4$-$C_8$-cycloalkenyl, a saturated, partially unsaturated or unsaturated 3- to 8-membered ring system which contains 1 to 4 heteroatoms selected from oxygen, nitrogen, sulfur, wherein the above groups are unsubstituted or substituted with any combination of from 1 to 6 groups $R^{11}$;

$R^{11}$ is halogen, cyano, nitro, hydroxy, mercapto, amino, formyl, $C_1$-$C_{10}$-alkylcarbonyl, $C_1$-$C_{10}$-alkoxy, $C_2$-$C_{10}$-alkenyloxy, $C_2$-$C_{10}$-alkynyloxy, $C_1$-$C_{10}$-haloalkoxy, $C_3$-$C_{10}$-haloalkenyloxy, $C_3$-$C_{10}$-haloalkynyloxy, $C_3$-$C_8$-cycloalkoxy, $C_4$-$C_8$-cycloalkenyloxy, $C_3$-$C_8$-halocycloalkoxy, $C_4$-$C_8$-halocycloalkenyloxy, $C_3$-$C_8$-cycloalkyl-$C_1$-$C_4$-alkoxy, $C_4$-$C_8$-cycloalkenyl-$C_1$-$C_4$-alkoxy, $C_3$-$C_8$- cycloalkyl-C$_2$-C$_4$-alkenyloxy, C$_4$-C$_8$-cycloalkenyl-C$_2$-C$_4$-alkenyloxy, C$_1$-C$_{10}$-alkyl-C$_3$-C$_8$-cycloalkoxy, C$_1$-C$_{10}$-alkenyl-C$_3$-C$_8$-cycloalkoxy, C$_1$-C$_{10}$-alkynyl-C$_3$-C$_8$-cycloalkoxy, C$_1$-C$_{10}$-alkyl-C$_3$-C$_8$-cycloalkenyloxy, C$_1$-C$_{10}$-alkenyl-C$_3$-C$_8$-cycloalkenyloxy, C$_1$-C$_4$-alkoxy-C$_1$-C$_{10}$-alkoxy, C$_1$-C$_4$-alkoxy-C$_2$-C$_{10}$-alkenyloxy, mono- or di(C$_1$-C$_{10}$-alkyl)carbamoyl, mono- or di(C$_1$-C$_4$-haloalkyl)carbamoyl, mono- or di(C$_3$-C$_8$-cycloalkyl)carbamoyl, C$_1$-C$_{10}$-alkoxycarbonyl, C$_3$-C$_8$-cycloalkoxycarbonyl, C$_1$-C$_{10}$-alkylcarbonyloxy, C$_3$-C$_8$-cycloalkylcarbonyloxy, C$_1$-C$_{10}$-haloalkoxycarbonyl, C$_1$-C$_{10}$-haloalkylcarbonyloxy, C$_1$-C$_{10}$-alkanamido, C$_1$-C$_{10}$-haloalkanamido, C$_2$-C$_{10}$-alkenamido, C$_3$-C$_8$-cycloalkanamido, C$_3$-C$_8$-cycloalkyl-C$_1$-C$_4$-alkanamido, C$_1$-C$_{10}$-alkylthio, C$_2$-C$_{10}$-alkenylthio, C$_2$-C$_{10}$-alkynylthio, C$_1$-C$_{10}$-haloalkylthio, C$_2$-C$_{10}$-haloalkenylthio, C$_2$-C$_{10}$-haloalkynylthio, C$_3$-C$_8$-cycloalkylthio, C$_3$-C$_8$-cycloalkenylthio, C$_3$-C$_8$-halocycloalkylthio, C$_3$-C$_8$-halocycloalkenylthio, C$_3$-C$_8$-cycloalkyl-C$_1$-C$_4$-alkylthio, C$_4$-C$_8$-cycloalkenyl-C$_1$-C$_4$-alkylthio, C$_3$-C$_8$-cycloalkyl-C$_2$-C$_4$-alkenylthio, C$_4$-C$_8$-cycloalkenyl-C$_2$-C$_4$-alkenylthio, C$_1$-C$_{10}$-alkyl-C$_3$-C$_8$-cycloalkylthio, C$_1$-C$_{10}$-alkenyl-C$_3$-C$_8$-cycloalkylthio, C$_1$-C$_{10}$-alkynyl-C$_3$-C$_8$-cycloalkylthio, C$_1$-C$_{10}$-alkyl-C$_3$-C$_8$-cycloalkenylthio, C$_1$-C$_{10}$-alkenyl-C$_3$-C$_8$-cycloalkenylthio, C$_1$-C$_{10}$-alkylsulfinyl, C$_2$-C$_{10}$-alkenylsulfinyl, C$_2$-C$_{10}$-alkynylsulfinyl, C$_1$-C$_{10}$-haloalkylsulfinyl, C$_2$-C$_{10}$-haloalkenylsulfinyl, C$_2$-C$_{10}$-haloalkynylsulfinyl, C$_3$-C$_8$-cycloalkylsulfinyl, C$_3$-C$_8$-cycloalkenylsulfinyl, C$_3$-C$_8$-halocycloalkylsulfinyl, C$_3$-C$_8$-halocycloalkenylsulfinyl, C$_3$-C$_8$-cycloalkyl-C$_1$-C$_4$-alkylsulfinyl, C$_4$-C$_8$-cycloalkenyl-C$_1$-C$_4$-alkylsulfinyl, C$_3$-C$_8$-cycloalkyl-C$_2$-C$_4$-alkenylsulfinyl, C$_4$-C$_8$-cycloalkenyl-C$_2$-C$_4$-alkenylsulfinyl, C$_1$-C$_{10}$-alkyl-C$_3$-C$_8$-cycloalkylsulfinyl, C$_1$-C$_{10}$-alkenyl-C$_3$-C$_8$-cycloalkylsulfinyl, C$_1$-C$_{10}$-alkynyl-C$_3$-C$_8$-cycloalkylsulfinyl, C$_1$-C$_{10}$-alkyl-C$_3$-C$_8$-cycloalkenylsulfinyl, C$_1$-C$_{10}$-alkenyl-C$_3$-C$_8$-cycloalkenylsulfinyl, C$_1$-C$_{10}$-alkylsulfonyl, C$_2$-C$_{10}$-alkenylsulfonyl, C$_2$-C$_{10}$-alkynylsulfonyl, C$_1$-C$_{10}$-haloalkylsulfonyl, C$_2$-C$_{10}$-haloalkenylsulfonyl, C$_2$-C$_{10}$-haloalkynylsulfonyl, C$_3$-C$_8$-cycloalkylsulfonyl, C$_3$-C$_8$-cycloalkenylsulfonyl, C$_3$-C$_8$-halocycloalkylsulfonyl, C$_3$-C$_8$-halocycloalkenylsulfonyl, C$_3$-C$_8$-cycloalkyl-C$_1$-C$_4$-alkylsulfonyl, C$_4$-C$_8$-cycloalkenyl-C$_1$-C$_4$-alkylsulfonyl, C$_3$-C$_8$-cycloalkyl-C$_2$-C$_4$-alkenylsulfonyl, C$_4$-C$_8$-cycloalkenyl-C$_2$-C$_4$-alkenylsulfonyl, C$_1$-C$_{10}$-alkyl-C$_3$-C$_8$-cycloalkylsulfonyl, C$_1$-C$_{10}$-alkenyl-C$_3$-C$_8$-cycloalkylsulfonyl, C$_1$-C$_{10}$-alkynyl-C$_3$-C$_8$-cycloalkylsulfonyl, C$_1$-C$_{10}$-alkyl-C$_3$-C$_8$-cycloalkenylsulfonyl, C$_1$-C$_{10}$-alkenyl-C$_3$-C$_8$-cycloalkenylsulfonyl, di(C$_1$-C$_{10}$-alkyl)amino, C$_1$-C$_{10}$-alkylamino, C$_2$-C$_{10}$-alkenylamino, C$_2$-C$_{10}$-alkynylamino, C$_1$-C$_{10}$-alkyl-C$_2$-C$_{10}$-alkenylamino, C$_1$-C$_{10}$-alkyl-C$_2$-C$_{10}$-alkynylamino, C$_1$-C$_{10}$-haloalkylamino, C$_2$-C$_{10}$-haloalkenylamino, C$_2$-C$_{10}$-haloalkynylamino, C$_3$-C$_8$-cycloalkylamino, C$_3$-C$_8$-cycloalkenylamino, C$_3$-C$_8$-halocycloalkylamino, C$_3$-C$_8$-halocycloalkenylamino, C$_3$-C$_8$-cycloalkyl-C$_4$-C$_8$-cycloalkenyl-C$_1$-C$_4$-alkylamino, C$_3$-C$_8$-cycloalkyl-C$_2$-C$_4$-alkenylamino, C$_4$-C$_8$-cycloalkenyl-C$_2$-C$_4$-alkenylamino, C$_1$-C$_{10}$-alkyl-C$_3$-C$_8$-cycloalkylamino, C$_1$-C$_{10}$-alkenyl-C$_3$-C$_8$-cycloalkylamino, C$_1$-C$_{10}$-alkynyl-C$_3$-C$_8$-cycloalkylamino, C$_1$-C$_{10}$-alkyl-C$_3$-C$_8$-cycloalkenylamino, C$_1$-C$_{10}$-alkenyl-C$_3$-C$_8$-cycloalkenylamino, tri(C$_1$-C$_{10}$-alkyl)silyl, aryl, aryloxy, arylthio, arylamino, aryl-C$_1$-C$_4$-alkoxy, aryl-C$_3$-C$_4$-alkenyloxy, aryl-C$_2$-C$_4$-alkenylthio, aryl-C$_1$-C$_4$-alkylamino, aryl-C$_3$-C$_4$-alkenylamino, triarylsilyl, wherein aryl is phenyl, naphthyl or biphenyl, or a saturated, partially unsaturated or unsaturated 3- to 8-membered ring system which contains 1 to 4 heteroatoms selected from oxygen, nitrogen, sulfur, wherein these aryl and these heterocyclic ring systems are unsubstituted or substituted with any combination of from 1 to 6 groups selected from halogen, cyano, nitro, amino, hydroxy, mercapto, C$_1$-C$_4$-alkyl, C$_1$-C$_4$-haloalkyl, C$_3$-C$_8$-cycloalkyl, C$_1$-C$_4$-alkoxy, C$_1$-C$_4$-haloalkoxy, C$_1$-C$_4$-alkylthio, C$_1$-C$_4$-haloalkylthio, di(C$_1$-C$_4$-alkyl)amino, C$_1$-C$_4$-alkylamino, C$_1$-C$_4$-haloalkylamino, formyl and C$_1$-C$_4$-alkylcarbonyl;

$R^4$ is $NR^{12}R^{13}$;

$R^{12}$ and $R^{13}$ are each independently hydrogen; or C$_1$-C$_{20}$-alkyl, C$_2$-C$_{20}$-alkenyl or C$_2$-C$_{20}$-alkynyl, each of which is unsubstituted or substituted with any combination of 1 to 6 groups selected from C$_1$-C$_4$-alkoxy, C$_1$-C$_4$-alkylthio, cyano, nitro, formyl, C$_1$-C$_4$-alkylcarbonyl, C$_1$-C$_4$-alkoxycarbonyl, C$_1$-C$_4$-alkylaminocarbonyl, alkyl)aminocarbonyl, C$_1$-C$_4$-alkylsulfinyl, C$_1$-C$_4$-alkylsulfonyl, C$_3$-C$_8$-cycloalkyl, and phenyl, wherein phenyl itself is unsubstituted or substituted by 1 to 4 substituents selected from halogen, C$_1$-C$_4$-alkyl, C$_1$-C$_4$-alkoxy, C$_1$-C$_4$-fluoroalkyl, C$_1$-C$_4$-alkyloxycarbonyl, trifluoromethylsulfonyl, formyl, nitro and cyano; or C$_1$-C$_{20}$-haloalkyl, C$_2$-C$_{20}$-haloalkenyl, C$_2$-C$_{20}$-haloalkynyl, C$_5$-C$_{10}$-cycloalkenyl, or a saturated or partially unsaturated or unsaturated 3- to 8-membered ring system which contains 1 to 4 heteroatoms selected from oxygen, nitrogen, sulfur, or phenyl or naphthyl, wherein this ring system and phenyl or naphthyl themselves are unsubstituted or substituted by 1 to 4 substituents selected from halogen, C$_1$-C$_4$-alkyl, C$_1$-C$_4$-alkoxy, C$_1$-C$_4$-fluoroalkyl, C$_1$-C$_4$-alkyloxycarbonyl, trifluoromethylsulfonyl, formyl, nitro and cyano; or $R^{12}$ and $R^{13}$ together with the nitrogen atom to which they are attached form a saturated or partially unsaturated 5- to 8-membered heterocycle which besides the one nitrogen atom contains 0 to 2 further heteroatoms selected from oxygen, nitrogen, sulfur, and may contain 1 or 2 carbonyl groups or thiocarbonyl groups and which is unsubstituted or substituted by from 1 to 4 groups selected from C$_1$-C$_4$-alkyl, C$_1$-C$_4$-alkoxy and C$_1$-C$_4$-haloalkyl;

$R^5$ is hydrogen; or C$_1$-C$_{20}$-alkyl, C$_2$-C$_{20}$-alkenyl, C$_2$-C$_{20}$-alkynyl, C$_1$-C$_4$-alkylcarbonyl, C$_1$-C$_4$-alkylaminocarbonyl, C$_1$-C$_4$-alkoxycarbonyl, each of which is unsubstituted or substituted by from 1 to 6 groups selected from C$_1$-C$_4$-alkoxy, cyano, nitro, formyl, C$_1$-C$_4$-alkylcarbonyl, C$_1$-C$_4$-alkoxycarbonyl, C$_1$-C$_4$-alkylaminocarbonyl, di(C$_1$-C$_4$-alkyl)aminocarbonyl, C$_1$-C$_4$-alkylsulfonyl, C$_3$-C$_8$-cycloalkyl, and phenyl, wherein phenyl itself is unsubstituted or substituted by 1 to 4 substituents selected from halogen, C$_1$-C$_4$-alkyl, alkoxy, C$_1$-C$_4$-fluoroalkyl, C$_1$-C$_4$-alkyloxycarbonyl, trifluoromethylsulfonyl, formyl, nitro and cyano; or C$_1$-C$_{20}$-haloalkyl, C$_2$-C$_{20}$-haloalkenyl, C$_2$-C$_{20}$-haloalkynyl, C$_5$-C$_{10}$-cycloalkenyl, or a saturated or partially unsaturated or unsaturated 3- to 8-membered ring system which contains 1 to 4 heteroatoms selected from oxygen, nitrogen, sulfur, or phenyl or naphthyl, wherein this ring system and phenyl or naphthyl themselves are unsubstituted or substituted by 1 to 4 substituents selected from halogen, C$_1$-C$_4$-alkyl, C$_1$-C$_4$-alkoxy, C$_1$-C$_4$-fluoroalkyl, C$_1$-C$_4$-alkyloxycarbonyl, trifluoromethylsulfonyl, formyl, nitro and cyano;

$Q^1$ and $Q^2$ each independently are hydrogen, halogen, cyano, SCN, nitro, hydroxy, C$_2$-C$_{10}$-alkenyl, C$_2$-C$_{10}$-haloalkenyl, $C_2$-$C_{10}$-alkynyl, $C_3$-$C_{10}$-haloalkynyl, $C_3$-$C_8$-cycloalkyl, $C_3$-$C_8$-halocycloalkyl, $C_1$-$C_{10}$-haloalkoxy, $C_1$-$C_{10}$-haloalkylthio, $C_1$-$C_{10}$-haloalkylsulfinyl, $C_1$-$C_{10}$-haloalkylsulfonyl, $C_1$-$C_{10}$-alkylsulfonyloxy, $C_1$-$C_{10}$-haloalkylsulfonyloxy, di($C_1$-$C_{10}$-alkyl)amino, $C_3$-$C_8$-cycloalkylamino, alkylcarbonyl, $C_1$-$C_{10}$-alkoxycarbonyl, $C_1$-$C_{10}$-alkylaminocarbonyl, di($C_1$-$C_{10}$-alkyl)aminocarbonyl, or tri($C_1$-$C_{10}$)-alkylsilyl, or $Q^1$ and $Q^2$ are each independently phenyl, benzyl or phenoxy, wherein each ring is unsubstituted or substituted with any combination of from 1 to 3 substituents independently selected from the group halogen, cyano, nitro, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_3$-$C_8$-cycloalkyl, $C_3$-$C_8$-halocycloalkyl, $C_1$-$C_{10}$-haloalkoxy, $C_1$-$C_{10}$-alkylthio, $C_3$-$C_8$-cycloalkylamino, $C_1$-$C_{10}$-alkyl-$C_3$-$C_8$-cycloalkylamino, alkylcarbonyl, $C_1$-$C_{10}$-alkoxycarbonyl, $C_1$-$C_{10}$-alkylaminocarbonyl, di($C_1$-$C_{10}$-alkyl)aminocarbonyl and tri($C_1$-$C_{10}$)-alkylsilyl;

$Q^3$ is halogen; or $C_1$-$C_{10}$-alkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_3$-$C_8$-cycloalkyl, $C_3$-$C_8$-halocycloalkyl, $C_1$-$C_{10}$-alkyl-$C_3$-$C_8$-cycloalkyl, $C_1$-$C_{10}$-haloalkyl-$C_3$-$C_8$-cycloalkyl, each unsubstituted or independently substituted with 1 to 2 groups selected from cyano, $C_1$-$C_{10}$-haloalkoxy, $C_1$-$C_{10}$-haloalkylsulfonyl, and $C_1$-$C_{10}$-alkoxycarbonyl; or $Q^3$ is $OR^{14}$, $S(O)_qR^{14}$, $NR^{15}R^{16}$, $OS(O)_2R^{17}$, $NR^{16}S(O)_2R^{17}$, $C(S)NH_2$, $C(R^{18})=NOR^{18}$, $C_1$-$C_{10}$-alkylaminothiocarbonyl, or di($C_1$-$C_{10}$-alkyl)aminothiocarbonyl;

$R^{14}$ is $C_1$-$C_{10}$-alkyl, $C_2$-$C_{10}$-alkenyl, $C_2$-$C_{10}$-haloalkenyl, alkynyl, $C_3$-$C_{10}$-haloalkynyl, $C_3$-$C_8$-cycloalkyl, $C_3$-$C_8$-halocycloalkyl, $C_3$-$C_8$-cycloalkyl-$C_1$-$C_4$-alkyl, $C_1$-$C_4$-alkyl-$C_3$-$C_8$-cycloalkyl, $C_3$-$C_8$-halocycloalkyl-$C_1$-$C_4$-alkyl, $C_1$-$C_4$-haloalkyl-$C_3$-$C_8$-cycloalkyl, or $C_1$-$C_{10}$-haloalkylcarbonyl, each unsubstituted or substituted with 1 $R^{19}$;

$R^{15}$ is $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_3$-$C_8$-cycloalkyl, $C_3$-$C_8$-halocycloalkyl, $C_1$-$C_4$-haloalkyl-$C_3$-$C_8$-cycloalkyl, or $C_1$-$C_{10}$-haloalkylcarbonyl, each unsubstituted or substituted with 1 $R^{19}$;

$R^{16}$ is hydrogen; or $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_3$-$C_8$-cycloalkyl, $C_3$-$C_8$-halocycloalkyl, $C_1$-$C_4$-alkyl-$C_3$-$C_8$-cycloalkyl, or $C_1$-$C_4$-haloalkyl-$C_3$-$C_8$-cycloalkyl, each unsubstituted or substituted with 1 $R^{19}$;

$R^{17}$ is $C_1$-$C_{10}$-alkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_3$-$C_8$-cycloalkyl, $C_3$-$C_8$-halocycloalkyl, $C_1$-$C_4$-alkyl-$C_3$-$C_8$-cycloalkyl, or $C_1$-$C_4$-haloalkyl-$C_3$-$C_8$-cycloalkyl, each unsubstituted or substituted with 1 $R^{19}$;

$R^{19}$ is cyano, nitro, $C_1$-$C_{10}$-alkoxy, $C_1$-$C_{10}$-haloalkoxy, $C_1$-$C_{10}$-haloalkylthio, $C_1$-$C_{10}$-haloalkylsulfinyl, alkylsulfonyl, $C_1$-$C_{10}$-haloalkylsulfonyl, $C_1$-$C_{10}$-alkoxycarbonyl, $C_1$-$C_{10}$-alkylamino, or di($C_1$-$C_{10}$-alkyl)amino; or $R^{19}$ is phenyl or a heteroaromatic 5- or 6-membered ring which contains 1 to 4 heteroatoms selected from oxygen, nitrogen, sulfur, the phenyl radical and the heteroaromatic ring being unsubstituted or substituted with any combination of from 1 to 3 groups selected from halogen, cyano, nitro, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_3$-$C_8$-cycloalkyl, $C_3$-$C_8$-halocycloalkyl, $C_1$-$C_{10}$-alkoxy, $C_1$-$C_{10}$-haloalkoxy, $C_1$-$C_{10}$-alkylthio, $C_1$-$C_{10}$-alkylsulfinyl, $C_1$-$C_{10}$-alkylsulfonyl, $C_1$-$C_{10}$-alkylamino, di($C_1$-$C_{10}$-alkyl)amino, $C_3$-$C_8$-cycloalkylamino, $C_1$-$C_{10}$-alkyl-$C_3$-$C_8$-cycloalkylamino, $C_1$-$C_{10}$-alkylcarbonyl, $C_1$-$C_{10}$-alkoxycarbonyl, $C_1$-$C_{10}$-alkylaminocarbonyl, di($C_1$-$C_{10}$-alkyl)aminocarbonyl and tri($C_1$-$C_{10}$)-alkylsilyl;

$R^{18}$ is the same or different: hydrogen, $C_1$-$C_{10}$-alkyl, or $C_1$-$C_{10}$-haloalkyl;

q is 0, 1 or 2;

$Q^4$ is halogen, cyano, nitro, hydroxy, COOH, $C(O)NH_2$, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_3$-$C_8$-cycloalkyl, $C_3$-$C_8$-halocycloalkyl, $C_1$-$C_{10}$-alkoxy, $C_1$-$C_{10}$-haloalkoxy, $C_1$-$C_{10}$-alkylthio, $C_1$-$C_{10}$-haloalkylthio, $C_1$-$C_{10}$-alkylsulfinyl, $C_1$-$C_{10}$-haloalkylsulfinyl, $C_1$-$C_{10}$-alkylsulfonyl, $C_1$-$C_{10}$-haloalkylsulfonyl, $C_1$-$C_{10}$-alkylamino, di($C_1$-$C_{10}$-alkyl)amino, $C_3$-$C_8$-cycloalkylamino, $C_1$-$C_{10}$-alkylcarbonyl, $C_1$-$C_{10}$-alkoxycarbonyl $C_1$-$C_{10}$-alkylaminocarbonyl, di($C_1$-$C_{10}$-alkyl)aminocarbonyl or tri($C_1$-$C_{10}$)-alkylsilyl; or $Q^4$ is phenyl, benzyl, benzyloxy, phenoxy, a 5- or 6-membered heteroaromatic ring which contains 1 to 4 heteroatoms selected from oxygen, nitrogen, sulfur or an aromatic 8-, 9- or 10-membered fused heterobicyclic ring system which contains 1 to 4 heteroatoms selected from oxygen, nitrogen, sulfur, wherein each of the above ring systems is unsubstituted or substituted with any combination of from 1 to 3 groups selected from halogen, cyano, nitro, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_3$-$C_8$-cycloalkyl, $C_3$-$C_8$-halocycloalkyl, $C_1$-$C_{10}$-alkoxy, $C_1$-$C_{10}$-haloalkoxy, $C_1$-$C_{10}$-alkylthio, $C_1$-$C_{10}$-alkylsulfinyl, $C_1$-$C_{10}$-alkylsulfonyl, $C_1$-$C_{10}$-alkylamino, di($C_1$-$C_{10}$-alkyl)amino, $C_3$-$C_8$-cycloalkylamino, $C_1$-$C_{10}$-alkyl-$C_3$-$C_8$-cycloalkylamino, $C_1$-$C_{10}$-alkylcarbonyl, $C_1$-$C_{10}$-alkoxycarbonyl, $C_1$-$C_{10}$-alkylaminocarbonyl, di($C_1$-$C_{10}$-alkyl)aminocarbonyl and tri($C_1$-$C_{10}$)-alkylsilyl;

X and Y are each independently oxygen or sulfur;

V and V' are each independently N or $CQ^2$;

W is N, CH or $CQ^4$;

m is 0, 1 or 2;

n is 0 or 1;

p is 0, 1, 2, 3, or 4;

or the enantiomers or salts or N-oxides thereof.

In addition, the present invention relates to processes for preparing the compounds I, pesticidal compositions comprising compounds I and methods for the control of insects, acarids or nematodes by contacting the insect, acarid or nematode or their food supply, habitat or breeding grounds with a pesticidally effective amount of compounds or compositions of formula I.

Moreover, the present invention also relates to a method of protecting growing plants from attack or infestation by insects or acarids by applying to the foliage of the plants, or to the soil or water in which they are growing, with a pesticidally effective amount of compositions or compounds of formula I.

This invention also provides a method for treating, controlling, preventing or protecting animals against infestation or infection by parasites which comprises orally, topically or parenterally administering or applying to the animals a parasiticidally effective amount of compositions or compounds of formula I.

In spite of the commercial insecticides, acaricides and nematicides available today, damage to crops, both growing and harvested, caused by insects and nematodes still occurs. Therefore, there is continuing need to develop new and more effective insecticidal, acaricidal and nematicidal agents.

It was therefore an object of the present invention to provide new pesticidal compositions, new compounds and new methods for the control of insects, acarids or nematodes and of protecting growing plants from attack or infestation by insects, arachnids or nematodes.

We have found that these objects are achieved by the compositions and the compounds of formula I. Furthermore, we have found processes for preparing the compounds of formula I.

Anthranilamide compounds have been described in a number of patent applications (WO 01/70671, WO 03/015518, WO 03/015519, WO 04/046129). N-Thioanthranilamide compounds have not been described in the prior art.

Compounds of the formula (I-1) wherein X and Y are oxygen and the other substituents are as defined above for formula (I)

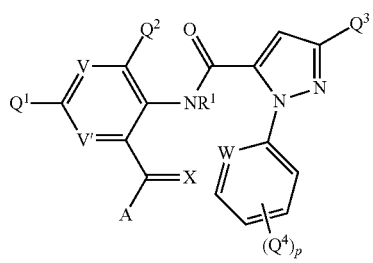

(I-1)

can be prepared by reacting a carboxylic acid of the formula (II)

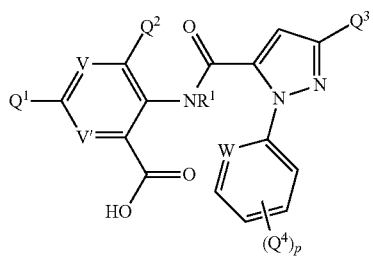

(II)

wherein the variables are as defined for formula (I) in the form of an activated derivative of this acid in the presence of a base with a compound of the formula $A^1$-H or $A^2$-H, respectively, wherein the variables are as defined for formula (I).

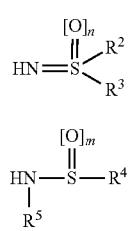

($A^1$-H)

($A^2$-H)

Suitable activated derivatives of the acid which may be used are, for example, anhydrides, azolides, or acid halides.

The activated derivatives of the acid can be obtained according to procedures known in the art, e.g. as listed in "Comprehensive Organic Reactions" VCH Publishers 1989, for the anhydride: pp 965-66, for the acid halides: p 978.

Suitable bases are, for example, amines such as triethylamine, diisopropylethylamine, pyridine or lutidine or else alkali hydrides, hydroxides, carbonates, or alkaline earth metal hydroxides, carbonates or bicarbonates.

The amount of the base that can be used in the reaction is usually 1 to 5 moles relative to 1 mole of compound (II).

The reaction is advantageously carried out in an inert solvent such as dichloromethane, chloroform, carbon tetrachloride, benzene, toluene, diethyl ether or tetrahydrofurane, or mixtures of these solvents, in a temperature range between 0° C. and 100° C., preferably between 20° C. and 50° C.

A preferred procedure for the preparation of specific compounds of formula (I-1) involves the reaction of $A^1$-H or $A^2$-H, respectively, with a benzoxazinone of formula (III)

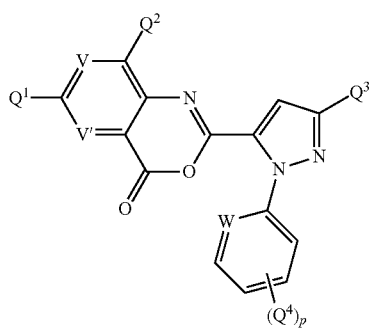

(III)

wherein the variables are as defined for formula (I). Typical procedures involve combination of the compounds $A^1$-H or $A^2$-H with the benzoxazinone of formula (III) in inert solvent such as dichloromethane, chloroform, carbon tetrachloride, benzene, toluene, diethyl ether or tetrahydrofurane, or mixtures of these solvents, in a temperature range between 0° C. and 100° C., preferably between 20° C. and 50° C. Addition of a base can be beneficial. Suitable bases are, for example, tertiary amines such as triethylamine, diisopropylethylamine, pyridine or lutidine or else alkali hydrides, hydroxides, carbonates, or alkaline earth metal hydroxides, carbonates or bicarbonates. The amount of the base that can be used in the reaction is usually 1 to 5 moles relative to 1 mole of compound (III).

Benzoxazinones are well documented in the chemical literature and are available via known methods that involve the coupling of either an anthranilic acid or an isatoic anhydride with an acid chloride. For references to the synthesis and chemistry of benzoxazinones see Jakobsen et al, *Bioorganic and Medicinal Chemistry*, 2000, 8, 2095-2103 and references cited therein. See also Coppola, *J. Heterocyclic Chemistry*, 1999, 36, 563-588. The benzoxazinones of formula III can also be prepared according to the procedures described in WO 04/046129 or WO 04/011447 as well as according to references cited therein and suitable modifications thereof.

Compounds of the formula (I-2) in which A is $A^1$, n is 0, X and Y are oxygen and the other variables are as defined for formula (I),

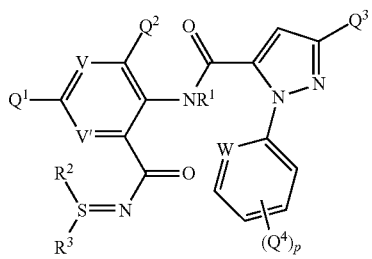

(I-2)

can be prepared by reacting an amide of the formula (IV)

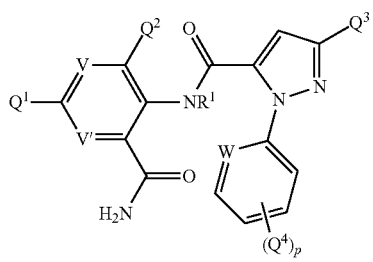

(IV)

wherein the variables are as defined for formula (I), with a sulfoxide of the formula (V),

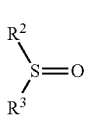

(V)

in the presence of a condensating agent, giving the compounds of formula (I-2) with elimination of water. Suitable condensing agents are, for example, phosphorous oxychloride, phosphorous (V) oxide, methanesulfonyl chloride, sulfuryl chloride, sulfur trichloride, boron triflouride, dicyclohexylcarbodiimide, aryl cyanates or acid anhydrides, preferably trifluoroacetic anhydride or trifluoromethanesulfonic anhydride.

In the compounds of the formula (I) prepared as described above in which A is $A^1$, n is 0, X and Y are oxygen and the other variables are as defined for formula (I) the sulfur atom can be oxidized to give the respective compounds of the formula (I) in which n is 1. Suitable oxidizing agents are, for example, sodium periodate or organic peracids, such as 3-chloroperbenzoic acid, see e.g. Houben-Weyl, Methoden der Organischen Chemie, Bd. E11, p. 1299 ff., G. Thieme Verlag, Stuttgart 1985.

The carboxylic acids of formula (II) and the amides of formula (IV) can be prepared, for example, according to the procedures described in WO 04/046129 or WO 04/011447 as well as according to references cited therein and suitable modifications thereof.

After completion of the reaction, the compounds of formula I can be isolated by employing conventional methods such as adding the reaction mixture to water, extracting with an organic solvent, concentrating the extract an the like. The isolated compound (I) can be purified by a technique such as chromatography, recrystallization and the like, if necessary.

Compounds of formula $A^1$-H can be prepared according to procedures known in the art, e.g. as described in U.S. Pat. No. 6,136,983 and references cited therein.

Compounds of formula $A^2$-H can be prepared according to procedures known in the art, e.g. as described in WO 03/097589 and references cited therein.

Sulfoxides of formula V can be obtained according to procedures known in the art, e.g. as described in J. March, Advanced Organic Chemistry, $4^{th}$ Edition, Wiley, 1992, p. 1297.

Compounds of formula I, II, III, IV, V, and compounds $A^1$-H and $A^2$-H which cannot be prepared according to the above procedures can be prepared according to suitable modifications of the above procedures.

The preparation of the compounds of formula I above may lead to them being obtained as isomer mixtures. If desired, these can be resolved by the methods customary for this purpose, such as crystallization or chromatography, also on optically active adsorbate, to give the pure isomers.

Agronomically acceptable salts of the compounds I can be formed in a customary manner, e.g. by reaction with an acid of the anion in question.

In this specification and in the claims, reference will be made to a number of terms that shall be defined to have the following meanings:

"Salt" as used herein includes adducts of compounds I with maleic acid, dimaleic acid, fumaric acid, difumaric acid, methane sulfenic acid, methane sulfonic acid, and succinic acid. Moreover, included as "salts" are those that can form with, for example, amines, metals, alkaline earth metal bases or quaternary ammonium bases, including zwitterions. Suitable metal and alkaline earth metal hydroxides as salt formers include the salts of barium, aluminum, nickel, copper, manganese, cobalt zinc, iron, silver, lithium, sodium, potassium, magnesium or calcium. Additional salt formers include chloride, sulfate, acetate, carbonate, hydride, and hydroxide. Desirable salts include adducts of compounds I with maleic acid, dimaleic acid, fumaric acid, difumaric acid, and methane sulfonic acid.

"Halogen" will be taken to mean fluoro, chloro, bromo and iodo.

The term "alkyl" as used herein refers to a branched or unbranched saturated hydrocarbon group having 1 to 10 carbon atoms, such as, and preferably, $C_1$-$C_6$-alkyl, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

The term "haloalkyl" as used herein refers to a straight-chain or branched alkyl group having 1 to 10 carbon atoms (as mentioned above), where some or all of the hydrogen atoms in these groups may be replaced by halogen atoms as mentioned above, for example $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Similarly, "alkoxy" and "alkylthio" refer to straight-chain or branched alkyl groups having 1 to 10 carbon atoms (as mentioned above) bonded through oxygen or sulfur linkages, respectively, at any bond in the alkyl group. Examples include methoxy, ethoxy, propoxy, isopropoxy, methylthio, ethylthio, propylthio, isopropylthio, and n-butylthio.

Similarly, "alkylamino" refers to a nitrogen atom which carries 1 or 2 straight-chain or branched alkyl groups having 1 to 10 carbon atoms (as mentioned above) which may be the same or different. Examples include methylamino, dimethylamino, ethylamino, diethylamino, methylethylamino, isopropylamino, or methylisopropylamino.

Similarly, "alkylsulfinyl" and "alkylsulfonyl" refer to straight-chain or branched alkyl groups having 1 to 10 carbon atoms (as mentioned above) bonded through —S(=O)— or —S(=O)$_2$-linkages, respectively, at any bond in the alkyl group. Examples include methylsulfinyl and methylsulfonyl.

The term "alkylcarbonyl" refers to straight-chain or branched alkyl groups having 1 to 10 carbon atoms (as mentioned above) bonded through a —C(=O)— linkage, respectively, at any bond in the alkyl group. Examples include acetyl, propionyl, buturyl, or 2-methylbuturyl.

The term "alkenyl" as used herein intends a branched or unbranched unsaturated hydrocarbon group having 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

The term "alkynyl" as used herein refers to a branched or unbranched unsaturated hydrocarbon group containing at least one triple bond, such as ethynyl, propynyl, 1-butynyl, 2-butynyl, and the like.

A saturated, partially unsaturated or unsaturated 3- to 8-membered ring system which contains 1 to 4 heteroatoms selected from oxygen, nitrogen, sulfur, is a ring system wherein two oxygen atoms must not be in adjacent positions and wherein at least 1 carbon atom must be in the ring system e.g. thiophen, furan, pyrrol, thiazol, oxazol, imidazol, isothiazol, isoxazol, pyrazol, 1,3,4-oxadiazol, 1,3,4-thiadiazol, 1,3,4-triazol, 1,2,4-oxadiazol, 1,2,4-thiadiazol, 1,2,4-triazol, 1,2,3-triazol, 1,2,3,4-tetrazol, benzo[b]thiophen, benzo[b]furan, indol, benzo[c]thiophen, benzo[c]furan, isoindol, benzoxazol, benzothiazol, benzimidazol, benzisoxazol, benzisothiazol, benzopyrazol, benzothiadiazol, benzotriazol, dibenzofuran, dibenzothiophen, carbazol, pyridin, pyrazin, pyrimidin, pyridazin, 1,3,5-triazin, 1,2,4-triazin, 1,2,4,5-tetrazin, chinolin, isochinolin, chinoxalin, chinazolin, cinnolin, 1,8-naphthyridin, 1,5-naphthyridin, 1,6-naphthyridin, 1,7-naphthyridin, phthalazin, pyridopyrimidin, purin, pteridin, 4H-chinolizin, piperidin, pyrrolidin, oxazolin, tetrahydrofuran, tetrahydropyran, isoxazolidin or thiazolidin.

A saturated, partially unsaturated or unsaturated 3- to 8-membered ring system which contains 1 to 4 heteroatoms selected from oxygen, nitrogen, sulfur also is e.g. a saturated, partially unsaturated or unsaturated 5- or 6-membered heterocycle which contains 1 to 4 heteroatoms selected from oxygen, nitrogen and sulfur, such as pyridine, pyrimidine, (1,2,4)-oxadiazole, (1,3,4)-oxadiazole, pyrrole, furan, thiophene, oxazole, thiazole, imidazole, pyrazole, isoxazole, 1,2,4-triazole, tetrazole, pyrazine, pyridazine, oxazoline, thiazoline, tetrahydrofuran, tetrahydropyran, morpholine, piperidine, piperazine, pyrroline, pyrrolidine, oxazolidine, thiazolidine, oxirane or oxetane; or a saturated, partially unsaturated or unsaturated 5- or 6-membered heterocycle which contains 1 nitrogen atom and 0 to 2 further heteroatoms selected from oxygen, nitrogen and sulfur, preferably from oxygen and nitrogen, such as piperidine, piperazin and morpholine.

Preferably, this ring system is a saturated, partially unsaturated or unsaturated 3- to 6-membered ring system which contains 1 to 4 heteroatoms selected from oxygen, nitrogen, sulfur, wherein two oxygen atoms must not be in adjacent positions and wherein at least 1 carbon atom must be in the ring system.

Most preferably, this ring system is a radical of pyridine, pyrimidine, (1,2,4)-oxadiazol, 1,3,4-oxadiazol, pyrrol, furan, thiophen, oxazol, thiazol, imidazol, pyrazol, isoxazol, 1,2,4-triazol, tetrazol, pyrazin, pyridazin, oxazolin, thiazolin, tetrahydrofuran, tetrahydropyran, morpholin, piperidin, piperazin, pyrrolin, pyrrolidin, oxazolidin, thiazolidin, oxiran or oxetan.

Tri($C_1$-$C_{10}$)alkylsilyl refers to a silicon atom having 3 straight-chain or branched $C_1$-$C_{10}$-alkyl groups as defined above which may be the same or different. Examples include trimethylsilyl, triethylsilyl, triphenylsilyl or triisopropylsilyl.

Cycloalkyl: monocyclic 3- to 6-, or 8-membered saturated carbon atom rings, e.g. $C_3$-$C_8$-cycloalkyl such as cyclopropyl, cyclobutyl, cyclopentyl, cyclohexyl, cycloheptyl, or cyclooctyl.

With respect to the intended use of the compounds of formula I, particular preference is given to the following meanings of the substituents, in each case on their own or in combination:

A compound of formula I wherein $R^1$ is hydrogen, $C_1$-$C_6$-alkyl, cyano, $C_1$-$C_6$-alkylsulfonyl, or $C_2$-$C_6$-alkoxycarbonyl, preferably hydrogen or $C_1$-$C_4$-alkyl, most preferably hydrogen.

A compound of formula I wherein A is $A^1$.

A compound of formula I wherein A is $A^2$.

A compound of formula I wherein $R^2$ and $R^3$ each independently are $R^6$, —C(=O)$R^7$, C(=NO$R^7$)$R^7$, —C(=NN$R^7_2$)$R^7$, —C(=O)O$R^7$, —C(=O)N$R^7_2$, —OC(=O)$R^7$, —OC(=O)O$R^7$, C(=O)N$R^7$—N$R^7_2$, —C(=O)N$R^7$—N$R^7$[C(=O)$R^7$], or $R^2$ and $R^3$ together with the sulfur atom to which they are attached form a saturated, partially unsaturated or unsaturated 3- to 8-membered ring which contains 1 to 4 heteroatoms selected from oxygen, nitrogen, sulfur, which ring can be fused with one or two saturated, partially unsaturated or unsaturated 5- to 6-membered rings which may contain 1 to 4 heteroatoms selected from oxygen, nitrogen, sulfur, wherein all of the above rings are unsubstituted or substituted by any combination of 1 to 6 groups $R^8$.

More preferably, $R^2$ and $R^3$ each independently are $R^6$ or $R^2$ and $R^3$ together with the sulfur atom to which they are attached form a saturated, partially unsaturated or unsaturated 3- to 8-membered ring which contains 1 to 4 heteroatoms selected from oxygen, nitrogen, sulfur, which ring can be fused with one or two saturated, partially unsaturated or unsaturated 5- to 6-membered rings which may contain 1 to 4 heteroatoms selected from oxygen, nitrogen, sulfur, wherein all of the above rings are unsubstituted or substituted by any combination of 1 to 6 groups $R^8$.

Even more preferred are compounds of formula I wherein $R^2$ and $R^3$ each independently are $R^6$, preferably hydrogen, $C_1$-$C_{20}$-alkyl, $C_2$-$C_{20}$-alkenyl, $C_2$-$C_{20}$-alkynyl, $C_3$-$C_8$-cycloalkyl, $C_3$-$C_8$-cycloalkenyl, $C_3$-$C_8$-cycloalkynyl, phenyl, naphthyl, biphenyl, or a saturated, partially unsaturated or unsaturated 3- to 8-membered ring which contains 1 to 4 heteroatoms selected from oxygen, nitrogen, sulfur, wherein all of these groups are unsubstituted or substituted by any combination of 1 to 6 groups $R^9$.

Especially preferred are compounds of formula I wherein $R^2$ and $R^3$ each independently are $C_1$-$C_{10}$-alkyl, $C_2$-$C_{10}$-alkenyl, $C_2$-$C_{10}$-alkynyl, $C_3$-$C_8$-cycloalkyl, or phenyl, wherein these groups are unsubstituted or substituted by any combination of 1 to 6 groups selected from $R^{10}$ or $R^{11}$, and $R^{10}$ is $C_1$-$C_{10}$-alkyl, $C_3$-$C_8$-cycloalkyl, $C_1$-$C_{10}$-alkyl-$C_3$-$C_8$-cycloalkyl or a saturated, partially unsaturated or unsaturated 3- to 8-membered ring which contains 1 to 4 heteroatoms selected from oxygen, nitrogen, sulfur, wherein these groups are unsubstituted or substituted with any combination of from 1 to 6 groups $R^{11}$, and $R^{11}$ is halogen, cyano, nitro, hydroxy, mercapto, amino, formyl, $C_1$-$C_{10}$-alkylcarbonyl, $C_1$-$C_{10}$-alkoxy, $C_2$-$C_{10}$-alkenyloxy, $C_2$-$C_{10}$-alkynyloxy, $C_1$-$C_{10}$-haloalkoxy, $C_3$-$C_8$-cycloalkoxy, $C_3$-$C_8$-halocycloalkoxy, $C_1$-$C_{10}$-alkoxycarbonyl, $C_3$-$C_8$-cycloalkoxycarbonyl, $C_1$-$C_{10}$-alkylcarbonyloxy, $C_3$-$C_8$-cyclo alkylcarbonyloxy, $C_1$-$C_{10}$-haloalkoxycarbonyl, $C_1$-$C_{10}$-haloalkylcarbonyloxy, $C_1$-$C_{10}$-alkanamido, $C_3$-$C_8$-cycloalkanamido, $C_1$-$C_{10}$-alkylthio, $C_2$-$C_{10}$-alkenylthio, $C_2$-$C_{10}$-alkynylthio, $C_1$-$C_{10}$-haloalkylthio, $C_3$-$C_8$-cycloalkylthio, $C_3$-$C_8$-halocycloalkylthio, $C_3$-$C_8$-cycloalkyl-$C_1$-$C_4$-alkylthio, $C_1$-$C_{10}$-alkylsulfinyl, $C_2$-$C_{10}$-alkenylsulfinyl, $C_2$-$C_{10}$-alkynylsulfinyl, $C_1$-$C_{10}$-haloalkylsulfinyl, $C_3$-$C_8$-cycloalkylsulfinyl, $C_3$-$C_8$-halocycloalkenylsulfinyl, $C_3$-$C_8$-cycloalkyl-$C_1$-$C_4$-alkylsulfinyl, $C_1$-$C_{10}$-alkylsulfonyl, $C_2$-$C_{10}$-alkenylsulfonyl, $C_2$-$C_{10}$-alkynylsulfonyl, $C_1$-$C_{10}$-haloalkylsulfonyl, $C_3$-$C_8$-cycloalkylsulfonyl, $C_3$-$C_8$-halocycloalkylsulfonyl, $C_3$-$C_8$-cycloalkyl-$C_1$-$C_4$-alkylsulfonyl, di($C_1$-$C_{10}$-alkyl)amino, $C_1$-$C_{10}$-alkylamino, $C_2$-$C_{10}$-alkenylamino, $C_2$-$C_{10}$-alkynylamino, $C_1$-$C_{10}$-alkyl-$C_2$-$C_{10}$-alkenylamino, $C_1$-$C_{10}$-alkyl-$C_2$-$C_{10}$-alkynylamino, $C_1$-$C_{10}$-haloalkylamino, $C_2$-$C_{10}$-haloalkenylamino, $C_3$-$C_8$-cycloalkylamino, tri($C_1$-$C_{10}$-alkyl)silyl, aryl, aryloxy, arylthio, arylamino, wherein aryl is phenyl, naphthyl or biphenyl, or a saturated, partially unsaturated or unsaturated 3- to 8-membered ring system which contains 1 to 4 heteroatoms selected from oxygen, nitrogen, sulfur, wherein these aryl and these heterocyclic ring systems are unsubstituted or substituted with any combination of from 1 to 6 groups selected from halogen, cyano, nitro, amino, hydroxy, mercapto, $C_1$-$C_4$-alkyl, $C_1$-$C_4$-haloalkyl, $C_1$-$C_4$-alkoxy, $C_1$-$C_4$-haloalkoxy, $C_1$-$C_4$-haloalkylthio, di($C_1$-$C_4$-alkyl)amino and $C_1$-$C_4$-alkylamino.

More preferred are compounds of formula I wherein $R^2$ and $R^3$ each independently are $C_1$-$C_{10}$-alkyl, $C_2$-$C_{10}$-alkenyl, $C_2$-$C_{10}$-alkynyl, $C_3$-$C_8$-cycloalkyl, or phenyl, wherein these groups are unsubstituted or substituted by any combination of 1 to 6 groups selected from $R^{11}$, and $R^{11}$ is halogen, cyano, nitro, hydroxy, mercapto, amino, $C_1$-$C_{10}$-alkoxy, $C_1$-$C_{10}$-haloalkoxy, $C_3$-$C_8$-cycloalkoxy, $C_1$-$C_{10}$-alkoxycarbonyl, $C_1$-$C_{10}$-alkylcarbonyloxy, $C_1$-$C_{10}$-alkanamido, $C_1$-$C_{10}$-alkylthio, $C_1$-$C_{10}$-alkylsulfinyl, $C_1$-$C_{10}$-alkylsulfonyl, di($C_1$-$C_{10}$-alkyl)amino or $C_1$-$C_{10}$-alkylamino.

Preferred are also compounds of formula I wherein $R^2$ and $R^3$ together with the sulfur atom to which they are attached form a 5- or 6-membered heterocycle which besides the sulfur atom contains 1 nitrogen or 1 oxygen atom, wherein these groups are unsubstituted or substituted by any combination of 1 to 6 groups selected from with any combination of from 1 to 6 groups selected from halogen, cyano, nitro, amino, hydroxy, mercapto, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, di($C_1$-$C_4$-alkyl)amino and $C_1$-$C_4$-alkylamino.

Preferred are also compounds of formula I wherein $R^2$ and $R^3$ together with the sulfur atom to which they are attached form a unit $SR^2R^3$ of the following formula:

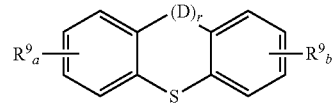

wherein
r is 0 or 1;
D is a direct bond, branched or straight $C_1$-$C_4$-alkylene, O, $S(O)_{0,1,2}$ or $NR^j$, preferably $CH_2$, O, or $NR^j$;
$R^9$ is as defined above for compounds of formula I;
$R^j$ is hydrogen, $C_1$-$C_4$-alkyl, $C_1$-$C_4$-alkylcarbonyl, $C_1$-$C_4$-alkoxycarbonyl, $C_1$-$C_4$-alkylaminocarbonyl, di($C_1$-$C_4$-alkyl)aminocarbonyl, or $C_1$-$C_4$-alkylsulfonyl;
a,b are the same or different 0, 1, 2, 3 or 4, preferably 0, 1, or 2.

When r=0 then the both arylgroups are unbridged.

Preferred are compounds of formula I wherein $R^9$ is $R^{10}$, $R^{11}$, or —C(=O)$R^{10}$, —C(=NOR$^{10}$)$R^{10}$, —C(=NNR$^{10}_2$)$R^{10}$, —C(=O)OR$^{10}$, —C(=O)NR$^{10}_2$, —C(=O)NR$^{10}$—NR$^{10}_2$, —C(=O)NR$^{10}$—NR$^{10}$[C(=O)R$^{10}$], —SO$_2$NR$^{10}_2$, —OR$^{10}$, —NR$^{10}_2$, or —SR$^{10}$.

Preferred are compounds of formula I wherein $R^4$ is $NR^{12}R^{13}$ and $R^{12}$ and $R^{13}$ are each independently hydrogen, $C_1$-$C_{20}$-alkyl, $C_2$-$C_{20}$-alkenyl or $C_2$-$C_{20}$-alkynyl, each of which is unsubstituted or substituted by from 1 to 6 groups selected from $C_1$-$C_4$-alkoxy, CN, NO$_2$, formyl, $C_1$-$C_4$-alkylcarbonyl, $C_1$-$C_4$-alkoxycarbonyl, $C_1$-$C_4$-alkylaminocarbonyl, di($C_1$-$C_4$-alkyl)aminocarbonyl, $C_1$-$C_4$-alkylsulfinyl, $C_1$-$C_4$-alkylsulfonyl, $C_3$-$C_8$-cycloalkyl, and phenyl, wherein phenyl itself is unsubstituted or substituted by 1 to 4 substituents selected from halogen, $C_1$-$C_4$-alkyl, $C_1$-$C_4$-alkoxy, $C_1$-$C_4$-fluoroalkyl, $C_1$-$C_4$-alkyloxycarbonyl, trifluoromethylsulfonyl, formyl, nitro and cyano; or $C_1$-$C_{20}$-haloalkyl, $C_2$-$C_{20}$-haloalkenyl, $C_2$-$C_{20}$-haloalkynyl, $C_5$-$C_{10}$-cycloalkenyl, or a saturated or partially unsaturated or unsaturated 3- to 8-membered ring system which contains 1 to 4 heteroatoms selected from oxygen, nitrogen, sulfur, wherein this ring system is unsubstituted or substituted by 1 to 4 substituents selected from halogen, $C_1$-$C_4$-alkyl, $C_1$-$C_4$-alkoxy, $C_1$-$C_4$-fluoroalkyl, $C_1$-$C_4$-alkyloxycarbonyl, trifluoromethylsulfonyl, formyl, nitro and cyano; or $R^{12}$ and $R^{13}$ together with the nitrogen atom to which they are attached may also form a saturated or partially unsaturated 5- to 8-membered heterocycle which besides the one nitrogen atom contains 0 to 2 further heteroatoms selected from oxygen, nitrogen, sulfur and may contain 1 or 2 carbonyl groups or thiocarbonyl groups and which is unsubstituted or substituted by from 1 to 4 groups selected from $C_1$-$C_4$-alkyl, $C_1$-$C_4$-alkoxy and $C_1$-$C_4$-haloalkyl.

More preferred are compounds of formula I wherein $R^4$ is $NR^{12}R^{13}$ and $R^{12}$ and $R^{13}$ are each independently hydrogen, $C_1$-$C_{20}$-alkyl, $C_2$-$C_{20}$-alkenyl or $C_2$-$C_{20}$-alkynyl, each of which is unsubstituted or substituted by from 1 to 3 CN, $C_1$-$C_{20}$-haloalkyl, or $R^{12}$ and $R^{13}$ together with the nitrogen atom to which they are attached may also form a saturated or partially unsaturated 5- to 8-membered heterocycle which besides the one nitrogen atom contains 0 to 2 further heteroatoms selected from oxygen, nitrogen, sulfur, and may contain 1 or 2 carbonyl groups or thiocarbonyl groups and which is unsubstituted or substituted by from 1 to 4 groups selected from $C_1$-$C_4$-alkoxy and $C_1$-$C_4$-haloalkyl.

Especially preferred are compounds of formula I wherein $R^4$ is $NR^{12}R^{13}$ and $R^{12}$ and $R^{13}$ together with the nitrogen atom to which they are attached are a saturated or partially unsaturated 5- or 6-membered nitrogen heterocycle which may be substituted by from 1 to 4 groups selected from $C_1$-$C_4$-alkyl, $C_1$-$C_4$-alkoxy and $C_1$-$C_4$-haloalkyl, in particular 2,5-dihydropyrrol-1-yl, 2,3-dihydropyrrol-1-yl, 1-pyrrolidinyl, 1-piperidinyl, 4-morpholinyl, 2-methylmorpholin-4-yl, 2,6-dimethylmorpholin-4-yl, or 1-methylpiperazin-4-yl.

Preferred are compounds of formula I wherein $R^5$ is hydrogen.

Preferred are compounds of formula I wherein $Q^1$ is hydrogen, halogen, cyano, SCN, nitro, hydroxy, $C_1$-$C_{10}$-alkyl, $C_1$-$C_{10}$-haloalkyl, $C_3$-$C_8$-cycloalkyl, $C_1$-$C_{10}$-alkoxy, $C_1$-$C_{10}$-haloalkoxy, $C_1$-$C_{10}$-alkylthio, $C_1$-$C_{10}$-haloalkylthio, $C_1$-$C_{10}$-alkylsulfonyl, $C_1$-$C_{10}$-alkylsulfonyloxy, $C_1$-$C_{10}$-alkylamino or di($C_1$-$C_{10}$-alkyl)amino, most preferably hydrogen, halogen, cyano, $C_1$-$C_4$-alkyl or $C_1$-$C_4$-haloalkyl.

Preferred are compounds of formula I wherein $Q^2$ is halogen, cyano, SCN, nitro, hydroxy, $C_1$-$C_{10}$-alkyl, $C_1$-$C_{10}$-haloalkyl, $C_3$-$C_8$-cycloalkyl, $C_1$-$C_{10}$-alkoxy, $C_1$-$C_{10}$-haloalkoxy, $C_1$-$C_{10}$-alkylthio, $C_1$-$C_{10}$-haloalkylthio, $C_1$-$C_{10}$-alkylsulfonyl, $C_1$-$C_{10}$-alkylsulfonyloxy, $C_1$-$C_{10}$-alkylamino or di($C_1$-$C_{10}$-alkyl)amino, most preferably halogen, cyano, $C_1$-$C_4$-alkyl or $C_1$-$C_4$-haloalkyl.

Preferred are compounds of formula I wherein $Q^3$ is halogen, $C_1$-$C_{10}$-alkyl, $C_1$-$C_{10}$-haloalkyl, $C_2$-$C_{10}$-alkynyl, $C_3$-$C_8$-cycloalkyl, $C_3$-$C_8$-halocycloalkyl, each unsubstituted or independently substituted with 1 to 2 groups selected from cyano, $C_1$-$C_{10}$-alkoxy, $C_1$-$C_{10}$-haloalkoxy or $C_1$-$C_{10}$-alkylthio, or $Q^3$ is $OR^{14}$, $S(O)_qR^{14}$, $NR^{15}R^{16}$, $OS(O)_2R^{17}$, $C(S)NH_2$, $C(R^{18})=NOR^{18}$; and $R^{14}$ is $C_1$-$C_{10}$-alkyl or $C_3$-$C_8$-cycloalkyl unsubstituted or substituted with 1 $R^{19}$; and $R^{15}$ is $C_1$-$C_{10}$-alkyl, $C_1$-$C_{10}$-haloalkyl, $C_2$-$C_{10}$-alkenyl, $C_2$-$C_{10}$-alkynyl, each unsubstituted or substituted with 1 $R^{19}$; and $R^{16}$ is hydrogen, $C_1$-$C_{10}$-alkyl, $C_1$-$C_{10}$-haloalkyl, $C_2$-$C_{10}$-alkenyl, $C_2$-$C_{10}$-alkynyl, each unsubstituted or substituted with 1 $R^{19}$; and $R^{17}$ is $C_1$-$C_{10}$-alkyl, $C_1$-$C_{10}$-haloalkyl, $C_2$-$C_{10}$-alkenyl, $C_2$-$C_{10}$-alkynyl, $C_3$-$C_8$-cycloalkyl, each unsubstituted or substituted with 1 $R^{19}$; and $R^{18}$ is hydrogen, $C_1$-$C_{10}$-alkyl, or $C_1$-$C_{10}$-haloalkyl; and $R^{19}$ is cyano, nitro, $C_1$-$C_{10}$-alkoxy, $C_1$-$C_{10}$-haloalkoxy, $C_1$-$C_{10}$-alkylthio, or $C_1$-$C_{10}$-haloalkylthio.

Most preferred are compounds of formula I wherein $Q^3$ is halogen, $C_1$-$C_4$-haloalkyl or $C_1$-$C_4$-haloalkoxy.

Preferred are compounds of formula I wherein $Q^4$ is halogen, cyano, nitro, $C_1$-$C_{10}$-alkyl, $C_1$-$C_{10}$-haloalkyl, $C_1$-$C_{10}$-alkoxy, $C_1$-$C_{10}$-haloalkoxy, $C_1$-$C_{10}$-alkylthio, $C_1$-$C_{10}$-haloalkylthio, $C_1$-$C_{10}$-alkylsulfinyl, $C_1$-$C_{10}$-haloalkylsulfinyl, $C_1$-$C_{10}$-alkylsulfonyl, $C_1$-$C_{10}$-haloalkylsulfonyl, or $C_1$-$C_{10}$-alkoxycarbonyl, preferably halogen or $C_1$-$C_4$-haloalkyl.

Preferred are compounds of formula I wherein X and Y are oxygen.

Preferred are compounds of formula I wherein W is N or $CQ^4$, preferably N.

Preferred are compounds of formula I wherein m is 2.

Preferred are compounds of formula I wherein n is 0.

Preferred are compounds of formula I wherein V and V' each independently are N or CH. Preferably, both V and V' are CH.

Especially preferred are N-thio-anthranilamid compounds of formula I wherein

W is N;

$R^1$ is hydrogen;

$Q^1$ is hydrogen, halogen, cyano, $C_1$-$C_4$-alkyl or $C_1$-$C_4$-haloalkyl;

$Q^2$ is halogen, cyano, $C_1$-$C_4$-alkyl or $C_1$-$C_4$-haloalkyl;

$Q^3$ is halogen, $C_1$-$C_4$-haloalkyl or $C_1$-$C_4$-haloalkoxy;

$Q^4$ is halogen or $C_1$-$C_4$-haloalkyl and is in the ortho-position; and p is 1.

Also, especially preferred are N-thio-anthranilamid compounds of formula I wherein A is $A^2$;

$R^4$ is $C_1$-$C_6$-alkylamino, $C_2$-$C_6$-alkenylamino, $C_2$-$C_6$-alkynylamino, di($C_1$-$C_6$-alkyl)amino, di($C_2$-$C_6$-alkenyl)amino, di($C_2$-$C_6$-alkynyl)amino, (phenyl)($C_1$-$C_6$-alkyl)amino, (phenyl)($C_2$-$C_6$-alkenyl)amino, (phenyl)($C_2$-$C_6$-alkynyl)amino, piperidine, piperazin or morpholine; and $R^5$ is hydrogen or $C_1$-$C_4$-alkyl.

Also, especially preferred are N-thio-anthranilamid compounds of formula I wherein A is $A^1$; and $R^2$ and $R^3$ each independently are phenyl, $C_1$-$C_6$-alkyl, $C_2$-$C_6$-alkenyl, or $C_2$-$C_6$-alkynyl, which are unsubstituted or substituted with any combination of 1 to 6 groups selected from halogen and cyano.

Most preferred are compounds of formula I wherein $R^2$ and $R^3$ each independently are $C_1$-$C_4$-alkyl, phenylmethyl, allylmethyl, propargylmethyl, or together with the sulfur atom to which they are attached form a 3- to 6-membered saturated ring which contains 1 to 3 heteroatoms selected from sulfur and oxygen.

With respect to their use, particular preference is given to the compounds IA compiled in the tables below. Moreover, the groups mentioned for a substituent in the tables are on their own, independently of the combination in which they are mentioned, a particularly preferred embodiment of the substituent in question.

Table 1

Compounds of the formula IA wherein $Q^1$ denotes hydrogen, $Q^3$ denotes $CF_3$, and A in each case corresponds to a row of Table A.

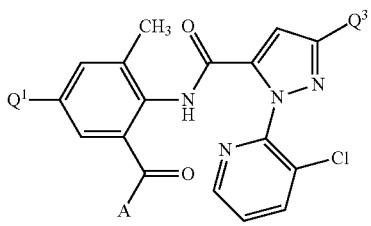

(IA)

Table 2
Compounds of the formula IA wherein $Q^1$ denotes hydrogen, $Q^3$ denotes bromine, and A in each case corresponds to a row of Table A.

Table 3
Compounds of the formula IA wherein $Q^1$ denotes hydrogen, $Q^3$ denotes chlorine, and A in each case corresponds to a row of Table A.

Table 4
Compounds of the formula IA wherein $Q^1$ denotes hydrogen, $Q^3$ denotes $CH_3$, and A in each case corresponds to a row of Table A.

Table 5
Compounds of the formula IA wherein $Q^1$ denotes hydrogen, $Q^3$ denotes $OCH_3$, and A in each case corresponds to a row of Table A.

Table 6
Compounds of the formula IA wherein $Q^1$ denotes hydrogen, $Q^3$ denotes $OCHCH_2$, and A in each case corresponds to a row of Table A.

Table 7
Compounds of the formula IA wherein $Q^1$ denotes hydrogen, $Q^3$ denotes ethoxy, and A in each case corresponds to a row of Table A.

Table 8
Compounds of the formula IA wherein $Q^1$ denotes hydrogen, $Q^3$ denotes $OCH_2CHFOCH_3$, and A in each case corresponds to a row of Table A.

Table 9
Compounds of the formula IA wherein $Q^1$ denotes hydrogen, $Q^3$ denotes $OCH_2CH=CH_2$, and A in each case corresponds to a row of Table A.

Table 10
Compounds of the formula IA wherein $Q^1$ denotes hydrogen, $Q^3$ denotes $OCH_2CCH$, and A in each case corresponds to a row of Table A.

Table 11
Compounds of the formula IA wherein $Q^1$ denotes hydrogen, $Q^3$ denotes $CH_2OCH_3$, and A in each case corresponds to a row of Table A.

Table 12
Compounds of the formula IA wherein $Q^1$ denotes hydrogen, $Q^3$ denotes $CH_2OCH_2CH_3$, and A in each case corresponds to a row of Table A.

Table 13
Compounds of the formula IA wherein $Q^1$ denotes hydrogen, $Q^3$ denotes $CH_2SCH_3$, and A in each case corresponds to a row of Table A.

Table 14
Compounds of the formula IA wherein $Q^1$ denotes hydrogen, $Q^3$ denotes $CH_2SCH_2CH_3$, and A in each case corresponds to a row of Table A.

Table 15
Compounds of the formula IA wherein $Q^1$ denotes hydrogen, $Q^3$ denotes $CH_2S(=O)CH_3$, and A in each case corresponds to a row of Table A.

Table 16
Compounds of the formula IA wherein $Q^1$ denotes hydrogen, $Q^3$ denotes $CH_2S(=O)CH_2CH_3$, and A in each case corresponds to a row of Table A.

Table 17
Compounds of the formula IA wherein $Q^1$ denotes hydrogen, $Q^3$ denotes $CH_2S(=O)_2CH_3$, and A in each case corresponds to a row of Table A.

Table 18
Compounds of the formula IA wherein $Q^1$ denotes hydrogen, $Q^3$ denotes $CH_2S(=O)_2CH_2CH_3$, and A in each case corresponds to a row of Table A.

Table 19
Compounds of the formula IA wherein $Q^1$ denotes hydrogen, $Q^3$ denotes $—OS(=O)_2CH_3$, and A in each case corresponds to a row of Table A.

Table 20
Compounds of the formula IA wherein $Q^1$ denotes hydrogen, $Q^3$ notes $—OS(=O)_2CH_2CH_3$, and A in each case corresponds to a row of Table A.

Table 21
Compounds of the formula IA wherein $Q^1$ denotes hydrogen, $Q^3$ notes $—OS(=O)_2CH_2CF_3$, and A in each case corresponds to a row of Table A.

Table 22
Compounds of the formula IA wherein $Q^1$ denotes hydrogen, $Q^3$ notes $—OS(=O)_2CClF_2$, and A in each case corresponds to a row of Table A.

Table 23
Compounds of the formula IA wherein $Q^1$ denotes hydrogen, $Q^3$ denotes $OC(=O)CF_3$, and A in each case corresponds to a row of Table A.

Table 24
Compounds of the formula IA wherein $Q^1$ denotes hydrogen, $Q^3$ denotes $NHCH_2CF_3$, and A in each case corresponds to a row of Table A.

Table 25
Compounds of the formula IA wherein $Q^1$ denotes hydrogen, $Q^3$ denotes $OCH_2$-cyclopropyl, and A in each case corresponds to a row of Table A.

Table 26
Compounds of the formula IA wherein $Q^1$ denotes hydrogen, $Q^3$ denotes $OCH_2C(Cl)=CH_2$, and A in each case corresponds to a row of Table A.

Table 27
Compounds of the formula IA wherein $Q^1$ denotes hydrogen, $Q^3$ denotes $OCH_2CH=CF_2$, and A in each case corresponds to a row of Table A.

Table 28
Compounds of the formula IA wherein $Q^1$ denotes hydrogen, $Q^3$ denotes $NHS(=O)_2CF_3$, and A in each case corresponds to a row of Table A.

Table 29
Compounds of the formula IA wherein $Q^1$ denotes hydrogen, $Q^3$ denotes $NHC(=O)CF_3$, and A in each case corresponds to a row of Table A.

Table 30
Compounds of the formula IA wherein $Q^1$ denotes hydrogen, $Q^3$ denotes $OCH_2CN$, and A in each case corresponds to a row of Table A.

Table 31
Compounds of the formula IA wherein $Q^1$ denotes hydrogen, $Q^3$ denotes $OCH_2NO_2$, and A in each case corresponds to a row of Table A.

Table 32
Compounds of the formula IA wherein $Q^1$ denotes hydrogen, $Q^3$ denotes cyclopropyloxy, and A in each case corresponds to a row of Table A.

Table 33
Compounds of the formula IA wherein $Q^1$ denotes hydrogen, $Q^3$ denotes $CH_2OCHF_2$, and A in each case corresponds to a row of Table A.

Table 34
Compounds of the formula IA wherein $Q^1$ denotes hydrogen, $Q^3$ denotes $CH_2S(=O)_2CHF_2$, and A in each case corresponds to a row of Table A.

Table 35
Compounds of the formula IA wherein $Q^1$ denotes hydrogen, $Q^3$ denotes $CH=NOCH_3$, and A in each case corresponds to a row of Table A.

Table 36
Compounds of the formula IA wherein $Q^1$ denotes hydrogen, $Q^3$ denotes $CH=NOCH_2CH_3$, and A in each case corresponds to a row of Table A.

Table 37
Compounds of the formula IA wherein $Q^1$ denotes hydrogen, $Q^3$ denotes $CH=NOCH(CH_3)_2$ and A in each case corresponds to a row of Table A.

Table 38
Compounds of the formula IA wherein $Q^1$ denotes hydrogen, $Q^3$ denotes $CH=NOC(CH_3)_3$, and A in each case corresponds to a row of Table A.

Table 39
Compounds of the formula IA wherein $Q^1$ denotes hydrogen, $Q^3$ denotes $C(CH_3)=NOCH_3$, and A in each case corresponds to a row of Table A.

Table 40
Compounds of the formula IA wherein $Q^1$ denotes hydrogen, $Q^3$ denotes $C(CH_3)=NOCH_2CH_3$, and A in each case corresponds to a row of Table A.

Table 41
Compounds of the formula IA wherein $Q^1$ denotes hydrogen, $Q^3$ denotes $C(CH_3)=NOCH(CH_3)_2$, and A in each case corresponds to a row of Table A.

Table 42
Compounds of the formula IA wherein $Q^1$ denotes hydrogen, $Q^3$ denotes $C(CH_3)=NOC(CH_3)_3$, and A in each case corresponds to a row of Table A.

Table 43
Compounds of the formula IA wherein $Q^1$ denotes chlorine, $Q^3$ denotes $CF_3$, and A in each case corresponds to a row of Table A.

Table 44
Compounds of the formula IA wherein $Q^1$ denotes chlorine, $Q^3$ denotes bromine, and A in each case corresponds to a row of Table A.

Table 45
Compounds of the formula IA wherein $Q^1$ denotes chlorine, $Q^3$ denotes chlorine, and A in each case corresponds to a row of Table A.

Table 46
Compounds of the formula IA wherein $Q^1$ denotes chlorine, $Q^3$ denotes $CH_3$, and A in each case corresponds to a row of Table A.

Table 47
Compounds of the formula IA wherein $Q^1$ denotes chlorine, $Q^3$ denotes $OCH_3$, and A in each case corresponds to a row of Table A.

Table 48
Compounds of the formula IA wherein $Q^1$ denotes chlorine, $Q^3$ denotes $OCHCH_2$, and A in each case corresponds to a row of Table A.

Table 49
Compounds of the formula IA wherein $Q^1$ denotes chlorine, $Q^3$ denotes ethoxy, and A in each case corresponds to a row of Table A.

Table 50
Compounds of the formula IA wherein $Q^1$ denotes chlorine, $Q^3$ denotes $OCH_2CHFOCH_3$, and A in each case corresponds to a row of Table A.

Table 51
Compounds of the formula IA wherein $Q^1$ denotes chlorine, $Q^3$ denotes $OCH_2CH=CH_2$, and A in each case corresponds to a row of Table A.

Table 52
Compounds of the formula IA wherein $Q^1$ denotes chlorine, $Q^3$ denotes $OCH_2CCH$, and A in each case corresponds to a row of Table A.

Table 53
Compounds of the formula IA wherein $Q^1$ denotes chlorine, $Q^3$ denotes $CH_2OCH_3$, and A in each case corresponds to a row of Table A.

Table 54
Compounds of the formula IA wherein $Q^1$ denotes chlorine, $Q^3$ denotes $CH_2OCH_2CH_3$, and A in each case corresponds to a row of Table A.

Table 55
Compounds of the formula IA wherein $Q^1$ denotes chlorine, $Q^3$ denotes $CH_2SCH_3$, and A in each case corresponds to a row of Table A.

Table 56
Compounds of the formula IA wherein $Q^1$ denotes chlorine, $Q^3$ denotes $CH_2SCH_2CH_3$, and A in each case corresponds to a row of Table A.

Table 57
Compounds of the formula IA wherein $Q^1$ denotes chlorine, $Q^3$ denotes $CH_2S(=O)CH_3$, and A in each case corresponds to a row of Table A.

Table 58
Compounds of the formula IA wherein $Q^1$ denotes chlorine, $Q^3$ denotes $CH_2S(=O)CH_2CH_3$, and A in each case corresponds to a row of Table A.

Table 59
Compounds of the formula IA wherein $Q^1$ denotes chlorine, $Q^3$ denotes $CH_2S(=O)_2CH_3$, and A in each case corresponds to a row of Table A.

Table 60
Compounds of the formula IA wherein $Q^1$ denotes chlorine, $Q^3$ denotes $CH_2S(=O)_2CH_2CH_3$, and A in each case corresponds to a row of Table A.

Table 61
Compounds of the formula IA wherein $Q^1$ denotes chlorine, $Q^3$ denotes $-OS(=O)_2CH_3$, and A in each case corresponds to a row of Table A.

Table 62
Compounds of the formula IA wherein $Q^1$ denotes chlorine, $Q^3$ notes $-OS(=O)_2CH_2CH_3$, and A in each case corresponds to a row of Table A.

Table 63
Compounds of the formula IA wherein $Q^1$ denotes chlorine, $Q^3$ notes $-OS(=O)_2CH_2CF_3$, and A in each case corresponds to a row of Table A.

Table 64
Compounds of the formula IA wherein $Q^1$ denotes chlorine, $Q^3$ notes $-OS(=O)_2CClF_2$, and A in each case corresponds to a row of Table A.

Table 65
Compounds of the formula IA wherein $Q^1$ denotes chlorine, $Q^3$ denotes $OC(=O)CF_3$, and A in each case corresponds to a row of Table A.

Table 66
Compounds of the formula IA wherein $Q^1$ denotes chlorine, $Q^3$ denotes $NHCH_2CF_3$, and A in each case corresponds to a row of Table A.

Table 67
Compounds of the formula IA wherein $Q^1$ denotes chlorine, $Q^3$ denotes $OCH_2$-cyclopropyl, and A in each case corresponds to a row of Table A.

Table 68
Compounds of the formula IA wherein $Q^1$ denotes chlorine, $Q^3$ denotes $OCH_2C(Cl)=CH_2$, and A in each case corresponds to a row of Table A.

Table 69
Compounds of the formula IA wherein $Q^1$ denotes chlorine, $Q^3$ denotes $OCH_2CH=CF_2$, and A in each case corresponds to a row of Table A.

Table 70
Compounds of the formula IA wherein $Q^1$ denotes chlorine, $Q^3$ denotes $NHS(=O)_2CF_3$, and A in each case corresponds to a row of Table A.

Table 71
Compounds of the formula IA wherein $Q^1$ denotes chlorine, $Q^3$ denotes $NHC(=O)CF_3$, and A in each case corresponds to a row of Table A.

Table 72
Compounds of the formula IA wherein $Q^1$ denotes chlorine, $Q^3$ denotes $OCH_2CN$, and A in each case corresponds to a row of Table A.

Table 73
Compounds of the formula IA wherein $Q^1$ denotes chlorine, $Q^3$ denotes $OCH_2NO_2$, and A in each case corresponds to a row of Table A.

Table 74
Compounds of the formula IA wherein $Q^1$ denotes chlorine, $Q^3$ denotes cyclopropyloxy, and A in each case corresponds to a row of Table A.

Table 75
Compounds of the formula IA wherein $Q^1$ denotes chlorine, $Q^3$ denotes $CH_2OCHF_2$, and A in each case corresponds to a row of Table A.

Table 76
Compounds of the formula IA wherein $Q^1$ denotes chlorine, $Q^3$ denotes $CH_2S(=O)_2CHF_2$, and A in each case corresponds to a row of Table A.

Table 77
Compounds of the formula IA wherein $Q^1$ denotes chlorine, $Q^3$ denotes $CH=NOCH_3$, and A in each case corresponds to a row of Table A.

Table 78
Compounds of the formula IA wherein $Q^1$ denotes chlorine, $Q^3$ denotes $CH=NOCH_2CH_3$, and A in each case corresponds to a row of Table A.

Table 79
Compounds of the formula IA wherein $Q^1$ denotes chlorine, $Q^3$ denotes $CH=NOCH(CH_3)_2$ and A in each case corresponds to a row of Table A.

Table 80
Compounds of the formula IA wherein $Q^1$ denotes chlorine, $Q^3$ denotes $CH=NOC(CH_3)_3$, and A in each case corresponds to a row of Table A.

Table 81
Compounds of the formula IA wherein $Q^1$ denotes chlorine, $Q^3$ denotes $C(CH_3)=NOCH_3$, and A in each case corresponds to a row of Table A.

Table 82
Compounds of the formula IA wherein $Q^1$ denotes chlorine, $Q^3$ denotes $C(CH_3)=NOCH_2CH_3$, and A in each case corresponds to a row of Table A.

Table 83
Compounds of the formula IA wherein $Q^1$ denotes chlorine, $Q^3$ denotes $C(CH_3)=NOCH(CH_3)_2$, and A in each case corresponds to a row of Table A.

Table 84
Compounds of the formula IA wherein $Q^1$ denotes chlorine, $Q^3$ denotes $C(CH_3)=NOC(CH_3)_3$, and A in each case corresponds to a row of Table A.

Table 85
Compounds of the formula IA wherein $Q^1$ denotes bromine, $Q^3$ denotes $CF_3$, and A in each case corresponds to a row of Table A.

Table 86
Compounds of the formula IA wherein $Q^1$ denotes bromine, $Q^3$ denotes bromine, and A in each case corresponds to a row of Table A.

Table 87
Compounds of the formula IA wherein $Q^1$ denotes bromine, $Q^3$ denotes chlorine, and A in each case corresponds to a row of Table A.

Table 88
Compounds of the formula IA wherein $Q^1$ denotes bromine, $Q^3$ denotes $CH_3$, and A in each case corresponds to a row of Table A.

Table 89
Compounds of the formula IA wherein $Q^1$ denotes bromine, $Q^3$ denotes $OCH_3$, and A in each case corresponds to a row of Table A.

Table 90
Compounds of the formula IA wherein $Q^1$ denotes bromine, $Q^3$ denotes $OCHCH_2$, and A in each case corresponds to a row of Table A.

Table 91
Compounds of the formula IA wherein $Q^1$ denotes bromine, $Q^3$ denotes ethoxy, and A in each case corresponds to a row of Table A.

Table 92
Compounds of the formula IA wherein $Q^1$ denotes bromine, $Q^3$ denotes $OCH_2CHFOCH_3$, and A in each case corresponds to a row of Table A.

Table 93
Compounds of the formula IA wherein $Q^1$ denotes bromine, $Q^3$ denotes $OCH_2CH=CH_2$, and A in each case corresponds to a row of Table A.

Table 94
Compounds of the formula IA wherein $Q^1$ denotes bromine, $Q^3$ denotes $OCH_2CCH$, and A in each case corresponds to a row of Table A.

Table 95
Compounds of the formula IA wherein $Q^1$ denotes bromine, $Q^3$ denotes $CH_2OCH_3$, and A in each case corresponds to a row of Table A.

Table 96
Compounds of the formula IA wherein $Q^1$ denotes bromine, $Q^3$ denotes $CH_2OCH_2CH_3$, and A in each case corresponds to a row of Table A.

Table 97
Compounds of the formula IA wherein $Q^1$ denotes bromine, $Q^3$ denotes $CH_2SCH_3$, and A in each case corresponds to a row of Table A.

Table 98
Compounds of the formula IA wherein $Q^1$ denotes bromine, $Q^3$ denotes $CH_2SCH_2CH_3$, and A in each case corresponds to a row of Table A.

Table 99
Compounds of the formula IA wherein $Q^1$ denotes bromine, $Q^3$ denotes $CH_2S(=O)CH_3$, and A in each case corresponds to a row of Table A.

Table 100
Compounds of the formula IA wherein $Q^1$ denotes bromine, $Q^3$ denotes $CH_2S(=O)CH_2CH_3$, and A in each case corresponds to a row of Table A.

Table 101
Compounds of the formula IA wherein $Q^1$ denotes bromine, $Q^3$ denotes $CH_2S(=O)_2CH_3$, and A in each case corresponds to a row of Table A.

Table 102
Compounds of the formula IA wherein $Q^1$ denotes bromine, $Q^3$ denotes $CH_2S(=O)_2CH_2CH_3$, and A in each case corresponds to a row of Table A.

Table 103
Compounds of the formula IA wherein $Q^1$ denotes bromine, $Q^3$ denotes $—OS(=O)_2CH_3$, and A in each case corresponds to a row of Table A.

Table 104
Compounds of the formula IA wherein $Q^1$ denotes bromine, $Q^3$ notes $—OS(=O)_2CH_2CH_3$, and A in each case corresponds to a row of Table A.

Table 105
Compounds of the formula IA wherein $Q^1$ denotes bromine, $Q^3$ notes $—OS(=O)_2CH_2CF_3$, and A in each case corresponds to a row of Table A.

Table 106
Compounds of the formula IA wherein $Q^1$ denotes bromine, $Q^3$ notes $—OS(=O)_2CClF_2$, and A in each case corresponds to a row of Table A.

Table 107
Compounds of the formula IA wherein $Q^1$ denotes bromine, $Q^3$ denotes $OC(=O)CF_3$, and A in each case corresponds to a row of Table A.

Table 108
Compounds of the formula IA wherein $Q^1$ denotes bromine, $Q^3$ denotes $NHCH_2CF_3$, and A in each case corresponds to a row of Table A.

Table 109
Compounds of the formula IA wherein $Q^1$ denotes bromine, $Q^3$ denotes $OCH_2$-cyclopropyl, and A in each case corresponds to a row of Table A.

Table 110
Compounds of the formula IA wherein $Q^1$ denotes bromine, $Q^3$ denotes $OCH_2C(Cl)=CH_2$, and A in each case corresponds to a row of Table A.

Table 111
Compounds of the formula IA wherein $Q^1$ denotes bromine, $Q^3$ denotes $OCH_2CH=CF_2$, and A in each case corresponds to a row of Table A.

Table 112
Compounds of the formula IA wherein $Q^1$ denotes bromine, $Q^3$ denotes $NHS(=O)_2CF_3$, and A in each case corresponds to a row of Table A.

Table 113
Compounds of the formula IA wherein $Q^1$ denotes bromine, $Q^3$ denotes $NHC(=O)CF_3$, and A in each case corresponds to a row of Table A.

Table 114
Compounds of the formula IA wherein $Q^1$ denotes bromine, $Q^3$ denotes $OCH_2CN$, and A in each case corresponds to a row of Table A.

Table 115
Compounds of the formula IA wherein $Q^1$ denotes bromine, $Q^3$ denotes $OCH_2NO_2$, and A in each case corresponds to a row of Table A.

Table 116
Compounds of the formula IA wherein $Q^1$ denotes bromine, $Q^3$ denotes cyclopropyloxy, and A in each case corresponds to a row of Table A.

Table 117
Compounds of the formula IA wherein $Q^1$ denotes bromine, $Q^3$ denotes $CH_2OCHF_2$, and A in each case corresponds to a row of Table A.

Table 118
Compounds of the formula IA wherein $Q^1$ denotes bromine, $Q^3$ denotes $CH_2S(=O)_2CHF_2$, and A in each case corresponds to a row of Table A.

Table 119
Compounds of the formula IA wherein $Q^1$ denotes bromine, $Q^3$ denotes $CH=NOCH_3$, and A in each case corresponds to a row of Table A.

Table 120
Compounds of the formula IA wherein $Q^1$ denotes bromine, $Q^3$ denotes $CH=NOCH_2CH_3$, and A in each case corresponds to a row of Table A.

Table 121
Compounds of the formula IA wherein $Q^1$ denotes bromine, $Q^3$ denotes $CH=NOCH(CH_3)_2$ and A in each case corresponds to a row of Table A.

Table 122
Compounds of the formula IA wherein $Q^1$ denotes bromine, $Q^3$ denotes $CH=NOC(CH_3)_3$, and A in each case corresponds to a row of Table A.

Table 123
Compounds of the formula IA wherein $Q^1$ denotes bromine, $Q^3$ denotes $C(CH_3)=NOCH_3$, and A in each case corresponds to a row of Table A.

Table 124
Compounds of the formula IA wherein $Q^1$ denotes bromine, $Q^3$ denotes $C(CH_3)=NOCH_2CH_3$, and A in each case corresponds to a row of Table A.

Table 125
Compounds of the formula IA wherein $Q^1$ denotes bromine, $Q^3$ denotes $C(CH_3)=NOCH(CH_3)_2$, and A in each case corresponds to a row of Table A.

Table 126
Compounds of the formula IA wherein $Q^1$ denotes bromine, $Q^3$ denotes $C(CH_3)=NOC(CH_3)_3$, and A in each case corresponds to a row of Table A.

Table 127
Compounds of the formula IA wherein $Q^1$ denotes fluorine, $Q^3$ denotes $CF_3$, and A in each case corresponds to a row of Table A.

Table 128
Compounds of the formula IA wherein $Q^1$ denotes fluorine, $Q^3$ denotes bromine, and A in each case corresponds to a row of Table A.

Table 129
Compounds of the formula IA wherein $Q^1$ denotes fluorine, $Q^3$ denotes chlorine, and A in each case corresponds to a row of Table A.

Table 130
Compounds of the formula IA wherein $Q^1$ denotes fluorine, $Q^3$ denotes $CH_3$, and A in each case corresponds to a row of Table A.

Table 131
Compounds of the formula IA wherein $Q^1$ denotes fluorine, $Q^3$ denotes $OCH_3$, and A in each case corresponds to a row of Table A.

Table 132
Compounds of the formula IA wherein $Q^1$ denotes fluorine, $Q^3$ denotes $OCHCH_2$, and A in each case corresponds to a row of Table A.

Table 133
Compounds of the formula IA wherein $Q^1$ denotes fluorine, $Q^3$ denotes ethoxy, and A in each case corresponds to a row of Table A.

Table 134
Compounds of the formula IA wherein $Q^1$ denotes fluorine, $Q^3$ denotes $OCH_2CHFOCH_3$, and A in each case corresponds to a row of Table A.

Table 135
Compounds of the formula IA wherein $Q^1$ denotes fluorine, $Q^3$ denotes $OCH_2CH=CH_2$, and A in each case corresponds to a row of Table A.

Table 136
Compounds of the formula IA wherein $Q^1$ denotes fluorine, $Q^3$ denotes $OCH_2CCH$, and A in each case corresponds to a row of Table A.

Table 137
Compounds of the formula IA wherein $Q^1$ denotes fluorine, $Q^3$ denotes $CH_2OCH_3$, and A in each case corresponds to a row of Table A.

Table 138
Compounds of the formula IA wherein $Q^1$ denotes fluorine, $Q^3$ denotes $CH_2OCH_2CH_3$, and A in each case corresponds to a row of Table A.

Table 139
Compounds of the formula IA wherein $Q^1$ denotes fluorine, $Q^3$ denotes $CH_2SCH_3$, and A in each case corresponds to a row of Table A.

Table 140
Compounds of the formula IA wherein $Q^1$ denotes fluorine, $Q^3$ denotes $CH_2SCH_2CH_3$, and A in each case corresponds to a row of Table A.

Table 141
Compounds of the formula IA wherein $Q^1$ denotes fluorine, $Q^3$ denotes $CH_2S(=O)CH_3$, and A in each case corresponds to a row of Table A.

Table 142
Compounds of the formula IA wherein $Q^1$ denotes fluorine, $Q^3$ denotes $CH_2S(=O)CH_2CH_3$, and A in each case corresponds to a row of Table A.

Table 143
Compounds of the formula IA wherein $Q^1$ denotes fluorine, $Q^3$ denotes $CH_2S(=O)_2CH_3$, and A in each case corresponds to a row of Table A.

Table 144
Compounds of the formula IA wherein $Q^1$ denotes fluorine, $Q^3$ denotes $CH_2S(=O)_2CH_2CH_3$, and A in each case corresponds to a row of Table A.

Table 145
Compounds of the formula IA wherein $Q^1$ denotes fluorine, $Q^3$ denotes $—OS(=O)_2CH_3$, and A in each case corresponds to a row of Table A.

Table 146
Compounds of the formula IA wherein $Q^1$ denotes fluorine, $Q^3$ notes $—OS(=O)_2CH_2CH_3$, and A in each case corresponds to a row of Table A.

Table 147
Compounds of the formula IA wherein $Q^1$ denotes fluorine, $Q^3$ notes $—OS(=O)_2CH_2CF_3$, and A in each case corresponds to a row of Table A.

Table 148
Compounds of the formula IA wherein $Q^1$ denotes fluorine, $Q^3$ denotes $—OS(=O)_2CClF_2$, and A in each case corresponds to a row of Table A.

Table 149
Compounds of the formula IA wherein $Q^1$ denotes fluorine, $Q^3$ denotes $OC(=O)CF_3$, and A in each case corresponds to a row of Table A.

Table 150
Compounds of the formula IA wherein $Q^1$ denotes fluorine, $Q^3$ denotes $NHCH_2CF_3$, and A in each case corresponds to a row of Table A.

Table 151
Compounds of the formula IA wherein $Q^1$ denotes fluorine, $Q^3$ denotes $OCH_2$-cyclopropyl, and A in each case corresponds to a row of Table A.

Table 152
Compounds of the formula IA wherein $Q^1$ denotes fluorine, $Q^3$ denotes $OCH_2C(Cl)=CH_2$, and A in each case corresponds to a row of Table A.

Table 153
Compounds of the formula IA wherein $Q^1$ denotes fluorine, $Q^3$ denotes $OCH_2CH=CF_2$, and A in each case corresponds to a row of Table A.

Table 154
Compounds of the formula IA wherein $Q^1$ denotes fluorine, $Q^3$ denotes $NHS(=O)_2CF_3$, and A in each case corresponds to a row of Table A.

Table 155
Compounds of the formula IA wherein $Q^1$ denotes fluorine, $Q^3$ denotes $NHC(=O)CF_3$, and A in each case corresponds to a row of Table A.

Table 156
Compounds of the formula IA wherein $Q^1$ denotes fluorine, $Q^3$ denotes $OCH_2CN$, and A in each case corresponds to a row of Table A.

Table 157
Compounds of the formula IA wherein $Q^1$ denotes fluorine, $Q^3$ denotes $OCH_2NO_2$, and A in each case corresponds to a row of Table A.

Table 158
Compounds of the formula IA wherein $Q^1$ denotes fluorine, $Q^3$ denotes cyclopropyloxy, and A in each case corresponds to a row of Table A.

Table 159
Compounds of the formula IA wherein $Q^1$ denotes fluorine, $Q^3$ denotes $CH_2OCHF_2$, and A in each case corresponds to a row of Table A.

Table 160
Compounds of the formula IA wherein $Q^1$ denotes fluorine, $Q^3$ denotes $CH_2S(=O)_2CHF_2$, and A in each case corresponds to a row of Table A.

Table 161
Compounds of the formula IA wherein $Q^1$ denotes fluorine, $Q^3$ denotes $CH=NOCH_3$, and A in each case corresponds to a row of Table A.

Table 162
Compounds of the formula IA wherein $Q^1$ denotes fluorine, $Q^3$ denotes $CH=NOCH_2CH_3$, and A in each case corresponds to a row of Table A.

Table 163
Compounds of the formula IA wherein $Q^1$ denotes fluorine, $Q^3$ denotes $CH=NOCH(CH_3)_2$ and A in each case corresponds to a row of Table A.

Table 164
Compounds of the formula IA wherein $Q^1$ denotes fluorine, $Q^3$ denotes CH=NOC(CH$_3$)$_3$, and A in each case corresponds to a row of Table A.

Table 165
Compounds of the formula IA wherein $Q^1$ denotes fluorine, $Q^3$ denotes C(CH$_3$)=NOCH$_3$, and A in each case corresponds to a row of Table A.

Table 166
Compounds of the formula IA wherein $Q^1$ denotes fluorine, $Q^3$ denotes C(CH$_3$)=NOCH$_2$CH$_3$, and A in each case corresponds to a row of Table A.

Table 167
Compounds of the formula IA wherein $Q^1$ denotes fluorine, $Q^3$ denotes C(CH$_3$)=NOCH(CH$_3$)$_2$, and A in each case corresponds to a row of Table A.

Table 168
Compounds of the formula IA wherein $Q^1$ denotes fluorine, $Q^3$ denotes C(CH$_3$)=NOC(CH$_3$)$_3$, and A in each case corresponds to a row of Table A.

Table 169
Compounds of the formula IA wherein $Q^1$ denotes iodine, $Q^3$ denotes CF$_3$, and A in each case corresponds to a row of Table A.

Table 170
Compounds of the formula IA wherein $Q^1$ denotes iodine, $Q^3$ denotes bromine, and A in each case corresponds to a row of Table A.

Table 171
Compounds of the formula IA wherein $Q^1$ denotes iodine, $Q^3$ denotes chlorine, and A in each case corresponds to a row of Table A.

Table 172
Compounds of the formula IA wherein $Q^1$ denotes iodine, $Q^3$ denotes CH$_3$, and A in each case corresponds to a row of Table A.

Table 173
Compounds of the formula IA wherein $Q^1$ denotes iodine, $Q^3$ denotes OCH$_3$, and A in each case corresponds to a row of Table A.

Table 174
Compounds of the formula IA wherein $Q^1$ denotes iodine, $Q^3$ denotes OCHCH$_2$, and A in each case corresponds to a row of Table A.

Table 175
Compounds of the formula IA wherein $Q^1$ denotes iodine, $Q^3$ denotes ethoxy, and A in each case corresponds to a row of Table A.

Table 176
Compounds of the formula IA wherein $Q^1$ denotes iodine, $Q^3$ denotes OCH$_2$CHFOCH$_3$, and A in each case corresponds to a row of Table A.

Table 177
Compounds of the formula IA wherein $Q^1$ denotes iodine, $Q^3$ denotes OCH$_2$CH=CH$_2$, and A in each case corresponds to a row of Table A.

Table 178
Compounds of the formula IA wherein $Q^1$ denotes iodine, $Q^3$ denotes OCH$_2$CCH, and A in each case corresponds to a row of Table A.

Table 179
Compounds of the formula IA wherein $Q^1$ denotes iodine, $Q^3$ denotes CH$_2$OCH$_3$, and A in each case corresponds to a row of Table A.

Table 180
Compounds of the formula IA wherein $Q^1$ denotes iodine, $Q^3$ denotes CH$_2$OCH$_2$CH$_3$, and A in each case corresponds to a row of Table A.

Table 181
Compounds of the formula IA wherein $Q^1$ denotes iodine, $Q^3$ denotes CH$_2$SCH$_3$, and A in each case corresponds to a row of Table A.

Table 182
Compounds of the formula IA wherein $Q^1$ denotes iodine, $Q^3$ denotes CH$_2$SCH$_2$CH$_3$, and A in each case corresponds to a row of Table A.

Table 183
Compounds of the formula IA wherein $Q^1$ denotes iodine, $Q^3$ denotes CH$_2$S(=O)CH$_3$, and A in each case corresponds to a row of Table A.

Table 184
Compounds of the formula IA wherein $Q^1$ denotes iodine, $Q^3$ denotes CH$_2$S(=O)CH$_2$CH$_3$, and A in each case corresponds to a row of Table A.

Table 185
Compounds of the formula IA wherein $Q^1$ denotes iodine, $Q^3$ denotes CH$_2$S(=O)$_2$CH$_3$, and A in each case corresponds to a row of Table A.

Table 186
Compounds of the formula IA wherein $Q^1$ denotes iodine, $Q^3$ denotes CH$_2$S(=O)$_2$CH$_2$CH$_3$, and A in each case corresponds to a row of Table A.

Table 187
Compounds of the formula IA wherein $Q^1$ denotes iodine, $Q^3$ denotes —OS(=O)$_2$CH$_3$, and A in each case corresponds to a row of Table A.

Table 188
Compounds of the formula IA wherein $Q^1$ denotes iodine, $Q^3$ notes —OS(=O)$_2$CH$_2$CH$_3$, and A in each case corresponds to a row of Table A.

Table 189
Compounds of the formula IA wherein $Q^1$ denotes iodine, $Q^3$ notes —OS(=O)$_2$CH$_2$CF$_3$, and A in each case corresponds to a row of Table A.

Table 190
Compounds of the formula IA wherein $Q^1$ denotes iodine, $Q^3$ denotes —OS(=O)$_2$CClF$_2$, and A in each case corresponds to a row of Table A.

Table 191
Compounds of the formula IA wherein $Q^1$ denotes iodine, $Q^3$ denotes OC(=O)CF$_3$, and A in each case corresponds to a row of Table A.

Table 192
Compounds of the formula IA wherein $Q^1$ denotes iodine, $Q^3$ denotes NHCH$_2$CF$_3$, and A in each case corresponds to a row of Table A.

Table 193
Compounds of the formula IA wherein $Q^1$ denotes iodine, $Q^3$ denotes OCH$_2$-cyclopropyl, and A in each case corresponds to a row of Table A.

Table 194
Compounds of the formula IA wherein $Q^1$ denotes iodine, $Q^3$ denotes OCH$_2$C(Cl)=CH$_2$, and A in each case corresponds to a row of Table A.

Table 195
Compounds of the formula IA wherein $Q^1$ denotes iodine, $Q^3$ denotes OCH$_2$CH=CF$_2$, and A in each case corresponds to a row of Table A.

Table 196
Compounds of the formula IA wherein $Q^1$ denotes iodine, $Q^3$ denotes NHS(=O)$_2$CF$_3$, and A in each case corresponds to a row of Table A.

Table 197
Compounds of the formula IA wherein $Q^1$ denotes iodine, $Q^3$ denotes NHC(=O)CF$_3$, and A in each case corresponds to a row of Table A.

Table 198
Compounds of the formula IA wherein $Q^1$ denotes iodine, $Q^3$ denotes OCH$_2$CN, and A in each case corresponds to a row of Table A.

Table 199
Compounds of the formula IA wherein $Q^1$ denotes iodine, $Q^3$ denotes OCH$_2$NO$_2$, and A in each case corresponds to a row of Table A.

Table 200
Compounds of the formula IA wherein $Q^1$ denotes iodine, $Q^3$ denotes cyclopropyloxy, and A in each case corresponds to a row of Table A.

Table 201
Compounds of the formula IA wherein $Q^1$ denotes iodine, $Q^3$ denotes CH$_2$OCHF$_2$, and A in each case corresponds to a row of Table A.

Table 202
Compounds of the formula IA wherein $Q^1$ denotes iodine, $Q^3$ denotes CH$_2$S(=O)$_2$CHF$_2$, and A in each case corresponds to a row of Table A.

Table 203
Compounds of the formula IA wherein $Q^1$ denotes iodine, $Q^3$ denotes CH=NOCH$_3$, and A in each case corresponds to a row of Table A.

Table 204
Compounds of the formula IA wherein $Q^1$ denotes iodine, $Q^3$ denotes CH=NOCH$_2$CH$_3$, and A in each case corresponds to a row of Table A.

Table 205
Compounds of the formula IA wherein $Q^1$ denotes iodine, $Q^3$ denotes CH=NOCH(CH$_3$)$_2$ and A in each case corresponds to a row of Table A.

Table 206
Compounds of the formula IA wherein $Q^1$ denotes iodine, $Q^3$ denotes CH=NOC(CH$_3$)$_3$, and A in each case corresponds to a row of Table A.

Table 207
Compounds of the formula IA wherein $Q^1$ denotes iodine, $Q^3$ denotes C(CH$_3$)=NOCH$_3$, and A in each case corresponds to a row of Table A.

Table 208
Compounds of the formula IA wherein $Q^1$ denotes iodine, $Q^3$ denotes C(CH$_3$)=NOCH$_2$CH$_3$, and A in each case corresponds to a row of Table A.

Table 209
Compounds of the formula IA wherein $Q^1$ denotes iodine, $Q^3$ denotes C(CH$_3$)=NOCH(CH$_3$)$_2$, and A in each case corresponds to a row of Table A.

Table 210
Compounds of the formula IA wherein $Q^1$ denotes iodine, $Q^3$ denotes C(CH$_3$)=NOC(CH$_3$)$_3$, and A in each case corresponds to a row of Table A.

Table 211
Compounds of the formula IA wherein $Q^1$ denotes cyano, $Q^3$ denotes CF$_3$, and A in each case corresponds to a row of Table A.

Table 212
Compounds of the formula IA wherein $Q^1$ denotes cyano, $Q^3$ denotes bromine, and A in each case corresponds to a row of Table A.

Table 213
Compounds of the formula IA wherein $Q^1$ denotes cyano, $Q^3$ denotes chlorine, and A in each case corresponds to a row of Table A.

Table 214
Compounds of the formula IA wherein $Q^1$ denotes cyano, $Q^3$ denotes CH$_3$, and A in each case corresponds to a row of Table A.

Table 215
Compounds of the formula IA wherein $Q^1$ denotes cyano, $Q^3$ denotes OCH$_3$, and A in each case corresponds to a row of Table A.

Table 216
Compounds of the formula IA wherein $Q^1$ denotes cyano, $Q^3$ denotes OCHCH$_2$, and A in each case corresponds to a row of Table A.

Table 217
Compounds of the formula IA wherein $Q^1$ denotes cyano, $Q^3$ denotes ethoxy, and A in each case corresponds to a row of Table A.

Table 218
Compounds of the formula IA wherein $Q^1$ denotes cyano, $Q^3$ denotes OCH$_2$CHFOCH$_3$, and A in each case corresponds to a row of Table A.

Table 219
Compounds of the formula IA wherein $Q^1$ denotes cyano, $Q^3$ denotes OCH$_2$CH=CH$_2$, and A in each case corresponds to a row of Table A.

Table 220
Compounds of the formula IA wherein $Q^1$ denotes cyano, $Q^3$ denotes OCH$_2$CCH, and A in each case corresponds to a row of Table A.

Table 221
Compounds of the formula IA wherein $Q^1$ denotes cyano, $Q^3$ denotes CH$_2$OCH$_3$, and A in each case corresponds to a row of Table A.

Table 222
Compounds of the formula IA wherein $Q^1$ denotes cyano, $Q^3$ denotes CH$_2$OCH$_2$CH$_3$, and A in each case corresponds to a row of Table A.

Table 223
Compounds of the formula IA wherein $Q^1$ denotes cyano, $Q^3$ denotes CH$_2$SCH$_3$, and A in each case corresponds to a row of Table A.

Table 224
Compounds of the formula IA wherein $Q^1$ denotes cyano, $Q^3$ denotes CH$_2$SCH$_2$CH$_3$, and A in each case corresponds to a row of Table A.

Table 225
Compounds of the formula IA wherein $Q^1$ denotes cyano, $Q^3$ denotes CH$_2$S(=O)CH$_3$, and A in each case corresponds to a row of Table A.

Table 226
Compounds of the formula IA wherein $Q^1$ denotes cyano, $Q^3$ denotes CH$_2$S(=O)CH$_2$CH$_3$, and A in each case corresponds to a row of Table A.

Table 227
Compounds of the formula IA wherein $Q^1$ denotes cyano, $Q^3$ denotes CH$_2$S(=O)$_2$CH$_3$, and A in each case corresponds to a row of Table A.

Table 228
Compounds of the formula IA wherein $Q^1$ denotes cyano, $Q^3$ denotes CH$_2$S(=O)$_2$CH$_2$CH$_3$, and A in each case corresponds to a row of Table A.

Table 229
Compounds of the formula IA wherein $Q^1$ denotes cyano, $Q^3$ denotes —OS(=O)$_2$CH$_3$, and A in each case corresponds to a row of Table A.

Table 230
Compounds of the formula IA wherein $Q^1$ denotes cyano, $Q^3$ notes —OS(=O)$_2$CH$_2$CH$_3$, and A in each case corresponds to a row of Table A.

Table 231
Compounds of the formula IA wherein $Q^1$ denotes cyano, $Q^3$ notes —OS(=O)$_2$CH$_2$CF$_3$, and A in each case corresponds to a row of Table A.

Table 232
Compounds of the formula IA wherein $Q^1$ denotes cyano, $Q^3$ denotes —OS(=O)$_2$CClF$_2$, and A in each case corresponds to a row of Table A.

Table 233
Compounds of the formula IA wherein $Q^1$ denotes cyano, $Q^3$ denotes OC(=O)CF$_3$, and A in each case corresponds to a row of Table A.

Table 234
Compounds of the formula IA wherein $Q^1$ denotes cyano, $Q^3$ denotes NHCH$_2$CF$_3$, and A in each case corresponds to a row of Table A.

Table 235
Compounds of the formula IA wherein $Q^1$ denotes cyano, $Q^3$ denotes OCH$_2$-cyclopropyl, and A in each case corresponds to a row of Table A.

Table 236
Compounds of the formula IA wherein $Q^1$ denotes cyano, $Q^3$ denotes OCH$_2$C(Cl)=CH$_2$, and A in each case corresponds to a row of Table A.

Table 237
Compounds of the formula IA wherein $Q^1$ denotes cyano, $Q^3$ denotes OCH$_2$CH=CF$_2$, and A in each case corresponds to a row of Table A.

Table 238
Compounds of the formula IA wherein $Q^1$ denotes cyano, $Q^3$ denotes NHS(=O)$_2$CF$_3$, and A in each case corresponds to a row of Table A.

Table 239
Compounds of the formula IA wherein $Q^1$ denotes cyano, $Q^3$ denotes NHC(=O)CF$_3$, and A in each case corresponds to a row of Table A.

Table 240
Compounds of the formula IA wherein $Q^1$ denotes cyano, $Q^3$ denotes OCH$_2$CN, and A in each case corresponds to a row of Table A.

Table 241
Compounds of the formula IA wherein $Q^1$ denotes cyano, $Q^3$ denotes OCH$_2$NO$_2$, and A in each case corresponds to a row of Table A.

Table 242
Compounds of the formula IA wherein $Q^1$ denotes cyano, $Q^3$ denotes cyclopropyloxy, and A in each case corresponds to a row of Table A.

Table 243
Compounds of the formula IA wherein $Q^1$ denotes cyano, $Q^3$ denotes CH$_2$OCHF$_2$, and A in each case corresponds to a row of Table A.

Table 244
Compounds of the formula IA wherein $Q^1$ denotes cyano, $Q^3$ denotes CH$_2$S(=O)$_2$CHF$_2$, and A in each case corresponds to a row of Table A.

Table 245
Compounds of the formula IA wherein $Q^1$ denotes cyano, $Q^3$ denotes CH=NOCH$_3$, and A in each case corresponds to a row of Table A.

Table 246
Compounds of the formula IA wherein $Q^1$ denotes cyano, $Q^3$ denotes CH=NOCH$_2$CH$_3$, and A in each case corresponds to a row of Table A.

Table 247
Compounds of the formula IA wherein $Q^1$ denotes cyano, $Q^3$ denotes CH=NOCH(CH$_3$)$_2$ and A in each case corresponds to a row of Table A.

Table 248
Compounds of the formula IA wherein $Q^1$ denotes cyano, $Q^3$ denotes CH=NOC(CH$_3$)$_3$, and A in each case corresponds to a row of Table A.

Table 249
Compounds of the formula IA wherein $Q^1$ denotes cyano, $Q^3$ denotes C(CH$_3$)=NOCH$_3$, and A in each case corresponds to a row of Table A.

Table 250
Compounds of the formula IA wherein $Q^1$ denotes cyano, $Q^3$ denotes C(CH$_3$)=NOCH$_2$CH$_3$, and A in each case corresponds to a row of Table A.

Table 251
Compounds of the formula IA wherein $Q^1$ denotes cyano, $Q^3$ denotes C(CH$_3$)=NOCH(CH$_3$)$_2$, and A in each case corresponds to a row of Table A.

Table 252
Compounds of the formula IA wherein $Q^1$ denotes cyano, $Q^3$ denotes C(CH$_3$)=NOC(CH$_3$)$_3$, and A in each case corresponds to a row of Table A.

Table 253
Compounds of the formula IA wherein $Q^1$ denotes methyl, $Q^3$ denotes CF$_3$, and A in each case corresponds to a row of Table A.

Table 254
Compounds of the formula IA wherein $Q^1$ denotes methyl, $Q^3$ denotes bromine, and A in each case corresponds to a row of Table A.

Table 255
Compounds of the formula IA wherein $Q^1$ denotes methyl, $Q^3$ denotes chlorine, and A in each case corresponds to a row of Table A.

Table 256
Compounds of the formula IA wherein $Q^1$ denotes methyl, $Q^3$ denotes CH$_3$, and A in each case corresponds to a row of Table A.

Table 257
Compounds of the formula IA wherein $Q^1$ denotes methyl, $Q^3$ denotes OCH$_3$, and A in each case corresponds to a row of Table A.

Table 258
Compounds of the formula IA wherein $Q^1$ denotes methyl, $Q^3$ denotes OCHCH$_2$, and A in each case corresponds to a row of Table A.

Table 259
Compounds of the formula IA wherein $Q^1$ denotes methyl, $Q^3$ denotes ethoxy, and A in each case corresponds to a row of Table A.

Table 260
Compounds of the formula IA wherein $Q^1$ denotes methyl, $Q^3$ denotes OCH$_2$CHFOCH$_3$, and A in each case corresponds to a row of Table A.

Table 261
Compounds of the formula IA wherein $Q^1$ denotes methyl, $Q^3$ denotes OCH$_2$CH=CH$_2$, and A in each case corresponds to a row of Table A.

Table 262
Compounds of the formula IA wherein $Q^1$ denotes methyl, $Q^3$ denotes OCH$_2$CCH, and A in each case corresponds to a row of Table A.

Table 263
Compounds of the formula IA wherein $Q^1$ denotes methyl, $Q^3$ denotes $CH_2OCH_3$, and A in each case corresponds to a row of Table A.

Table 264
Compounds of the formula IA wherein $Q^1$ denotes methyl, $Q^3$ denotes $CH_2OCH_2CH_3$, and A in each case corresponds to a row of Table A.

Table 265
Compounds of the formula IA wherein $Q^1$ denotes methyl, $Q^3$ denotes $CH_2SCH_3$, and A in each case corresponds to a row of Table A.

Table 266
Compounds of the formula IA wherein $Q^1$ denotes methyl, $Q^3$ denotes $CH_2SCH_2CH_3$, and A in each case corresponds to a row of Table A.

Table 267
Compounds of the formula IA wherein $Q^1$ denotes methyl, $Q^3$ denotes $CH_2S(=O)CH_3$, and A in each case corresponds to a row of Table A.

Table 268
Compounds of the formula IA wherein $Q^1$ denotes methyl, $Q^3$ denotes $CH_2S(=O)CH_2CH_3$, and A in each case corresponds to a row of Table A.

Table 269
Compounds of the formula IA wherein $Q^1$ denotes methyl, $Q^3$ denotes $CH_2S(=O)_2CH_3$, and A in each case corresponds to a row of Table A.

Table 270
Compounds of the formula IA wherein $Q^1$ denotes methyl, $Q^3$ denotes $CH_2S(=O)_2CH_2CH_3$, and A in each case corresponds to a row of Table A.

Table 271
Compounds of the formula IA wherein $Q^1$ denotes methyl, $Q^3$ denotes $—OS(=O)_2CH_3$, and A in each case corresponds to a row of Table A.

Table 272
Compounds of the formula IA wherein $Q^1$ denotes methyl, $Q^3$ notes $—OS(=O)_2CH_2CH_3$, and A in each case corresponds to a row of Table A.

Table 273
Compounds of the formula IA wherein $Q^1$ denotes methyl, $Q^3$ notes $—OS(=O)_2CH_2CF_3$, and A in each case corresponds to a row of Table A.

Table 274
Compounds of the formula IA wherein $Q^1$ denotes methyl, $Q^3$ denotes $—OS(=O)_2CClF_2$, and A in each case corresponds to a row of Table A.

Table 275
Compounds of the formula IA wherein $Q^1$ denotes methyl, $Q^3$ denotes $OC(=O)CF_3$, and A in each case corresponds to a row of Table A.

Table 276
Compounds of the formula IA wherein $Q^1$ denotes methyl, $Q^3$ denotes $NHCH_2CF_3$, and A in each case corresponds to a row of Table A.

Table 277
Compounds of the formula IA wherein $Q^1$ denotes methyl, $Q^3$ denotes $OCH_2$-cyclopropyl, and A in each case corresponds to a row of Table A.

Table 278
Compounds of the formula IA wherein $Q^1$ denotes methyl, $Q^3$ denotes $OCH_2C(Cl)=CH_2$, and A in each case corresponds to a row of Table A.

Table 279
Compounds of the formula IA wherein $Q^1$ denotes methyl, $Q^3$ denotes $OCH_2CH=CF_2$, and A in each case corresponds to a row of Table A.

Table 280
Compounds of the formula IA wherein $Q^1$ denotes methyl, $Q^3$ denotes $NHS(=O)_2CF_3$, and A in each case corresponds to a row of Table A.

Table 281
Compounds of the formula IA wherein $Q^1$ denotes methyl, $Q^3$ denotes $NHC(=O)CF_3$, and A in each case corresponds to a row of Table A.

Table 282
Compounds of the formula IA wherein $Q^1$ denotes methyl, $Q^3$ denotes $OCH_2CN$, and A in each case corresponds to a row of Table A.

Table 283
Compounds of the formula IA wherein $Q^1$ denotes methyl, $Q^3$ denotes $OCH_2NO_2$, and A in each case corresponds to a row of Table A.

Table 284
Compounds of the formula IA wherein $Q^1$ denotes methyl, $Q^3$ denotes cyclopropyloxy, and A in each case corresponds to a row of Table A.

Table 285
Compounds of the formula IA wherein $Q^1$ denotes methyl, $Q^3$ denotes $CH_2OCHF_2$, and A in each case corresponds to a row of Table A.

Table 286
Compounds of the formula IA wherein $Q^1$ denotes methyl, $Q^3$ denotes $CH_2S(=O)_2CHF_2$, and A in each case corresponds to a row of Table A.

Table 287
Compounds of the formula IA wherein $Q^1$ denotes methyl, $Q^3$ denotes $CH=NOCH_3$, and A in each case corresponds to a row of Table A.

Table 288
Compounds of the formula IA wherein $Q^1$ denotes methyl, $Q^3$ denotes $CH=NOCH_2CH_3$, and A in each case corresponds to a row of Table A.

Table 289
Compounds of the formula IA wherein $Q^1$ denotes methyl, $Q^3$ denotes $CH=NOCH(CH_3)_2$ and A in each case corresponds to a row of Table A.

Table 290
Compounds of the formula IA wherein $Q^1$ denotes methyl, $Q^3$ denotes $CH=NOC(CH_3)_3$, and A in each case corresponds to a row of Table A.

Table 291
Compounds of the formula IA wherein $Q^1$ denotes methyl, $Q^3$ denotes $C(CH_3)=NOCH_3$, and A in each case corresponds to a row of Table A.

Table 292
Compounds of the formula IA wherein $Q^1$ denotes methyl, $Q^3$ denotes $C(CH_3)=NOCH_2CH_3$, and A in each case corresponds to a row of Table A.

Table 293
Compounds of the formula IA wherein $Q^1$ denotes methyl, $Q^3$ denotes $C(CH_3)=NOCH(CH_3)_2$, and A in each case corresponds to a row of Table A.

Table 294
Compounds of the formula IA wherein $Q^1$ denotes methyl, $Q^3$ denotes $C(CH_3)=NOC(CH_3)_3$, and A in each case corresponds to a row of Table A.

TABLE A

| No. | A | $R^a$ | $R^b$ | $R^c$ |
|---|---|---|---|---|
| IA-1 | $-N(R^a)-S(=O)_2-N(R^b)(R^c)$ ($A^2.1$) | H | $CH_3$ | $CH_3$ |
| IA-2 | $A^2.1$ | H | $CH_2CH_3$ | $CH_3$ |
| IA-3 | $A^2.1$ | H | $CH_2CH_2CH_3$ | $CH_3$ |
| IA-4 | $A^2.1$ | H | $CH(CH_3)_2$ | $CH_3$ |
| IA-5 | $A^2.1$ | H | $CH_2CH_2CH_2CH_3$ | $CH_3$ |
| IA-6 | $A^2.1$ | H | $CH_2CH(CH_3)_2$ | $CH_3$ |
| IA-7 | $A^2.1$ | H | $CH_2CHCH_2$ | $CH_3$ |
| IA-8 | $A^2.1$ | H | $CH_2CCH$ | $CH_3$ |
| IA-9 | $A^2.1$ | H | $C_6H_5$ | $CH_3$ |
| IA-10 | $A^2.1$ | $CH_3$ | $CH_3$ | $CH_3$ |
| IA-11 | $A^2.1$ | $CH_3$ | $CH_2CH_3$ | $CH_3$ |
| IA-12 | $A^2.1$ | $CH_3$ | $CH_2CH_2CH_3$ | $CH_3$ |
| IA-13 | $A^2.1$ | $CH_3$ | $CH(CH_3)_2$ | $CH_3$ |
| IA-14 | $A^2.1$ | $CH_3$ | $CH_2CH_2CH_2CH_3$ | $CH_3$ |
| IA-15 | $A^2.1$ | $CH_3$ | $CH_2CH(CH_3)_2$ | $CH_3$ |
| IA-16 | $A^2.1$ | $CH_3$ | $CH_2CHCH_2$ | $CH_3$ |
| IA-17 | $A^2.1$ | $CH_3$ | $CH_2CCH$ | $CH_3$ |
| IA-18 | $A^2.1$ | $CH_3$ | $C_6H_5$ | $CH_3$ |
| IA-19 | $A^2.1$ | $CH(CH_3)_2$ | $CH_3$ | $CH_3$ |
| IA-20 | $A^2.1$ | $CH(CH_3)_2$ | $CH_2CH_3$ | $CH_3$ |
| IA-21 | $A^2.1$ | $CH(CH_3)_2$ | $CH_2CH_2CH_3$ | $CH_3$ |
| IA-22 | $A^2.1$ | $CH(CH_3)_2$ | $CH(CH_3)_2$ | $CH_3$ |
| IA-23 | $A^2.1$ | $CH(CH_3)_2$ | $CH_2CH_2CH_2CH_3$ | $CH_3$ |
| IA-24 | $A^2.1$ | $CH(CH_3)_2$ | $CH_2CH(CH_3)_2$ | $CH_3$ |
| IA-25 | $A^2.1$ | $CH(CH_3)_2$ | $CH_2CHCH_2$ | $CH_3$ |
| IA-26 | $A^2.1$ | $CH(CH_3)_2$ | $CH_2CCH$ | $CH_3$ |
| IA-27 | $A^2.1$ | $CH(CH_3)_2$ | $C_6H_5$ | $CH_3$ |
| IA-28 | $A^2.1$ | H | $CH_2CH_3$ | $CH_2CH_3$ |
| IA-29 | $A^2.1$ | H | $CH_2CH_2CH_3$ | $CH_2CH_3$ |
| IA-30 | $A^2.1$ | H | $CH(CH_3)_2$ | $CH_2CH_3$ |
| IA-31 | $A^2.1$ | H | $CH_2CH_2CH_2CH_3$ | $CH_2CH_3$ |
| IA-32 | $A^2.1$ | H | $CH_2CH(CH_3)_2$ | $CH_2CH_3$ |
| IA-33 | $A^2.1$ | H | $CH_2CHCH_2$ | $CH_2CH_3$ |
| IA-34 | $A^2.1$ | H | $CH_2CCH$ | $CH_2CH_3$ |
| IA-35 | $A^2.1$ | H | $C_6H_5$ | $CH_2CH_3$ |
| IA-36 | $A^2.1$ | $CH_3$ | $CH_2CH_3$ | $CH_2CH_3$ |
| IA-37 | $A^2.1$ | $CH_3$ | $CH_2CH_2CH_3$ | $CH_2CH_3$ |
| IA-38 | $A^2.1$ | $CH_3$ | $CH(CH_3)_2$ | $CH_2CH_3$ |
| IA-39 | $A^2.1$ | $CH_3$ | $CH_2CH_2CH_2CH_3$ | $CH_2CH_3$ |
| IA-40 | $A^2.1$ | $CH_3$ | $CH_2CH(CH_3)_2$ | $CH_2CH_3$ |
| IA-41 | $A^2.1$ | $CH_3$ | $CH_2CHCH_2$ | $CH_2CH_3$ |
| IA-42 | $A^2.1$ | $CH_3$ | $CH_2CCH$ | $CH_2CH_3$ |
| IA-43 | $A^2.1$ | $CH_3$ | $C_6H_5$ | $CH_2CH_3$ |
| IA-44 | $A^2.1$ | $CH(CH_3)_2$ | $CH_2CH_3$ | $CH_2CH_3$ |
| IA-45 | $A^2.1$ | $CH(CH_3)_2$ | $CH_2CH_2CH_3$ | $CH_2CH_3$ |
| IA-46 | $A^2.1$ | $CH(CH_3)_2$ | $CH(CH_3)_2$ | $CH_2CH_3$ |
| IA-47 | $A^2.1$ | $CH(CH_3)_2$ | $CH_2CH_2CH_2CH_3$ | $CH_2CH_3$ |
| IA-48 | $A^2.1$ | $CH(CH_3)_2$ | $CH_2CH(CH_3)_2$ | $CH_2CH_3$ |
| IA-49 | $A^2.1$ | $CH(CH_3)_2$ | $CH_2CHCH_2$ | $CH_2CH_3$ |
| IA-50 | $A^2.1$ | $CH(CH_3)_2$ | $CH_2CCH$ | $CH_2CH_3$ |
| IA-51 | $A^2.1$ | $CH(CH_3)_2$ | $C_6H_5$ | $CH_2CH_3$ |
| IA-52 | $A^2.1$ | H | $CH_2CH_2CH_3$ | $CH_2CH_2CH_3$ |
| IA-53 | $A^2.1$ | H | $CH(CH_3)_2$ | $CH_2CH_2CH_3$ |
| IA-54 | $A^2.1$ | H | $CH_2CH_2CH_2CH_3$ | $CH_2CH_2CH_3$ |
| IA-55 | $A^2.1$ | H | $CH_2CH(CH_3)_2$ | $CH_2CH_2CH_3$ |
| IA-56 | $A^2.1$ | H | $CH_2CHCH_2$ | $CH_2CH_2CH_3$ |
| IA-57 | $A^2.1$ | H | $CH_2CCH$ | $CH_2CH_2CH_3$ |
| IA-58 | $A^2.1$ | H | $C_6H_5$ | $CH_2CH_2CH_3$ |
| IA-59 | $A^2.1$ | $CH_3$ | $CH_2CH_2CH_3$ | $CH_2CH_2CH_3$ |
| IA-60 | $A^2.1$ | $CH_3$ | $CH(CH_3)_2$ | $CH_2CH_2CH_3$ |
| IA-61 | $A^2.1$ | $CH_3$ | $CH_2CH_2CH_2CH_3$ | $CH_2CH_2CH_3$ |
| IA-62 | $A^2.1$ | $CH_3$ | $CH_2CH(CH_3)_2$ | $CH_2CH_2CH_3$ |
| IA-63 | $A^2.1$ | $CH_3$ | $CH_2CHCH_2$ | $CH_2CH_2CH_3$ |
| IA-64 | $A^2.1$ | $CH_3$ | $CH_2CCH$ | $CH_2CH_2CH_3$ |
| IA-65 | $A^2.1$ | $CH_3$ | $C_6H_5$ | $CH_2CH_2CH_3$ |
| IA-66 | $A^2.1$ | $CH(CH_3)_2$ | $CH_2CH_2CH_3$ | $CH_2CH_2CH_3$ |
| IA-67 | $A^2.1$ | $CH(CH_3)_2$ | $CH(CH_3)_2$ | $CH_2CH_2CH_3$ |
| IA-68 | $A^2.1$ | $CH(CH_3)_2$ | $CH_2CH_2CH_2CH_3$ | $CH_2CH_2CH_3$ |
| IA-69 | $A^2.1$ | $CH(CH_3)_2$ | $CH_2CH(CH_3)_2$ | $CH_2CH_2CH_3$ |
| IA-70 | $A^2.1$ | $CH(CH_3)_2$ | $CH_2CHCH_2$ | $CH_2CH_2CH_3$ |
| IA-71 | $A^2.1$ | $CH(CH_3)_2$ | $CH_2CCH$ | $CH_2CH_2CH_3$ |

TABLE A-continued

| No. | A | R$^a$ | R$^b$ | R$^c$ |
|---|---|---|---|---|
| IA-72 | A$^2$.1 | CH(CH$_3$)$_2$ | C$_6$H$_5$ | CH$_2$CH$_2$CH$_3$ |
| IA-73 | A$^2$.1 | H | CH(CH$_3$)$_2$ | CH(CH$_3$)$_2$ |
| IA-74 | A$^2$.1 | H | CH$_2$CH$_2$CH$_2$CH$_3$ | CH(CH$_3$)$_2$ |
| IA-75 | A$^2$.1 | H | CH$_2$CH(CH$_3$)$_2$ | CH(CH$_3$)$_2$ |
| IA-76 | A$^2$.1 | H | CH$_2$CHCH$_2$ | CH(CH$_3$)$_2$ |
| IA-77 | A$^2$.1 | H | CH$_2$CCH | CH(CH$_3$)$_2$ |
| IA-78 | A$^2$.1 | H | C$_6$H$_5$ | CH(CH$_3$)$_2$ |
| IA-79 | A$^2$.1 | CH$_3$ | CH(CH$_3$)$_2$ | CH(CH$_3$)$_2$ |
| IA-80 | A$^2$.1 | CH$_3$ | CH$_2$CH$_2$CH$_2$CH$_3$ | CH(CH$_3$)$_2$ |
| IA-81 | A$^2$.1 | CH$_3$ | CH$_2$CH(CH$_3$)$_2$ | CH(CH$_3$)$_2$ |
| IA-82 | A$^2$.1 | CH$_3$ | CH$_2$CHCH$_2$ | CH(CH$_3$)$_2$ |
| IA-83 | A$^2$.1 | CH$_3$ | CH$_2$CCH | CH(CH$_3$)$_2$ |
| IA-84 | A$^2$.1 | CH$_3$ | C$_6$H$_5$ | CH(CH$_3$)$_2$ |
| IA-85 | A$^2$.1 | CH(CH$_3$)$_2$ | CH(CH$_3$)$_2$ | CH(CH$_3$)$_2$ |
| IA-86 | A$^2$.1 | CH(CH$_3$)$_2$ | CH$_2$CH$_2$CH$_2$CH$_3$ | CH(CH$_3$)$_2$ |
| IA-87 | A$^2$.1 | CH(CH$_3$)$_2$ | CH$_2$CH(CH$_3$)$_2$ | CH(CH$_3$)$_2$ |
| IA-88 | A$^2$.1 | CH(CH$_3$)$_2$ | CH$_2$CHCH$_2$ | CH(CH$_3$)$_2$ |
| IA-89 | A$^2$.1 | CH(CH$_3$)$_2$ | CH$_2$CCH | CH(CH$_3$)$_2$ |
| IA-90 | A$^2$.1 | CH(CH$_3$)$_2$ | C$_6$H$_5$ | CH(CH$_3$)$_2$ |
| IA-91 | A$^2$.1 | H | CH$_2$CH$_2$CH$_3$ | CH$_2$CH$_2$CH$_2$CH$_3$ |
| IA-92 | A$^2$.1 | H | CH$_2$CH(CH$_3$)$_2$ | CH$_2$CH$_2$CH$_2$CH$_3$ |
| IA-93 | A$^2$.1 | H | CH$_2$CHCH$_2$ | CH$_2$CH$_2$CH$_2$CH$_3$ |
| IA-94 | A$^2$.1 | H | CH$_2$CCH | CH$_2$CH$_2$CH$_2$CH$_3$ |
| IA-95 | A$^2$.1 | H | C$_6$H$_5$ | CH$_2$CH$_2$CH$_2$CH$_3$ |
| IA-96 | A$^2$.1 | CH$_3$ | CH$_2$CH$_2$CH$_2$CH$_3$ | CH$_2$CH$_2$CH$_2$CH$_3$ |
| IA-97 | A$^2$.1 | CH$_3$ | CH$_2$CH(CH$_3$)$_2$ | CH$_2$CH$_2$CH$_2$CH$_3$ |
| IA-98 | A$^2$.1 | CH$_3$ | CH$_2$CHCH$_2$ | CH$_2$CH$_2$CH$_2$CH$_3$ |
| IA-99 | A$^2$.1 | CH$_3$ | CH$_2$CCH | CH$_2$CH$_2$CH$_2$CH$_3$ |
| IA-100 | A$^2$.1 | CH$_3$ | C$_6$H$_5$ | CH$_2$CH$_2$CH$_2$CH$_3$ |
| IA-101 | A$^2$.1 | CH(CH$_3$)$_2$ | CH$_2$CH$_2$CH$_2$CH$_3$ | CH$_2$CH$_2$CH$_2$CH$_3$ |
| IA-102 | A$^2$.1 | CH(CH$_3$)$_2$ | CH$_2$CH(CH$_3$)$_2$ | CH$_2$CH$_2$CH$_2$CH$_3$ |
| IA-103 | A$^2$.1 | CH(CH$_3$)$_2$ | CH$_2$CHCH$_2$ | CH$_2$CH$_2$CH$_2$CH$_3$ |
| IA-104 | A$^2$.1 | CH(CH$_3$)$_2$ | CH$_2$CCH | CH$_2$CH$_2$CH$_2$CH$_3$ |
| IA-105 | A$^2$.1 | CH(CH$_3$)$_2$ | C$_6$H$_5$ | CH$_2$CH$_2$CH$_2$CH$_3$ |
| IA-106 | A$^2$.1 | H | CH$_2$CH(CH$_3$)$_2$ | CH$_2$CH(CH$_3$)$_2$ |
| IA-107 | A$^2$.1 | H | CH$_2$CHCH$_2$ | CH$_2$CH(CH$_3$)$_2$ |
| IA-108 | A$^2$.1 | H | CH$_2$CCH | CH$_2$CH(CH$_3$)$_2$ |
| IA-109 | A$^2$.1 | H | C$_6$H$_5$ | CH$_2$CH(CH$_3$)$_2$ |
| IA-110 | A$^2$.1 | CH$_3$ | CH$_2$CH(CH$_3$)$_2$ | CH$_2$CH(CH$_3$)$_2$ |
| IA-111 | A$^2$.1 | CH$_3$ | CH$_2$CHCH$_2$ | CH$_2$CH(CH$_3$)$_2$ |
| IA-112 | A$^2$.1 | CH$_3$ | CH$_2$CCH | CH$_2$CH(CH$_3$)$_2$ |
| IA-113 | A$^2$.1 | CH$_3$ | C$_6$H$_5$ | CH$_2$CH(CH$_3$)$_2$ |
| IA-114 | A$^2$.1 | CH(CH$_3$)$_2$ | CH$_2$CH(CH$_3$)$_2$ | CH$_2$CH(CH$_3$)$_2$ |
| IA-115 | A$^2$.1 | CH(CH$_3$)$_2$ | CH$_2$CHCH$_2$ | CH$_2$CH(CH$_3$)$_2$ |
| IA-116 | A$^2$.1 | CH(CH$_3$)$_2$ | CH$_2$CCH | CH$_2$CH(CH$_3$)$_2$ |
| IA-117 | A$^2$.1 | CH(CH$_3$)$_2$ | C$_6$H$_5$ | CH$_2$CH(CH$_3$)$_2$ |
| IA-118 | A$^2$.1 | H | CH$_2$CHCH$_2$ | CH$_2$CHCH$_2$ |
| IA-119 | A$^2$.1 | H | CH$_2$CCH | CH$_2$CHCH$_2$ |
| IA-120 | A$^2$.1 | H | C$_6$H$_5$ | CH$_2$CHCH$_2$ |
| IA-121 | A$^2$.1 | CH$_3$ | CH$_2$CHCH$_2$ | CH$_2$CHCH$_2$ |
| IA-122 | A$^2$.1 | CH$_3$ | CH$_2$CCH | CH$_2$CHCH$_2$ |
| IA-123 | A$^2$.1 | CH$_3$ | C$_6$H$_5$ | CH$_2$CHCH$_2$ |
| IA-124 | A$^2$.1 | CH(CH$_3$)$_2$ | CH$_2$CHCH$_2$ | CH$_2$CHCH$_2$ |
| IA-125 | A$^2$.1 | CH(CH$_3$)$_2$ | CH$_2$CCH | CH$_2$CHCH$_2$ |
| IA-126 | A$^2$.1 | CH(CH$_3$)$_2$ | C$_6$H$_5$ | CH$_2$CHCH$_2$ |
| IA-127 | A$^2$.1 | H | CH$_2$CCH | CH$_2$CCH |
| IA-128 | A$^2$.1 | H | C$_6$H$_5$ | CH$_2$CCH |
| IA-129 | A$^2$.1 | CH$_3$ | CH$_2$CCH | CH$_2$CCH |
| IA-130 | A$^2$.1 | CH$_3$ | C$_6$H$_5$ | CH$_2$CCH |
| IA-131 | A$^2$.1 | CH(CH$_3$)$_2$ | CH$_2$CCH | CH$_2$CCH |
| IA-132 | A$^2$.1 | CH(CH$_3$)$_2$ | C$_6$H$_5$ | CH$_2$CCH |
| IA-133 | A$^2$.1 | H | C$_6$H$_5$ | C$_6$H$_5$ |
| IA-134 | A$^2$.1 | CH$_3$ | C$_6$H$_5$ | C$_6$H$_5$ |
| IA-135 | A$^2$.1 | CH(CH$_3$)$_2$ | C$_6$H$_5$ | C$_6$H$_5$ |

Table 295
Compounds of the formula IA (as defined above) wherein $Q^1$ denotes hydrogen, $Q^3$ denotes $CF_3$, and A in each case corresponds to a row of Table B.

Table 296
Compounds of the formula IA wherein $Q^1$ denotes hydrogen, $Q^3$ denotes bromine, and A in each case corresponds to a row of Table B.

Table 297
Compounds of the formula IA wherein $Q^1$ denotes hydrogen, $Q^3$ denotes chlorine, and A in each case corresponds to a row of Table B.

Table 298
Compounds of the formula IA wherein $Q^1$ denotes hydrogen, $Q^3$ denotes $CH_3$, and A in each case corresponds to a row of Table B.

Table 299
Compounds of the formula IA wherein $Q^1$ denotes hydrogen, $Q^3$ denotes $OCH_3$, and A in each case corresponds to a row of Table B.

Table 300
Compounds of the formula IA wherein $Q^1$ denotes hydrogen, $Q^3$ denotes $OCHCH_2$, and A in each case corresponds to a row of Table B.

Table 301
Compounds of the formula IA wherein $Q^1$ denotes hydrogen, $Q^3$ denotes ethoxy, and A in each case corresponds to a row of Table B.

Table 302
Compounds of the formula IA wherein $Q^1$ denotes hydrogen, $Q^3$ denotes $OCH_2CHFOCH_3$, and A in each case corresponds to a row of Table B.

Table 303
Compounds of the formula IA wherein $Q^1$ denotes hydrogen, $Q^3$ denotes $OCH_2CH=CH_2$, and A in each case corresponds to a row of Table B.

Table 304
Compounds of the formula IA wherein $Q^1$ denotes hydrogen, $Q^3$ denotes $OCH_2CCH$, and A in each case corresponds to a row of Table B.

Table 305
Compounds of the formula IA wherein $Q^1$ denotes hydrogen, $Q^3$ denotes $CH_2OCH_3$, and A in each case corresponds to a row of Table B.

Table 306
Compounds of the formula IA wherein $Q^1$ denotes hydrogen, $Q^3$ denotes $CH_2OCH_2CH_3$, and A in each case corresponds to a row of Table B.

Table 307
Compounds of the formula IA wherein $Q^1$ denotes hydrogen, $Q^3$ denotes $CH_2SCH_3$, and A in each case corresponds to a row of Table B.

Table 308
Compounds of the formula IA wherein $Q^1$ denotes hydrogen, $Q^3$ denotes $CH_2SCH_2CH_3$, and A in each case corresponds to a row of Table B.

Table 309
Compounds of the formula IA wherein $Q^1$ denotes hydrogen, $Q^3$ denotes $CH_2S(=O)CH_3$, and A in each case corresponds to a row of Table B.

Table 310
Compounds of the formula IA wherein $Q^1$ denotes hydrogen, $Q^3$ denotes $CH_2S(=O)CH_2CH_3$, and A in each case corresponds to a row of Table B.

Table 311
Compounds of the formula IA wherein $Q^1$ denotes hydrogen, $Q^3$ denotes $CH_2S(=O)_2CH_3$, and A in each case corresponds to a row of Table B.

Table 312
Compounds of the formula IA wherein $Q^1$ denotes hydrogen, $Q^3$ denotes $CH_2S(=O)_2CH_2CH_3$, and A in each case corresponds to a row of Table B.

Table 313
Compounds of the formula IA wherein $Q^1$ denotes hydrogen, $Q^3$ denotes $—OS(=O)_2CH_3$, and A in each case corresponds to a row of Table B.

Table 314
Compounds of the formula IA wherein $Q^1$ denotes hydrogen, $Q^3$ notes $—OS(=O)_2CH_2CH_3$, and A in each case corresponds to a row of Table B.

Table 315
Compounds of the formula IA wherein $Q^1$ denotes hydrogen, $Q^3$ notes $—OS(=O)_2CH_2CF_3$, and A in each case corresponds to a row of Table B.

Table 316
Compounds of the formula IA wherein $Q^1$ denotes hydrogen, $Q^3$ notes $—OS(=O)_2CClF_2$, and A in each case corresponds to a row of Table B.

Table 317
Compounds of the formula IA wherein $Q^1$ denotes hydrogen, $Q^3$ denotes $OC(=O)CF_3$, and A in each case corresponds to a row of Table B.

Table 318
Compounds of the formula IA wherein $Q^1$ denotes hydrogen, $Q^3$ denotes $NHCH_2CF_3$, and A in each case corresponds to a row of Table B.

Table 319
Compounds of the formula IA wherein $Q^1$ denotes hydrogen, $Q^3$ denotes $OCH_2$-cyclopropyl, and A in each case corresponds to a row of Table B.

Table 320
Compounds of the formula IA wherein $Q^1$ denotes hydrogen, $Q^3$ denotes $OCH_2C(Cl)=CH_2$, and A in each case corresponds to a row of Table B.

Table 321
Compounds of the formula IA wherein $Q^1$ denotes hydrogen, $Q^3$ denotes $OCH_2CH=CF_2$, and A in each case corresponds to a row of Table B.

Table 322
Compounds of the formula IA wherein $Q^1$ denotes hydrogen, $Q^3$ denotes $NHS(=O)_2CF_3$, and A in each case corresponds to a row of Table B.

Table 323
Compounds of the formula IA wherein $Q^1$ denotes hydrogen, $Q^3$ denotes $NHC(=O)CF_3$, and A in each case corresponds to a row of Table B.

Table 324
Compounds of the formula IA wherein $Q^1$ denotes hydrogen, $Q^3$ denotes $OCH_2CN$, and A in each case corresponds to a row of Table B.

Table 325
Compounds of the formula IA wherein $Q^1$ denotes hydrogen, $Q^3$ denotes $OCH_2NO_2$, and A in each case corresponds to a row of Table B.

Table 326
Compounds of the formula IA wherein $Q^1$ denotes hydrogen, $Q^3$ denotes cyclopropyloxy, and A in each case corresponds to a row of Table B.

Table 327
Compounds of the formula IA wherein $Q^1$ denotes hydrogen, $Q^3$ denotes $CH_2OCHF_2$, and A in each case corresponds to a row of Table B.

Table 328
Compounds of the formula IA wherein $Q^1$ denotes hydrogen, $Q^3$ denotes $CH_2S(=O)_2CHF_2$, and A in each case corresponds to a row of Table B.

Table 329
Compounds of the formula IA wherein $Q^1$ denotes hydrogen, $Q^3$ denotes $CH=NOCH_3$, and A in each case corresponds to a row of Table B.

Table 330
Compounds of the formula IA wherein $Q^1$ denotes hydrogen, $Q^3$ denotes $CH=NOCH_2CH_3$, and A in each case corresponds to a row of Table B.

Table 331
Compounds of the formula IA wherein $Q^1$ denotes hydrogen, $Q^3$ denotes $CH=NOCH(CH_3)_2$ and A in each case corresponds to a row of Table B.

Table 332
Compounds of the formula IA wherein $Q^1$ denotes hydrogen, $Q^3$ denotes $CH=NOC(CH_3)_3$, and A in each case corresponds to a row of Table B.

Table 333
Compounds of the formula IA wherein $Q^1$ denotes hydrogen, $Q^3$ denotes $C(CH_3)=NOCH_3$, and A in each case corresponds to a row of Table B.

Table 334
Compounds of the formula IA wherein $Q^1$ denotes hydrogen, $Q^3$ denotes $C(CH_3)=NOCH_2CH_3$, and A in each case corresponds to a row of Table B.

Table 335
Compounds of the formula IA wherein $Q^1$ denotes hydrogen, $Q^3$ denotes $C(CH_3)=NOCH(CH_3)_2$, and A in each case corresponds to a row of Table B.

Table 336
Compounds of the formula IA wherein $Q^1$ denotes hydrogen, $Q^3$ denotes $C(CH_3)=NOC(CH_3)_3$, and A in each case corresponds to a row of Table B.

Table 337
Compounds of the formula IA wherein $Q^1$ denotes chlorine, $Q^3$ denotes $CF_3$, and A in each case corresponds to a row of Table B.

Table 338
Compounds of the formula IA wherein $Q^1$ denotes chlorine, $Q^3$ denotes bromine, and A in each case corresponds to a row of Table B.

Table 339
Compounds of the formula IA wherein $Q^1$ denotes chlorine, $Q^3$ denotes chlorine, and A in each case corresponds to a row of Table B.

Table 340
Compounds of the formula IA wherein $Q^1$ denotes chlorine, $Q^3$ denotes $CH_3$, and A in each case corresponds to a row of Table B.

Table 341
Compounds of the formula IA wherein $Q^1$ denotes chlorine, $Q^3$ denotes $OCH_3$, and A in each case corresponds to a row of Table B.

Table 342
Compounds of the formula IA wherein $Q^1$ denotes chlorine, $Q^3$ denotes $OCHCH_2$, and A in each case corresponds to a row of Table B.

Table 343
Compounds of the formula IA wherein $Q^1$ denotes chlorine, $Q^3$ denotes ethoxy, and A in each case corresponds to a row of Table B.

Table 344
Compounds of the formula IA wherein $Q^1$ denotes chlorine, $Q^3$ denotes $OCH_2CHFOCH_3$, and A in each case corresponds to a row of Table B.

Table 345
Compounds of the formula IA wherein $Q^1$ denotes chlorine, $Q^3$ denotes $OCH_2CH=CH_2$, and A in each case corresponds to a row of Table B.

Table 346
Compounds of the formula IA wherein $Q^1$ denotes chlorine, $Q^3$ denotes $OCH_2CCH$, and A in each case corresponds to a row of Table B.

Table 347
Compounds of the formula IA wherein $Q^1$ denotes chlorine, $Q^3$ denotes $CH_2OCH_3$, and A in each case corresponds to a row of Table B.

Table 348
Compounds of the formula IA wherein $Q^1$ denotes chlorine, $Q^3$ denotes $CH_2OCH_2CH_3$, and A in each case corresponds to a row of Table B.

Table 349
Compounds of the formula IA wherein $Q^1$ denotes chlorine, $Q^3$ denotes $CH_2SCH_3$, and A in each case corresponds to a row of Table B.

Table 350
Compounds of the formula IA wherein $Q^1$ denotes chlorine, $Q^3$ denotes $CH_2SCH_2CH_3$, and A in each case corresponds to a row of Table B.

Table 351
Compounds of the formula IA wherein $Q^1$ denotes chlorine, $Q^3$ denotes $CH_2S(=O)CH_3$, and A in each case corresponds to a row of Table B.

Table 352
Compounds of the formula IA wherein $Q^1$ denotes chlorine, $Q^3$ denotes $CH_2S(=O)CH_2CH_3$, and A in each case corresponds to a row of Table B.

Table 353
Compounds of the formula IA wherein $Q^1$ denotes chlorine, $Q^3$ denotes $CH_2S(=O)_2CH_3$, and A in each case corresponds to a row of Table B.

Table 354
Compounds of the formula IA wherein $Q^1$ denotes chlorine, $Q^3$ denotes $CH_2S(=O)_2CH_2CH_3$, and A in each case corresponds to a row of Table B.

Table 355
Compounds of the formula IA wherein $Q^1$ denotes chlorine, $Q^3$ denotes $-OS(=O)_2CH_3$, and A in each case corresponds to a row of Table B.

Table 356
Compounds of the formula IA wherein $Q^1$ denotes chlorine, $Q^3$ notes $-OS(=O)_2CH_2CH_3$, and A in each case corresponds to a row of Table B.

Table 357
Compounds of the formula IA wherein $Q^1$ denotes chlorine, $Q^3$ notes $-OS(=O)_2CH_2CF_3$, and A in each case corresponds to a row of Table B.

Table 358
Compounds of the formula IA wherein $Q^1$ denotes chlorine, $Q^3$ notes $-OS(=O)_2CClF_2$, and A in each case corresponds to a row of Table B.

Table 359
Compounds of the formula IA wherein $Q^1$ denotes chlorine, $Q^3$ denotes $OC(=O)CF_3$, and A in each case corresponds to a row of Table B.

Table 360
Compounds of the formula IA wherein $Q^1$ denotes chlorine, $Q^3$ denotes $NHCH_2CF_3$, and A in each case corresponds to a row of Table B.

Table 361
Compounds of the formula IA wherein $Q^1$ denotes chlorine, $Q^3$ denotes $OCH_2$-cyclopropyl, and A in each case corresponds to a row of Table B.

Table 362
Compounds of the formula IA wherein $Q^1$ denotes chlorine, $Q^3$ denotes $OCH_2C(Cl)=CH_2$, and A in each case corresponds to a row of Table B.

Table 363
Compounds of the formula IA wherein $Q^1$ denotes chlorine, $Q^3$ denotes $OCH_2CH=CF_2$, and A in each case corresponds to a row of Table B.

Table 364
Compounds of the formula IA wherein $Q^1$ denotes chlorine, $Q^3$ denotes $NHS(=O)_2CF_3$, and A in each case corresponds to a row of Table B.

Table 365
Compounds of the formula IA wherein $Q^1$ denotes chlorine, $Q^3$ denotes $NHC(=O)CF_3$, and A in each case corresponds to a row of Table B.

Table 366
Compounds of the formula IA wherein $Q^1$ denotes chlorine, $Q^3$ denotes $OCH_2CN$, and A in each case corresponds to a row of Table B.

Table 367
Compounds of the formula IA wherein $Q^1$ denotes chlorine, $Q^3$ denotes $OCH_2NO_2$, and A in each case corresponds to a row of Table B.

Table 368
Compounds of the formula IA wherein $Q^1$ denotes chlorine, $Q^3$ denotes cyclopropyloxy, and A in each case corresponds to a row of Table B.

Table 369
Compounds of the formula IA wherein $Q^1$ denotes chlorine, $Q^3$ denotes $CH_2OCHF_2$, and A in each case corresponds to a row of Table B.

Table 370
Compounds of the formula IA wherein $Q^1$ denotes chlorine, $Q^3$ denotes $CH_2S(=O)_2CHF_2$, and A in each case corresponds to a row of Table B.

Table 371
Compounds of the formula IA wherein $Q^1$ denotes chlorine, $Q^3$ denotes $CH=NOCH_3$, and A in each case corresponds to a row of Table B.

Table 372
Compounds of the formula IA wherein $Q^1$ denotes chlorine, $Q^3$ denotes $CH=NOCH_2CH_3$, and A in each case corresponds to a row of Table B.

Table 373
Compounds of the formula IA wherein $Q^1$ denotes chlorine, $Q^3$ denotes $CH=NOCH(CH_3)_2$ and A in each case corresponds to a row of Table B.

Table 374
Compounds of the formula IA wherein $Q^1$ denotes chlorine, $Q^3$ denotes $CH=NOC(CH_3)_3$, and A in each case corresponds to a row of Table B.

Table 375
Compounds of the formula IA wherein $Q^1$ denotes chlorine, $Q^3$ denotes $C(CH_3)=NOCH_3$, and A in each case corresponds to a row of Table B.

Table 376
Compounds of the formula IA wherein $Q^1$ denotes chlorine, $Q^3$ denotes $C(CH_3)=NOCH_2CH_3$, and A in each case corresponds to a row of Table B.

Table 377
Compounds of the formula IA wherein $Q^1$ denotes chlorine, $Q^3$ denotes $C(CH_3)=NOCH(CH_3)_2$, and A in each case corresponds to a row of Table B.

Table 378
Compounds of the formula IA wherein $Q^1$ denotes chlorine, $Q^3$ denotes $C(CH_3)=NOC(CH_3)_3$, and A in each case corresponds to a row of Table B.

Table 379
Compounds of the formula IA wherein $Q^1$ denotes bromine, $Q^3$ denotes $CF_3$, and A in each case corresponds to a row of Table B.

Table 380
Compounds of the formula IA wherein $Q^1$ denotes bromine, $Q^3$ denotes bromine, and A in each case corresponds to a row of Table B.

Table 381
Compounds of the formula IA wherein $Q^1$ denotes bromine, $Q^3$ denotes chlorine, and A in each case corresponds to a row of Table B.

Table 382
Compounds of the formula IA wherein $Q^1$ denotes bromine, $Q^3$ denotes $CH_3$, and A in each case corresponds to a row of Table B.

Table 383
Compounds of the formula IA wherein $Q^1$ denotes bromine, $Q^3$ denotes $OCH_3$, and A in each case corresponds to a row of Table B.

Table 384
Compounds of the formula IA wherein $Q^1$ denotes bromine, $Q^3$ denotes $OCHCH_2$, and A in each case corresponds to a row of Table B.

Table 385
Compounds of the formula IA wherein $Q^1$ denotes bromine, $Q^3$ denotes ethoxy, and A in each case corresponds to a row of Table B.

Table 386
Compounds of the formula IA wherein $Q^1$ denotes bromine, $Q^3$ denotes $OCH_2CHFOCH_3$, and A in each case corresponds to a row of Table B.

Table 387
Compounds of the formula IA wherein $Q^1$ denotes bromine, $Q^3$ denotes $OCH_2CH=CH_2$, and A in each case corresponds to a row of Table B.

Table 388
Compounds of the formula IA wherein $Q^1$ denotes bromine, $Q^3$ denotes $OCH_2CCH$, and A in each case corresponds to a row of Table B.

Table 389
Compounds of the formula IA wherein $Q^1$ denotes bromine, $Q^3$ denotes $CH_2OCH_3$, and A in each case corresponds to a row of Table B.

Table 390
Compounds of the formula IA wherein $Q^1$ denotes bromine, $Q^3$ denotes $CH_2OCH_2CH_3$, and A in each case corresponds to a row of Table B.

Table 391
Compounds of the formula IA wherein $Q^1$ denotes bromine, $Q^3$ denotes $CH_2SCH_3$, and A in each case corresponds to a row of Table B.

Table 392
Compounds of the formula IA wherein $Q^1$ denotes bromine, $Q^3$ denotes $CH_2SCH_2CH_3$, and A in each case corresponds to a row of Table B.

Table 393
Compounds of the formula IA wherein $Q^1$ denotes bromine, $Q^3$ denotes $CH_2S(=O)CH_3$, and A in each case corresponds to a row of Table B.

Table 394
Compounds of the formula IA wherein $Q^1$ denotes bromine, $Q^3$ denotes $CH_2S(=O)CH_2CH_3$, and A in each case corresponds to a row of Table B.

Table 395
Compounds of the formula IA wherein $Q^1$ denotes bromine, $Q^3$ denotes $CH_2S(=O)_2CH_3$, and A in each case corresponds to a row of Table B.

Table 396
Compounds of the formula IA wherein $Q^1$ denotes bromine, $Q^3$ denotes $CH_2S(=O)_2CH_2CH_3$, and A in each case corresponds to a row of Table B.

Table 397
Compounds of the formula IA wherein $Q^1$ denotes bromine, $Q^3$ denotes $—OS(=O)_2CH_3$, and A in each case corresponds to a row of Table B.

Table 398
Compounds of the formula IA wherein $Q^1$ denotes bromine, $Q^3$ notes $—OS(=O)_2CH_2CH_3$, and A in each case corresponds to a row of Table B.

Table 399
Compounds of the formula IA wherein $Q^1$ denotes bromine, $Q^3$ notes $—OS(=O)_2CH_2CF_3$, and A in each case corresponds to a row of Table B.

Table 400
Compounds of the formula IA wherein $Q^1$ denotes bromine, $Q^3$ notes $—OS(=O)_2CClF_2$, and A in each case corresponds to a row of Table B.

Table 401
Compounds of the formula IA wherein $Q^1$ denotes bromine, $Q^3$ denotes $OC(=O)CF_3$, and A in each case corresponds to a row of Table B.

Table 402
Compounds of the formula IA wherein $Q^1$ denotes bromine, $Q^3$ denotes $NHCH_2CF_3$, and A in each case corresponds to a row of Table B.

Table 403
Compounds of the formula IA wherein $Q^1$ denotes bromine, $Q^3$ denotes $OCH_2$-cyclopropyl, and A in each case corresponds to a row of Table B.

Table 404
Compounds of the formula IA wherein $Q^1$ denotes bromine, $Q^3$ denotes $OCH_2C(Cl)=CH_2$, and A in each case corresponds to a row of Table B.

Table 405
Compounds of the formula IA wherein $Q^1$ denotes bromine, $Q^3$ denotes $OCH_2CH=CF_2$, and A in each case corresponds to a row of Table B.

Table 406
Compounds of the formula IA wherein $Q^1$ denotes bromine, $Q^3$ denotes $NHS(=O)_2CF_3$, and A in each case corresponds to a row of Table B.

Table 407
Compounds of the formula IA wherein $Q^1$ denotes bromine, $Q^3$ denotes $NHC(=O)CF_3$, and A in each case corresponds to a row of Table B.

Table 408
Compounds of the formula IA wherein $Q^1$ denotes bromine, $Q^3$ denotes $OCH_2CN$, and A in each case corresponds to a row of Table B.

Table 409
Compounds of the formula IA wherein $Q^1$ denotes bromine, $Q^3$ denotes $OCH_2NO_2$, and A in each case corresponds to a row of Table B.

Table 410
Compounds of the formula IA wherein $Q^1$ denotes bromine, $Q^3$ denotes cyclopropyloxy, and A in each case corresponds to a row of Table B.

Table 411
Compounds of the formula IA wherein $Q^1$ denotes bromine, $Q^3$ denotes $CH_2OCHF_2$, and A in each case corresponds to a row of Table B.

Table 412
Compounds of the formula IA wherein $Q^1$ denotes bromine, $Q^3$ denotes $CH_2S(=O)_2CHF_2$, and A in each case corresponds to a row of Table B.

Table 413
Compounds of the formula IA wherein $Q^1$ denotes bromine, $Q^3$ denotes $CH=NOCH_3$, and A in each case corresponds to a row of Table B.

Table 414
Compounds of the formula IA wherein $Q^1$ denotes bromine, $Q^3$ denotes $CH=NOCH_2CH_3$, and A in each case corresponds to a row of Table B.

Table 415
Compounds of the formula IA wherein $Q^1$ denotes bromine, $Q^3$ denotes $CH=NOCH(CH_3)_2$ and A in each case corresponds to a row of Table B.

Table 416
Compounds of the formula IA wherein $Q^1$ denotes bromine, $Q^3$ denotes $CH=NOC(CH_3)_3$, and A in each case corresponds to a row of Table B.

Table 417
Compounds of the formula IA wherein $Q^1$ denotes bromine, $Q^3$ denotes $C(CH_3)=NOCH_3$, and A in each case corresponds to a row of Table B.

Table 418
Compounds of the formula IA wherein $Q^1$ denotes bromine, $Q^3$ denotes $C(CH_3)=NOCH_2CH_3$, and A in each case corresponds to a row of Table B.

Table 419
Compounds of the formula IA wherein $Q^1$ denotes bromine, $Q^3$ denotes $C(CH_3)=NOCH(CH_3)_2$, and A in each case corresponds to a row of Table B.

Table 420
Compounds of the formula IA wherein $Q^1$ denotes bromine, $Q^3$ denotes $C(CH_3)=NOC(CH_3)_3$, and A in each case corresponds to a row of Table B.

Table 421
Compounds of the formula IA wherein $Q^1$ denotes fluorine, $Q^3$ denotes $CF_3$, and A in each case corresponds to a row of Table B.

Table 422
Compounds of the formula IA wherein $Q^1$ denotes fluorine, $Q^3$ denotes bromine, and A in each case corresponds to a row of Table B.

Table 423
Compounds of the formula IA wherein $Q^1$ denotes fluorine, $Q^3$ denotes chlorine, and A in each case corresponds to a row of Table B.

Table 424
Compounds of the formula IA wherein $Q^1$ denotes fluorine, $Q^3$ denotes $CH_3$, and A in each case corresponds to a row of Table B.

Table 425
Compounds of the formula IA wherein $Q^1$ denotes fluorine, $Q^3$ denotes $OCH_3$, and A in each case corresponds to a row of Table B.

Table 426
Compounds of the formula IA wherein $Q^1$ denotes fluorine, $Q^3$ denotes $OCHCH_2$, and A in each case corresponds to a row of Table B.

Table 427
Compounds of the formula IA wherein $Q^1$ denotes fluorine, $Q^3$ denotes ethoxy, and A in each case corresponds to a row of Table B.

Table 428
Compounds of the formula IA wherein $Q^1$ denotes fluorine, $Q^3$ denotes $OCH_2CHFOCH_3$, and A in each case corresponds to a row of Table B.

Table 429
Compounds of the formula IA wherein $Q^1$ denotes fluorine, $Q^3$ denotes $OCH_2CH=CH_2$, and A in each case corresponds to a row of Table B.

Table 430
Compounds of the formula IA wherein $Q^1$ denotes fluorine, $Q^3$ denotes $OCH_2CCH$, and A in each case corresponds to a row of Table B.

Table 431
Compounds of the formula IA wherein $Q^1$ denotes fluorine, $Q^3$ denotes $CH_2OCH_3$, and A in each case corresponds to a row of Table B.

Table 432
Compounds of the formula IA wherein $Q^1$ denotes fluorine, $Q^3$ denotes $CH_2OCH_2CH_3$, and A in each case corresponds to a row of Table B.

Table 433
Compounds of the formula IA wherein $Q^1$ denotes fluorine, $Q^3$ denotes $CH_2SCH_3$, and A in each case corresponds to a row of Table B.

Table 434
Compounds of the formula IA wherein $Q^1$ denotes fluorine, $Q^3$ denotes $CH_2SCH_2CH_3$, and A in each case corresponds to a row of Table B.

Table 435
Compounds of the formula IA wherein $Q^1$ denotes fluorine, $Q^3$ denotes $CH_2S(=O)CH_3$, and A in each case corresponds to a row of Table B.

Table 436
Compounds of the formula IA wherein $Q^1$ denotes fluorine, $Q^3$ denotes $CH_2S(=O)CH_2CH_3$, and A in each case corresponds to a row of Table B.

Table 437
Compounds of the formula IA wherein $Q^1$ denotes fluorine, $Q^3$ denotes $CH_2S(=O)_2CH_3$, and A in each case corresponds to a row of Table B.

Table 438
Compounds of the formula IA wherein $Q^1$ denotes fluorine, $Q^3$ denotes $CH_2S(=O)_2CH_2CH_3$, and A in each case corresponds to a row of Table B.

Table 439
Compounds of the formula IA wherein $Q^1$ denotes fluorine, $Q^3$ denotes $—OS(=O)_2CH_3$, and A in each case corresponds to a row of Table B.

Table 440
Compounds of the formula IA wherein $Q^1$ denotes fluorine, $Q^3$ notes $—OS(=O)_2CH_2CH_3$, and A in each case corresponds to a row of Table B.

Table 441
Compounds of the formula IA wherein $Q^1$ denotes fluorine, $Q^3$ notes $—OS(=O)_2CH_2CF_3$, and A in each case corresponds to a row of Table B.

Table 442
Compounds of the formula IA wherein $Q^1$ denotes fluorine, $Q^3$ denotes $—OS(=O)_2CClF_2$, and A in each case corresponds to a row of Table B.

Table 443
Compounds of the formula IA wherein $Q^1$ denotes fluorine, $Q^3$ denotes $OC(=O)CF_3$, and A in each case corresponds to a row of Table B.

Table 444
Compounds of the formula IA wherein $Q^1$ denotes fluorine, $Q^3$ denotes $NHCH_2CF_3$, and A in each case corresponds to a row of Table B.

Table 445
Compounds of the formula IA wherein $Q^1$ denotes fluorine, $Q^3$ denotes $OCH_2$-cyclopropyl, and A in each case corresponds to a row of Table B.

Table 446
Compounds of the formula IA wherein $Q^1$ denotes fluorine, $Q^3$ denotes $OCH_2C(Cl)=CH_2$, and A in each case corresponds to a row of Table B.

Table 447
Compounds of the formula IA wherein $Q^1$ denotes fluorine, $Q^3$ denotes $OCH_2CH=CF_2$, and A in each case corresponds to a row of Table B.

Table 448
Compounds of the formula IA wherein $Q^1$ denotes fluorine, $Q^3$ denotes $NHS(=O)_2CF_3$, and A in each case corresponds to a row of Table B.

Table 449
Compounds of the formula IA wherein $Q^1$ denotes fluorine, $Q^3$ denotes $NHC(=O)CF_3$, and A in each case corresponds to a row of Table B.

Table 450
Compounds of the formula IA wherein $Q^1$ denotes fluorine, $Q^3$ denotes $OCH_2CN$, and A in each case corresponds to a row of Table B.

Table 451
Compounds of the formula IA wherein $Q^1$ denotes fluorine, $Q^3$ denotes $OCH_2NO_2$, and A in each case corresponds to a row of Table B.

Table 452
Compounds of the formula IA wherein $Q^1$ denotes fluorine, $Q^3$ denotes cyclopropyloxy, and A in each case corresponds to a row of Table B.

Table 453
Compounds of the formula IA wherein $Q^1$ denotes fluorine, $Q^3$ denotes $CH_2OCHF_2$, and A in each case corresponds to a row of Table B.

Table 454
Compounds of the formula IA wherein $Q^1$ denotes fluorine, $Q^3$ denotes $CH_2S(=O)_2CHF_2$, and A in each case corresponds to a row of Table B.

Table 455
Compounds of the formula IA wherein $Q^1$ denotes fluorine, $Q^3$ denotes $CH=NOCH_3$, and A in each case corresponds to a row of Table B.

Table 456
Compounds of the formula IA wherein $Q^1$ denotes fluorine, $Q^3$ denotes $CH=NOCH_2CH_3$, and A in each case corresponds to a row of Table B.

Table 457
Compounds of the formula IA wherein $Q^1$ denotes fluorine, $Q^3$ denotes $CH=NOCH(CH_3)_2$ and A in each case corresponds to a row of Table B.

Table 458
Compounds of the formula IA wherein $Q^1$ denotes fluorine, $Q^3$ denotes $CH=NOC(CH_3)_3$, and A in each case corresponds to a row of Table B.

Table 459
Compounds of the formula IA wherein $Q^1$ denotes fluorine, $Q^3$ denotes $C(CH_3)=NOCH_3$, and A in each case corresponds to a row of Table B.

Table 460
Compounds of the formula IA wherein $Q^1$ denotes fluorine, $Q^3$ denotes $C(CH_3)=NOCH_2CH_3$, and A in each case corresponds to a row of Table B.

Table 461
Compounds of the formula IA wherein $Q^1$ denotes fluorine, $Q^3$ denotes $C(CH_3)=NOCH(CH_3)_2$, and A in each case corresponds to a row of Table B.

Table 462
Compounds of the formula IA wherein $Q^1$ denotes fluorine, $Q^3$ denotes $C(CH_3)=NOC(CH_3)_3$, and A in each case corresponds to a row of Table B.

Table 463
Compounds of the formula IA wherein $Q^1$ denotes iodine, $Q^3$ denotes $CF_3$, and A in each case corresponds to a row of Table B.

Table 464
Compounds of the formula IA wherein $Q^1$ denotes iodine, $Q^3$ denotes bromine, and A in each case corresponds to a row of Table B.

Table 465
Compounds of the formula IA wherein $Q^1$ denotes iodine, $Q^3$ denotes chlorine, and A in each case corresponds to a row of Table B.

Table 466
Compounds of the formula IA wherein $Q^1$ denotes iodine, $Q^3$ denotes $CH_3$, and A in each case corresponds to a row of Table B.

Table 467
Compounds of the formula IA wherein $Q^1$ denotes iodine, $Q^3$ denotes $OCH_3$, and A in each case corresponds to a row of Table B.

Table 468
Compounds of the formula IA wherein $Q^1$ denotes iodine, $Q^3$ denotes $OCHCH_2$, and A in each case corresponds to a row of Table B.

Table 469
Compounds of the formula IA wherein $Q^1$ denotes iodine, $Q^3$ denotes ethoxy, and A in each case corresponds to a row of Table B.

Table 470
Compounds of the formula IA wherein $Q^1$ denotes iodine, $Q^3$ denotes $OCH_2CHFOCH_3$, and A in each case corresponds to a row of Table B.

Table 471
Compounds of the formula IA wherein $Q^1$ denotes iodine, $Q^3$ denotes $OCH_2CH=CH_2$, and A in each case corresponds to a row of Table B.

Table 472
Compounds of the formula IA wherein $Q^1$ denotes iodine, $Q^3$ denotes $OCH_2CCH$, and A in each case corresponds to a row of Table B.

Table 473
Compounds of the formula IA wherein $Q^1$ denotes iodine, $Q^3$ denotes $CH_2OCH_3$, and A in each case corresponds to a row of Table B.

Table 474
Compounds of the formula IA wherein $Q^1$ denotes iodine, $Q^3$ denotes $CH_2OCH_2CH_3$, and A in each case corresponds to a row of Table B.

Table 475
Compounds of the formula IA wherein $Q^1$ denotes iodine, $Q^3$ denotes $CH_2SCH_3$, and A in each case corresponds to a row of Table B.

Table 476
Compounds of the formula IA wherein $Q^1$ denotes iodine, $Q^3$ denotes $CH_2SCH_2CH_3$, and A in each case corresponds to a row of Table B.

Table 477
Compounds of the formula IA wherein $Q^1$ denotes iodine, $Q^3$ denotes $CH_2S(=O)CH_3$, and A in each case corresponds to a row of Table B.

Table 478
Compounds of the formula IA wherein $Q^1$ denotes iodine, $Q^3$ denotes $CH_2S(=O)CH_2CH_3$, and A in each case corresponds to a row of Table B.

Table 479
Compounds of the formula IA wherein $Q^1$ denotes iodine, $Q^3$ denotes $CH_2S(=O)_2CH_3$, and A in each case corresponds to a row of Table B.

Table 480
Compounds of the formula IA wherein $Q^1$ denotes iodine, $Q^3$ denotes $CH_2S(=O)_2CH_2CH_3$, and A in each case corresponds to a row of Table B.

Table 481
Compounds of the formula IA wherein $Q^1$ denotes iodine, $Q^3$ denotes $—OS(=O)_2CH_3$, and A in each case corresponds to a row of Table B.

Table 482
Compounds of the formula IA wherein $Q^1$ denotes iodine, $Q^3$ notes $—OS(=O)_2CH_2CH_3$, and A in each case corresponds to a row of Table B.

Table 483
Compounds of the formula IA wherein $Q^1$ denotes iodine, $Q^3$ notes $—OS(=O)_2CH_2CF_3$, and A in each case corresponds to a row of Table B.

Table 484
Compounds of the formula IA wherein $Q^1$ denotes iodine, $Q^3$ denotes $—OS(=O)_2CClF_2$, and A in each case corresponds to a row of Table B.

Table 485
Compounds of the formula IA wherein $Q^1$ denotes iodine, $Q^3$ denotes $OC(=O)CF_3$, and A in each case corresponds to a row of Table B.

Table 486
Compounds of the formula IA wherein $Q^1$ denotes iodine, $Q^3$ denotes $NHCH_2CF_3$, and A in each case corresponds to a row of Table B.

Table 487
Compounds of the formula IA wherein $Q^1$ denotes iodine, $Q^3$ denotes $OCH_2$-cyclopropyl, and A in each case corresponds to a row of Table B.

Table 488
Compounds of the formula IA wherein $Q^1$ denotes iodine, $Q^3$ denotes $OCH_2C(Cl)=CH_2$, and A in each case corresponds to a row of Table B.

Table 489
Compounds of the formula IA wherein $Q^1$ denotes iodine, $Q^3$ denotes $OCH_2CH=CF_2$, and A in each case corresponds to a row of Table B.

Table 490
Compounds of the formula IA wherein $Q^1$ denotes iodine, $Q^3$ denotes $NHS(=O)_2CF_3$, and A in each case corresponds to a row of Table B.

Table 491
Compounds of the formula IA wherein $Q^1$ denotes iodine, $Q^3$ denotes $NHC(=O)CF_3$, and A in each case corresponds to a row of Table B.

Table 492
Compounds of the formula IA wherein $Q^1$ denotes iodine, $Q^3$ denotes $OCH_2CN$, and A in each case corresponds to a row of Table B.

Table 493
Compounds of the formula IA wherein $Q^1$ denotes iodine, $Q^3$ denotes $OCH_2NO_2$, and A in each case corresponds to a row of Table B.

Table 494
Compounds of the formula IA wherein $Q^1$ denotes iodine, $Q^3$ denotes cyclopropyloxy, and A in each case corresponds to a row of Table B.

Table 495
Compounds of the formula IA wherein $Q^1$ denotes iodine, $Q^3$ denotes $CH_2OCHF_2$, and A in each case corresponds to a row of Table B.

Table 496
Compounds of the formula IA wherein $Q^1$ denotes iodine, $Q^3$ denotes $CH_2S(=O)_2CHF_2$, and A in each case corresponds to a row of Table B.

Table 497
Compounds of the formula IA wherein $Q^1$ denotes iodine, $Q^3$ denotes $CH=NOCH_3$, and A in each case corresponds to a row of Table B.

Table 498
Compounds of the formula IA wherein $Q^1$ denotes iodine, $Q^3$ denotes $CH=NOCH_2CH_3$, and A in each case corresponds to a row of Table B.

Table 499
Compounds of the formula IA wherein $Q^1$ denotes iodine, $Q^3$ denotes $CH=NOCH(CH_3)_2$ and A in each case corresponds to a row of Table B.

Table 500
Compounds of the formula IA wherein $Q^1$ denotes iodine, $Q^3$ denotes $CH=NOC(CH_3)_3$, and A in each case corresponds to a row of Table B.

Table 501
Compounds of the formula IA wherein $Q^1$ denotes iodine, $Q^3$ denotes $C(CH_3)=NOCH_3$, and A in each case corresponds to a row of Table B.

Table 502
Compounds of the formula IA wherein $Q^1$ denotes iodine, $Q^3$ denotes $C(CH_3)=NOCH_2CH_3$, and A in each case corresponds to a row of Table B.

Table 503
Compounds of the formula IA wherein $Q^1$ denotes iodine, $Q^3$ denotes $C(CH_3)=NOCH(CH_3)_2$, and A in each case corresponds to a row of Table B.

Table 504
Compounds of the formula IA wherein $Q^1$ denotes iodine, $Q^3$ denotes $C(CH_3)=NOC(CH_3)_3$, and A in each case corresponds to a row of Table B.

Table 505
Compounds of the formula IA wherein $Q^1$ denotes cyano, $Q^3$ denotes $CF_3$, and A in each case corresponds to a row of Table B.

Table 506
Compounds of the formula IA wherein $Q^1$ denotes cyano, $Q^3$ denotes bromine, and A in each case corresponds to a row of Table B.

Table 507
Compounds of the formula IA wherein $Q^1$ denotes cyano, $Q^3$ denotes chlorine, and A in each case corresponds to a row of Table B.

Table 508
Compounds of the formula IA wherein $Q^1$ denotes cyano, $Q^3$ denotes $CH_3$, and A in each case corresponds to a row of Table B.

Table 509
Compounds of the formula IA wherein $Q^1$ denotes cyano, $Q^3$ denotes $OCH_3$, and A in each case corresponds to a row of Table B.

Table 510
Compounds of the formula IA wherein $Q^1$ denotes cyano, $Q^3$ denotes $OCHCH_2$, and A in each case corresponds to a row of Table B.

Table 511
Compounds of the formula IA wherein $Q^1$ denotes cyano, $Q^3$ denotes ethoxy, and A in each case corresponds to a row of Table B.

Table 512
Compounds of the formula IA wherein $Q^1$ denotes cyano, $Q^3$ denotes $OCH_2CHFOCH_3$, and A in each case corresponds to a row of Table B.

Table 513
Compounds of the formula IA wherein $Q^1$ denotes cyano, $Q^3$ denotes $OCH_2CH=CH_2$, and A in each case corresponds to a row of Table B.

Table 514
Compounds of the formula IA wherein $Q^1$ denotes cyano, $Q^3$ denotes $OCH_2CCH$, and A in each case corresponds to a row of Table B.

Table 515
Compounds of the formula IA wherein $Q^1$ denotes cyano, $Q^3$ denotes $CH_2OCH_3$, and A in each case corresponds to a row of Table B.

Table 516
Compounds of the formula IA wherein $Q^1$ denotes cyano, $Q^3$ denotes $CH_2OCH_2CH_3$, and A in each case corresponds to a row of Table B.

Table 517
Compounds of the formula IA wherein $Q^1$ denotes cyano, $Q^3$ denotes $CH_2SCH_3$, and A in each case corresponds to a row of Table B.

Table 518
Compounds of the formula IA wherein $Q^1$ denotes cyano, $Q^3$ denotes $CH_2SCH_2CH_3$, and A in each case corresponds to a row of Table B.

Table 519
Compounds of the formula IA wherein $Q^1$ denotes cyano, $Q^3$ denotes $CH_2S(=O)CH_3$, and A in each case corresponds to a row of Table B.

Table 520
Compounds of the formula IA wherein $Q^1$ denotes cyano, $Q^3$ denotes $CH_2S(=O)CH_2CH_3$, and A in each case corresponds to a row of Table B.

Table 521
Compounds of the formula IA wherein $Q^1$ denotes cyano, $Q^3$ denotes $CH_2S(=O)_2CH_3$, and A in each case corresponds to a row of Table B.

Table 522
Compounds of the formula IA wherein $Q^1$ denotes cyano, $Q^3$ denotes $CH_2S(=O)_2CH_2CH_3$, and A in each case corresponds to a row of Table B.

Table 523
Compounds of the formula IA wherein $Q^1$ denotes cyano, $Q^3$ denotes $-OS(=O)_2CH_3$, and A in each case corresponds to a row of Table B.

Table 524
Compounds of the formula IA wherein $Q^1$ denotes cyano, $Q^3$ notes $-OS(=O)_2CH_2CH_3$, and A in each case corresponds to a row of Table B.

Table 525
Compounds of the formula IA wherein $Q^1$ denotes cyano, $Q^3$ notes $-OS(=O)_2CH_2CF_3$, and A in each case corresponds to a row of Table B.

Table 526
Compounds of the formula IA wherein $Q^1$ denotes cyano, $Q^3$ denotes $-OS(=O)_2CClF_2$, and A in each case corresponds to a row of Table B.

Table 527
Compounds of the formula IA wherein $Q^1$ denotes cyano, $Q^3$ denotes $OC(=O)CF_3$, and A in each case corresponds to a row of Table B.

Table 528
Compounds of the formula IA wherein $Q^1$ denotes cyano, $Q^3$ denotes $NHCH_2CF_3$, and A in each case corresponds to a row of Table B.

Table 529
Compounds of the formula IA wherein $Q^1$ denotes cyano, $Q^3$ denotes $OCH_2$-cyclopropyl, and A in each case corresponds to a row of Table B.

Table 530
Compounds of the formula IA wherein $Q^1$ denotes cyano, $Q^3$ denotes $OCH_2C(Cl)=CH_2$, and A in each case corresponds to a row of Table B.

Table 531
Compounds of the formula IA wherein $Q^1$ denotes cyano, $Q^3$ denotes $OCH_2CH=CF_2$, and A in each case corresponds to a row of Table B.

Table 532
Compounds of the formula IA wherein $Q^1$ denotes cyano, $Q^3$ denotes $NHS(=O)_2CF_3$, and A in each case corresponds to a row of Table B.

Table 533
Compounds of the formula IA wherein $Q^1$ denotes cyano, $Q^3$ denotes $NHC(=O)CF_3$, and A in each case corresponds to a row of Table B.

Table 534
Compounds of the formula IA wherein $Q^1$ denotes cyano, $Q^3$ denotes $OCH_2CN$, and A in each case corresponds to a row of Table B.

Table 535
Compounds of the formula IA wherein $Q^1$ denotes cyano, $Q^3$ denotes $OCH_2NO_2$, and A in each case corresponds to a row of Table B.

Table 536
Compounds of the formula IA wherein $Q^1$ denotes cyano, $Q^3$ denotes cyclopropyloxy, and A in each case corresponds to a row of Table B.

Table 537
Compounds of the formula IA wherein $Q^1$ denotes cyano, $Q^3$ denotes $CH_2OCHF_2$, and A in each case corresponds to a row of Table B.

Table 538
Compounds of the formula IA wherein $Q^1$ denotes cyano, $Q^3$ denotes $CH_2S(=O)_2CHF_2$, and A in each case corresponds to a row of Table B.

Table 539
Compounds of the formula IA wherein $Q^1$ denotes cyano, $Q^3$ denotes $CH=NOCH_3$, and A in each case corresponds to a row of Table B.

Table 540
Compounds of the formula IA wherein $Q^1$ denotes cyano, $Q^3$ denotes $CH=NOCH_2CH_3$, and A in each case corresponds to a row of Table B.

Table 541
Compounds of the formula IA wherein $Q^1$ denotes cyano, $Q^3$ denotes $CH=NOCH(CH_3)_2$ and A in each case corresponds to a row of Table B.

Table 542
Compounds of the formula IA wherein $Q^1$ denotes cyano, $Q^3$ denotes $CH=NOC(CH_3)_3$, and A in each case corresponds to a row of Table B.

Table 543
Compounds of the formula IA wherein $Q^1$ denotes cyano, $Q^3$ denotes $C(CH_3)=NOCH_3$, and A in each case corresponds to a row of Table B.

Table 544
Compounds of the formula IA wherein $Q^1$ denotes cyano, $Q^3$ denotes $C(CH_3)=NOCH_2CH_3$, and A in each case corresponds to a row of Table B.

Table 545
Compounds of the formula IA wherein $Q^1$ denotes cyano, $Q^3$ denotes $C(CH_3)=NOCH(CH_3)_2$, and A in each case corresponds to a row of Table B.

Table 546
Compounds of the formula IA wherein $Q^1$ denotes cyano, $Q^3$ denotes $C(CH_3)=NOC(CH_3)_3$, and A in each case corresponds to a row of Table B.

Table 547
Compounds of the formula IA wherein $Q^1$ denotes methyl, $Q^3$ denotes $CF_3$, and A in each case corresponds to a row of Table B.

Table 548
Compounds of the formula IA wherein $Q^1$ denotes methyl, $Q^3$ denotes bromine, and A in each case corresponds to a row of Table B.

Table 549
Compounds of the formula IA wherein $Q^1$ denotes methyl, $Q^3$ denotes chlorine, and A in each case corresponds to a row of Table B.

Table 550
Compounds of the formula IA wherein $Q^1$ denotes methyl, $Q^3$ denotes $CH_3$, and A in each case corresponds to a row of Table B.

Table 551
Compounds of the formula IA wherein $Q^1$ denotes methyl, $Q^3$ denotes $OCH_3$, and A in each case corresponds to a row of Table B.

Table 552
Compounds of the formula IA wherein $Q^1$ denotes methyl, $Q^3$ denotes $OCHCH_2$, and A in each case corresponds to a row of Table B.

Table 553
Compounds of the formula IA wherein $Q^1$ denotes methyl, $Q^3$ denotes ethoxy, and A in each case corresponds to a row of Table B.

Table 554
Compounds of the formula IA wherein $Q^1$ denotes methyl, $Q^3$ denotes $OCH_2CHFOCH_3$, and A in each case corresponds to a row of Table B.

Table 555
Compounds of the formula IA wherein $Q^1$ denotes methyl, $Q^3$ denotes $OCH_2CH=CH_2$, and A in each case corresponds to a row of Table B.

Table 556
Compounds of the formula IA wherein $Q^1$ denotes methyl, $Q^3$ denotes $OCH_2CCH$, and A in each case corresponds to a row of Table B.

Table 557
Compounds of the formula IA wherein $Q^1$ denotes methyl, $Q^3$ denotes $CH_2OCH_3$, and A in each case corresponds to a row of Table B.

Table 558
Compounds of the formula IA wherein $Q^1$ denotes methyl, $Q^3$ denotes $CH_2OCH_2CH_3$, and A in each case corresponds to a row of Table B.

Table 559
Compounds of the formula IA wherein $Q^1$ denotes methyl, $Q^3$ denotes $CH_2SCH_3$, and A in each case corresponds to a row of Table B.

Table 560
Compounds of the formula IA wherein $Q^1$ denotes methyl, $Q^3$ denotes $CH_2SCH_2CH_3$, and A in each case corresponds to a row of Table B.

Table 561
Compounds of the formula IA wherein $Q^1$ denotes methyl, $Q^3$ denotes $CH_2S(=O)CH_3$, and A in each case corresponds to a row of Table B.

Table 562
Compounds of the formula IA wherein $Q^1$ denotes methyl, $Q^3$ denotes $CH_2S(=O)CH_2CH_3$, and A in each case corresponds to a row of Table B.

Table 563
Compounds of the formula IA wherein $Q^1$ denotes methyl, $Q^3$ denotes $CH_2S(=O)_2CH_3$, and A in each case corresponds to a row of Table B.

Table 564
Compounds of the formula IA wherein $Q^1$ denotes methyl, $Q^3$ denotes $CH_2S(=O)_2CH_2CH_3$, and A in each case corresponds to a row of Table B.

Table 565
Compounds of the formula IA wherein $Q^1$ denotes methyl, $Q^3$ denotes $-OS(=O)_2CH_3$, and A in each case corresponds to a row of Table B.

Table 566
Compounds of the formula IA wherein $Q^1$ denotes methyl, $Q^3$ notes $-OS(=O)_2CH_2CH_3$, and A in each case corresponds to a row of Table B.

Table 567
Compounds of the formula IA wherein $Q^1$ denotes methyl, $Q^3$ notes $-OS(=O)_2CH_2CF_3$, and A in each case corresponds to a row of Table B.

Table 568
Compounds of the formula IA wherein $Q^1$ denotes methyl, $Q^3$ denotes $-OS(=O)_2CClF_2$, and A in each case corresponds to a row of Table B.

Table 569
Compounds of the formula IA wherein $Q^1$ denotes methyl, $Q^3$ denotes $OC(=O)CF_3$, and A in each case corresponds to a row of Table B.

Table 570
Compounds of the formula IA wherein $Q^1$ denotes methyl, $Q^3$ denotes $NHCH_2CF_3$, and A in each case corresponds to a row of Table B.

Table 571
Compounds of the formula IA wherein $Q^1$ denotes methyl, $Q^3$ denotes $OCH_2$-cyclopropyl, and A in each case corresponds to a row of Table B.

Table 572
Compounds of the formula IA wherein $Q^1$ denotes methyl, $Q^3$ denotes $OCH_2C(Cl)=CH_2$, and A in each case corresponds to a row of Table B.

Table 573
Compounds of the formula IA wherein $Q^1$ denotes methyl, $Q^3$ denotes $OCH_2CH=CF_2$, and A in each case corresponds to a row of Table B.

Table 574
Compounds of the formula IA wherein $Q^1$ denotes methyl, $Q^3$ denotes $NHS(=O)_2CF_3$, and A in each case corresponds to a row of Table B.

Table 575
Compounds of the formula IA wherein $Q^1$ denotes methyl, $Q^3$ denotes $NHC(=O)CF_3$, and A in each case corresponds to a row of Table B.

Table 576
Compounds of the formula IA wherein $Q^1$ denotes methyl, $Q^3$ denotes $OCH_2CN$, and A in each case corresponds to a row of Table B.

Table 577
Compounds of the formula IA wherein $Q^1$ denotes methyl, $Q^3$ denotes $OCH_2NO_2$, and A in each case corresponds to a row of Table B.

Table 578
Compounds of the formula IA wherein $Q^1$ denotes methyl, $Q^3$ denotes cyclopropyloxy, and A in each case corresponds to a row of Table B.

Table 579
Compounds of the formula IA wherein $Q^1$ denotes methyl, $Q^3$ denotes $CH_2OCHF_2$, and A in each case corresponds to a row of Table B.

Table 580
Compounds of the formula IA wherein $Q^1$ denotes methyl, $Q^3$ denotes $CH_2S(=O)_2CHF_2$, and A in each case corresponds to a row of Table B.

Table 581
Compounds of the formula IA wherein $Q^1$ denotes methyl, $Q^3$ denotes $CH=NOCH_3$, and A in each case corresponds to a row of Table B.

Table 582
Compounds of the formula IA wherein $Q^1$ denotes methyl, $Q^3$ denotes $CH=NOCH_2CH_3$, and A in each case corresponds to a row of Table B.

Table 583
Compounds of the formula IA wherein $Q^1$ denotes methyl, $Q^3$ denotes $CH=NOCH(CH_3)_2$ and A in each case corresponds to a row of Table B.

Table 584
Compounds of the formula IA wherein $Q^1$ denotes methyl, $Q^3$ denotes $CH=NOC(CH_3)_3$, and A in each case corresponds to a row of Table B.

Table 585
Compounds of the formula IA wherein $Q^1$ denotes methyl, $Q^3$ denotes $C(CH_3)=NOCH_3$, and A in each case corresponds to a row of Table B.

Table 586
Compounds of the formula IA wherein $Q^1$ denotes methyl, $Q^3$ denotes $C(CH_3)=NOCH_2CH_3$, and A in each case corresponds to a row of Table B.

Table 587
Compounds of the formula IA wherein $Q^1$ denotes methyl, $Q^3$ denotes $C(CH_3)=NOCH(CH_3)_2$, and A in each case corresponds to a row of Table B.

Table 588
Compounds of the formula IA wherein $Q^1$ denotes methyl, $Q^3$ denotes $C(CH_3)=NOC(CH_3)_3$, and A in each case corresponds to a row of Table B.

TABLE B

| No. | A | $R^{a\#}$ | $R^d$ |
|---|---|---|---|
| IA-136 |  | H | * N (piperidine) |
| | $A^2.2$ | | |

TABLE B-continued

| No. | A | R$^{a\#}$ | R$^d$ |
|---|---|---|---|
| IA-137 | A$^2$.2 | CH$_3$ | morpholinyl* |
| IA-138 | A$^2$.2 | CH(CH$_3$)$_2$ | tetrahydropyridinyl* |

*denotes the binding site.

Table 589
Compounds of the formula IA (as defined above) wherein Q$^1$ denotes hydrogen, Q$^3$ denotes CF$_3$, and A in each case corresponds to a row of Table C.

Table 590
Compounds of the formula IA wherein Q$^1$ denotes hydrogen, Q$^3$ denotes bromine, and A in each case corresponds to a row of Table C.

Table 591
Compounds of the formula IA wherein Q$^1$ denotes hydrogen, Q$^3$ denotes chlorine, and A in each case corresponds to a row of Table C.

Table 592
Compounds of the formula IA wherein Q$^1$ denotes hydrogen, Q$^3$ denotes CH$_3$, and A in each case corresponds to a row of Table C.

Table 593
Compounds of the formula IA wherein Q$^1$ denotes hydrogen, Q$^3$ denotes OCH$_3$, and A in each case corresponds to a row of Table C.

Table 594
Compounds of the formula IA wherein Q$^1$ denotes hydrogen, Q$^3$ denotes OCHCH$_2$, and A in each case corresponds to a row of Table C.

Table 595
Compounds of the formula IA wherein Q$^1$ denotes hydrogen, Q$^3$ denotes ethoxy, and A in each case corresponds to a row of Table C.

Table 596
Compounds of the formula IA wherein Q$^1$ denotes hydrogen, Q$^3$ denotes OCH$_2$CHFOCH$_3$, and A in each case corresponds to a row of Table C.

Table 597
Compounds of the formula IA wherein Q$^1$ denotes hydrogen, Q$^3$ denotes OCH$_2$CH=CH$_2$, and A in each case corresponds to a row of Table C.

Table 598
Compounds of the formula IA wherein Q$^1$ denotes hydrogen, Q$^3$ denotes OCH$_2$CCH, and A in each case corresponds to a row of Table C.

Table 599
Compounds of the formula IA wherein Q$^1$ denotes hydrogen, Q$^3$ denotes CH$_2$OCH$_3$, and A in each case corresponds to a row of Table C.

Table 600
Compounds of the formula IA wherein Q$^1$ denotes hydrogen, Q$^3$ denotes CH$_2$OCH$_2$CH$_3$, and A in each case corresponds to a row of Table C.

Table 601
Compounds of the formula IA wherein Q$^1$ denotes hydrogen, Q$^3$ denotes CH$_2$SCH$_3$, and A in each case corresponds to a row of Table C.

Table 602
Compounds of the formula IA wherein Q$^1$ denotes hydrogen, Q$^3$ denotes CH$_2$SCH$_2$CH$_3$, and A in each case corresponds to a row of Table C.

Table 603
Compounds of the formula IA wherein Q$^1$ denotes hydrogen, Q$^3$ denotes CH$_2$S(=O)CH$_3$, and A in each case corresponds to a row of Table C.

Table 604
Compounds of the formula IA wherein Q$^1$ denotes hydrogen, Q$^3$ denotes CH$_2$S(=O)CH$_2$CH$_3$, and A in each case corresponds to a row of Table C.

Table 605
Compounds of the formula IA wherein Q$^1$ denotes hydrogen, Q$^3$ denotes CH$_2$S(=O)$_2$CH$_3$, and A in each case corresponds to a row of Table C.

Table 606
Compounds of the formula IA wherein Q$^1$ denotes hydrogen, Q$^3$ denotes CH$_2$S(=O)$_2$CH$_2$CH$_3$, and A in each case corresponds to a row of Table C.

Table 607
Compounds of the formula IA wherein Q$^1$ denotes hydrogen, Q$^3$ denotes —OS(=O)$_2$CH$_3$, and A in each case corresponds to a row of Table C.

Table 608
Compounds of the formula IA wherein Q$^1$ denotes hydrogen, Q$^3$ notes —OS(=O)$_2$CH$_2$CH$_3$, and A in each case corresponds to a row of Table C.

Table 609
Compounds of the formula IA wherein Q$^1$ denotes hydrogen, Q$^3$ notes —OS(=O)$_2$CH$_2$CF$_3$, and A in each case corresponds to a row of Table C.

Table 610
Compounds of the formula IA wherein Q$^1$ denotes hydrogen, Q$^3$ notes —OS(=O)$_2$CClF$_2$, and A in each case corresponds to a row of Table C.

Table 611
Compounds of the formula IA wherein Q$^1$ denotes hydrogen, Q$^3$ denotes OC(=O)CF$_3$, and A in each case corresponds to a row of Table C.

Table 612
Compounds of the formula IA wherein Q$^1$ denotes hydrogen, Q$^3$ denotes NHCH$_2$CF$_3$, and A in each case corresponds to a row of Table C.

Table 613
Compounds of the formula IA wherein Q$^1$ denotes hydrogen, Q$^3$ denotes OCH$_2$-cyclopropyl, and A in each case corresponds to a row of Table C.

Table 614
Compounds of the formula IA wherein Q$^1$ denotes hydrogen, Q$^3$ denotes OCH$_2$C(Cl)=CH$_2$, and A in each case corresponds to a row of Table C.

Table 615
Compounds of the formula IA wherein Q$^1$ denotes hydrogen, Q$^3$ denotes OCH$_2$CH=CF$_2$, and A in each case corresponds to a row of Table C.

Table 616
Compounds of the formula IA wherein Q$^1$ denotes hydrogen, Q$^3$ denotes NHS(=O)$_2$CF$_3$, and A in each case corresponds to a row of Table C.

Table 617
Compounds of the formula IA wherein Q$^1$ denotes hydrogen, Q$^3$ denotes NHC(=O)CF$_3$, and A in each case corresponds to a row of Table C.

Table 618
Compounds of the formula IA wherein $Q^1$ denotes hydrogen, $Q^3$ denotes $OCH_2CN$, and A in each case corresponds to a row of Table C.

Table 619
Compounds of the formula IA wherein $Q^1$ denotes hydrogen, $Q^3$ denotes $OCH_2NO_2$, and A in each case corresponds to a row of Table C.

Table 620
Compounds of the formula IA wherein $Q^1$ denotes hydrogen, $Q^3$ denotes cyclopropyloxy, and A in each case corresponds to a row of Table C.

Table 621
Compounds of the formula IA wherein $Q^1$ denotes hydrogen, $Q^3$ denotes $CH_2OCHF_2$, and A in each case corresponds to a row of Table C.

Table 622
Compounds of the formula IA wherein $Q^1$ denotes hydrogen, $Q^3$ denotes $CH_2S(=O)_2CHF_2$, and A in each case corresponds to a row of Table C.

Table 623
Compounds of the formula IA wherein $Q^1$ denotes hydrogen, $Q^3$ denotes $CH=NOCH_3$, and A in each case corresponds to a row of Table C.

Table 624
Compounds of the formula IA wherein $Q^1$ denotes hydrogen, $Q^3$ denotes $CH=NOCH_2CH_3$, and A in each case corresponds to a row of Table C.

Table 625
Compounds of the formula IA wherein $Q^1$ denotes hydrogen, $Q^3$ denotes $CH=NOCH(CH_3)_2$ and A in each case corresponds to a row of Table C.

Table 626
Compounds of the formula IA wherein $Q^1$ denotes hydrogen, $Q^3$ denotes $CH=NOC(CH_3)_3$, and A in each case corresponds to a row of Table C.

Table 627
Compounds of the formula IA wherein $Q^1$ denotes hydrogen, $Q^3$ denotes $C(CH_3)=NOCH_3$, and A in each case corresponds to a row of Table C.

Table 628
Compounds of the formula IA wherein $Q^1$ denotes hydrogen, $Q^3$ denotes $C(CH_3)=NOCH_2CH_3$, and A in each case corresponds to a row of Table C.

Table 629
Compounds of the formula IA wherein $Q^1$ denotes hydrogen, $Q^3$ denotes $C(CH_3)=NOCH(CH_3)_2$, and A in each case corresponds to a row of Table C.

Table 630
Compounds of the formula IA wherein $Q^1$ denotes hydrogen, $Q^3$ denotes $C(CH_3)=NOC(CH_3)_3$, and A in each case corresponds to a row of Table C.

Table 631
Compounds of the formula IA wherein $Q^1$ denotes chlorine, $Q^3$ denotes $CF_3$, and A in each case corresponds to a row of Table C.

Table 632
Compounds of the formula IA wherein $Q^1$ denotes chlorine, $Q^3$ denotes bromine, and A in each case corresponds to a row of Table C.

Table 633
Compounds of the formula IA wherein $Q^1$ denotes chlorine, $Q^3$ denotes chlorine, and A in each case corresponds to a row of Table C.

Table 634
Compounds of the formula IA wherein $Q^1$ denotes chlorine, $Q^3$ denotes $CH_3$, and A in each case corresponds to a row of Table C.

Table 635
Compounds of the formula IA wherein $Q^1$ denotes chlorine, $Q^3$ denotes $OCH_3$, and A in each case corresponds to a row of Table C.

Table 636
Compounds of the formula IA wherein $Q^1$ denotes chlorine, $Q^3$ denotes $OCHCH_2$, and A in each case corresponds to a row of Table C.

Table 637
Compounds of the formula IA wherein $Q^1$ denotes chlorine, $Q^3$ denotes ethoxy, and A in each case corresponds to a row of Table C.

Table 638
Compounds of the formula IA wherein $Q^1$ denotes chlorine, $Q^3$ denotes $OCH_2CHFOCH_3$, and A in each case corresponds to a row of Table C.

Table 639
Compounds of the formula IA wherein $Q^1$ denotes chlorine, $Q^3$ denotes $OCH_2CH=CH_2$, and A in each case corresponds to a row of Table C.

Table 640
Compounds of the formula IA wherein $Q^1$ denotes chlorine, $Q^3$ denotes $OCH_2CCH$, and A in each case corresponds to a row of Table C.

Table 641
Compounds of the formula IA wherein $Q^1$ denotes chlorine, $Q^3$ denotes $CH_2OCH_3$, and A in each case corresponds to a row of Table C.

Table 642
Compounds of the formula IA wherein $Q^1$ denotes chlorine, $Q^3$ denotes $CH_2OCH_2CH_3$, and A in each case corresponds to a row of Table C.

Table 643
Compounds of the formula IA wherein $Q^1$ denotes chlorine, $Q^3$ denotes $CH_2SCH_3$, and A in each case corresponds to a row of Table C.

Table 644
Compounds of the formula IA wherein $Q^1$ denotes chlorine, $Q^3$ denotes $CH_2SCH_2CH_3$, and A in each case corresponds to a row of Table C.

Table 645
Compounds of the formula IA wherein $Q^1$ denotes chlorine, $Q^3$ denotes $CH_2S(=O)CH_3$, and A in each case corresponds to a row of Table C.

Table 646
Compounds of the formula IA wherein $Q^1$ denotes chlorine, $Q^3$ denotes $CH_2S(=O)CH_2CH_3$, and A in each case corresponds to a row of Table C.

Table 647
Compounds of the formula IA wherein $Q^1$ denotes chlorine, $Q^3$ denotes $CH_2S(=O)_2CH_3$, and A in each case corresponds to a row of Table C.

Table 648
Compounds of the formula IA wherein $Q^1$ denotes chlorine, $Q^3$ denotes $CH_2S(=O)_2CH_2CH_3$, and A in each case corresponds to a row of Table C.

Table 649
Compounds of the formula IA wherein $Q^1$ denotes chlorine, $Q^3$ denotes $—OS(=O)_2CH_3$, and A in each case corresponds to a row of Table C.

Table 650
Compounds of the formula IA wherein $Q^1$ denotes chlorine, $Q^3$ notes $—OS(=O)_2CH_2CH_3$, and A in each case corresponds to a row of Table C.

Table 651
Compounds of the formula IA wherein $Q^1$ denotes chlorine, $Q^3$ notes —OS(=O)$_2$CH$_2$CF$_3$, and A in each case corresponds to a row of Table C.

Table 652
Compounds of the formula IA wherein $Q^1$ denotes chlorine, $Q^3$ notes —OS(=O)$_2$CClF$_2$, and A in each case corresponds to a row of Table C.

Table 653
Compounds of the formula IA wherein $Q^1$ denotes chlorine, $Q^3$ denotes OC(=O)CF$_3$, and A in each case corresponds to a row of Table C.

Table 654
Compounds of the formula IA wherein $Q^1$ denotes chlorine, $Q^3$ denotes NHCH$_2$CF$_3$, and A in each case corresponds to a row of Table C.

Table 655
Compounds of the formula IA wherein $Q^1$ denotes chlorine, $Q^3$ denotes OCH$_2$-cyclopropyl, and A in each case corresponds to a row of Table C.

Table 656
Compounds of the formula IA wherein $Q^1$ denotes chlorine, $Q^3$ denotes OCH$_2$C(Cl)=CH$_2$, and A in each case corresponds to a row of Table C.

Table 657
Compounds of the formula IA wherein $Q^1$ denotes chlorine, $Q^3$ denotes OCH$_2$CH=CF$_2$, and A in each case corresponds to a row of Table C.

Table 658
Compounds of the formula IA wherein $Q^1$ denotes chlorine, $Q^3$ denotes NHS(=O)$_2$CF$_3$, and A in each case corresponds to a row of Table C.

Table 659
Compounds of the formula IA wherein $Q^1$ denotes chlorine, $Q^3$ denotes NHC(=O)CF$_3$, and A in each case corresponds to a row of Table C.

Table 660
Compounds of the formula IA wherein $Q^1$ denotes chlorine, $Q^3$ denotes OCH$_2$CN, and A in each case corresponds to a row of Table C.

Table 661
Compounds of the formula IA wherein $Q^1$ denotes chlorine, $Q^3$ denotes OCH$_2$NO$_2$, and A in each case corresponds to a row of Table C.

Table 662
Compounds of the formula IA wherein $Q^1$ denotes chlorine, $Q^3$ denotes cyclopropyloxy, and A in each case corresponds to a row of Table C.

Table 663
Compounds of the formula IA wherein $Q^1$ denotes chlorine, $Q^3$ denotes CH$_2$OCHF$_2$, and A in each case corresponds to a row of Table C.

Table 664
Compounds of the formula IA wherein $Q^1$ denotes chlorine, $Q^3$ denotes CH$_2$S(=O)$_2$CHF$_2$, and A in each case corresponds to a row of Table C.

Table 665
Compounds of the formula IA wherein $Q^1$ denotes chlorine, $Q^3$ denotes CH=NOCH$_3$, and A in each case corresponds to a row of Table C.

Table 666
Compounds of the formula IA wherein $Q^1$ denotes chlorine, $Q^3$ denotes CH=NOCH$_2$CH$_3$, and A in each case corresponds to a row of Table C.

Table 667
Compounds of the formula IA wherein $Q^1$ denotes chlorine, $Q^3$ denotes CH=NOCH(CH$_3$)$_2$ and A in each case corresponds to a row of Table C.

Table 668
Compounds of the formula IA wherein $Q^1$ denotes chlorine, $Q^3$ denotes CH=NOC(CH$_3$)$_3$, and A in each case corresponds to a row of Table C.

Table 669
Compounds of the formula IA wherein $Q^1$ denotes chlorine, $Q^3$ denotes C(CH$_3$)=NOCH$_3$, and A in each case corresponds to a row of Table C.

Table 670
Compounds of the formula IA wherein $Q^1$ denotes chlorine, $Q^3$ denotes C(CH$_3$)=NOCH$_2$CH$_3$, and A in each case corresponds to a row of Table C.

Table 671
Compounds of the formula IA wherein $Q^1$ denotes chlorine, $Q^3$ denotes C(CH$_3$)=NOCH(CH$_3$)$_2$, and A in each case corresponds to a row of Table C.

Table 672
Compounds of the formula IA wherein $Q^1$ denotes chlorine, $Q^3$ denotes C(CH$_3$)=NOC(CH$_3$)$_3$, and A in each case corresponds to a row of Table C.

Table 673
Compounds of the formula IA wherein $Q^1$ denotes bromine, $Q^3$ denotes CF$_3$, and A in each case corresponds to a row of Table C.

Table 674
Compounds of the formula IA wherein $Q^1$ denotes bromine, $Q^3$ denotes bromine, and A in each case corresponds to a row of Table C.

Table 675
Compounds of the formula IA wherein $Q^1$ denotes bromine, $Q^3$ denotes chlorine, and A in each case corresponds to a row of Table C.

Table 676
Compounds of the formula IA wherein $Q^1$ denotes bromine, $Q^3$ denotes CH$_3$, and A in each case corresponds to a row of Table C.

Table 677
Compounds of the formula IA wherein $Q^1$ denotes bromine, $Q^3$ denotes OCH$_3$, and A in each case corresponds to a row of Table C.

Table 678
Compounds of the formula IA wherein $Q^1$ denotes bromine, $Q^3$ denotes OCHCH$_2$, and A in each case corresponds to a row of Table C.

Table 679
Compounds of the formula IA wherein $Q^1$ denotes bromine, $Q^3$ denotes ethoxy, and A in each case corresponds to a row of Table C.

Table 680
Compounds of the formula IA wherein $Q^1$ denotes bromine, $Q^3$ denotes OCH$_2$CHFOCH$_3$, and A in each case corresponds to a row of Table C.

Table 681
Compounds of the formula IA wherein $Q^1$ denotes bromine, $Q^3$ denotes OCH$_2$CH=CH$_2$, and A in each case corresponds to a row of Table C.

Table 682
Compounds of the formula IA wherein $Q^1$ denotes bromine, $Q^3$ denotes OCH$_2$CCH, and A in each case corresponds to a row of Table C.

Table 683
Compounds of the formula IA wherein $Q^1$ denotes bromine, $Q^3$ denotes CH$_2$OCH$_3$, and A in each case corresponds to a row of Table C.

Table 684
Compounds of the formula IA wherein $Q^1$ denotes bromine, $Q^3$ denotes $CH_2OCH_2CH_3$, and A in each case corresponds to a row of Table C.

Table 685
Compounds of the formula IA wherein $Q^1$ denotes bromine, $Q^3$ denotes $CH_2SCH_3$, and A in each case corresponds to a row of Table C.

Table 686
Compounds of the formula IA wherein $Q^1$ denotes bromine, $Q^3$ denotes $CH_2SCH_2CH_3$, and A in each case corresponds to a row of Table C.

Table 687
Compounds of the formula IA wherein $Q^1$ denotes bromine, $Q^3$ denotes $CH_2S(=O)CH_3$, and A in each case corresponds to a row of Table C.

Table 688
Compounds of the formula IA wherein $Q^1$ denotes bromine, $Q^3$ denotes $CH_2S(=O)CH_2CH_3$, and A in each case corresponds to a row of Table C.

Table 689
Compounds of the formula IA wherein $Q^1$ denotes bromine, $Q^3$ denotes $CH_2S(=O)_2CH_3$, and A in each case corresponds to a row of Table C.

Table 690
Compounds of the formula IA wherein $Q^1$ denotes bromine, $Q^3$ denotes $CH_2S(=O)_2CH_2CH_3$, and A in each case corresponds to a row of Table C.

Table 691
Compounds of the formula IA wherein $Q^1$ denotes bromine, $Q^3$ denotes $—OS(=O)_2CH_3$, and A in each case corresponds to a row of Table C.

Table 692
Compounds of the formula IA wherein $Q^1$ denotes bromine, $Q^3$ notes $—OS(=O)_2CH_2CH_3$, and A in each case corresponds to a row of Table C.

Table 693
Compounds of the formula IA wherein $Q^1$ denotes bromine, $Q^3$ notes $—OS(=O)_2CH_2CF_3$, and A in each case corresponds to a row of Table C.

Table 694
Compounds of the formula IA wherein $Q^1$ denotes bromine, $Q^3$ notes $—OS(=O)_2CClF_2$, and A in each case corresponds to a row of Table C.

Table 695
Compounds of the formula IA wherein $Q^1$ denotes bromine, $Q^3$ denotes $OC(=O)CF_3$, and A in each case corresponds to a row of Table C.

Table 696
Compounds of the formula IA wherein $Q^1$ denotes bromine, $Q^3$ denotes $NHCH_2CF_3$, and A in each case corresponds to a row of Table C.

Table 697
Compounds of the formula IA wherein $Q^1$ denotes bromine, $Q^3$ denotes $OCH_2$-cyclopropyl, and A in each case corresponds to a row of Table C.

Table 698
Compounds of the formula IA wherein $Q^1$ denotes bromine, $Q^3$ denotes $OCH_2C(Cl)=CH_2$, and A in each case corresponds to a row of Table C.

Table 699
Compounds of the formula IA wherein $Q^1$ denotes bromine, $Q^3$ denotes $OCH_2CH=CF_2$, and A in each case corresponds to a row of Table C.

Table 700
Compounds of the formula IA wherein $Q^1$ denotes bromine, $Q^3$ denotes $NHS(=O)_2CF_3$, and A in each case corresponds to a row of Table C.

Table 701
Compounds of the formula IA wherein $Q^1$ denotes bromine, $Q^3$ denotes $NHC(=O)CF_3$, and A in each case corresponds to a row of Table C.

Table 702
Compounds of the formula IA wherein $Q^1$ denotes bromine, $Q^3$ denotes $OCH_2CN$, and A in each case corresponds to a row of Table C.

Table 703
Compounds of the formula IA wherein $Q^1$ denotes bromine, $Q^3$ denotes $OCH_2NO_2$, and A in each case corresponds to a row of Table C.

Table 704
Compounds of the formula IA wherein $Q^1$ denotes bromine, $Q^3$ denotes cyclopropyloxy, and A in each case corresponds to a row of Table C.

Table 705
Compounds of the formula IA wherein $Q^1$ denotes bromine, $Q^3$ denotes $CH_2OCHF_2$, and A in each case corresponds to a row of Table C.

Table 706
Compounds of the formula IA wherein $Q^1$ denotes bromine, $Q^3$ denotes $CH_2S(=O)_2CHF_2$, and A in each case corresponds to a row of Table C.

Table 707
Compounds of the formula IA wherein $Q^1$ denotes bromine, $Q^3$ denotes $CH=NOCH_3$, and A in each case corresponds to a row of Table C.

Table 708
Compounds of the formula IA wherein $Q^1$ denotes bromine, $Q^3$ denotes $CH=NOCH_2CH_3$, and A in each case corresponds to a row of Table C.

Table 709
Compounds of the formula IA wherein $Q^1$ denotes bromine, $Q^3$ denotes $CH=NOCH(CH_3)_2$ and A in each case corresponds to a row of Table C.

Table 710
Compounds of the formula IA wherein $Q^1$ denotes bromine, $Q^3$ denotes $CH=NOC(CH_3)_3$, and A in each case corresponds to a row of Table C.

Table 711
Compounds of the formula IA wherein $Q^1$ denotes bromine, $Q^3$ denotes $C(CH_3)=NOCH_3$, and A in each case corresponds to a row of Table C.

Table 712
Compounds of the formula IA wherein $Q^1$ denotes bromine, $Q^3$ denotes $C(CH_3)=NOCH_2CH_3$, and A in each case corresponds to a row of Table C.

Table 713
Compounds of the formula IA wherein $Q^1$ denotes bromine, $Q^3$ denotes $C(CH_3)=NOCH(CH_3)_2$, and A in each case corresponds to a row of Table C.

Table 714
Compounds of the formula IA wherein $Q^1$ denotes bromine, $Q^3$ denotes $C(CH_3)=NOC(CH_3)_3$, and A in each case corresponds to a row of Table C.

Table 715
Compounds of the formula IA wherein $Q^1$ denotes fluorine, $Q^3$ denotes $CF_3$, and A in each case corresponds to a row of Table C.

Table 716
Compounds of the formula IA wherein $Q^1$ denotes fluorine, $Q^3$ denotes bromine, and A in each case corresponds to a row of Table C.

Table 717

Compounds of the formula IA wherein $Q^1$ denotes fluorine, $Q^3$ denotes chlorine, and A in each case corresponds to a row of Table C.

Table 718

Compounds of the formula IA wherein $Q^1$ denotes fluorine, $Q^3$ denotes $CH_3$, and A in each case corresponds to a row of Table C.

Table 719

Compounds of the formula IA wherein $Q^1$ denotes fluorine, $Q^3$ denotes $OCH_3$, and A in each case corresponds to a row of Table C.

Table 720

Compounds of the formula IA wherein $Q^1$ denotes fluorine, $Q^3$ denotes $OCHCH_2$, and A in each case corresponds to a row of Table C.

Table 721

Compounds of the formula IA wherein $Q^1$ denotes fluorine, $Q^3$ denotes ethoxy, and A in each case corresponds to a row of Table C.

Table 722

Compounds of the formula IA wherein $Q^1$ denotes fluorine, $Q^3$ denotes $OCH_2CHFOCH_3$, and A in each case corresponds to a row of Table C.

Table 723

Compounds of the formula IA wherein $Q^1$ denotes fluorine, $Q^3$ denotes $OCH_2CH=CH_2$, and A in each case corresponds to a row of Table C.

Table 724

Compounds of the formula IA wherein $Q^1$ denotes fluorine, $Q^3$ denotes $OCH_2CCH$, and A in each case corresponds to a row of Table C.

Table 725

Compounds of the formula IA wherein $Q^1$ denotes fluorine, $Q^3$ denotes $CH_2OCH_3$, and A in each case corresponds to a row of Table C.

Table 726

Compounds of the formula IA wherein $Q^1$ denotes fluorine, $Q^3$ denotes $CH_2OCH_2CH_3$, and A in each case corresponds to a row of Table C.

Table 727

Compounds of the formula IA wherein $Q^1$ denotes fluorine, $Q^3$ denotes $CH_2SCH_3$, and A in each case corresponds to a row of Table C.

Table 728

Compounds of the formula IA wherein $Q^1$ denotes fluorine, $Q^3$ denotes $CH_2SCH_2CH_3$, and A in each case corresponds to a row of Table C.

Table 729

Compounds of the formula IA wherein $Q^1$ denotes fluorine, $Q^3$ denotes $CH_2S(=O)CH_3$, and A in each case corresponds to a row of Table C.

Table 730

Compounds of the formula IA wherein $Q^1$ denotes fluorine, $Q^3$ denotes $CH_2S(=O)CH_2CH_3$, and A in each case corresponds to a row of Table C.

Table 731

Compounds of the formula IA wherein $Q^1$ denotes fluorine, $Q^3$ denotes $CH_2S(=O)_2CH_3$, and A in each case corresponds to a row of Table C.

Table 732

Compounds of the formula IA wherein $Q^1$ denotes fluorine, $Q^3$ denotes $CH_2S(=O)_2CH_2CH_3$, and A in each case corresponds to a row of Table C.

Table 733

Compounds of the formula IA wherein $Q^1$ denotes fluorine, $Q^3$ denotes $—OS(=O)_2CH_3$, and A in each case corresponds to a row of Table C.

Table 734

Compounds of the formula IA wherein $Q^1$ denotes fluorine, $Q^3$ notes $—OS(=O)_2CH_2CH_3$, and A in each case corresponds to a row of Table C.

Table 735

Compounds of the formula IA wherein $Q^1$ denotes fluorine, $Q^3$ notes $—OS(=O)_2CH_2CF_3$, and A in each case corresponds to a row of Table C.

Table 736

Compounds of the formula IA wherein $Q^1$ denotes fluorine, $Q^3$ denotes $—OS(=O)_2CClF_2$, and A in each case corresponds to a row of Table C.

Table 737

Compounds of the formula IA wherein $Q^1$ denotes fluorine, $Q^3$ denotes $OC(=O)CF_3$, and A in each case corresponds to a row of Table C.

Table 738

Compounds of the formula IA wherein $Q^1$ denotes fluorine, $Q^3$ denotes $NHCH_2CF_3$, and A in each case corresponds to a row of Table C.

Table 739

Compounds of the formula IA wherein $Q^1$ denotes fluorine, $Q^3$ denotes $OCH_2$-cyclopropyl, and A in each case corresponds to a row of Table C.

Table 740

Compounds of the formula IA wherein $Q^1$ denotes fluorine, $Q^3$ denotes $OCH_2C(Cl)=CH_2$, and A in each case corresponds to a row of Table C.

Table 741

Compounds of the formula IA wherein $Q^1$ denotes fluorine, $Q^3$ denotes $OCH_2CH=CF_2$, and A in each case corresponds to a row of Table C.

Table 742

Compounds of the formula IA wherein $Q^1$ denotes fluorine, $Q^3$ denotes $NHS(=O)_2CF_3$, and A in each case corresponds to a row of Table C.

Table 743

Compounds of the formula IA wherein $Q^1$ denotes fluorine, $Q^3$ denotes $NHC(=O)CF_3$, and A in each case corresponds to a row of Table C.

Table 744

Compounds of the formula IA wherein $Q^1$ denotes fluorine, $Q^3$ denotes $OCH_2CN$, and A in each case corresponds to a row of Table C.

Table 745

Compounds of the formula IA wherein $Q^1$ denotes fluorine, $Q^3$ denotes $OCH_2NO_2$, and A in each case corresponds to a row of Table C.

Table 746

Compounds of the formula IA wherein $Q^1$ denotes fluorine, $Q^3$ denotes cyclopropyloxy, and A in each case corresponds to a row of Table C.

Table 747

Compounds of the formula IA wherein $Q^1$ denotes fluorine, $Q^3$ denotes $CH_2OCHF_2$, and A in each case corresponds to a row of Table C.

Table 748

Compounds of the formula IA wherein $Q^1$ denotes fluorine, $Q^3$ denotes $CH_2S(=O)_2CHF_2$, and A in each case corresponds to a row of Table C.

Table 749

Compounds of the formula IA wherein $Q^1$ denotes fluorine, $Q^3$ denotes $CH=NOCH_3$, and A in each case corresponds to a row of Table C.

Table 750
Compounds of the formula IA wherein $Q^1$ denotes fluorine, $Q^3$ denotes CH=NOCH$_2$CH$_3$, and A in each case corresponds to a row of Table C.

Table 751
Compounds of the formula IA wherein $Q^1$ denotes fluorine, $Q^3$ denotes CH=NOCH(CH$_3$)$_2$ and A in each case corresponds to a row of Table C.

Table 752
Compounds of the formula IA wherein $Q^1$ denotes fluorine, $Q^3$ denotes CH=NOC(CH$_3$)$_3$, and A in each case corresponds to a row of Table C.

Table 753
Compounds of the formula IA wherein $Q^1$ denotes fluorine, $Q^3$ denotes C(CH$_3$)=NOCH$_3$, and A in each case corresponds to a row of Table C.

Table 754
Compounds of the formula IA wherein $Q^1$ denotes fluorine, $Q^3$ denotes C(CH$_3$)=NOCH$_2$CH$_3$, and A in each case corresponds to a row of Table C.

Table 755
Compounds of the formula IA wherein $Q^1$ denotes fluorine, $Q^3$ denotes C(CH$_3$)=NOCH(CH$_3$)$_2$, and A in each case corresponds to a row of Table C.

Table 756
Compounds of the formula IA wherein $Q^1$ denotes fluorine, $Q^3$ denotes C(CH$_3$)=NOC(CH$_3$)$_3$, and A in each case corresponds to a row of Table C.

Table 757
Compounds of the formula IA wherein $Q^1$ denotes iodine, $Q^3$ denotes CF$_3$, and A in each case corresponds to a row of Table C.

Table 758
Compounds of the formula IA wherein $Q^1$ denotes iodine, $Q^3$ denotes bromine, and A in each case corresponds to a row of Table C.

Table 759
Compounds of the formula IA wherein $Q^1$ denotes iodine, $Q^3$ denotes chlorine, and A in each case corresponds to a row of Table C.

Table 760
Compounds of the formula IA wherein $Q^1$ denotes iodine, $Q^3$ denotes CH$_3$, and A in each case corresponds to a row of Table C.

Table 761
Compounds of the formula IA wherein $Q^1$ denotes iodine, $Q^3$ denotes OCH$_3$, and A in each case corresponds to a row of Table C.

Table 762
Compounds of the formula IA wherein $Q^1$ denotes iodine, $Q^3$ denotes OCHCH$_2$, and A in each case corresponds to a row of Table C.

Table 763
Compounds of the formula IA wherein $Q^1$ denotes iodine, $Q^3$ denotes ethoxy, and A in each case corresponds to a row of Table C.

Table 764
Compounds of the formula IA wherein $Q^1$ denotes iodine, $Q^3$ denotes OCH$_2$CHFOCH$_3$, and A in each case corresponds to a row of Table C.

Table 765
Compounds of the formula IA wherein $Q^1$ denotes iodine, $Q^3$ denotes OCH$_2$CH=CH$_2$, and A in each case corresponds to a row of Table C.

Table 766
Compounds of the formula IA wherein $Q^1$ denotes iodine, $Q^3$ denotes OCH$_2$CCH, and A in each case corresponds to a row of Table C.

Table 767
Compounds of the formula IA wherein $Q^1$ denotes iodine, $Q^3$ denotes CH$_2$OCH$_3$, and A in each case corresponds to a row of Table C.

Table 768
Compounds of the formula IA wherein $Q^1$ denotes iodine, $Q^3$ denotes CH$_2$OCH$_2$CH$_3$, and A in each case corresponds to a row of Table C.

Table 769
Compounds of the formula IA wherein $Q^1$ denotes iodine, $Q^3$ denotes CH$_2$SCH$_3$, and A in each case corresponds to a row of Table C.

Table 770
Compounds of the formula IA wherein $Q^1$ denotes iodine, $Q^3$ denotes CH$_2$SCH$_2$CH$_3$, and A in each case corresponds to a row of Table C.

Table 771
Compounds of the formula IA wherein $Q^1$ denotes iodine, $Q^3$ denotes CH$_2$S(=O)CH$_3$, and A in each case corresponds to a row of Table C.

Table 772
Compounds of the formula IA wherein $Q^1$ denotes iodine, $Q^3$ denotes CH$_2$S(=O)CH$_2$CH$_3$, and A in each case corresponds to a row of Table C.

Table 773
Compounds of the formula IA wherein $Q^1$ denotes iodine, $Q^3$ denotes CH$_2$S(=O)$_2$CH$_3$, and A in each case corresponds to a row of Table C.

Table 774
Compounds of the formula IA wherein $Q^1$ denotes iodine, $Q^3$ denotes CH$_2$S(=O)$_2$CH$_2$CH$_3$, and A in each case corresponds to a row of Table C.

Table 775
Compounds of the formula IA wherein $Q^1$ denotes iodine, $Q^3$ denotes —OS(=O)$_2$CH$_3$, and A in each case corresponds to a row of Table C.

Table 776
Compounds of the formula IA wherein $Q^1$ denotes iodine, $Q^3$ notes —OS(=O)$_2$CH$_2$CH$_3$, and A in each case corresponds to a row of Table C.

Table 777
Compounds of the formula IA wherein $Q^1$ denotes iodine, $Q^3$ notes —OS(=O)$_2$CH$_2$CF$_3$, and A in each case corresponds to a row of Table C.

Table 778
Compounds of the formula IA wherein $Q^1$ denotes iodine, $Q^3$ denotes —OS(=O)$_2$CClF$_2$, and A in each case corresponds to a row of Table C.

Table 779
Compounds of the formula IA wherein $Q^1$ denotes iodine, $Q^3$ denotes OC(=O)CF$_3$, and A in each case corresponds to a row of Table C.

Table 780
Compounds of the formula IA wherein $Q^1$ denotes iodine, $Q^3$ denotes NHCH$_2$CF$_3$, and A in each case corresponds to a row of Table C.

Table 781
Compounds of the formula IA wherein $Q^1$ denotes iodine, $Q^3$ denotes OCH$_2$-cyclopropyl, and A in each case corresponds to a row of Table C.

Table 782
Compounds of the formula IA wherein $Q^1$ denotes iodine, $Q^3$ denotes OCH$_2$C(Cl)=CH$_2$, and A in each case corresponds to a row of Table C.

Table 783
Compounds of the formula IA wherein $Q^1$ denotes iodine, $Q^3$ denotes $OCH_2CH=CF_2$, and A in each case corresponds to a row of Table C.

Table 784
Compounds of the formula IA wherein $Q^1$ denotes iodine, $Q^3$ denotes $NHS(=O)_2CF_3$, and A in each case corresponds to a row of Table C.

Table 785
Compounds of the formula IA wherein $Q^1$ denotes iodine, $Q^3$ denotes $NHC(=O)CF_3$, and A in each case corresponds to a row of Table C.

Table 786
Compounds of the formula IA wherein $Q^1$ denotes iodine, $Q^3$ denotes $OCH_2CN$, and A in each case corresponds to a row of Table C.

Table 787
Compounds of the formula IA wherein $Q^1$ denotes iodine, $Q^3$ denotes $OCH_2NO_2$, and A in each case corresponds to a row of Table C.

Table 788
Compounds of the formula IA wherein $Q^1$ denotes iodine, $Q^3$ denotes cyclopropyloxy, and A in each case corresponds to a row of Table C.

Table 789
Compounds of the formula IA wherein $Q^1$ denotes iodine, $Q^3$ denotes $CH_2OCHF_2$, and A in each case corresponds to a row of Table C.

Table 790
Compounds of the formula IA wherein $Q^1$ denotes iodine, $Q^3$ denotes $CH_2S(=O)_2CHF_2$, and A in each case corresponds to a row of Table C.

Table 791
Compounds of the formula IA wherein $Q^1$ denotes iodine, $Q^3$ denotes $CH=NOCH_3$, and A in each case corresponds to a row of Table C.

Table 792
Compounds of the formula IA wherein $Q^1$ denotes iodine, $Q^3$ denotes $CH=NOCH_2CH_3$, and A in each case corresponds to a row of Table C.

Table 793
Compounds of the formula IA wherein $Q^1$ denotes iodine, $Q^3$ denotes $CH=NOCH(CH_3)_2$ and A in each case corresponds to a row of Table C.

Table 794
Compounds of the formula IA wherein $Q^1$ denotes iodine, $Q^3$ denotes $CH=NOC(CH_3)_3$, and A in each case corresponds to a row of Table C.

Table 795
Compounds of the formula IA wherein $Q^1$ denotes iodine, $Q^3$ denotes $C(CH_3)=NOCH_3$, and A in each case corresponds to a row of Table C.

Table 796
Compounds of the formula IA wherein $Q^1$ denotes iodine, $Q^3$ denotes $C(CH_3)=NOCH_2CH_3$, and A in each case corresponds to a row of Table C.

Table 797
Compounds of the formula IA wherein $Q^1$ denotes iodine, $Q^3$ denotes $C(CH_3)=NOCH(CH_3)_2$, and A in each case corresponds to a row of Table C.

Table 798
Compounds of the formula IA wherein $Q^1$ denotes iodine, $Q^3$ denotes $C(CH_3)=NOC(CH_3)_3$, and A in each case corresponds to a row of Table C.

Table 799
Compounds of the formula IA wherein $Q^1$ denotes cyano, $Q^3$ denotes $CF_3$, and A in each case corresponds to a row of Table C.

Table 800
Compounds of the formula IA wherein $Q^1$ denotes cyano, $Q^3$ denotes bromine, and A in each case corresponds to a row of Table C.

Table 801
Compounds of the formula IA wherein $Q^1$ denotes cyano, $Q^3$ denotes chlorine, and A in each case corresponds to a row of Table C.

Table 802
Compounds of the formula IA wherein $Q^1$ denotes cyano, $Q^3$ denotes $CH_3$, and A in each case corresponds to a row of Table C.

Table 803
Compounds of the formula IA wherein $Q^1$ denotes cyano, $Q^3$ denotes $OCH_3$, and A in each case corresponds to a row of Table C.

Table 804
Compounds of the formula IA wherein $Q^1$ denotes cyano, $Q^3$ denotes $OCHCH_2$, and A in each case corresponds to a row of Table C.

Table 805
Compounds of the formula IA wherein $Q^1$ denotes cyano, $Q^3$ denotes ethoxy, and A in each case corresponds to a row of Table C.

Table 806
Compounds of the formula IA wherein $Q^1$ denotes cyano, $Q^3$ denotes $OCH_2CHFOCH_3$, and A in each case corresponds to a row of Table C.

Table 807
Compounds of the formula IA wherein $Q^1$ denotes cyano, $Q^3$ denotes $OCH_2CH=CH_2$, and A in each case corresponds to a row of Table C.

Table 808
Compounds of the formula IA wherein $Q^1$ denotes cyano, $Q^3$ denotes $OCH_2CCH$, and A in each case corresponds to a row of Table C.

Table 809
Compounds of the formula IA wherein $Q^1$ denotes cyano, $Q^3$ denotes $CH_2OCH_3$, and A in each case corresponds to a row of Table C.

Table 810
Compounds of the formula IA wherein $Q^1$ denotes cyano, $Q^3$ denotes $CH_2OCH_2CH_3$, and A in each case corresponds to a row of Table C.

Table 811
Compounds of the formula IA wherein $Q^1$ denotes cyano, $Q^3$ denotes $CH_2SCH_3$, and A in each case corresponds to a row of Table C.

Table 812
Compounds of the formula IA wherein $Q^1$ denotes cyano, $Q^3$ denotes $CH_2SCH_2CH_3$, and A in each case corresponds to a row of Table C.

Table 813
Compounds of the formula IA wherein $Q^1$ denotes cyano, $Q^3$ denotes $CH_2S(=O)CH_3$, and A in each case corresponds to a row of Table C.

Table 814
Compounds of the formula IA wherein $Q^1$ denotes cyano, $Q^3$ denotes $CH_2S(=O)CH_2CH_3$, and A in each case corresponds to a row of Table C.

Table 815
Compounds of the formula IA wherein $Q^1$ denotes cyano, $Q^3$ denotes $CH_2S(=O)_2CH_3$, and A in each case corresponds to a row of Table C.

Table 816
Compounds of the formula IA wherein $Q^1$ denotes cyano, $Q^3$ denotes $CH_2S(=O)_2CH_2CH_3$, and A in each case corresponds to a row of Table C.

Table 817
Compounds of the formula IA wherein $Q^1$ denotes cyano, $Q^3$ denotes —$OS(=O)_2CH_3$, and A in each case corresponds to a row of Table C.

Table 818
Compounds of the formula IA wherein $Q^1$ denotes cyano, $Q^3$ notes —$OS(=O)_2CH_2CH_3$, and A in each case corresponds to a row of Table C.

Table 819
Compounds of the formula IA wherein $Q^1$ denotes cyano, $Q^3$ notes —$OS(=O)_2CH_2CF_3$, and A in each case corresponds to a row of Table C.

Table 820
Compounds of the formula IA wherein $Q^1$ denotes cyano, $Q^3$ denotes —$OS(=O)_2CClF_2$, and A in each case corresponds to a row of Table C.

Table 821
Compounds of the formula IA wherein $Q^1$ denotes cyano, $Q^3$ denotes $OC(=O)CF_3$, and A in each case corresponds to a row of Table C.

Table 822
Compounds of the formula IA wherein $Q^1$ denotes cyano, $Q^3$ denotes $NHCH_2CF_3$, and A in each case corresponds to a row of Table C.

Table 823
Compounds of the formula IA wherein $Q^1$ denotes cyano, $Q^3$ denotes $OCH_2$-cyclopropyl, and A in each case corresponds to a row of Table C.

Table 824
Compounds of the formula IA wherein $Q^1$ denotes cyano, $Q^3$ denotes $OCH_2C(Cl)=CH_2$, and A in each case corresponds to a row of Table C.

Table 825
Compounds of the formula IA wherein $Q^1$ denotes cyano, $Q^3$ denotes $OCH_2CH=CF_2$, and A in each case corresponds to a row of Table C.

Table 826
Compounds of the formula IA wherein $Q^1$ denotes cyano, $Q^3$ denotes $NHS(=O)_2CF_3$, and A in each case corresponds to a row of Table C.

Table 827
Compounds of the formula IA wherein $Q^1$ denotes cyano, $Q^3$ denotes $NHC(=O)CF_3$, and A in each case corresponds to a row of Table C.

Table 828
Compounds of the formula IA wherein $Q^1$ denotes cyano, $Q^3$ denotes $OCH_2CN$, and A in each case corresponds to a row of Table C.

Table 829
Compounds of the formula IA wherein $Q^1$ denotes cyano, $Q^3$ denotes $OCH_2NO_2$, and A in each case corresponds to a row of Table C.

Table 830
Compounds of the formula IA wherein $Q^1$ denotes cyano, $Q^3$ denotes cyclopropyloxy, and A in each case corresponds to a row of Table C.

Table 831
Compounds of the formula IA wherein $Q^1$ denotes cyano, $Q^3$ denotes $CH_2OCHF_2$, and A in each case corresponds to a row of Table C.

Table 832
Compounds of the formula IA wherein $Q^1$ denotes cyano, $Q^3$ denotes $CH_2S(=O)_2CHF_2$, and A in each case corresponds to a row of Table C.

Table 833
Compounds of the formula IA wherein $Q^1$ denotes cyano, $Q^3$ denotes $CH=NOCH_3$, and A in each case corresponds to a row of Table C.

Table 834
Compounds of the formula IA wherein $Q^1$ denotes cyano, $Q^3$ denotes $CH=NOCH_2CH_3$, and A in each case corresponds to a row of Table C.

Table 835
Compounds of the formula IA wherein $Q^1$ denotes cyano, $Q^3$ denotes $CH=NOCH(CH_3)_2$ and A in each case corresponds to a row of Table C.

Table 836
Compounds of the formula IA wherein $Q^1$ denotes cyano, $Q^3$ denotes $CH=NOC(CH_3)_3$, and A in each case corresponds to a row of Table C.

Table 837
Compounds of the formula IA wherein $Q^1$ denotes cyano, $Q^3$ denotes $C(CH_3)=NOCH_3$, and A in each case corresponds to a row of Table C.

Table 838
Compounds of the formula IA wherein $Q^1$ denotes cyano, $Q^3$ denotes $C(CH_3)=NOCH_2CH_3$, and A in each case corresponds to a row of Table C.

Table 839
Compounds of the formula IA wherein $Q^1$ denotes cyano, $Q^3$ denotes $C(CH_3)=NOCH(CH_3)_2$, and A in each case corresponds to a row of Table C.

Table 840
Compounds of the formula IA wherein $Q^1$ denotes cyano, $Q^3$ denotes $C(CH_3)=NOC(CH_3)_3$, and A in each case corresponds to a row of Table C.

Table 841
Compounds of the formula IA wherein $Q^1$ denotes methyl, $Q^3$ denotes $CF_3$, and A in each case corresponds to a row of Table C.

Table 842
Compounds of the formula IA wherein $Q^1$ denotes methyl, $Q^3$ denotes bromine, and A in each case corresponds to a row of Table C.

Table 843
Compounds of the formula IA wherein $Q^1$ denotes methyl, $Q^3$ denotes chlorine, and A in each case corresponds to a row of Table C.

Table 844
Compounds of the formula IA wherein $Q^1$ denotes methyl, $Q^3$ denotes $CH_3$, and A in each case corresponds to a row of Table C.

Table 845
Compounds of the formula IA wherein $Q^1$ denotes methyl, $Q^3$ denotes $OCH_3$, and A in each case corresponds to a row of Table C.

Table 846
Compounds of the formula IA wherein $Q^1$ denotes methyl, $Q^3$ denotes $OCHCH_2$, and A in each case corresponds to a row of Table C.

Table 847
Compounds of the formula IA wherein $Q^1$ denotes methyl, $Q^3$ denotes ethoxy, and A in each case corresponds to a row of Table C.

Table 848
Compounds of the formula IA wherein $Q^1$ denotes methyl, $Q^3$ denotes $OCH_2CHFOCH_3$, and A in each case corresponds to a row of Table C.

Table 849
Compounds of the formula IA wherein $Q^1$ denotes methyl, $Q^3$ denotes $OCH_2CH=CH_2$, and A in each case corresponds to a row of Table C.

Table 850
Compounds of the formula IA wherein $Q^1$ denotes methyl, $Q^3$ denotes $OCH_2CCH$, and A in each case corresponds to a row of Table C.

Table 851
Compounds of the formula IA wherein $Q^1$ denotes methyl, $Q^3$ denotes $CH_2OCH_3$, and A in each case corresponds to a row of Table C.

Table 852
Compounds of the formula IA wherein $Q^1$ denotes methyl, $Q^3$ denotes $CH_2OCH_2CH_3$, and A in each case corresponds to a row of Table C.

Table 853
Compounds of the formula IA wherein $Q^1$ denotes methyl, $Q^3$ denotes $CH_2SCH_3$, and A in each case corresponds to a row of Table C.

Table 854
Compounds of the formula IA wherein $Q^1$ denotes methyl, $Q^3$ denotes $CH_2SCH_2CH_3$, and A in each case corresponds to a row of Table C.

Table 855
Compounds of the formula IA wherein $Q^1$ denotes methyl, $Q^3$ denotes $CH_2S(=O)CH_3$, and A in each case corresponds to a row of Table C.

Table 856
Compounds of the formula IA wherein $Q^1$ denotes methyl, $Q^3$ denotes $CH_2S(=O)CH_2CH_3$, and A in each case corresponds to a row of Table C.

Table 857
Compounds of the formula IA wherein $Q^1$ denotes methyl, $Q^3$ denotes $CH_2S(=O)_2CH_3$, and A in each case corresponds to a row of Table C.

Table 858
Compounds of the formula IA wherein $Q^1$ denotes methyl, $Q^3$ denotes $CH_2S(=O)_2CH_2CH_3$, and A in each case corresponds to a row of Table C.

Table 859
Compounds of the formula IA wherein $Q^1$ denotes methyl, $Q^3$ denotes $—OS(=O)_2CH_3$, and A in each case corresponds to a row of Table C.

Table 860
Compounds of the formula IA wherein $Q^1$ denotes methyl, $Q^3$ notes $—OS(=O)_2CH_2CH_3$, and A in each case corresponds to a row of Table C.

Table 861
Compounds of the formula IA wherein $Q^1$ denotes methyl, $Q^3$ notes $—OS(=O)_2CH_2CF_3$, and A in each case corresponds to a row of Table C.

Table 862
Compounds of the formula IA wherein $Q^1$ denotes methyl, $Q^3$ denotes $—OS(=O)_2CClF_2$, and A in each case corresponds to a row of Table C.

Table 863
Compounds of the formula IA wherein $Q^1$ denotes methyl, $Q^3$ denotes $OC(=O)CF_3$, and A in each case corresponds to a row of Table C.

Table 864
Compounds of the formula IA wherein $Q^1$ denotes methyl, $Q^3$ denotes $NHCH_2CF_3$, and A in each case corresponds to a row of Table C.

Table 865
Compounds of the formula IA wherein $Q^1$ denotes methyl, $Q^3$ denotes $OCH_2$-cyclopropyl, and A in each case corresponds to a row of Table C.

Table 866
Compounds of the formula IA wherein $Q^1$ denotes methyl, $Q^3$ denotes $OCH_2C(Cl)=CH_2$, and A in each case corresponds to a row of Table C.

Table 867
Compounds of the formula IA wherein $Q^1$ denotes methyl, $Q^3$ denotes $OCH_2CH=CF_2$, and A in each case corresponds to a row of Table C.

Table 868
Compounds of the formula IA wherein $Q^1$ denotes methyl, $Q^3$ denotes $NHS(=O)_2CF_3$, and A in each case corresponds to a row of Table C.

Table 869
Compounds of the formula IA wherein $Q^1$ denotes methyl, $Q^3$ denotes $NHC(=O)CF_3$, and A in each case corresponds to a row of Table C.

Table 870
Compounds of the formula IA wherein $Q^1$ denotes methyl, $Q^3$ denotes $OCH_2CN$, and A in each case corresponds to a row of Table C.

Table 871
Compounds of the formula IA wherein $Q^1$ denotes methyl, $Q^3$ denotes $OCH_2NO_2$, and A in each case corresponds to a row of Table C.

Table 872
Compounds of the formula IA wherein $Q^1$ denotes methyl, $Q^3$ denotes cyclopropyloxy, and A in each case corresponds to a row of Table C.

Table 873
Compounds of the formula IA wherein $Q^1$ denotes methyl, $Q^3$ denotes $CH_2OCHF_2$, and A in each case corresponds to a row of Table C.

Table 874
Compounds of the formula IA wherein $Q^1$ denotes methyl, $Q^3$ denotes $CH_2S(=O)_2CHF_2$, and A in each case corresponds to a row of Table C.

Table 875
Compounds of the formula IA wherein $Q^1$ denotes methyl, $Q^3$ denotes $CH=NOCH_3$, and A in each case corresponds to a row of Table C.

Table 876
Compounds of the formula IA wherein $Q^1$ denotes methyl, $Q^3$ denotes $CH=NOCH_2CH_3$, and A in each case corresponds to a row of Table C.

Table 877
Compounds of the formula IA wherein $Q^1$ denotes methyl, $Q^3$ denotes $CH=NOCH(CH_3)_2$ and A in each case corresponds to a row of Table C.

Table 878
Compounds of the formula IA wherein $Q^1$ denotes methyl, $Q^3$ denotes $CH=NOC(CH_3)_3$, and A in each case corresponds to a row of Table C.

Table 879
Compounds of the formula IA wherein $Q^1$ denotes methyl, $Q^3$ denotes $C(CH_3)=NOCH_3$, and A in each case corresponds to a row of Table C.

Table 880
Compounds of the formula IA wherein $Q^1$ denotes methyl, $Q^3$ denotes $C(CH_3)=NOCH_2CH_3$, and A in each case corresponds to a row of Table C.

Table 881
Compounds of the formula IA wherein $Q^1$ denotes methyl, $Q^3$ denotes $C(CH_3)=NOCH(CH_3)_2$, and A in each case corresponds to a row of Table C.

Table 882

Compounds of the formula IA wherein $Q^1$ denotes methyl, $Q^3$ denotes $C(CH_3)=NOC(CH_3)_3$, and A in each case corresponds to a row of Table C.

TABLE C

| No. | A | $R^e$ | $R^f$ |
|---|---|---|---|
| IA-139 | $-N=S\begin{smallmatrix}R^e\\R^f\end{smallmatrix}$  $A^1.1$ | $CH_3$ | $CH_3$ |
| IA-140 | $A^1.1$ | $CH_2CH_3$ | $CH_3$ |
| IA-141 | $A^1.1$ | $CH=CH_2$ | $CH_3$ |
| IA-142 | $A^1.1$ | $CH_2CH_2CH_3$ | $CH_3$ |
| IA-143 | $A^1.1$ | $CH(CH_3)_2$ | $CH_3$ |
| IA-144 | $A^1.1$ | $CH_2CH_2CH_2CH_3$ | $CH_3$ |
| IA-145 | $A^1.1$ | $C(CH_3)_3$ | $CH_3$ |
| IA-146 | $A^1.1$ | $CH_2CH(CH_3)_2$ | $CH_3$ |
| IA-147 | $A^1.1$ | $CH(CH_3)CH_2CH_3$ | $CH_3$ |
| IA-148 | $A^1.1$ | $CH_2CHCH_2$ | $CH_3$ |
| IA-149 | $A^1.1$ | $CH_2CCH$ | $CH_3$ |
| IA-150 | $A^1.1$ | $CH(CH_3)CH=CH_2$ | $CH_3$ |
| IA-151 | $A^1.1$ | $CHF_2$ | $CH_3$ |
| IA-152 | $A^1.1$ | $CH_2Cl$ | $CH_3$ |
| IA-153 | $A^1.1$ | $CH_2CH_2CN$ | $CH_3$ |
| IA-154 | $A^1.1$ | $CH_2CH_2Cl$ | $CH_3$ |
| IA-155 | $A^1.1$ | $CH_2CH_2OH$ | $CH_3$ |
| IA-156 | $A^1.1$ | $CH_2CH_2CH_2OH$ | $CH_3$ |
| IA-157 | $A^1.1$ | $CH_2CH(OH)CH_2OH$ | $CH_3$ |
| IA-158 | $A^1.1$ | $CH_2CH(OCH_3)_2$ | $CH_3$ |
| IA-159 | $A^1.1$ | $CH_2SCH_3$ | $CH_3$ |
| IA-160 | $A^1.1$ | $(CH_2)_3SCH_3$ | $CH_3$ |
| IA-161 | $A^1.1$ | $CH_2S(=O)CH_3$ | $CH_3$ |
| IA-162 | $A^1.1$ | $CH_2S(=O)_2CH_3$ | $CH_3$ |
| IA-163 | $A^1.1$ | $CH_2C(=O)CH_3$ | $CH_3$ |
| IA-164 | $A^1.1$ | $CH_2C(=O)CH_2CH_3$ | $CH_3$ |
| IA-165 | $A^1.1$ | $CH_2COOH$ | $CH_3$ |
| IA-166 | $A^1.1$ | $CH_2COOCH_3$ | $CH_3$ |
| IA-167 | $A^1.1$ | $CH_2COOCH_2CH_3$ | $CH_3$ |
| IA-168 | $A^1.1$ | cyclo-$C_3H_5$ | $CH_3$ |
| IA-169 | $A^1.1$ | cyclo-$C_4H_7$ | $CH_3$ |
| IA-170 | $A^1.1$ | cyclo-$C_5H_9$ | $CH_3$ |
| IA-171 | $A^1.1$ | cyclo-$C_6H_{11}$ | $CH_3$ |
| IA-172 | $A^1.1$ | $C_6H_5$ | $CH_3$ |
| IA-173 | $A^1.1$ | $CH_2CH_3$ | $CH_2CH_3$ |
| IA-174 | $A^1.1$ | $CH=CH_2$ | $CH_2CH_3$ |
| IA-175 | $A^1.1$ | $CH_2CH_2CH_3$ | $CH_2CH_3$ |
| IA-176 | $A^1.1$ | $CH(CH_3)_2$ | $CH_2CH_3$ |
| IA-177 | $A^1.1$ | $CH_2CH_2CH_2CH_3$ | $CH_2CH_3$ |
| IA-178 | $A^1.1$ | $C(CH_3)_3$ | $CH_2CH_3$ |
| IA-179 | $A^1.1$ | $CH_2CH(CH_3)_2$ | $CH_2CH_3$ |
| IA-180 | $A^1.1$ | $CH(CH_3)CH_2CH_3$ | $CH_2CH_3$ |
| IA-181 | $A^1.1$ | $CH_2CHCH_2$ | $CH_2CH_3$ |
| IA-182 | $A^1.1$ | $CH_2CCH$ | $CH_2CH_3$ |
| IA-183 | $A^1.1$ | $CH(CH_3)CH=CH_2$ | $CH_2CH_3$ |
| IA-184 | $A^1.1$ | $CHF_2$ | $CH_2CH_3$ |
| IA-185 | $A^1.1$ | $CH_2Cl$ | $CH_2CH_3$ |
| IA-186 | $A^1.1$ | $CH_2CH_2CN$ | $CH_2CH_3$ |
| IA-187 | $A^1.1$ | $CH_2CH_2Cl$ | $CH_2CH_3$ |
| IA-188 | $A^1.1$ | $CH_2CH_2OH$ | $CH_2CH_3$ |
| IA-189 | $A^1.1$ | $CH_2CH_2CH_2OH$ | $CH_2CH_3$ |
| IA-190 | $A^1.1$ | $CH_2CH(OH)CH_2OH$ | $CH_2CH_3$ |
| IA-191 | $A^1.1$ | $CH_2CH(OCH_3)_2$ | $CH_2CH_3$ |
| IA-192 | $A^1.1$ | $CH_2SCH_3$ | $CH_2CH_3$ |
| IA-193 | $A^1.1$ | $(CH_2)_3SCH_3$ | $CH_2CH_3$ |
| IA-194 | $A^1.1$ | $CH_2S(=O)CH_3$ | $CH_2CH_3$ |
| IA-195 | $A^1.1$ | $CH_2S(=O)_2CH_3$ | $CH_2CH_3$ |
| IA-196 | $A^1.1$ | $CH_2C(=O)CH_3$ | $CH_2CH_3$ |
| IA-197 | $A^1.1$ | $CH_2C(=O)CH_2CH_3$ | $CH_2CH_3$ |
| IA-198 | $A^1.1$ | $CH_2COOH$ | $CH_2CH_3$ |
| IA-199 | $A^1.1$ | $CH_2COOCH_3$ | $CH_2CH_3$ |
| IA-200 | $A^1.1$ | $CH_2COOCH_2CH_3$ | $CH_2CH_3$ |
| IA-201 | $A^1.1$ | cyclo-$C_3H_5$ | $CH_2CH_3$ |
| IA-202 | $A^1.1$ | cyclo-$C_4H_7$ | $CH_2CH_3$ |
| IA-203 | $A^1.1$ | cyclo-$C_5H_9$ | $CH_2CH_3$ |
| IA-204 | $A^1.1$ | cyclo-$C_6H_{11}$ | $CH_2CH_3$ |
| IA-205 | $A^1.1$ | $C_6H_5$ | $CH_2CH_3$ |
| IA-206 | $A^1.1$ | $CH=CH_2$ | $CH=CH_2$ |
| IA-207 | $A^1.1$ | $CH_2CH_2CH_3$ | $CH=CH_2$ |
| IA-208 | $A^1.1$ | $CH(CH_3)_2$ | $CH=CH_2$ |
| IA-209 | $A^1.1$ | $CH_2CH_2CH_2CH_3$ | $CH=CH_2$ |
| IA-210 | $A^1.1$ | $C(CH_3)_3$ | $CH=CH_2$ |
| IA-211 | $A^1.1$ | $CH_2CH(CH_3)_2$ | $CH=CH_2$ |
| IA-212 | $A^1.1$ | $CH(CH_3)CH_2CH_3$ | $CH=CH_2$ |
| IA-213 | $A^1.1$ | $CH_2CHCH_2$ | $CH=CH_2$ |
| IA-214 | $A^1.1$ | $CH_2CCH$ | $CH=CH_2$ |
| IA-215 | $A^1.1$ | $CH(CH_3)CH=CH_2$ | $CH=CH_2$ |
| IA-216 | $A^1.1$ | $CHF_2$ | $CH=CH_2$ |
| IA-217 | $A^1.1$ | $CH_2Cl$ | $CH=CH_2$ |
| IA-218 | $A^1.1$ | $CH_2CH_2CN$ | $CH=CH_2$ |
| IA-219 | $A^1.1$ | $CH_2CH_2Cl$ | $CH=CH_2$ |
| IA-220 | $A^1.1$ | $CH_2CH_2OH$ | $CH=CH_2$ |
| IA-221 | $A^1.1$ | $CH_2CH_2CH_2OH$ | $CH=CH_2$ |
| IA-222 | $A^1.1$ | $CH_2CH(OH)CH_2OH$ | $CH=CH_2$ |
| IA-223 | $A^1.1$ | $CH_2CH(OCH_3)_2$ | $CH=CH_2$ |
| IA-224 | $A^1.1$ | $CH_2SCH_3$ | $CH=CH_2$ |
| IA-225 | $A^1.1$ | $(CH_2)_3SCH_3$ | $CH=CH_2$ |
| IA-226 | $A^1.1$ | $CH_2S(=O)CH_3$ | $CH=CH_2$ |
| IA-227 | $A^1.1$ | $CH_2S(=O)_2CH_3$ | $CH=CH_2$ |
| IA-228 | $A^1.1$ | $CH_2C(=O)CH_3$ | $CH=CH_2$ |
| IA-229 | $A^1.1$ | $CH_2C(=O)CH_2CH_3$ | $CH=CH_2$ |
| IA-230 | $A^1.1$ | $CH_2COOH$ | $CH=CH_2$ |
| IA-231 | $A^1.1$ | $CH_2COOCH_3$ | $CH=CH_2$ |
| IA-232 | $A^1.1$ | $CH_2COOCH_2CH_3$ | $CH=CH_2$ |
| IA-233 | $A^1.1$ | cyclo-$C_3H_5$ | $CH=CH_2$ |
| IA-234 | $A^1.1$ | cyclo-$C_4H_7$ | $CH=CH_2$ |
| IA-235 | $A^1.1$ | cyclo-$C_5H_9$ | $CH=CH_2$ |
| IA-236 | $A^1.1$ | cyclo-$C_6H_{11}$ | $CH=CH_2$ |
| IA-237 | $A^1.1$ | $C_6H_5$ | $CH=CH_2$ |
| IA-238 | $A^1.1$ | $CH_2CH_3$ | $CH_2CH_2CH_3$ |
| IA-239 | $A^1.1$ | $CH(CH_3)_2$ | $CH_2CH_2CH_3$ |
| IA-240 | $A^1.1$ | $CH_2CH_2CH_3$ | $CH_2CH_2CH_3$ |
| IA-241 | $A^1.1$ | $C(CH_3)_3$ | $CH_2CH_2CH_3$ |
| IA-242 | $A^1.1$ | $CH_2CH(CH_3)_2$ | $CH_2CH_2CH_3$ |
| IA-243 | $A^1.1$ | $CH(CH_3)CH_2CH_3$ | $CH_2CH_2CH_3$ |
| IA-244 | $A^1.1$ | $CH_2CHCH_2$ | $CH_2CH_2CH_3$ |
| IA-245 | $A^1.1$ | $CH_2CCH$ | $CH_2CH_2CH_3$ |
| IA-246 | $A^1.1$ | $CH(CH_3)CH=CH_2$ | $CH_2CH_2CH_3$ |
| IA-247 | $A^1.1$ | $CHF_2$ | $CH_2CH_2CH_3$ |
| IA-248 | $A^1.1$ | $CH_2Cl$ | $CH_2CH_2CH_3$ |
| IA-249 | $A^1.1$ | $CH_2CH_2CN$ | $CH_2CH_2CH_3$ |
| IA-250 | $A^1.1$ | $CH_2CH_2Cl$ | $CH_2CH_2CH_3$ |
| IA-251 | $A^1.1$ | $CH_2CH_2OH$ | $CH_2CH_2CH_3$ |
| IA-252 | $A^1.1$ | $CH_2CH_2CH_2OH$ | $CH_2CH_2CH_3$ |
| IA-253 | $A^1.1$ | $CH_2CH(OH)CH_2OH$ | $CH_2CH_2CH_3$ |
| IA-254 | $A^1.1$ | $CH_2CH(OCH_3)_2$ | $CH_2CH_2CH_3$ |
| IA-255 | $A^1.1$ | $CH_2SCH_3$ | $CH_2CH_2CH_3$ |
| IA-256 | $A^1.1$ | $(CH_2)_3SCH_3$ | $CH_2CH_2CH_3$ |
| IA-257 | $A^1.1$ | $CH_2S(=O)CH_3$ | $CH_2CH_2CH_3$ |
| IA-258 | $A^1.1$ | $CH_2S(=O)_2CH_3$ | $CH_2CH_2CH_3$ |
| IA-259 | $A^1.1$ | $CH_2C(=O)CH_3$ | $CH_2CH_2CH_3$ |
| IA-260 | $A^1.1$ | $CH_2C(=O)CH_2CH_3$ | $CH_2CH_2CH_3$ |
| IA-261 | $A^1.1$ | $CH_2COOH$ | $CH_2CH_2CH_3$ |
| IA-262 | $A^1.1$ | $CH_2COOCH_3$ | $CH_2CH_2CH_3$ |
| IA-263 | $A^1.1$ | $CH_2COOCH_2CH_3$ | $CH_2CH_2CH_3$ |
| IA-264 | $A^1.1$ | cyclo-$C_3H_5$ | $CH_2CH_2CH_3$ |
| IA-265 | $A^1.1$ | cyclo-$C_4H_7$ | $CH_2CH_2CH_3$ |
| IA-266 | $A^1.1$ | cyclo-$C_5H_9$ | $CH_2CH_2CH_3$ |
| IA-267 | $A^1.1$ | cyclo-$C_6H_{11}$ | $CH_2CH_2CH_3$ |
| IA-268 | $A^1.1$ | $C_6H_5$ | $CH_2CH_2CH_3$ |
| IA-269 | $A^1.1$ | $CH(CH_3)_2$ | $CH(CH_3)_2$ |
| IA-270 | $A^1.1$ | $CH_2CH_2CH_3$ | $CH(CH_3)_2$ |
| IA-271 | $A^1.1$ | $C(CH_3)_3$ | $CH(CH_3)_2$ |
| IA-272 | $A^1.1$ | $CH_2CH(CH_3)_2$ | $CH(CH_3)_2$ |
| IA-273 | $A^1.1$ | $CH(CH_3)CH_2CH_3$ | $CH(CH_3)_2$ |
| IA-274 | $A^1.1$ | $CH_2CHCH_2$ | $CH(CH_3)_2$ |
| IA-275 | $A^1.1$ | $CH_2CCH$ | $CH(CH_3)_2$ |
| IA-276 | $A^1.1$ | $CH(CH_3)CH=CH_2$ | $CH(CH_3)_2$ |
| IA-277 | $A^1.1$ | $CHF_2$ | $CH(CH_3)_2$ |
| IA-278 | $A^1.1$ | $CH_2Cl$ | $CH(CH_3)_2$ |
| IA-279 | $A^1.1$ | $CH_2CH_2CN$ | $CH(CH_3)_2$ |
| IA-280 | $A^1.1$ | $CH_2CH_2Cl$ | $CH(CH_3)_2$ |
| IA-281 | $A^1.1$ | $CH_2CH_2OH$ | $CH(CH_3)_2$ |

TABLE C-continued

| No. | A | $R^e$ | $R^f$ |
|---|---|---|---|
| IA-282 | $A^1.1$ | $CH_2CH_2CH_2OH$ | $CH(CH_3)_2$ |
| IA-283 | $A^1.1$ | $CH_2CH(OH)CH_2OH$ | $CH(CH_3)_2$ |
| IA-284 | $A^1.1$ | $CH_2CH(OCH_3)_2$ | $CH(CH_3)_2$ |
| IA-285 | $A^1.1$ | $CH_2SCH_3$ | $CH(CH_3)_2$ |
| IA-286 | $A^1.1$ | $(CH_2)_3SCH_3$ | $CH(CH_3)_2$ |
| IA-287 | $A^1.1$ | $CH_2S(=O)CH_3$ | $CH(CH_3)_2$ |
| IA-288 | $A^1.1$ | $CH_2S(=O)_2CH_3$ | $CH(CH_3)_2$ |
| IA-289 | $A^1.1$ | $CH_2C(=O)CH_3$ | $CH(CH_3)_2$ |
| IA-290 | $A^1.1$ | $CH_2C(=O)CH_2CH_3$ | $CH(CH_3)_2$ |
| IA-291 | $A^1.1$ | $CH_2COOH$ | $CH(CH_3)_2$ |
| IA-292 | $A^1.1$ | $CH_2COOCH_3$ | $CH(CH_3)_2$ |
| IA-293 | $A^1.1$ | $CH_2COOCH_2CH_3$ | $CH(CH_3)_2$ |
| IA-294 | $A^1.1$ | cyclo-$C_3H_5$ | $CH(CH_3)_2$ |
| IA-295 | $A^1.1$ | cyclo-$C_4H_7$ | $CH(CH_3)_2$ |
| IA-296 | $A^1.1$ | cyclo-$C_5H_9$ | $CH(CH_3)_2$ |
| IA-297 | $A^1.1$ | cyclo-$C_6H_{11}$ | $CH(CH_3)_2$ |
| IA-298 | $A^1.1$ | $C_6H_5$ | $CH(CH_3)_2$ |
| IA-299 | $A^1.1$ | $CH_2CH_2CH_2CH_3$ | $CH_2CH_2CH_2CH_3$ |
| IA-300 | $A^1.1$ | $C(CH_3)_3$ | $CH_2CH_2CH_2CH_3$ |
| IA-301 | $A^1.1$ | $CH_2CH(CH_3)_2$ | $CH_2CH_2CH_2CH_3$ |
| IA-302 | $A^1.1$ | $CH(CH_3)CH_2CH_3$ | $CH_2CH_2CH_2CH_3$ |
| IA-303 | $A^1.1$ | $CH_2CHCH_2$ | $CH_2CH_2CH_2CH_3$ |
| IA-304 | $A^1.1$ | $CH_2CCH$ | $CH_2CH_2CH_2CH_3$ |
| IA-305 | $A^1.1$ | $CH(CH_3)CH=CH_2$ | $CH_2CH_2CH_2CH_3$ |
| IA-306 | $A^1.1$ | $CHF_2$ | $CH_2CH_2CH_2CH_3$ |
| IA-307 | $A^1.1$ | $CH_2Cl$ | $CH_2CH_2CH_2CH_3$ |
| IA-308 | $A^1.1$ | $CH_2CH_2CN$ | $CH_2CH_2CH_2CH_3$ |
| IA-309 | $A^1.1$ | $CH_2CH_2Cl$ | $CH_2CH_2CH_2CH_3$ |
| IA-310 | $A^1.1$ | $CH_2CH_2OH$ | $CH_2CH_2CH_2CH_3$ |
| IA-311 | $A^1.1$ | $CH_2CH_2CH_2OH$ | $CH_2CH_2CH_2CH_3$ |
| IA-312 | $A^1.1$ | $CH_2CH(OH)CH_2OH$ | $CH_2CH_2CH_2CH_3$ |
| IA-313 | $A^1.1$ | $CH_2CH(OCH_3)_2$ | $CH_2CH_2CH_2CH_3$ |
| IA-314 | $A^1.1$ | $CH_2SCH_3$ | $CH_2CH_2CH_2CH_3$ |
| IA-315 | $A^1.1$ | $(CH_2)_3SCH_3$ | $CH_2CH_2CH_2CH_3$ |
| IA-316 | $A^1.1$ | $CH_2S(=O)CH_3$ | $CH_2CH_2CH_2CH_3$ |
| IA-317 | $A^1.1$ | $CH_2S(=O)_2CH_3$ | $CH_2CH_2CH_2CH_3$ |
| IA-318 | $A^1.1$ | $CH_2C(=O)CH_3$ | $CH_2CH_2CH_2CH_3$ |
| IA-319 | $A^1.1$ | $CH_2C(=O)CH_2CH_3$ | $CH_2CH_2CH_2CH_3$ |
| IA-320 | $A^1.1$ | $CH_2COOH$ | $CH_2CH_2CH_2CH_3$ |
| IA-321 | $A^1.1$ | $CH_2COOCH_3$ | $CH_2CH_2CH_2CH_3$ |
| IA-322 | $A^1.1$ | $CH_2COOCH_2CH_3$ | $CH_2CH_2CH_2CH_3$ |
| IA-323 | $A^1.1$ | cyclo-$C_3H_5$ | $CH_2CH_2CH_2CH_3$ |
| IA-324 | $A^1.1$ | cyclo-$C_4H_7$ | $CH_2CH_2CH_2CH_3$ |
| IA-325 | $A^1.1$ | cyclo-$C_5H_9$ | $CH_2CH_2CH_2CH_3$ |
| IA-326 | $A^1.1$ | cyclo-$C_6H_{11}$ | $CH_2CH_2CH_2CH_3$ |
| IA-327 | $A^1.1$ | $C_6H_5$ | $CH_2CH_2CH_2CH_3$ |
| IA-328 | $A^1.1$ | $C(CH_3)_3$ | $C(CH_3)_3$ |
| IA-329 | $A^1.1$ | $CH_2CH(CH_3)_2$ | $C(CH_3)_3$ |
| IA-330 | $A^1.1$ | $CH(CH_3)CH_2CH_3$ | $C(CH_3)_3$ |
| IA-331 | $A^1.1$ | $CH_2CHCH_2$ | $C(CH_3)_3$ |
| IA-332 | $A^1.1$ | $CH_2CCH$ | $C(CH_3)_3$ |
| IA-333 | $A^1.1$ | $CH(CH_3)CH=CH_2$ | $C(CH_3)_3$ |
| IA-334 | $A^1.1$ | $CHF_2$ | $C(CH_3)_3$ |
| IA-335 | $A^1.1$ | $CH_2Cl$ | $C(CH_3)_3$ |
| IA-336 | $A^1.1$ | $CH_2CH_2CN$ | $C(CH_3)_3$ |
| IA-337 | $A^1.1$ | $CH_2CH_2Cl$ | $C(CH_3)_3$ |
| IA-338 | $A^1.1$ | $CH_2CH_2OH$ | $C(CH_3)_3$ |
| IA-339 | $A^1.1$ | $CH_2CH_2CH_2OH$ | $C(CH_3)_3$ |
| IA-340 | $A^1.1$ | $CH_2CH(OH)CH_2OH$ | $C(CH_3)_3$ |
| IA-341 | $A^1.1$ | $CH_2CH(OCH_3)_2$ | $C(CH_3)_3$ |
| IA-342 | $A^1.1$ | $CH_2SCH_3$ | $C(CH_3)_3$ |
| IA-343 | $A^1.1$ | $(CH_2)_3SCH_3$ | $C(CH_3)_3$ |
| IA-344 | $A^1.1$ | $CH_2S(=O)CH_3$ | $C(CH_3)_3$ |
| IA-345 | $A^1.1$ | $CH_2S(=O)_2CH_3$ | $C(CH_3)_3$ |
| IA-346 | $A^1.1$ | $CH_2C(=O)CH_3$ | $C(CH_3)_3$ |
| IA-347 | $A^1.1$ | $CH_2C(=O)CH_2CH_3$ | $C(CH_3)_3$ |
| IA-348 | $A^1.1$ | $CH_2COOH$ | $C(CH_3)_3$ |
| IA-349 | $A^1.1$ | $CH_2COOCH_3$ | $C(CH_3)_3$ |
| IA-350 | $A^1.1$ | $CH_2COOCH_2CH_3$ | $C(CH_3)_3$ |
| IA-351 | $A^1.1$ | cyclo-$C_3H_5$ | $C(CH_3)_3$ |
| IA-352 | $A^1.1$ | cyclo-$C_4H_7$ | $C(CH_3)_3$ |
| IA-353 | $A^1.1$ | cyclo-$C_5H_9$ | $C(CH_3)_3$ |
| IA-354 | $A^1.1$ | cyclo-$C_6H_{11}$ | $C(CH_3)_3$ |
| IA-355 | $A^1.1$ | $C_6H_5$ | $C(CH_3)_3$ |
| IA-356 | $A^1.1$ | $CH_2CH(CH_3)_2$ | $CH_2CH(CH_3)_2$ |
| IA-357 | $A^1.1$ | $CH(CH_3)CH_2CH_3$ | $CH_2CH(CH_3)_2$ |
| IA-358 | $A^1.1$ | $CH_2CHCH_2$ | $CH_2CH(CH_3)_2$ |
| IA-359 | $A^1.1$ | $CH_2CCH$ | $CH_2CH(CH_3)_2$ |
| IA-360 | $A^1.1$ | $CH(CH_3)CH=CH_2$ | $CH_2CH(CH_3)_2$ |
| IA-361 | $A^1.1$ | $CHF_2$ | $CH_2CH(CH_3)_2$ |
| IA-362 | $A^1.1$ | $CH_2Cl$ | $CH_2CH(CH_3)_2$ |
| IA-363 | $A^1.1$ | $CH_2CH_2CN$ | $CH_2CH(CH_3)_2$ |
| IA-364 | $A^1.1$ | $CH_2CH_2Cl$ | $CH_2CH(CH_3)_2$ |
| IA-365 | $A^1.1$ | $CH_2CH_2OH$ | $CH_2CH(CH_3)_2$ |
| IA-366 | $A^1.1$ | $CH_2CH_2CH_2OH$ | $CH_2CH(CH_3)_2$ |
| IA-367 | $A^1.1$ | $CH_2CH(OH)CH_2OH$ | $CH_2CH(CH_3)_2$ |
| IA-368 | $A^1.1$ | $CH_2CH(OCH_3)_2$ | $CH_2CH(CH_3)_2$ |
| IA-369 | $A^1.1$ | $CH_2SCH_3$ | $CH_2CH(CH_3)_2$ |
| IA-370 | $A^1.1$ | $(CH_2)_3SCH_3$ | $CH_2CH(CH_3)_2$ |
| IA-371 | $A^1.1$ | $CH_2S(=O)CH_3$ | $CH_2CH(CH_3)_2$ |
| IA-372 | $A^1.1$ | $CH_2S(=O)_2CH_3$ | $CH_2CH(CH_3)_2$ |
| IA-373 | $A^1.1$ | $CH_2C(=O)CH_3$ | $CH_2CH(CH_3)_2$ |
| IA-374 | $A^1.1$ | $CH_2C(=O)CH_2CH_3$ | $CH_2CH(CH_3)_2$ |
| IA-375 | $A^1.1$ | $CH_2COOH$ | $CH_2CH(CH_3)_2$ |
| IA-376 | $A^1.1$ | $CH_2COOCH_3$ | $CH_2CH(CH_3)_2$ |
| IA-377 | $A^1.1$ | $CH_2COOCH_2CH_3$ | $CH_2CH(CH_3)_2$ |
| IA-378 | $A^1.1$ | cyclo-$C_3H_5$ | $CH_2CH(CH_3)_2$ |
| IA-379 | $A^1.1$ | cyclo-$C_4H_7$ | $CH_2CH(CH_3)_2$ |
| IA-380 | $A^1.1$ | cyclo-$C_5H_9$ | $CH_2CH(CH_3)_2$ |
| IA-381 | $A^1.1$ | cyclo-$C_6H_{11}$ | $CH_2CH(CH_3)_2$ |
| IA-382 | $A^1.1$ | $C_6H_5$ | $CH_2CH(CH_3)_2$ |
| IA-383 | $A^1.1$ | $CH(CH_3)CH_2CH_3$ | $CH(CH_3)CH_2CH_3$ |
| IA-384 | $A^1.1$ | $CH_2CHCH_2$ | $CH(CH_3)CH_2CH_3$ |
| IA-385 | $A^1.1$ | $CH_2CCH$ | $CH(CH_3)CH_2CH_3$ |
| IA-386 | $A^1.1$ | $CH(CH_3)CH=CH_2$ | $CH(CH_3)CH_2CH_3$ |
| IA-387 | $A^1.1$ | $CHF_2$ | $CH(CH_3)CH_2CH_3$ |
| IA-388 | $A^1.1$ | $CH_2Cl$ | $CH(CH_3)CH_2CH_3$ |
| IA-389 | $A^1.1$ | $CH_2CH_2CN$ | $CH(CH_3)CH_2CH_3$ |
| IA-390 | $A^1.1$ | $CH_2CH_2Cl$ | $CH(CH_3)CH_2CH_3$ |
| IA-391 | $A^1.1$ | $CH_2CH_2OH$ | $CH(CH_3)CH_2CH_3$ |
| IA-392 | $A^1.1$ | $CH_2CH_2CH_2OH$ | $CH(CH_3)CH_2CH_3$ |
| IA-393 | $A^1.1$ | $CH_2CH(OH)CH_2OH$ | $CH(CH_3)CH_2CH_3$ |
| IA-394 | $A^1.1$ | $CH_2CH(OCH_3)_2$ | $CH(CH_3)CH_2CH_3$ |
| IA-395 | $A^1.1$ | $CH_2SCH_3$ | $CH(CH_3)CH_2CH_3$ |
| IA-396 | $A^1.1$ | $(CH_2)_3SCH_3$ | $CH(CH_3)CH_2CH_3$ |
| IA-397 | $A^1.1$ | $CH_2S(=O)CH_3$ | $CH(CH_3)CH_2CH_3$ |
| IA-398 | $A^1.1$ | $CH_2S(=O)_2CH_3$ | $CH(CH_3)CH_2CH_3$ |
| IA-399 | $A^1.1$ | $CH_2C(=O)CH_3$ | $CH(CH_3)CH_2CH_3$ |
| IA-400 | $A^1.1$ | $CH_2C(=O)CH_2CH_3$ | $CH(CH_3)CH_2CH_3$ |
| IA-401 | $A^1.1$ | $CH_2COOH$ | $CH(CH_3)CH_2CH_3$ |
| IA-402 | $A^1.1$ | $CH_2COOCH_3$ | $CH(CH_3)CH_2CH_3$ |
| IA-403 | $A^1.1$ | $CH_2COOCH_2CH_3$ | $CH(CH_3)CH_2CH_3$ |
| IA-404 | $A^1.1$ | cyclo-$C_3H_5$ | $CH(CH_3)CH_2CH_3$ |
| IA-405 | $A^1.1$ | cyclo-$C_4H_7$ | $CH(CH_3)CH_2CH_3$ |
| IA-406 | $A^1.1$ | cyclo-$C_5H_9$ | $CH(CH_3)CH_2CH_3$ |
| IA-407 | $A^1.1$ | cyclo-$C_6H_{11}$ | $CH(CH_3)CH_2CH_3$ |
| IA-408 | $A^1.1$ | $C_6H_5$ | $CH(CH_3)CH_2CH_3$ |
| IA-409 | $A^1.1$ | $CH_2CHCH_2$ | $CH_2CHCH_2$ |
| IA-410 | $A^1.1$ | $CH_2CCH$ | $CH_2CHCH_2$ |
| IA-411 | $A^1.1$ | $CH(CH_3)CH=CH_2$ | $CH_2CHCH_2$ |
| IA-412 | $A^1.1$ | $CHF_2$ | $CH_2CHCH_2$ |
| IA-413 | $A^1.1$ | $CH_2Cl$ | $CH_2CHCH_2$ |
| IA-414 | $A^1.1$ | $CH_2CH_2CN$ | $CH_2CHCH_2$ |
| IA-415 | $A^1.1$ | $CH_2CH_2Cl$ | $CH_2CHCH_2$ |
| IA-416 | $A^1.1$ | $CH_2CH_2OH$ | $CH_2CHCH_2$ |
| IA-417 | $A^1.1$ | $CH_2CH_2CH_2OH$ | $CH_2CHCH_2$ |
| IA-418 | $A^1.1$ | $CH_2CH(OH)CH_2OH$ | $CH_2CHCH_2$ |
| IA-419 | $A^1.1$ | $CH_2CH(OCH_3)_2$ | $CH_2CHCH_2$ |
| IA-420 | $A^1.1$ | $CH_2SCH_3$ | $CH_2CHCH_2$ |
| IA-421 | $A^1.1$ | $(CH_2)_3SCH_3$ | $CH_2CHCH_2$ |
| IA-422 | $A^1.1$ | $CH_2S(=O)CH_3$ | $CH_2CHCH_2$ |
| IA-423 | $A^1.1$ | $CH_2S(=O)_2CH_3$ | $CH_2CHCH_2$ |
| IA-424 | $A^1.1$ | $CH_2C(=O)CH_3$ | $CH_2CHCH_2$ |
| IA-425 | $A^1.1$ | $CH_2C(=O)CH_2CH_3$ | $CH_2CHCH_2$ |
| IA-426 | $A^1.1$ | $CH_2COOH$ | $CH_2CHCH_2$ |
| IA-427 | $A^1.1$ | $CH_2COOCH_3$ | $CH_2CHCH_2$ |
| IA-428 | $A^1.1$ | $CH_2COOCH_2CH_3$ | $CH_2CHCH_2$ |
| IA-429 | $A^1.1$ | cyclo-$C_3H_5$ | $CH_2CHCH_2$ |
| IA-430 | $A^1.1$ | cyclo-$C_4H_7$ | $CH_2CHCH_2$ |
| IA-431 | $A^1.1$ | cyclo-$C_5H_9$ | $CH_2CHCH_2$ |
| IA-432 | $A^1.1$ | cyclo-$C_6H_{11}$ | $CH_2CHCH_2$ |
| IA-433 | $A^1.1$ | $C_6H_5$ | $CH_2CHCH_2$ |
| IA-434 | $A^1.1$ | $CH_2CCH$ | $CH_2CCH$ |
| IA-435 | $A^1.1$ | $CH(CH_3)CH=CH_2$ | $CH_2CCH$ |
| IA-436 | $A^1.1$ | $CHF_2$ | $CH_2CCH$ |
| IA-437 | $A^1.1$ | $CH_2Cl$ | $CH_2CCH$ |

TABLE C-continued

| No. | A | R$^e$ | R$^f$ |
|---|---|---|---|
| IA-438 | A$^1$.1 | CH$_2$CH$_2$CN | CH$_2$CCH |
| IA-439 | A$^1$.1 | CH$_2$CH$_2$Cl | CH$_2$CCH |
| IA-440 | A$^1$.1 | CH$_2$CH$_2$OH | CH$_2$CCH |
| IA-441 | A$^1$.1 | CH$_2$CH$_2$CH$_2$OH | CH$_2$CCH |
| IA-442 | A$^1$.1 | CH$_2$CH(OH)CH$_2$OH | CH$_2$CCH |
| IA-443 | A$^1$.1 | CH$_2$CH(OCH$_3$)$_2$ | CH$_2$CCH |
| IA-444 | A$^1$.1 | CH$_2$SCH$_3$ | CH$_2$CCH |
| IA-445 | A$^1$.1 | (CH$_2$)$_3$SCH$_3$ | CH$_2$CCH |
| IA-446 | A$^1$.1 | CH$_2$S(=O)CH$_3$ | CH$_2$CCH |
| IA-447 | A$^1$.1 | CH$_2$S(=O)$_2$CH$_3$ | CH$_2$CCH |
| IA-448 | A$^1$.1 | CH$_2$C(=O)CH$_3$ | CH$_2$CCH |
| IA-449 | A$^1$.1 | CH$_2$C(=O)CH$_2$CH$_3$ | CH$_2$CCH |
| IA-450 | A$^1$.1 | CH$_2$COOH | CH$_2$CCH |
| IA-451 | A$^1$.1 | CH$_2$COOCH$_3$ | CH$_2$CCH |
| IA-452 | A$^1$.1 | CH$_2$COOCH$_2$CH$_3$ | CH$_2$CCH |
| IA-453 | A$^1$.1 | cyclo-C$_3$H$_5$ | CH$_2$CCH |
| IA-454 | A$^1$.1 | cyclo-C$_4$H$_7$ | CH$_2$CCH |
| IA-455 | A$^1$.1 | cyclo-C$_5$H$_9$ | CH$_2$CCH |
| IA-456 | A$^1$.1 | cyclo-C$_6$H$_{11}$ | CH$_2$CCH |
| IA-457 | A$^1$.1 | C$_6$H$_5$ | CH$_2$CCH |
| IA-458 | A$^1$.1 | CH(CH$_3$)CH=CH$_2$ | CH(CH$_3$)CH=CH$_2$ |
| IA-459 | A$^1$.1 | CHF$_2$ | CH(CH$_3$)CH=CH$_2$ |
| IA-460 | A$^1$.1 | CH$_2$Cl | CH(CH$_3$)CH=CH$_2$ |
| IA-461 | A$^1$.1 | CH$_2$CH$_2$CN | CH(CH$_3$)CH=CH$_2$ |
| IA-462 | A$^1$.1 | CH$_2$CH$_2$Cl | CH(CH$_3$)CH=CH$_2$ |
| IA-463 | A$^1$.1 | CH$_2$CH$_2$OH | CH(CH$_3$)CH=CH$_2$ |
| IA-464 | A$^1$.1 | CH$_2$CH$_2$CH$_2$OH | CH(CH$_3$)CH=CH$_2$ |
| IA-465 | A$^1$.1 | CH$_2$CH(OH)CH$_2$OH | CH(CH$_3$)CH=CH$_2$ |
| IA-466 | A$^1$.1 | CH$_2$CH(OCH$_3$)$_2$ | CH(CH$_3$)CH=CH$_2$ |
| IA-467 | A$^1$.1 | CH$_2$SCH$_3$ | CH(CH$_3$)CH=CH$_2$ |
| IA-468 | A$^1$.1 | (CH$_2$)$_3$SCH$_3$ | CH(CH$_3$)CH=CH$_2$ |
| IA-469 | A$^1$.1 | CH$_2$S(=O)CH$_3$ | CH(CH$_3$)CH=CH$_2$ |
| IA-470 | A$^1$.1 | CH$_2$S(=O)$_2$CH$_3$ | CH(CH$_3$)CH=CH$_2$ |
| IA-471 | A$^1$.1 | CH$_2$C(=O)CH$_3$ | CH(CH$_3$)CH=CH$_2$ |
| IA-472 | A$^1$.1 | CH$_2$C(=O)CH$_2$CH$_3$ | CH(CH$_3$)CH=CH$_2$ |
| IA-473 | A$^1$.1 | CH$_2$COOH | CH(CH$_3$)CH=CH$_2$ |
| IA-474 | A$^1$.1 | CH$_2$COOCH$_3$ | CH(CH$_3$)CH=CH$_2$ |
| IA-475 | A$^1$.1 | CH$_2$COOCH$_2$CH$_3$ | CH(CH$_3$)CH=CH$_2$ |
| IA-476 | A$^1$.1 | cyclo-C$_3$H$_5$ | CH(CH$_3$)CH=CH$_2$ |
| IA-477 | A$^1$.1 | cyclo-C$_4$H$_7$ | CH(CH$_3$)CH=CH$_2$ |
| IA-478 | A$^1$.1 | cyclo-C$_5$H$_9$ | CH(CH$_3$)CH=CH$_2$ |
| IA-479 | A$^1$.1 | cyclo-C$_6$H$_{11}$ | CH(CH$_3$)CH=CH$_2$ |
| IA-480 | A$^1$.1 | C$_6$H$_5$ | CH(CH$_3$)CH=CH$_2$ |
| IA-481 | A$^1$.1 | CHF$_2$ | CHF$_2$ |
| IA-482 | A$^1$.1 | CH$_2$Cl | CHF$_2$ |
| IA-483 | A$^1$.1 | CH$_2$CH$_2$CN | CHF$_2$ |
| IA-484 | A$^1$.1 | CH$_2$CH$_2$Cl | CHF$_2$ |
| IA-485 | A$^1$.1 | CH$_2$CH$_2$OH | CHF$_2$ |
| IA-486 | A$^1$.1 | CH$_2$CH$_2$CH$_2$OH | CHF$_2$ |
| IA-487 | A$^1$.1 | CH$_2$CH(OH)CH$_2$OH | CHF$_2$ |
| IA-488 | A$^1$.1 | CH$_2$CH(OCH$_3$)$_2$ | CHF$_2$ |
| IA-489 | A$^1$.1 | CH$_2$SCH$_3$ | CHF$_2$ |
| IA-490 | A$^1$.1 | (CH$_2$)$_3$SCH$_3$ | CHF$_2$ |
| IA-491 | A$^1$.1 | CH$_2$S(=O)CH$_3$ | CHF$_2$ |
| IA-492 | A$^1$.1 | CH$_2$S(=O)$_2$CH$_3$ | CHF$_2$ |
| IA-493 | A$^1$.1 | CH$_2$C(=O)CH$_3$ | CHF$_2$ |
| IA-494 | A$^1$.1 | CH$_2$C(=O)CH$_2$CH$_3$ | CHF$_2$ |
| IA-495 | A$^1$.1 | CH$_2$COOH | CHF$_2$ |
| IA-496 | A$^1$.1 | CH$_2$COOCH$_3$ | CHF$_2$ |
| IA-497 | A$^1$.1 | CH$_2$COOCH$_2$CH$_3$ | CHF$_2$ |
| IA-498 | A$^1$.1 | cyclo-C$_3$H$_5$ | CHF$_2$ |
| IA-499 | A$^1$.1 | cyclo-C$_4$H$_7$ | CHF$_2$ |
| IA-500 | A$^1$.1 | cyclo-C$_5$H$_9$ | CHF$_2$ |
| IA-501 | A$^1$.1 | cyclo-C$_6$H$_{11}$ | CHF$_2$ |
| IA-502 | A$^1$.1 | C$_6$H$_5$ | CHF$_2$ |
| IA-503 | A$^1$.1 | CH$_2$Cl | CH$_2$Cl |
| IA-504 | A$^1$.1 | CH$_2$CH$_2$CN | CH$_2$Cl |
| IA-505 | A$^1$.1 | CH$_2$CH$_2$Cl | CH$_2$Cl |
| IA-506 | A$^1$.1 | CH$_2$CH$_2$OH | CH$_2$Cl |
| IA-507 | A$^1$.1 | CH$_2$CH$_2$CH$_2$OH | CH$_2$Cl |
| IA-508 | A$^1$.1 | CH$_2$CH(OH)CH$_2$OH | CH$_2$Cl |
| IA-509 | A$^1$.1 | CH$_2$CH(OCH$_3$)$_2$ | CH$_2$Cl |
| IA-510 | A$^1$.1 | CH$_2$SCH$_3$ | CH$_2$Cl |
| IA-511 | A$^1$.1 | (CH$_2$)$_3$SCH$_3$ | CH$_2$Cl |
| IA-512 | A$^1$.1 | CH$_2$S(=O)CH$_3$ | CH$_2$Cl |
| IA-513 | A$^1$.1 | CH$_2$S(=O)$_2$CH$_3$ | CH$_2$Cl |
| IA-514 | A$^1$.1 | CH$_2$C(=O)CH$_3$ | CH$_2$Cl |
| IA-515 | A$^1$.1 | CH$_2$C(=O)CH$_2$CH$_3$ | CH$_2$Cl |
| IA-516 | A$^1$.1 | CH$_2$COOH | CH$_2$Cl |
| IA-517 | A$^1$.1 | CH$_2$COOCH$_3$ | CH$_2$Cl |
| IA-518 | A$^1$.1 | CH$_2$COOCH$_2$CH$_3$ | CH$_2$Cl |
| IA-519 | A$^1$.1 | cyclo-C$_3$H$_5$ | CH$_2$Cl |
| IA-520 | A$^1$.1 | cyclo-C$_4$H$_7$ | CH$_2$Cl |
| IA-521 | A$^1$.1 | cyclo-C$_5$H$_9$ | CH$_2$Cl |
| IA-522 | A$^1$.1 | cyclo-C$_6$H$_{11}$ | CH$_2$Cl |
| IA-523 | A$^1$.1 | C$_6$H$_5$ | CH$_2$Cl |
| IA-524 | A$^1$.1 | CH$_2$CH$_2$CN | CH$_2$CH$_2$CN |
| IA-525 | A$^1$.1 | CH$_2$CH$_2$Cl | CH$_2$CH$_2$CN |
| IA-526 | A$^1$.1 | CH$_2$CH$_2$OH | CH$_2$CH$_2$CN |
| IA-527 | A$^1$.1 | CH$_2$CH$_2$CH$_2$OH | CH$_2$CH$_2$CN |
| IA-528 | A$^1$.1 | CH$_2$CH(OH)CH$_2$OH | CH$_2$CH$_2$CN |
| IA-529 | A$^1$.1 | CH$_2$CH(OCH$_3$)$_2$ | CH$_2$CH$_2$CN |
| IA-530 | A$^1$.1 | CH$_2$SCH$_3$ | CH$_2$CH$_2$CN |
| IA-531 | A$^1$.1 | (CH$_2$)$_3$SCH$_3$ | CH$_2$CH$_2$CN |
| IA-532 | A$^1$.1 | CH$_2$S(=O)CH$_3$ | CH$_2$CH$_2$CN |
| IA-533 | A$^1$.1 | CH$_2$S(=O)$_2$CH$_3$ | CH$_2$CH$_2$CN |
| IA-534 | A$^1$.1 | CH$_2$C(=O)CH$_3$ | CH$_2$CH$_2$CN |
| IA-535 | A$^1$.1 | CH$_2$C(=O)CH$_2$CH$_3$ | CH$_2$CH$_2$CN |
| IA-536 | A$^1$.1 | CH$_2$COOH | CH$_2$CH$_2$CN |
| IA-537 | A$^1$.1 | CH$_2$COOCH$_3$ | CH$_2$CH$_2$CN |
| IA-538 | A$^1$.1 | CH$_2$COOCH$_2$CH$_3$ | CH$_2$CH$_2$CN |
| IA-539 | A$^1$.1 | cyclo-C$_3$H$_5$ | CH$_2$CH$_2$CN |
| IA-540 | A$^1$.1 | cyclo-C$_4$H$_7$ | CH$_2$CH$_2$CN |
| IA-541 | A$^1$.1 | cyclo-C$_5$H$_9$ | CH$_2$CH$_2$CN |
| IA-542 | A$^1$.1 | cyclo-C$_6$H$_{11}$ | CH$_2$CH$_2$CN |
| IA-543 | A$^1$.1 | C$_6$H$_5$ | CH$_2$CH$_2$CN |
| IA-544 | A$^1$.1 | CH$_2$CH$_2$Cl | CH$_2$CH$_2$Cl |
| IA-545 | A$^1$.1 | CH$_2$CH$_2$OH | CH$_2$CH$_2$Cl |
| IA-546 | A$^1$.1 | CH$_2$CH$_2$CH$_2$OH | CH$_2$CH$_2$Cl |
| IA-547 | A$^1$.1 | CH$_2$CH(OH)CH$_2$OH | CH$_2$CH$_2$Cl |
| IA-548 | A$^1$.1 | CH$_2$CH(OCH$_3$)$_2$ | CH$_2$CH$_2$Cl |
| IA-549 | A$^1$.1 | CH$_2$SCH$_3$ | CH$_2$CH$_2$Cl |
| IA-550 | A$^1$.1 | (CH$_2$)$_3$SCH$_3$ | CH$_2$CH$_2$Cl |
| IA-551 | A$^1$.1 | CH$_2$S(=O)CH$_3$ | CH$_2$CH$_2$Cl |
| IA-552 | A$^1$.1 | CH$_2$S(=O)$_2$CH$_3$ | CH$_2$CH$_2$Cl |
| IA-553 | A$^1$.1 | CH$_2$C(=O)CH$_3$ | CH$_2$CH$_2$Cl |
| IA-554 | A$^1$.1 | CH$_2$C(=O)CH$_2$CH$_3$ | CH$_2$CH$_2$Cl |
| IA-555 | A$^1$.1 | CH$_2$COOH | CH$_2$CH$_2$Cl |
| IA-556 | A$^1$.1 | CH$_2$COOCH$_3$ | CH$_2$CH$_2$Cl |
| IA-557 | A$^1$.1 | CH$_2$COOCH$_2$CH$_3$ | CH$_2$CH$_2$Cl |
| IA-558 | A$^1$.1 | cyclo-C$_3$H$_5$ | CH$_2$CH$_2$Cl |
| IA-559 | A$^1$.1 | cyclo-C$_4$H$_7$ | CH$_2$CH$_2$Cl |
| IA-560 | A$^1$.1 | cyclo-C$_5$H$_9$ | CH$_2$CH$_2$Cl |
| IA-561 | A$^1$.1 | cyclo-C$_6$H$_{11}$ | CH$_2$CH$_2$Cl |
| IA-562 | A$^1$.1 | C$_6$H$_5$ | CH$_2$CH$_2$Cl |
| IA-563 | A$^1$.1 | CH$_2$CH$_2$OH | CH$_2$CH$_2$OH |
| IA-564 | A$^1$.1 | CH$_2$CH$_2$CH$_2$OH | CH$_2$CH$_2$OH |
| IA-565 | A$^1$.1 | CH$_2$CH(OH)CH$_2$OH | CH$_2$CH$_2$OH |
| IA-566 | A$^1$.1 | CH$_2$CH(OCH$_3$)$_2$ | CH$_2$CH$_2$OH |
| IA-567 | A$^1$.1 | CH$_2$SCH$_3$ | CH$_2$CH$_2$OH |
| IA-568 | A$^1$.1 | (CH$_2$)$_3$SCH$_3$ | CH$_2$CH$_2$OH |
| IA-569 | A$^1$.1 | CH$_2$S(=O)CH$_3$ | CH$_2$CH$_2$OH |
| IA-570 | A$^1$.1 | CH$_2$S(=O)$_2$CH$_3$ | CH$_2$CH$_2$OH |
| IA-571 | A$^1$.1 | CH$_2$C(=O)CH$_3$ | CH$_2$CH$_2$OH |
| IA-572 | A$^1$.1 | CH$_2$C(=O)CH$_2$CH$_3$ | CH$_2$CH$_2$OH |
| IA-573 | A$^1$.1 | CH$_2$COOH | CH$_2$CH$_2$OH |
| IA-574 | A$^1$.1 | CH$_2$COOCH$_3$ | CH$_2$CH$_2$OH |
| IA-575 | A$^1$.1 | CH$_2$COOCH$_2$CH$_3$ | CH$_2$CH$_2$OH |
| IA-576 | A$^1$.1 | cyclo-C$_3$H$_5$ | CH$_2$CH$_2$OH |
| IA-577 | A$^1$.1 | cyclo-C$_4$H$_7$ | CH$_2$CH$_2$OH |
| IA-578 | A$^1$.1 | cyclo-C$_5$H$_9$ | CH$_2$CH$_2$OH |
| IA-579 | A$^1$.1 | cyclo-C$_6$H$_{11}$ | CH$_2$CH$_2$OH |
| IA-580 | A$^1$.1 | C$_6$H$_5$ | CH$_2$CH$_2$OH |
| IA-581 | A$^1$.1 | CH$_2$CH$_2$CH$_2$OH | CH$_2$CH$_2$CH$_2$OH |
| IA-582 | A$^1$.1 | CH$_2$CH(OH)CH$_2$OH | CH$_2$CH$_2$CH$_2$OH |
| IA-583 | A$^1$.1 | CH$_2$CH(OCH$_3$)$_2$ | CH$_2$CH$_2$CH$_2$OH |
| IA-584 | A$^1$.1 | CH$_2$SCH$_3$ | CH$_2$CH$_2$CH$_2$OH |
| IA-585 | A$^1$.1 | (CH$_2$)$_3$SCH$_3$ | CH$_2$CH$_2$CH$_2$OH |
| IA-586 | A$^1$.1 | CH$_2$S(=O)CH$_3$ | CH$_2$CH$_2$CH$_2$OH |
| IA-587 | A$^1$.1 | CH$_2$S(=O)$_2$CH$_3$ | CH$_2$CH$_2$CH$_2$OH |
| IA-588 | A$^1$.1 | CH$_2$C(=O)CH$_3$ | CH$_2$CH$_2$CH$_2$OH |
| IA-589 | A$^1$.1 | CH$_2$C(=O)CH$_2$CH$_3$ | CH$_2$CH$_2$CH$_2$OH |
| IA-590 | A$^1$.1 | CH$_2$COOH | CH$_2$CH$_2$CH$_2$OH |
| IA-591 | A$^1$.1 | CH$_2$COOCH$_3$ | CH$_2$CH$_2$CH$_2$OH |
| IA-592 | A$^1$.1 | CH$_2$COOCH$_2$CH$_3$ | CH$_2$CH$_2$CH$_2$OH |
| IA-593 | A$^1$.1 | cyclo-C$_3$H$_5$ | CH$_2$CH$_2$CH$_2$OH |

TABLE C-continued

| No. | A | R$^e$ | R$^f$ |
|---|---|---|---|
| IA-594 | A$^1$.1 | cyclo-C$_4$H$_7$ | CH$_2$CH$_2$CH$_2$OH |
| IA-595 | A$^1$.1 | cyclo-C$_5$H$_9$ | CH$_2$CH$_2$CH$_2$OH |
| IA-596 | A$^1$.1 | cyclo-C$_6$H$_{11}$ | CH$_2$CH$_2$CH$_2$OH |
| IA-597 | A$^1$.1 | C$_6$H$_5$ | CH$_2$CH$_2$CH$_2$OH |
| IA-598 | A$^1$.1 | CH$_2$CH(OH)CH$_2$OH | CH$_2$CH(OH)CH$_2$OH |
| IA-599 | A$^1$.1 | CH$_2$CH(OCH$_3$)$_2$ | CH$_2$CH(OH)CH$_2$OH |
| IA-600 | A$^1$.1 | CH$_2$SCH$_3$ | CH$_2$CH(OH)CH$_2$OH |
| IA-601 | A$^1$.1 | (CH$_2$)$_3$SCH$_3$ | CH$_2$CH(OH)CH$_2$OH |
| IA-602 | A$^1$.1 | CH$_2$S(=O)CH$_3$ | CH$_2$CH(OH)CH$_2$OH |
| IA-603 | A$^1$.1 | CH$_2$S(=O)$_2$CH$_3$ | CH$_2$CH(OH)CH$_2$OH |
| IA-604 | A$^1$.1 | CH$_2$C(=O)CH$_3$ | CH$_2$CH(OH)CH$_2$OH |
| IA-605 | A$^1$.1 | CH$_2$C(=O)CH$_2$CH$_3$ | CH$_2$CH(OH)CH$_2$OH |
| IA-606 | A$^1$.1 | CH$_2$COOH | CH$_2$CH(OH)CH$_2$OH |
| IA-607 | A$^1$.1 | CH$_2$COOCH$_3$ | CH$_2$CH(OH)CH$_2$OH |
| IA-608 | A$^1$.1 | CH$_2$COOCH$_2$CH$_3$ | CH$_2$CH(OH)CH$_2$OH |
| IA-609 | A$^1$.1 | cyclo-C$_3$H$_5$ | CH$_2$CH(OH)CH$_2$OH |
| IA-610 | A$^1$.1 | cyclo-C$_4$H$_7$ | CH$_2$CH(OH)CH$_2$OH |
| IA-611 | A$^1$.1 | cyclo-C$_5$H$_9$ | CH$_2$CH(OH)CH$_2$OH |
| IA-612 | A$^1$.1 | cyclo-C$_6$H$_{11}$ | CH$_2$CH(OH)CH$_2$OH |
| IA-613 | A$^1$.1 | C$_6$H$_5$ | CH$_2$CH(OH)CH$_2$OH |
| IA-614 | A$^1$.1 | CH$_2$CH(OCH$_3$)$_2$ | CH$_2$CH(OCH$_3$)$_2$ |
| IA-615 | A$^1$.1 | CH$_2$SCH$_3$ | CH$_2$CH(OCH$_3$)$_2$ |
| IA-616 | A$^1$.1 | (CH$_2$)$_3$SCH$_3$ | CH$_2$CH(OCH$_3$)$_2$ |
| IA-617 | A$^1$.1 | CH$_2$S(=O)CH$_3$ | CH$_2$CH(OCH$_3$)$_2$ |
| IA-618 | A$^1$.1 | CH$_2$S(=O)$_2$CH$_3$ | CH$_2$CH(OCH$_3$)$_2$ |
| IA-619 | A$^1$.1 | CH$_2$C(=O)CH$_3$ | CH$_2$CH(OCH$_3$)$_2$ |
| IA-620 | A$^1$.1 | CH$_2$C(=O)CH$_2$CH$_3$ | CH$_2$CH(OCH$_3$)$_2$ |
| IA-621 | A$^1$.1 | CH$_2$COOH | CH$_2$CH(OCH$_3$)$_2$ |
| IA-622 | A$^1$.1 | CH$_2$COOCH$_3$ | CH$_2$CH(OCH$_3$)$_2$ |
| IA-623 | A$^1$.1 | CH$_2$COOCH$_2$CH$_3$ | CH$_2$CH(OCH$_3$)$_2$ |
| IA-624 | A$^1$.1 | cyclo-C$_3$H$_5$ | CH$_2$CH(OCH$_3$)$_2$ |
| IA-625 | A$^1$.1 | cyclo-C$_4$H$_7$ | CH$_2$CH(OCH$_3$)$_2$ |
| IA-626 | A$^1$.1 | cyclo-C$_5$H$_9$ | CH$_2$CH(OCH$_3$)$_2$ |
| IA-627 | A$^1$.1 | cyclo-C$_6$H$_{11}$ | CH$_2$CH(OCH$_3$)$_2$ |
| IA-628 | A$^1$.1 | C$_6$H$_5$ | CH$_2$CH(OCH$_3$)$_2$ |
| IA-629 | A$^1$.1 | CH$_2$SCH$_3$ | CH$_2$SCH$_3$ |
| IA-630 | A$^1$.1 | (CH$_2$)$_3$SCH$_3$ | CH$_2$SCH$_3$ |
| IA-631 | A$^1$.1 | CH$_2$S(=O)CH$_3$ | CH$_2$SCH$_3$ |
| IA-632 | A$^1$.1 | CH$_2$S(=O)$_2$CH$_3$ | CH$_2$SCH$_3$ |
| IA-633 | A$^1$.1 | CH$_2$C(=O)CH$_3$ | CH$_2$SCH$_3$ |
| IA-634 | A$^1$.1 | CH$_2$C(=O)CH$_2$CH$_3$ | CH$_2$SCH$_3$ |
| IA-635 | A$^1$.1 | CH$_2$COOH | CH$_2$SCH$_3$ |
| IA-636 | A$^1$.1 | CH$_2$COOCH$_3$ | CH$_2$SCH$_3$ |
| IA-637 | A$^1$.1 | CH$_2$COOCH$_2$CH$_3$ | CH$_2$SCH$_3$ |
| IA-638 | A$^1$.1 | cyclo-C$_3$H$_5$ | CH$_2$SCH$_3$ |
| IA-639 | A$^1$.1 | cyclo-C$_4$H$_7$ | CH$_2$SCH$_3$ |
| IA-640 | A$^1$.1 | cyclo-C$_5$H$_9$ | CH$_2$SCH$_3$ |
| IA-641 | A$^1$.1 | cyclo-C$_6$H$_{11}$ | CH$_2$SCH$_3$ |
| IA-642 | A$^1$.1 | C$_6$H$_5$ | CH$_2$SCH$_3$ |
| IA-643 | A$^1$.1 | (CH$_2$)$_3$SCH$_3$ | (CH$_2$)$_3$SCH$_3$ |
| IA-644 | A$^1$.1 | CH$_2$S(=O)CH$_3$ | (CH$_2$)$_3$SCH$_3$ |
| IA-645 | A$^1$.1 | CH$_2$S(=O)$_2$CH$_3$ | (CH$_2$)$_3$SCH$_3$ |
| IA-646 | A$^1$.1 | CH$_2$C(=O)CH$_3$ | (CH$_2$)$_3$SCH$_3$ |
| IA-647 | A$^1$.1 | CH$_2$C(=O)CH$_2$CH$_3$ | (CH$_2$)$_3$SCH$_3$ |
| IA-648 | A$^1$.1 | CH$_2$COOH | (CH$_2$)$_3$SCH$_3$ |
| IA-649 | A$^1$.1 | CH$_2$COOCH$_3$ | (CH$_2$)$_3$SCH$_3$ |
| IA-650 | A$^1$.1 | CH$_2$COOCH$_2$CH$_3$ | (CH$_2$)$_3$SCH$_3$ |
| IA-651 | A$^1$.1 | cyclo-C$_3$H$_5$ | (CH$_2$)$_3$SCH$_3$ |
| IA-652 | A$^1$.1 | cyclo-C$_4$H$_7$ | (CH$_2$)$_3$SCH$_3$ |
| IA-653 | A$^1$.1 | cyclo-C$_5$H$_9$ | (CH$_2$)$_3$SCH$_3$ |
| IA-654 | A$^1$.1 | cyclo-C$_6$H$_{11}$ | (CH$_2$)$_3$SCH$_3$ |
| IA-655 | A$^1$.1 | C$_6$H$_5$ | (CH$_2$)$_3$SCH$_3$ |
| IA-656 | A$^1$.1 | CH$_2$S(=O)CH$_3$ | CH$_2$S(=O)CH$_3$ |
| IA-657 | A$^1$.1 | CH$_2$S(=O)$_2$CH$_3$ | CH$_2$S(=O)CH$_3$ |
| IA-658 | A$^1$.1 | CH$_2$C(=O)CH$_3$ | CH$_2$S(=O)CH$_3$ |
| IA-659 | A$^1$.1 | CH$_2$C(=O)CH$_2$CH$_3$ | CH$_2$S(=O)CH$_3$ |
| IA-660 | A$^1$.1 | CH$_2$COOH | CH$_2$S(=O)CH$_3$ |
| IA-661 | A$^1$.1 | CH$_2$COOCH$_3$ | CH$_2$S(=O)CH$_3$ |
| IA-662 | A$^1$.1 | CH$_2$COOCH$_2$CH$_3$ | CH$_2$S(=O)CH$_3$ |
| IA-663 | A$^1$.1 | cyclo-C$_3$H$_5$ | CH$_2$S(=O)CH$_3$ |
| IA-664 | A$^1$.1 | cyclo-C$_4$H$_7$ | CH$_2$S(=O)CH$_3$ |
| IA-665 | A$^1$.1 | cyclo-C$_5$H$_9$ | CH$_2$S(=O)CH$_3$ |
| IA-666 | A$^1$.1 | cyclo-C$_6$H$_{11}$ | CH$_2$S(=O)CH$_3$ |
| IA-667 | A$^1$.1 | C$_6$H$_5$ | CH$_2$S(=O)CH$_3$ |
| IA-668 | A$^1$.1 | CH$_2$S(=O)$_2$CH$_3$ | CH$_2$S(=O)$_2$CH$_3$ |
| IA-669 | A$^1$.1 | CH$_2$C(=O)CH$_3$ | CH$_2$S(=O)$_2$CH$_3$ |
| IA-670 | A$^1$.1 | CH$_2$C(=O)CH$_2$CH$_3$ | CH$_2$S(=O)$_2$CH$_3$ |
| IA-671 | A$^1$.1 | CH$_2$COOH | CH$_2$S(=O)$_2$CH$_3$ |
| IA-672 | A$^1$.1 | CH$_2$COOCH$_3$ | CH$_2$S(=O)$_2$CH$_3$ |
| IA-673 | A$^1$.1 | CH$_2$COOCH$_2$CH$_3$ | CH$_2$S(=O)$_2$CH$_3$ |
| IA-674 | A$^1$.1 | cyclo-C$_3$H$_5$ | CH$_2$S(=O)$_2$CH$_3$ |
| IA-675 | A$^1$.1 | cyclo-C$_4$H$_7$ | CH$_2$S(=O)$_2$CH$_3$ |
| IA-676 | A$^1$.1 | cyclo-C$_5$H$_9$ | CH$_2$S(=O)$_2$CH$_3$ |
| IA-677 | A$^1$.1 | cyclo-C$_6$H$_{11}$ | CH$_2$S(=O)$_2$CH$_3$ |
| IA-678 | A$^1$.1 | C$_6$H$_5$ | CH$_2$S(=O)$_2$CH$_3$ |
| IA-679 | A$^1$.1 | CH$_2$C(=O)CH$_3$ | CH$_2$C(=O)CH$_3$ |
| IA-680 | A$^1$.1 | CH$_2$C(=O)CH$_2$CH$_3$ | CH$_2$C(=O)CH$_3$ |
| IA-681 | A$^1$.1 | CH$_2$COOH | CH$_2$C(=O)CH$_3$ |
| IA-682 | A$^1$.1 | CH$_2$COOCH$_3$ | CH$_2$C(=O)CH$_3$ |
| IA-683 | A$^1$.1 | CH$_2$COOCH$_2$CH$_3$ | CH$_2$C(=O)CH$_3$ |
| IA-684 | A$^1$.1 | cyclo-C$_3$H$_5$ | CH$_2$C(=O)CH$_3$ |
| IA-685 | A$^1$.1 | cyclo-C$_4$H$_7$ | CH$_2$C(=O)CH$_3$ |
| IA-686 | A$^1$.1 | cyclo-C$_5$H$_9$ | CH$_2$C(=O)CH$_3$ |
| IA-687 | A$^1$.1 | cyclo-C$_6$H$_{11}$ | CH$_2$C(=O)CH$_3$ |
| IA-688 | A$^1$.1 | C$_6$H$_5$ | CH$_2$C(=O)CH$_3$ |
| IA-689 | A$^1$.1 | CH$_2$C(=O)CH$_2$CH$_3$ | CH$_2$C(=O)CH$_2$CH$_3$ |
| IA-690 | A$^1$.1 | CH$_2$COOH | CH$_2$C(=O)CH$_2$CH$_3$ |
| IA-691 | A$^1$.1 | CH$_2$COOCH$_3$ | CH$_2$C(=O)CH$_2$CH$_3$ |
| IA-692 | A$^1$.1 | CH$_2$COOCH$_2$CH$_3$ | CH$_2$C(=O)CH$_2$CH$_3$ |
| IA-693 | A$^1$.1 | cyclo-C$_3$H$_5$ | CH$_2$C(=O)CH$_2$CH$_3$ |
| IA-694 | A$^1$.1 | cyclo-C$_4$H$_7$ | CH$_2$C(=O)CH$_2$CH$_3$ |
| IA-695 | A$^1$.1 | cyclo-C$_5$H$_9$ | CH$_2$C(=O)CH$_2$CH$_3$ |
| IA-696 | A$^1$.1 | cyclo-C$_6$H$_{11}$ | CH$_2$C(=O)CH$_2$CH$_3$ |
| IA-697 | A$^1$.1 | C$_6$H$_5$ | CH$_2$C(=O)CH$_2$CH$_3$ |
| IA-698 | A$^1$.1 | CH$_2$COOH | CH$_2$COOH |
| IA-699 | A$^1$.1 | CH$_2$COOCH$_3$ | CH$_2$COOH |
| IA-700 | A$^1$.1 | CH$_2$COOCH$_2$CH$_3$ | CH$_2$COOH |
| IA-701 | A$^1$.1 | cyclo-C$_3$H$_5$ | CH$_2$COOH |
| IA-702 | A$^1$.1 | cyclo-C$_4$H$_7$ | CH$_2$COOH |
| IA-703 | A$^1$.1 | cyclo-C$_5$H$_9$ | CH$_2$COOH |
| IA-704 | A$^1$.1 | cyclo-C$_6$H$_{11}$ | CH$_2$COOH |
| IA-705 | A$^1$.1 | C$_6$H$_5$ | CH$_2$COOH |
| IA-706 | A$^1$.1 | CH$_2$COOCH$_3$ | CH$_2$COOCH$_3$ |
| IA-707 | A$^1$.1 | CH$_2$COOCH$_2$CH$_3$ | CH$_2$COOCH$_3$ |
| IA-708 | A$^1$.1 | cyclo-C$_3$H$_5$ | CH$_2$COOCH$_3$ |
| IA-709 | A$^1$.1 | cyclo-C$_4$H$_7$ | CH$_2$COOCH$_3$ |
| IA-710 | A$^1$.1 | cyclo-C$_5$H$_9$ | CH$_2$COOCH$_3$ |
| IA-711 | A$^1$.1 | cyclo-C$_6$H$_{11}$ | CH$_2$COOCH$_3$ |
| IA-712 | A$^1$.1 | C$_6$H$_5$ | CH$_2$COOCH$_3$ |
| IA-713 | A$^1$.1 | CH$_2$COOCH$_2$CH$_3$ | CH$_2$COOCH$_2$CH$_3$ |
| IA-714 | A$^1$.1 | cyclo-C$_3$H$_5$ | CH$_2$COOCH$_2$CH$_3$ |
| IA-715 | A$^1$.1 | cyclo-C$_4$H$_7$ | CH$_2$COOCH$_2$CH$_3$ |
| IA-716 | A$^1$.1 | cyclo-C$_5$H$_9$ | CH$_2$COOCH$_2$CH$_3$ |
| IA-717 | A$^1$.1 | cyclo-C$_6$H$_{11}$ | CH$_2$COOCH$_2$CH$_3$ |
| IA-718 | A$^1$.1 | C$_6$H$_5$ | CH$_2$COOCH$_2$CH$_3$ |
| IA-719 | A$^1$.1 | cyclo-C$_3$H$_5$ | cyclo-C$_3$H$_5$ |
| IA-720 | A$^1$.1 | cyclo-C$_4$H$_7$ | cyclo-C$_3$H$_5$ |
| IA-721 | A$^1$.1 | cyclo-C$_5$H$_9$ | cyclo-C$_3$H$_5$ |
| IA-722 | A$^1$.1 | cyclo-C$_6$H$_{11}$ | cyclo-C$_3$H$_5$ |
| IA-723 | A$^1$.1 | C$_6$H$_5$ | cyclo-C$_3$H$_5$ |
| IA-724 | A$^1$.1 | cyclo-C$_4$H$_7$ | cyclo-C$_4$H$_7$ |
| IA-725 | A$^1$.1 | cyclo-C$_5$H$_9$ | cyclo-C$_4$H$_7$ |
| IA-726 | A$^1$.1 | cyclo-C$_6$H$_{11}$ | cyclo-C$_4$H$_7$ |
| IA-727 | A$^1$.1 | C$_6$H$_5$ | cyclo-C$_4$H$_7$ |
| IA-728 | A$^1$.1 | cyclo-C$_5$H$_9$ | cyclo-C$_5$H$_9$ |
| IA-729 | A$^1$.1 | cyclo-C$_6$H$_{11}$ | cyclo-C$_5$H$_9$ |
| IA-730 | A$^1$.1 | C$_6$H$_5$ | cyclo-C$_5$H$_9$ |
| IA-731 | A$^1$.1 | cyclo-C$_6$H$_{11}$ | cyclo-C$_6$H$_{11}$ |
| IA-732 | A$^1$.1 | C$_6$H$_5$ | cyclo-C$_6$H$_{11}$ |
| IA-733 | A$^1$.1 | C$_6$H$_5$ | C$_6$H$_5$ |
| IA-734 | A$^1$.2 (—N=S(=O)(R$^e$)(R$^f$)) | CH$_3$ | CH$_3$ |
| IA-735 | A$^1$.2 | CH$_2$CH$_3$ | CH$_3$ |
| IA-736 | A$^1$.2 | CH=CH$_2$ | CH$_3$ |
| IA-737 | A$^1$.2 | CH$_2$CH$_2$CH$_3$ | CH$_3$ |
| IA-738 | A$^1$.2 | CH(CH$_3$)$_2$ | CH$_3$ |
| IA-739 | A$^1$.2 | CH$_2$CH$_2$CH$_2$CH$_3$ | CH$_3$ |
| IA-740 | A$^1$.2 | C(CH$_3$)$_3$ | CH$_3$ |
| IA-741 | A$^1$.2 | CH$_2$CH(CH$_3$)$_2$ | CH$_3$ |
| IA-742 | A$^1$.2 | CH(CH$_3$)CH$_2$CH$_3$ | CH$_3$ |

TABLE C-continued

| No. | A | $R^e$ | $R^f$ |
|---|---|---|---|
| IA-743 | $A^1.2$ | $CH_2CHCH_2$ | $CH_3$ |
| IA-744 | $A^1.2$ | $CH_2CCH$ | $CH_3$ |
| IA-745 | $A^1.2$ | $CH(CH_3)CH=CH_2$ | $CH_3$ |
| IA-746 | $A^1.2$ | $CHF_2$ | $CH_3$ |
| IA-747 | $A^1.2$ | $CH_2Cl$ | $CH_3$ |
| IA-748 | $A^1.2$ | $CH_2CH_2CN$ | $CH_3$ |
| IA-749 | $A^1.2$ | $CH_2CH_2Cl$ | $CH_3$ |
| IA-750 | $A^1.2$ | $CH_2CH_2OH$ | $CH_3$ |
| IA-751 | $A^1.2$ | $CH_2CH_2CH_2OH$ | $CH_3$ |
| IA-752 | $A^1.2$ | $CH_2CH(OH)CH_2OH$ | $CH_3$ |
| IA-753 | $A^1.2$ | $CH_2CH(OCH_3)_2$ | $CH_3$ |
| IA-754 | $A^1.2$ | $CH_2SCH_3$ | $CH_3$ |
| IA-755 | $A^1.2$ | $(CH_2)_3SCH_3$ | $CH_3$ |
| IA-756 | $A^1.2$ | $CH_2S(=O)CH_3$ | $CH_3$ |
| IA-757 | $A^1.2$ | $CH_2S(=O)_2CH_3$ | $CH_3$ |
| IA-758 | $A^1.2$ | $CH_2C(=O)CH_3$ | $CH_3$ |
| IA-759 | $A^1.2$ | $CH_2C(=O)CH_2CH_3$ | $CH_3$ |
| IA-760 | $A^1.2$ | $CH_2COOH$ | $CH_3$ |
| IA-761 | $A^1.2$ | $CH_2COOCH_3$ | $CH_3$ |
| IA-762 | $A^1.2$ | $CH_2COOCH_2CH_3$ | $CH_3$ |
| IA-763 | $A^1.2$ | cyclo-$C_3H_5$ | $CH_3$ |
| IA-764 | $A^1.2$ | cyclo-$C_4H_7$ | $CH_3$ |
| IA-765 | $A^1.2$ | cyclo-$C_5H_9$ | $CH_3$ |
| IA-766 | $A^1.2$ | cyclo-$C_6H_{11}$ | $CH_3$ |
| IA-767 | $A^1.2$ | $C_6H_5$ | $CH_3$ |
| IA-768 | $A^1.2$ | $CH_2CH_3$ | $CH_2CH_3$ |
| IA-769 | $A^1.2$ | $CH=CH_2$ | $CH_2CH_3$ |
| IA-770 | $A^1.2$ | $CH_2CH_2CH_3$ | $CH_2CH_3$ |
| IA-771 | $A^1.2$ | $CH(CH_3)_2$ | $CH_2CH_3$ |
| IA-772 | $A^1.2$ | $CH_2CH_2CH_2CH_3$ | $CH_2CH_3$ |
| IA-773 | $A^1.2$ | $C(CH_3)_3$ | $CH_2CH_3$ |
| IA-774 | $A^1.2$ | $CH_2CH(CH_3)_2$ | $CH_2CH_3$ |
| IA-775 | $A^1.2$ | $CH(CH_3)CH_2CH_3$ | $CH_2CH_3$ |
| IA-776 | $A^1.2$ | $CH_2CHCH_2$ | $CH_2CH_3$ |
| IA-777 | $A^1.2$ | $CH_2CCH$ | $CH_2CH_3$ |
| IA-778 | $A^1.2$ | $CH(CH_3)CH=CH_2$ | $CH_2CH_3$ |
| IA-779 | $A^1.2$ | $CHF_2$ | $CH_2CH_3$ |
| IA-780 | $A^1.2$ | $CH_2Cl$ | $CH_2CH_3$ |
| IA-781 | $A^1.2$ | $CH_2CH_2CN$ | $CH_2CH_3$ |
| IA-782 | $A^1.2$ | $CH_2CH_2Cl$ | $CH_2CH_3$ |
| IA-783 | $A^1.2$ | $CH_2CH_2OH$ | $CH_2CH_3$ |
| IA-784 | $A^1.2$ | $CH_2CH_2CH_2OH$ | $CH_2CH_3$ |
| IA-785 | $A^1.2$ | $CH_2CH(OH)CH_2OH$ | $CH_2CH_3$ |
| IA-786 | $A^1.2$ | $CH_2CH(OCH_3)_2$ | $CH_2CH_3$ |
| IA-787 | $A^1.2$ | $CH_2SCH_3$ | $CH_2CH_3$ |
| IA-788 | $A^1.2$ | $(CH_2)_3SCH_3$ | $CH_2CH_3$ |
| IA-789 | $A^1.2$ | $CH_2S(=O)CH_3$ | $CH_2CH_3$ |
| IA-790 | $A^1.2$ | $CH_2S(=O)_2CH_3$ | $CH_2CH_3$ |
| IA-791 | $A^1.2$ | $CH_2C(=O)CH_3$ | $CH_2CH_3$ |
| IA-792 | $A^1.2$ | $CH_2C(=O)CH_2CH_3$ | $CH_2CH_3$ |
| IA-793 | $A^1.2$ | $CH_2COOH$ | $CH_2CH_3$ |
| IA-794 | $A^1.2$ | $CH_2COOCH_3$ | $CH_2CH_3$ |
| IA-795 | $A^1.2$ | $CH_2COOCH_2CH_3$ | $CH_2CH_3$ |
| IA-796 | $A^1.2$ | cyclo-$C_3H_5$ | $CH_2CH_3$ |
| IA-797 | $A^1.2$ | cyclo-$C_4H_7$ | $CH_2CH_3$ |
| IA-798 | $A^1.2$ | cyclo-$C_5H_9$ | $CH_2CH_3$ |
| IA-799 | $A^1.2$ | cyclo-$C_6H_{11}$ | $CH_2CH_3$ |
| IA-800 | $A^1.2$ | $C_6H_5$ | $CH_2CH_3$ |
| IA-801 | $A^1.2$ | $CH=CH_2$ | $CH=CH_2$ |
| IA-802 | $A^1.2$ | $CH_2CH_2CH_3$ | $CH=CH_2$ |
| IA-803 | $A^1.2$ | $CH(CH_3)_2$ | $CH=CH_2$ |
| IA-804 | $A^1.2$ | $CH_2CH_2CH_2CH_3$ | $CH=CH_2$ |
| IA-805 | $A^1.2$ | $C(CH_3)_3$ | $CH=CH_2$ |
| IA-806 | $A^1.2$ | $CH_2CH(CH_3)_2$ | $CH=CH_2$ |
| IA-807 | $A^1.2$ | $CH(CH_3)CH_2CH_3$ | $CH=CH_2$ |
| IA-808 | $A^1.2$ | $CH_2CHCH_2$ | $CH=CH_2$ |
| IA-809 | $A^1.2$ | $CH_2CCH$ | $CH=CH_2$ |
| IA-810 | $A^1.2$ | $CH(CH_3)CH=CH_2$ | $CH=CH_2$ |
| IA-811 | $A^1.2$ | $CHF_2$ | $CH=CH_2$ |
| IA-812 | $A^1.2$ | $CH_2Cl$ | $CH=CH_2$ |
| IA-813 | $A^1.2$ | $CH_2CH_2CN$ | $CH=CH_2$ |
| IA-814 | $A^1.2$ | $CH_2CH_2Cl$ | $CH=CH_2$ |
| IA-815 | $A^1.2$ | $CH_2CH_2OH$ | $CH=CH_2$ |
| IA-816 | $A^1.2$ | $CH_2CH_2CH_2OH$ | $CH=CH_2$ |
| IA-817 | $A^1.2$ | $CH_2CH(OH)CH_2OH$ | $CH=CH_2$ |
| IA-818 | $A^1.2$ | $CH_2CH(OCH_3)_2$ | $CH=CH_2$ |
| IA-819 | $A^1.2$ | $CH_2SCH_3$ | $CH=CH_2$ |
| IA-820 | $A^1.2$ | $(CH_2)_3SCH_3$ | $CH=CH_2$ |
| IA-821 | $A^1.2$ | $CH_2S(=O)CH_3$ | $CH=CH_2$ |
| IA-822 | $A^1.2$ | $CH_2S(=O)_2CH_3$ | $CH=CH_2$ |
| IA-823 | $A^1.2$ | $CH_2C(=O)CH_3$ | $CH=CH_2$ |
| IA-824 | $A^1.2$ | $CH_2C(=O)CH_2CH_3$ | $CH=CH_2$ |
| IA-825 | $A^1.2$ | $CH_2COOH$ | $CH=CH_2$ |
| IA-826 | $A^1.2$ | $CH_2COOCH_3$ | $CH=CH_2$ |
| IA-827 | $A^1.2$ | $CH_2COOCH_2CH_3$ | $CH=CH_2$ |
| IA-828 | $A^1.2$ | cyclo-$C_3H_5$ | $CH=CH_2$ |
| IA-829 | $A^1.2$ | cyclo-$C_4H_7$ | $CH=CH_2$ |
| IA-830 | $A^1.2$ | cyclo-$C_5H_9$ | $CH=CH_2$ |
| IA-831 | $A^1.2$ | cyclo-$C_6H_{11}$ | $CH=CH_2$ |
| IA-832 | $A^1.2$ | $C_6H_5$ | $CH=CH_2$ |
| IA-833 | $A^1.2$ | $CH_2CH_2CH_3$ | $CH_2CH_2CH_3$ |
| IA-834 | $A^1.2$ | $CH(CH_3)_2$ | $CH_2CH_2CH_3$ |
| IA-835 | $A^1.2$ | $CH_2CH_2CH_2CH_3$ | $CH_2CH_2CH_3$ |
| IA-836 | $A^1.2$ | $C(CH_3)_3$ | $CH_2CH_2CH_3$ |
| IA-837 | $A^1.2$ | $CH_2CH(CH_3)_2$ | $CH_2CH_2CH_3$ |
| IA-838 | $A^1.2$ | $CH(CH_3)CH_2CH_3$ | $CH_2CH_2CH_3$ |
| IA-839 | $A^1.2$ | $CH_2CHCH_2$ | $CH_2CH_2CH_3$ |
| IA-840 | $A^1.2$ | $CH_2CCH$ | $CH_2CH_2CH_3$ |
| IA-841 | $A^1.2$ | $CH(CH_3)CH=CH_2$ | $CH_2CH_2CH_3$ |
| IA-842 | $A^1.2$ | $CHF_2$ | $CH_2CH_2CH_3$ |
| IA-843 | $A^1.2$ | $CH_2Cl$ | $CH_2CH_2CH_3$ |
| IA-844 | $A^1.2$ | $CH_2CH_2CN$ | $CH_2CH_2CH_3$ |
| IA-845 | $A^1.2$ | $CH_2CH_2Cl$ | $CH_2CH_2CH_3$ |
| IA-846 | $A^1.2$ | $CH_2CH_2OH$ | $CH_2CH_2CH_3$ |
| IA-847 | $A^1.2$ | $CH_2CH_2CH_2OH$ | $CH_2CH_2CH_3$ |
| IA-848 | $A^1.2$ | $CH_2CH(OH)CH_2OH$ | $CH_2CH_2CH_3$ |
| IA-849 | $A^1.2$ | $CH_2CH(OCH_3)_2$ | $CH_2CH_2CH_3$ |
| IA-850 | $A^1.2$ | $CH_2SCH_3$ | $CH_2CH_2CH_3$ |
| IA-851 | $A^1.2$ | $(CH_2)_3SCH_3$ | $CH_2CH_2CH_3$ |
| IA-852 | $A^1.2$ | $CH_2S(=O)CH_3$ | $CH_2CH_2CH_3$ |
| IA-853 | $A^1.2$ | $CH_2S(=O)_2CH_3$ | $CH_2CH_2CH_3$ |
| IA-854 | $A^1.2$ | $CH_2C(=O)CH_3$ | $CH_2CH_2CH_3$ |
| IA-855 | $A^1.2$ | $CH_2C(=O)CH_2CH_3$ | $CH_2CH_2CH_3$ |
| IA-856 | $A^1.2$ | $CH_2COOH$ | $CH_2CH_2CH_3$ |
| IA-857 | $A^1.2$ | $CH_2COOCH_3$ | $CH_2CH_2CH_3$ |
| IA-858 | $A^1.2$ | $CH_2COOCH_2CH_3$ | $CH_2CH_2CH_3$ |
| IA-859 | $A^1.2$ | cyclo-$C_3H_5$ | $CH_2CH_2CH_3$ |
| IA-860 | $A^1.2$ | cyclo-$C_4H_7$ | $CH_2CH_2CH_3$ |
| IA-861 | $A^1.2$ | cyclo-$C_5H_9$ | $CH_2CH_2CH_3$ |
| IA-862 | $A^1.2$ | cyclo-$C_6H_{11}$ | $CH_2CH_2CH_3$ |
| IA-863 | $A^1.2$ | $C_6H_5$ | $CH_2CH_2CH_3$ |
| IA-864 | $A^1.2$ | $CH(CH_3)_2$ | $CH(CH_3)_2$ |
| IA-865 | $A^1.2$ | $CH_2CH_2CH_2CH_3$ | $CH(CH_3)_2$ |
| IA-866 | $A^1.2$ | $C(CH_3)_3$ | $CH(CH_3)_2$ |
| IA-867 | $A^1.2$ | $CH_2CH(CH_3)_2$ | $CH(CH_3)_2$ |
| IA-868 | $A^1.2$ | $CH(CH_3)CH_2CH_3$ | $CH(CH_3)_2$ |
| IA-869 | $A^1.2$ | $CH_2CHCH_2$ | $CH(CH_3)_2$ |
| IA-870 | $A^1.2$ | $CH_2CCH$ | $CH(CH_3)_2$ |
| IA-871 | $A^1.2$ | $CH(CH_3)CH=CH_2$ | $CH(CH_3)_2$ |
| IA-872 | $A^1.2$ | $CHF_2$ | $CH(CH_3)_2$ |
| IA-873 | $A^1.2$ | $CH_2Cl$ | $CH(CH_3)_2$ |
| IA-874 | $A^1.2$ | $CH_2CH_2CN$ | $CH(CH_3)_2$ |
| IA-875 | $A^1.2$ | $CH_2CH_2Cl$ | $CH(CH_3)_2$ |
| IA-876 | $A^1.2$ | $CH_2CH_2OH$ | $CH(CH_3)_2$ |
| IA-877 | $A^1.2$ | $CH_2CH_2CH_2OH$ | $CH(CH_3)_2$ |
| IA-878 | $A^1.2$ | $CH_2CH(OH)CH_2OH$ | $CH(CH_3)_2$ |
| IA-879 | $A^1.2$ | $CH_2CH(OCH_3)_2$ | $CH(CH_3)_2$ |
| IA-880 | $A^1.2$ | $CH_2SCH_3$ | $CH(CH_3)_2$ |
| IA-881 | $A^1.2$ | $(CH_2)_3SCH_3$ | $CH(CH_3)_2$ |
| IA-882 | $A^1.2$ | $CH_2S(=O)CH_3$ | $CH(CH_3)_2$ |
| IA-883 | $A^1.2$ | $CH_2S(=O)_2CH_3$ | $CH(CH_3)_2$ |
| IA-884 | $A^1.2$ | $CH_2C(=O)CH_3$ | $CH(CH_3)_2$ |
| IA-885 | $A^1.2$ | $CH_2C(=O)CH_2CH_3$ | $CH(CH_3)_2$ |
| IA-886 | $A^1.2$ | $CH_2COOH$ | $CH(CH_3)_2$ |
| IA-887 | $A^1.2$ | $CH_2COOCH_3$ | $CH(CH_3)_2$ |
| IA-888 | $A^1.2$ | $CH_2COOCH_2CH_3$ | $CH(CH_3)_2$ |
| IA-889 | $A^1.2$ | cyclo-$C_3H_5$ | $CH(CH_3)_2$ |
| IA-890 | $A^1.2$ | cyclo-$C_4H_7$ | $CH(CH_3)_2$ |
| IA-891 | $A^1.2$ | cyclo-$C_5H_9$ | $CH(CH_3)_2$ |
| IA-892 | $A^1.2$ | cyclo-$C_6H_{11}$ | $CH(CH_3)_2$ |
| IA-893 | $A^1.2$ | $C_6H_5$ | $CH(CH_3)_2$ |
| IA-894 | $A^1.2$ | $CH_2CH_2CH_3$ | $CH_2CH_2CH_2CH_3$ |
| IA-895 | $A^1.2$ | $C(CH_3)_3$ | $CH_2CH_2CH_2CH_3$ |
| IA-896 | $A^1.2$ | $CH_2CH(CH_3)_2$ | $CH_2CH_2CH_2CH_3$ |
| IA-897 | $A^1.2$ | $CH(CH_3)CH_2CH_3$ | $CH_2CH_2CH_2CH_3$ |
| IA-898 | $A^1.2$ | $CH_2CHCH_2$ | $CH_2CH_2CH_2CH_3$ |

TABLE C-continued

| No. | A | R$^e$ | R$^f$ |
|---|---|---|---|
| IA-899 | A$^1$.2 | CH$_2$CCH | CH$_2$CH$_2$CH$_2$CH$_3$ |
| IA-900 | A$^1$.2 | CH(CH$_3$)CH=CH$_2$ | CH$_2$CH$_2$CH$_2$CH$_3$ |
| IA-901 | A$^1$.2 | CHF$_2$ | CH$_2$CH$_2$CH$_2$CH$_3$ |
| IA-902 | A$^1$.2 | CH$_2$Cl | CH$_2$CH$_2$CH$_2$CH$_3$ |
| IA-903 | A$^1$.2 | CH$_2$CH$_2$CN | CH$_2$CH$_2$CH$_2$CH$_3$ |
| IA-904 | A$^1$.2 | CH$_2$CH$_2$Cl | CH$_2$CH$_2$CH$_2$CH$_3$ |
| IA-905 | A$^1$.2 | CH$_2$CH$_2$OH | CH$_2$CH$_2$CH$_2$CH$_3$ |
| IA-906 | A$^1$.2 | CH$_2$CH$_2$CH$_2$OH | CH$_2$CH$_2$CH$_2$CH$_3$ |
| IA-907 | A$^1$.2 | CH$_2$CH(OH)CH$_2$OH | CH$_2$CH$_2$CH$_2$CH$_3$ |
| IA-908 | A$^1$.2 | CH$_2$CH(OCH$_3$)$_2$ | CH$_2$CH$_2$CH$_2$CH$_3$ |
| IA-909 | A$^1$.2 | CH$_2$SCH$_3$ | CH$_2$CH$_2$CH$_2$CH$_3$ |
| IA-910 | A$^1$.2 | (CH$_2$)$_3$SCH$_3$ | CH$_2$CH$_2$CH$_2$CH$_3$ |
| IA-911 | A$^1$.2 | CH$_2$S(=O)CH$_3$ | CH$_2$CH$_2$CH$_2$CH$_3$ |
| IA-912 | A$^1$.2 | CH$_2$S(=O)$_2$CH$_3$ | CH$_2$CH$_2$CH$_2$CH$_3$ |
| IA-913 | A$^1$.2 | CH$_2$C(=O)CH$_3$ | CH$_2$CH$_2$CH$_2$CH$_3$ |
| IA-914 | A$^1$.2 | CH$_2$C(=O)CH$_2$CH$_3$ | CH$_2$CH$_2$CH$_2$CH$_3$ |
| IA-915 | A$^1$.2 | CH$_2$COOH | CH$_2$CH$_2$CH$_2$CH$_3$ |
| IA-916 | A$^1$.2 | CH$_2$COOCH$_3$ | CH$_2$CH$_2$CH$_2$CH$_3$ |
| IA-917 | A$^1$.2 | CH$_2$COOCH$_2$CH$_3$ | CH$_2$CH$_2$CH$_2$CH$_3$ |
| IA-918 | A$^1$.2 | cyclo-C$_3$H$_5$ | CH$_2$CH$_2$CH$_2$CH$_3$ |
| IA-919 | A$^1$.2 | cyclo-C$_4$H$_7$ | CH$_2$CH$_2$CH$_2$CH$_3$ |
| IA-920 | A$^1$.2 | cyclo-C$_5$H$_9$ | CH$_2$CH$_2$CH$_2$CH$_3$ |
| IA-921 | A$^1$.2 | cyclo-C$_6$H$_{11}$ | CH$_2$CH$_2$CH$_2$CH$_3$ |
| IA-922 | A$^1$.2 | C$_6$H$_5$ | CH$_2$CH$_2$CH$_2$CH$_3$ |
| IA-923 | A$^1$.2 | C(CH$_3$)$_3$ | C(CH$_3$)$_3$ |
| IA-924 | A$^1$.2 | CH$_2$CH(CH$_3$)$_2$ | C(CH$_3$)$_3$ |
| IA-925 | A$^1$.2 | CH(CH$_3$)CH$_2$CH$_3$ | C(CH$_3$)$_3$ |
| IA-926 | A$^1$.2 | CH$_2$CHCH$_2$ | C(CH$_3$)$_3$ |
| IA-927 | A$^1$.2 | CH$_2$CCH | C(CH$_3$)$_3$ |
| IA-928 | A$^1$.2 | CH(CH$_3$)CH=CH$_2$ | C(CH$_3$)$_3$ |
| IA-929 | A$^1$.2 | CHF$_2$ | C(CH$_3$)$_3$ |
| IA-930 | A$^1$.2 | CH$_2$Cl | C(CH$_3$)$_3$ |
| IA-931 | A$^1$.2 | CH$_2$CH$_2$CN | C(CH$_3$)$_3$ |
| IA-932 | A$^1$.2 | CH$_2$CH$_2$Cl | C(CH$_3$)$_3$ |
| IA-933 | A$^1$.2 | CH$_2$CH$_2$OH | C(CH$_3$)$_3$ |
| IA-934 | A$^1$.2 | CH$_2$CH$_2$CH$_2$OH | C(CH$_3$)$_3$ |
| IA-935 | A$^1$.2 | CH$_2$CH(OH)CH$_2$OH | C(CH$_3$)$_3$ |
| IA-936 | A$^1$.2 | CH$_2$CH(OCH$_3$)$_2$ | C(CH$_3$)$_3$ |
| IA-937 | A$^1$.2 | CH$_2$SCH$_3$ | C(CH$_3$)$_3$ |
| IA-938 | A$^1$.2 | (CH$_2$)$_3$SCH$_3$ | C(CH$_3$)$_3$ |
| IA-939 | A$^1$.2 | CH$_2$S(=O)CH$_3$ | C(CH$_3$)$_3$ |
| IA-940 | A$^1$.2 | CH$_2$S(=O)$_2$CH$_3$ | C(CH$_3$)$_3$ |
| IA-941 | A$^1$.2 | CH$_2$C(=O)CH$_3$ | C(CH$_3$)$_3$ |
| IA-942 | A$^1$.2 | CH$_2$C(=O)CH$_2$CH$_3$ | C(CH$_3$)$_3$ |
| IA-943 | A$^1$.2 | CH$_2$COOH | C(CH$_3$)$_3$ |
| IA-944 | A$^1$.2 | CH$_2$COOCH$_3$ | C(CH$_3$)$_3$ |
| IA-945 | A$^1$.2 | CH$_2$COOCH$_2$CH$_3$ | C(CH$_3$)$_3$ |
| IA-946 | A$^1$.2 | cyclo-C$_3$H$_5$ | C(CH$_3$)$_3$ |
| IA-947 | A$^1$.2 | cyclo-C$_4$H$_7$ | C(CH$_3$)$_3$ |
| IA-948 | A$^1$.2 | cyclo-C$_5$H$_9$ | C(CH$_3$)$_3$ |
| IA-949 | A$^1$.2 | cyclo-C$_6$H$_{11}$ | C(CH$_3$)$_3$ |
| IA-950 | A$^1$.2 | C$_6$H$_5$ | C(CH$_3$)$_3$ |
| IA-951 | A$^1$.2 | CH$_2$CH(CH$_3$)$_2$ | CH$_2$CH(CH$_3$)$_2$ |
| IA-952 | A$^1$.2 | CH(CH$_3$)CH$_2$CH$_3$ | CH$_2$CH(CH$_3$)$_2$ |
| IA-953 | A$^1$.2 | CH$_2$CHCH$_2$ | CH$_2$CH(CH$_3$)$_2$ |
| IA-954 | A$^1$.2 | CH$_2$CCH | CH$_2$CH(CH$_3$)$_2$ |
| IA-955 | A$^1$.2 | CH(CH$_3$)CH=CH$_2$ | CH$_2$CH(CH$_3$)$_2$ |
| IA-956 | A$^1$.2 | CHF$_2$ | CH$_2$CH(CH$_3$)$_2$ |
| IA-957 | A$^1$.2 | CH$_2$Cl | CH$_2$CH(CH$_3$)$_2$ |
| IA-958 | A$^1$.2 | CH$_2$CH$_2$CN | CH$_2$CH(CH$_3$)$_2$ |
| IA-959 | A$^1$.2 | CH$_2$CH$_2$Cl | CH$_2$CH(CH$_3$)$_2$ |
| IA-960 | A$^1$.2 | CH$_2$CH$_2$OH | CH$_2$CH(CH$_3$)$_2$ |
| IA-961 | A$^1$.2 | CH$_2$CH$_2$CH$_2$OH | CH$_2$CH(CH$_3$)$_2$ |
| IA-962 | A$^1$.2 | CH$_2$CH(OH)CH$_2$OH | CH$_2$CH(CH$_3$)$_2$ |
| IA-963 | A$^1$.2 | CH$_2$CH(OCH$_3$)$_2$ | CH$_2$CH(CH$_3$)$_2$ |
| IA-964 | A$^1$.2 | CH$_2$SCH$_3$ | CH$_2$CH(CH$_3$)$_2$ |
| IA-965 | A$^1$.2 | (CH$_2$)$_3$SCH$_3$ | CH$_2$CH(CH$_3$)$_2$ |
| IA-966 | A$^1$.2 | CH$_2$S(=O)CH$_3$ | CH$_2$CH(CH$_3$)$_2$ |
| IA-967 | A$^1$.2 | CH$_2$S(=O)$_2$CH$_3$ | CH$_2$CH(CH$_3$)$_2$ |
| IA-968 | A$^1$.2 | CH$_2$C(=O)CH$_3$ | CH$_2$CH(CH$_3$)$_2$ |
| IA-969 | A$^1$.2 | CH$_2$C(=O)CH$_2$CH$_3$ | CH$_2$CH(CH$_3$)$_2$ |
| IA-970 | A$^1$.2 | CH$_2$COOH | CH$_2$CH(CH$_3$)$_2$ |
| IA-971 | A$^1$.2 | CH$_2$COOCH$_3$ | CH$_2$CH(CH$_3$)$_2$ |
| IA-972 | A$^1$.2 | CH$_2$COOCH$_2$CH$_3$ | CH$_2$CH(CH$_3$)$_2$ |
| IA-973 | A$^1$.2 | cyclo-C$_3$H$_5$ | CH$_2$CH(CH$_3$)$_2$ |
| IA-974 | A$^1$.2 | cyclo-C$_4$H$_7$ | CH$_2$CH(CH$_3$)$_2$ |
| IA-975 | A$^1$.2 | cyclo-C$_5$H$_9$ | CH$_2$CH(CH$_3$)$_2$ |
| IA-976 | A$^1$.2 | cyclo-C$_6$H$_{11}$ | CH$_2$CH(CH$_3$)$_2$ |
| IA-977 | A$^1$.2 | C$_6$H$_5$ | CH$_2$CH(CH$_3$)$_2$ |
| IA-978 | A$^1$.2 | CH(CH$_3$)CH$_2$CH$_3$ | CH(CH$_3$)CH$_2$CH$_3$ |
| IA-979 | A$^1$.2 | CH$_2$CHCH$_2$ | CH(CH$_3$)CH$_2$CH$_3$ |
| IA-980 | A$^1$.2 | CH$_2$CCH | CH(CH$_3$)CH$_2$CH$_3$ |
| IA-981 | A$^1$.2 | CH(CH$_3$)CH=CH$_2$ | CH(CH$_3$)CH$_2$CH$_3$ |
| IA-982 | A$^1$.2 | CHF$_2$ | CH(CH$_3$)CH$_2$CH$_3$ |
| IA-983 | A$^1$.2 | CH$_2$Cl | CH(CH$_3$)CH$_2$CH$_3$ |
| IA-984 | A$^1$.2 | CH$_2$CH$_2$CN | CH(CH$_3$)CH$_2$CH$_3$ |
| IA-985 | A$^1$.2 | CH$_2$CH$_2$Cl | CH(CH$_3$)CH$_2$CH$_3$ |
| IA-986 | A$^1$.2 | CH$_2$CH$_2$OH | CH(CH$_3$)CH$_2$CH$_3$ |
| IA-987 | A$^1$.2 | CH$_2$CH$_2$CH$_2$OH | CH(CH$_3$)CH$_2$CH$_3$ |
| IA-988 | A$^1$.2 | CH$_2$CH(OH)CH$_2$OH | CH(CH$_3$)CH$_2$CH$_3$ |
| IA-989 | A$^1$.2 | CH$_2$CH(OCH$_3$)$_2$ | CH(CH$_3$)CH$_2$CH$_3$ |
| IA-990 | A$^1$.2 | CH$_2$SCH$_3$ | CH(CH$_3$)CH$_2$CH$_3$ |
| IA-991 | A$^1$.2 | (CH$_2$)$_3$SCH$_3$ | CH(CH$_3$)CH$_2$CH$_3$ |
| IA-992 | A$^1$.2 | CH$_2$S(=O)CH$_3$ | CH(CH$_3$)CH$_2$CH$_3$ |
| IA-993 | A$^1$.2 | CH$_2$S(=O)$_2$CH$_3$ | CH(CH$_3$)CH$_2$CH$_3$ |
| IA-994 | A$^1$.2 | CH$_2$C(=O)CH$_3$ | CH(CH$_3$)CH$_2$CH$_3$ |
| IA-995 | A$^1$.2 | CH$_2$C(=O)CH$_2$CH$_3$ | CH(CH$_3$)CH$_2$CH$_3$ |
| IA-996 | A$^1$.2 | CH$_2$COOH | CH(CH$_3$)CH$_2$CH$_3$ |
| IA-997 | A$^1$.2 | CH$_2$COOCH$_3$ | CH(CH$_3$)CH$_2$CH$_3$ |
| IA-998 | A$^1$.2 | CH$_2$COOCH$_2$CH$_3$ | CH(CH$_3$)CH$_2$CH$_3$ |
| IA-999 | A$^1$.2 | cyclo-C$_3$H$_5$ | CH(CH$_3$)CH$_2$CH$_3$ |
| IA-1000 | A$^1$.2 | cyclo-C$_4$H$_7$ | CH(CH$_3$)CH$_2$CH$_3$ |
| IA-1001 | A$^1$.2 | cyclo-C$_5$H$_9$ | CH(CH$_3$)CH$_2$CH$_3$ |
| IA-1002 | A$^1$.2 | cyclo-C$_6$H$_{11}$ | CH(CH$_3$)CH$_2$CH$_3$ |
| IA-1003 | A$^1$.2 | C$_6$H$_5$ | CH(CH$_3$)CH$_2$CH$_3$ |
| IA-1004 | A$^1$.2 | CH$_2$CHCH$_2$ | CH$_2$CHCH$_2$ |
| IA-1005 | A$^1$.2 | CH$_2$CCH | CH$_2$CHCH$_2$ |
| IA-1006 | A$^1$.2 | CH(CH$_3$)CH=CH$_2$ | CH$_2$CHCH$_2$ |
| IA-1007 | A$^1$.2 | CHF$_2$ | CH$_2$CHCH$_2$ |
| IA-1008 | A$^1$.2 | CH$_2$Cl | CH$_2$CHCH$_2$ |
| IA-1009 | A$^1$.2 | CH$_2$CH$_2$CN | CH$_2$CHCH$_2$ |
| IA-1010 | A$^1$.2 | CH$_2$CH$_2$Cl | CH$_2$CHCH$_2$ |
| IA-1011 | A$^1$.2 | CH$_2$CH$_2$OH | CH$_2$CHCH$_2$ |
| IA-1012 | A$^1$.2 | CH$_2$CH$_2$CH$_2$OH | CH$_2$CHCH$_2$ |
| IA-1013 | A$^1$.2 | CH$_2$CH(OH)CH$_2$OH | CH$_2$CHCH$_2$ |
| IA-1014 | A$^1$.2 | CH$_2$CH(OCH$_3$)$_2$ | CH$_2$CHCH$_2$ |
| IA-1015 | A$^1$.2 | CH$_2$SCH$_3$ | CH$_2$CHCH$_2$ |
| IA-1016 | A$^1$.2 | (CH$_2$)$_3$SCH$_3$ | CH$_2$CHCH$_2$ |
| IA-1017 | A$^1$.2 | CH$_2$S(=O)CH$_3$ | CH$_2$CHCH$_2$ |
| IA-1018 | A$^1$.2 | CH$_2$S(=O)$_2$CH$_3$ | CH$_2$CHCH$_2$ |
| IA-1019 | A$^1$.2 | CH$_2$C(=O)CH$_3$ | CH$_2$CHCH$_2$ |
| IA-1020 | A$^1$.2 | CH$_2$C(=O)CH$_2$CH$_3$ | CH$_2$CHCH$_2$ |
| IA-1021 | A$^1$.2 | CH$_2$COOH | CH$_2$CHCH$_2$ |
| IA-1022 | A$^1$.2 | CH$_2$COOCH$_3$ | CH$_2$CHCH$_2$ |
| IA-1023 | A$^1$.2 | CH$_2$COOCH$_2$CH$_3$ | CH$_2$CHCH$_2$ |
| IA-1024 | A$^1$.2 | cyclo-C$_3$H$_5$ | CH$_2$CHCH$_2$ |
| IA-1025 | A$^1$.2 | cyclo-C$_4$H$_7$ | CH$_2$CHCH$_2$ |
| IA-1026 | A$^1$.2 | cyclo-C$_5$H$_9$ | CH$_2$CHCH$_2$ |
| IA-1027 | A$^1$.2 | cyclo-C$_6$H$_{11}$ | CH$_2$CHCH$_2$ |
| IA-1028 | A$^1$.2 | C$_6$H$_5$ | CH$_2$CHCH$_2$ |
| IA-1029 | A$^1$.2 | CH$_2$CCH | CH$_2$CCH |
| IA-1030 | A$^1$.2 | CH(CH$_3$)CH=CH$_2$ | CH$_2$CCH |
| IA-1031 | A$^1$.2 | CHF$_2$ | CH$_2$CCH |
| IA-1032 | A$^1$.2 | CH$_2$Cl | CH$_2$CCH |
| IA-1033 | A$^1$.2 | CH$_2$CH$_2$CN | CH$_2$CCH |
| IA-1034 | A$^1$.2 | CH$_2$CH$_2$Cl | CH$_2$CCH |
| IA-1035 | A$^1$.2 | CH$_2$CH$_2$OH | CH$_2$CCH |
| IA-1036 | A$^1$.2 | CH$_2$CH$_2$CH$_2$OH | CH$_2$CCH |
| IA-1037 | A$^1$.2 | CH$_2$CH(OH)CH$_2$OH | CH$_2$CCH |
| IA-1038 | A$^1$.2 | CH$_2$CH(OCH$_3$)$_2$ | CH$_2$CCH |
| IA-1039 | A$^1$.2 | CH$_2$SCH$_3$ | CH$_2$CCH |
| IA-1040 | A$^1$.2 | (CH$_2$)$_3$SCH$_3$ | CH$_2$CCH |
| IA-1041 | A$^1$.2 | CH$_2$S(=O)CH$_3$ | CH$_2$CCH |
| IA-1042 | A$^1$.2 | CH$_2$S(=O)$_2$CH$_3$ | CH$_2$CCH |
| IA-1043 | A$^1$.2 | CH$_2$C(=O)CH$_3$ | CH$_2$CCH |
| IA-1044 | A$^1$.2 | CH$_2$C(=O)CH$_2$CH$_3$ | CH$_2$CCH |
| IA-1045 | A$^1$.2 | CH$_2$COOH | CH$_2$CCH |
| IA-1046 | A$^1$.2 | CH$_2$COOCH$_3$ | CH$_2$CCH |
| IA-1047 | A$^1$.2 | CH$_2$COOCH$_2$CH$_3$ | CH$_2$CCH |
| IA-1048 | A$^1$.2 | cyclo-C$_3$H$_5$ | CH$_2$CCH |
| IA-1049 | A$^1$.2 | cyclo-C$_4$H$_7$ | CH$_2$CCH |
| IA-1050 | A$^1$.2 | cyclo-C$_5$H$_9$ | CH$_2$CCH |
| IA-1051 | A$^1$.2 | cyclo-C$_6$H$_{11}$ | CH$_2$CCH |
| IA-1052 | A$^1$.2 | C$_6$H$_5$ | CH$_2$CCH |
| IA-1053 | A$^1$.2 | CH(CH$_3$)CH=CH$_2$ | CH(CH$_3$)CH=CH$_2$ |
| IA-1054 | A$^1$.2 | CHF$_2$ | CH(CH$_3$)CH=CH$_2$ |

TABLE C-continued

| No. | A | R$^e$ | R$^f$ |
|---|---|---|---|
| IA-1055 | A$^1$.2 | CH$_2$Cl | CH(CH$_3$)CH=CH$_2$ |
| IA-1056 | A$^1$.2 | CH$_2$CH$_2$CN | CH(CH$_3$)CH=CH$_2$ |
| IA-1057 | A$^1$.2 | CH$_2$CH$_2$Cl | CH(CH$_3$)CH=CH$_2$ |
| IA-1058 | A$^1$.2 | CH$_2$CH$_2$OH | CH(CH$_3$)CH=CH$_2$ |
| IA-1059 | A$^1$.2 | CH$_2$CH$_2$CH$_2$OH | CH(CH$_3$)CH=CH$_2$ |
| IA-1060 | A$^1$.2 | CH$_2$CH(OH)CH$_2$OH | CH(CH$_3$)CH=CH$_2$ |
| IA-1061 | A$^1$.2 | CH$_2$CH(OCH$_3$)$_2$ | CH(CH$_3$)CH=CH$_2$ |
| IA-1062 | A$^1$.2 | CH$_2$SCH$_3$ | CH(CH$_3$)CH=CH$_2$ |
| IA-1063 | A$^1$.2 | (CH$_2$)$_3$SCH$_3$ | CH(CH$_3$)CH=CH$_2$ |
| IA-1064 | A$^1$.2 | CH$_2$S(=O)CH$_3$ | CH(CH$_3$)CH=CH$_2$ |
| IA-1065 | A$^1$.2 | CH$_2$S(=O)$_2$CH$_3$ | CH(CH$_3$)CH=CH$_2$ |
| IA-1066 | A$^1$.2 | CH$_2$C(=O)CH$_3$ | CH(CH$_3$)CH=CH$_2$ |
| IA-1067 | A$^1$.2 | CH$_2$C(=O)CH$_2$CH$_3$ | CH(CH$_3$)CH=CH$_2$ |
| IA-1068 | A$^1$.2 | CH$_2$COOH | CH(CH$_3$)CH=CH$_2$ |
| IA-1069 | A$^1$.2 | CH$_2$COOCH$_3$ | CH(CH$_3$)CH=CH$_2$ |
| IA-1070 | A$^1$.2 | CH$_2$COOCH$_2$CH$_3$ | CH(CH$_3$)CH=CH$_2$ |
| IA-1071 | A$^1$.2 | cyclo-C$_3$H$_5$ | CH(CH$_3$)CH=CH$_2$ |
| IA-1072 | A$^1$.2 | cyclo-C$_4$H$_7$ | CH(CH$_3$)CH=CH$_2$ |
| IA-1073 | A$^1$.2 | cyclo-C$_5$H$_9$ | CH(CH$_3$)CH=CH$_2$ |
| IA-1074 | A$^1$.2 | cyclo-C$_6$H$_{11}$ | CH(CH$_3$)CH=CH$_2$ |
| IA-1075 | A$^1$.2 | C$_6$H$_5$ | CH(CH$_3$)CH=CH$_2$ |
| IA-1076 | A$^1$.2 | CHF$_2$ | CHF$_2$ |
| IA-1077 | A$^1$.2 | CH$_2$Cl | CHF$_2$ |
| IA-1078 | A$^1$.2 | CH$_2$CH$_2$CN | CHF$_2$ |
| IA-1079 | A$^1$.2 | CH$_2$CH$_2$Cl | CHF$_2$ |
| IA-1080 | A$^1$.2 | CH$_2$CH$_2$OH | CHF$_2$ |
| IA-1081 | A$^1$.2 | CH$_2$CH$_2$CH$_2$OH | CHF$_2$ |
| IA-1082 | A$^1$.2 | CH$_2$CH(OH)CH$_2$OH | CHF$_2$ |
| IA-1083 | A$^1$.2 | CH$_2$CH(OCH$_3$)$_2$ | CHF$_2$ |
| IA-1084 | A$^1$.2 | CH$_2$SCH$_3$ | CHF$_2$ |
| IA-1085 | A$^1$.2 | (CH$_2$)$_3$SCH$_3$ | CHF$_2$ |
| IA-1086 | A$^1$.2 | CH$_2$S(=O)CH$_3$ | CHF$_2$ |
| IA-1087 | A$^1$.2 | CH$_2$S(=O)$_2$CH$_3$ | CHF$_2$ |
| IA-1088 | A$^1$.2 | CH$_2$C(=O)CH$_3$ | CHF$_2$ |
| IA-1089 | A$^1$.2 | CH$_2$C(=O)CH$_2$CH$_3$ | CHF$_2$ |
| IA-1090 | A$^1$.2 | CH$_2$COOH | CHF$_2$ |
| IA-1091 | A$^1$.2 | CH$_2$COOCH$_3$ | CHF$_2$ |
| IA-1092 | A$^1$.2 | CH$_2$COOCH$_2$CH$_3$ | CHF$_2$ |
| IA-1093 | A$^1$.2 | cyclo-C$_3$H$_5$ | CHF$_2$ |
| IA-1094 | A$^1$.2 | cyclo-C$_4$H$_7$ | CHF$_2$ |
| IA-1095 | A$^1$.2 | cyclo-C$_5$H$_9$ | CHF$_2$ |
| IA-1096 | A$^1$.2 | cyclo-C$_6$H$_{11}$ | CHF$_2$ |
| IA-1097 | A$^1$.2 | C$_6$H$_5$ | CHF$_2$ |
| IA-1098 | A$^1$.2 | CH$_2$Cl | CH$_2$Cl |
| IA-1099 | A$^1$.2 | CH$_2$CH$_2$CN | CH$_2$Cl |
| IA-1100 | A$^1$.2 | CH$_2$CH$_2$Cl | CH$_2$Cl |
| IA-1101 | A$^1$.2 | CH$_2$CH$_2$OH | CH$_2$Cl |
| IA-1102 | A$^1$.2 | CH$_2$CH$_2$CH$_2$OH | CH$_2$Cl |
| IA-1103 | A$^1$.2 | CH$_2$CH(OH)CH$_2$OH | CH$_2$Cl |
| IA-1104 | A$^1$.2 | CH$_2$CH(OCH$_3$)$_2$ | CH$_2$Cl |
| IA-1105 | A$^1$.2 | CH$_2$SCH$_3$ | CH$_2$Cl |
| IA-1106 | A$^1$.2 | (CH$_2$)$_3$SCH$_3$ | CH$_2$Cl |
| IA-1107 | A$^1$.2 | CH$_2$S(=O)CH$_3$ | CH$_2$Cl |
| IA-1108 | A$^1$.2 | CH$_2$S(=O)$_2$CH$_3$ | CH$_2$Cl |
| IA-1109 | A$^1$.2 | CH$_2$C(=O)CH$_3$ | CH$_2$Cl |
| IA-1110 | A$^1$.2 | CH$_2$C(=O)CH$_2$CH$_3$ | CH$_2$Cl |
| IA-1111 | A$^1$.2 | CH$_2$COOH | CH$_2$Cl |
| IA-1112 | A$^1$.2 | CH$_2$COOCH$_3$ | CH$_2$Cl |
| IA-1113 | A$^1$.2 | CH$_2$COOCH$_2$CH$_3$ | CH$_2$Cl |
| IA-1114 | A$^1$.2 | cyclo-C$_3$H$_5$ | CH$_2$Cl |
| IA-1115 | A$^1$.2 | cyclo-C$_4$H$_7$ | CH$_2$Cl |
| IA-1116 | A$^1$.2 | cyclo-C$_5$H$_9$ | CH$_2$Cl |
| IA-1117 | A$^1$.2 | cyclo-C$_6$H$_{11}$ | CH$_2$Cl |
| IA-1118 | A$^1$.2 | C$_6$H$_5$ | CH$_2$Cl |
| IA-1119 | A$^1$.2 | CH$_2$CH$_2$CN | CH$_2$CH$_2$CN |
| IA-1120 | A$^1$.2 | CH$_2$CH$_2$Cl | CH$_2$CH$_2$CN |
| IA-1121 | A$^1$.2 | CH$_2$CH$_2$OH | CH$_2$CH$_2$CN |
| IA-1122 | A$^1$.2 | CH$_2$CH$_2$CH$_2$OH | CH$_2$CH$_2$CN |
| IA-1123 | A$^1$.2 | CH$_2$CH(OH)CH$_2$OH | CH$_2$CH$_2$CN |
| IA-1124 | A$^1$.2 | CH$_2$CH(OCH$_3$)$_2$ | CH$_2$CH$_2$CN |
| IA-1125 | A$^1$.2 | CH$_2$SCH$_3$ | CH$_2$CH$_2$CN |
| IA-1126 | A$^1$.2 | (CH$_2$)$_3$SCH$_3$ | CH$_2$CH$_2$CN |
| IA-1127 | A$^1$.2 | CH$_2$S(=O)CH$_3$ | CH$_2$CH$_2$CN |
| IA-1128 | A$^1$.2 | CH$_2$S(=O)$_2$CH$_3$ | CH$_2$CH$_2$CN |
| IA-1129 | A$^1$.2 | CH$_2$C(=O)CH$_3$ | CH$_2$CH$_2$CN |
| IA-1130 | A$^1$.2 | CH$_2$C(=O)CH$_2$CH$_3$ | CH$_2$CH$_2$CN |
| IA-1131 | A$^1$.2 | CH$_2$COOH | CH$_2$CH$_2$CN |
| IA-1132 | A$^1$.2 | CH$_2$COOCH$_3$ | CH$_2$CH$_2$CN |
| IA-1133 | A$^1$.2 | CH$_2$COOCH$_2$CH$_3$ | CH$_2$CH$_2$CN |
| IA-1134 | A$^1$.2 | cyclo-C$_3$H$_5$ | CH$_2$CH$_2$CN |
| IA-1135 | A$^1$.2 | cyclo-C$_4$H$_7$ | CH$_2$CH$_2$CN |
| IA-1136 | A$^1$.2 | cyclo-C$_5$H$_9$ | CH$_2$CH$_2$CN |
| IA-1137 | A$^1$.2 | cyclo-C$_6$H$_{11}$ | CH$_2$CH$_2$CN |
| IA-1138 | A$^1$.2 | C$_6$H$_5$ | CH$_2$CH$_2$CN |
| IA-1139 | A$^1$.2 | CH$_2$CH$_2$Cl | CH$_2$CH$_2$Cl |
| IA-1140 | A$^1$.2 | CH$_2$CH$_2$OH | CH$_2$CH$_2$Cl |
| IA-1141 | A$^1$.2 | CH$_2$CH$_2$CH$_2$OH | CH$_2$CH$_2$Cl |
| IA-1142 | A$^1$.2 | CH$_2$CH(OH)CH$_2$OH | CH$_2$CH$_2$Cl |
| IA-1143 | A$^1$.2 | CH$_2$CH(OCH$_3$)$_2$ | CH$_2$CH$_2$Cl |
| IA-1144 | A$^1$.2 | CH$_2$SCH$_3$ | CH$_2$CH$_2$Cl |
| IA-1145 | A$^1$.2 | (CH$_2$)$_3$SCH$_3$ | CH$_2$CH$_2$Cl |
| IA-1146 | A$^1$.2 | CH$_2$S(=O)CH$_3$ | CH$_2$CH$_2$Cl |
| IA-1147 | A$^1$.2 | CH$_2$S(=O)$_2$CH$_3$ | CH$_2$CH$_2$Cl |
| IA-1148 | A$^1$.2 | CH$_2$C(=O)CH$_3$ | CH$_2$CH$_2$Cl |
| IA-1149 | A$^1$.2 | CH$_2$C(=O)CH$_2$CH$_3$ | CH$_2$CH$_2$Cl |
| IA-1150 | A$^1$.2 | CH$_2$COOH | CH$_2$CH$_2$Cl |
| IA-1151 | A$^1$.2 | CH$_2$COOCH$_3$ | CH$_2$CH$_2$Cl |
| IA-1152 | A$^1$.2 | CH$_2$COOCH$_2$CH$_3$ | CH$_2$CH$_2$Cl |
| IA-1153 | A$^1$.2 | cyclo-C$_3$H$_5$ | CH$_2$CH$_2$Cl |
| IA-1154 | A$^1$.2 | cyclo-C$_4$H$_7$ | CH$_2$CH$_2$Cl |
| IA-1155 | A$^1$.2 | cyclo-C$_5$H$_9$ | CH$_2$CH$_2$Cl |
| IA-1156 | A$^1$.2 | cyclo-C$_6$H$_{11}$ | CH$_2$CH$_2$Cl |
| IA-1157 | A$^1$.2 | C$_6$H$_5$ | CH$_2$CH$_2$Cl |
| IA-1158 | A$^1$.2 | CH$_2$CH$_2$OH | CH$_2$CH$_2$OH |
| IA-1159 | A$^1$.2 | CH$_2$CH$_2$CH$_2$OH | CH$_2$CH$_2$OH |
| IA-1160 | A$^1$.2 | CH$_2$CH(OH)CH$_2$OH | CH$_2$CH$_2$OH |
| IA-1161 | A$^1$.2 | CH$_2$CH(OCH$_3$)$_2$ | CH$_2$CH$_2$OH |
| IA-1162 | A$^1$.2 | CH$_2$SCH$_3$ | CH$_2$CH$_2$OH |
| IA-1163 | A$^1$.2 | (CH$_2$)$_3$SCH$_3$ | CH$_2$CH$_2$OH |
| IA-1164 | A$^1$.2 | CH$_2$S(=O)CH$_3$ | CH$_2$CH$_2$OH |
| IA-1165 | A$^1$.2 | CH$_2$S(=O)$_2$CH$_3$ | CH$_2$CH$_2$OH |
| IA-1166 | A$^1$.2 | CH$_2$C(=O)CH$_3$ | CH$_2$CH$_2$OH |
| IA-1167 | A$^1$.2 | CH$_2$C(=O)CH$_2$CH$_3$ | CH$_2$CH$_2$OH |
| IA-1168 | A$^1$.2 | CH$_2$COOH | CH$_2$CH$_2$OH |
| IA-1169 | A$^1$.2 | CH$_2$COOCH$_3$ | CH$_2$CH$_2$OH |
| IA-1170 | A$^1$.2 | CH$_2$COOCH$_2$CH$_3$ | CH$_2$CH$_2$OH |
| IA-1171 | A$^1$.2 | cyclo-C$_3$H$_5$ | CH$_2$CH$_2$OH |
| IA-1172 | A$^1$.2 | cyclo-C$_4$H$_7$ | CH$_2$CH$_2$OH |
| IA-1173 | A$^1$.2 | cyclo-C$_5$H$_9$ | CH$_2$CH$_2$OH |
| IA-1174 | A$^1$.2 | cyclo-C$_6$H$_{11}$ | CH$_2$CH$_2$OH |
| IA-1175 | A$^1$.2 | C$_6$H$_5$ | CH$_2$CH$_2$OH |
| IA-1176 | A$^1$.2 | CH$_2$CH$_2$CH$_2$OH | CH$_2$CH$_2$CH$_2$OH |
| IA-1177 | A$^1$.2 | CH$_2$CH(OH)CH$_2$OH | CH$_2$CH$_2$CH$_2$OH |
| IA-1178 | A$^1$.2 | CH$_2$CH(OCH$_3$)$_2$ | CH$_2$CH$_2$CH$_2$OH |
| IA-1179 | A$^1$.2 | CH$_2$SCH$_3$ | CH$_2$CH$_2$CH$_2$OH |
| IA-1180 | A$^1$.2 | (CH$_2$)$_3$SCH$_3$ | CH$_2$CH$_2$CH$_2$OH |
| IA-1181 | A$^1$.2 | CH$_2$S(=O)CH$_3$ | CH$_2$CH$_2$CH$_2$OH |
| IA-1182 | A$^1$.2 | CH$_2$S(=O)$_2$CH$_3$ | CH$_2$CH$_2$CH$_2$OH |
| IA-1183 | A$^1$.2 | CH$_2$C(=O)CH$_3$ | CH$_2$CH$_2$CH$_2$OH |
| IA-1184 | A$^1$.2 | CH$_2$C(=O)CH$_2$CH$_3$ | CH$_2$CH$_2$CH$_2$OH |
| IA-1185 | A$^1$.2 | CH$_2$COOH | CH$_2$CH$_2$CH$_2$OH |
| IA-1186 | A$^1$.2 | CH$_2$COOCH$_3$ | CH$_2$CH$_2$CH$_2$OH |
| IA-1187 | A$^1$.2 | CH$_2$COOCH$_2$CH$_3$ | CH$_2$CH$_2$CH$_2$OH |
| IA-1188 | A$^1$.2 | cyclo-C$_3$H$_5$ | CH$_2$CH$_2$CH$_2$OH |
| IA-1189 | A$^1$.2 | cyclo-C$_4$H$_7$ | CH$_2$CH$_2$CH$_2$OH |
| IA-1190 | A$^1$.2 | cyclo-C$_5$H$_9$ | CH$_2$CH$_2$CH$_2$OH |
| IA-1191 | A$^1$.2 | cyclo-C$_6$H$_{11}$ | CH$_2$CH$_2$CH$_2$OH |
| IA-1192 | A$^1$.2 | C$_6$H$_5$ | CH$_2$CH$_2$CH$_2$OH |
| IA-1193 | A$^1$.2 | CH$_2$CH(OH)CH$_2$OH | CH$_2$CH(OH)CH$_2$OH |
| IA-1194 | A$^1$.2 | CH$_2$CH(OCH$_3$)$_2$ | CH$_2$CH(OH)CH$_2$OH |
| IA-1195 | A$^1$.2 | CH$_2$SCH$_3$ | CH$_2$CH(OH)CH$_2$OH |
| IA-1196 | A$^1$.2 | (CH$_2$)$_3$SCH$_3$ | CH$_2$CH(OH)CH$_2$OH |
| IA-1197 | A$^1$.2 | CH$_2$S(=O)CH$_3$ | CH$_2$CH(OH)CH$_2$OH |
| IA-1198 | A$^1$.2 | CH$_2$S(=O)$_2$CH$_3$ | CH$_2$CH(OH)CH$_2$OH |
| IA-1199 | A$^1$.2 | CH$_2$C(=O)CH$_3$ | CH$_2$CH(OH)CH$_2$OH |
| IA-1200 | A$^1$.2 | CH$_2$C(=O)CH$_2$CH$_3$ | CH$_2$CH(OH)CH$_2$OH |
| IA-1201 | A$^1$.2 | CH$_2$COOH | CH$_2$CH(OH)CH$_2$OH |
| IA-1202 | A$^1$.2 | CH$_2$COOCH$_3$ | CH$_2$CH(OH)CH$_2$OH |
| IA-1203 | A$^1$.2 | CH$_2$COOCH$_2$CH$_3$ | CH$_2$CH(OH)CH$_2$OH |
| IA-1204 | A$^1$.2 | cyclo-C$_3$H$_5$ | CH$_2$CH(OH)CH$_2$OH |
| IA-1205 | A$^1$.2 | cyclo-C$_4$H$_7$ | CH$_2$CH(OH)CH$_2$OH |
| IA-1206 | A$^1$.2 | cyclo-C$_5$H$_9$ | CH$_2$CH(OH)CH$_2$OH |
| IA-1207 | A$^1$.2 | cyclo-C$_6$H$_{11}$ | CH$_2$CH(OH)CH$_2$OH |
| IA-1208 | A$^1$.2 | C$_6$H$_5$ | CH$_2$CH(OH)CH$_2$OH |
| IA-1209 | A$^1$.2 | CH$_2$CH(OCH$_3$)$_2$ | CH$_2$CH(OCH$_3$)$_2$ |
| IA-1210 | A$^1$.2 | CH$_2$SCH$_3$ | CH$_2$CH(OCH$_3$)$_2$ |

TABLE C-continued

| No. | A | R$^e$ | R$^f$ |
|---|---|---|---|
| IA-1211 | A$^1$.2 | (CH$_2$)$_3$SCH$_3$ | CH$_2$CH(OCH$_3$)$_2$ |
| IA-1212 | A$^1$.2 | CH$_2$S(=O)CH$_3$ | CH$_2$CH(OCH$_3$)$_2$ |
| IA-1213 | A$^1$.2 | CH$_2$S(=O)$_2$CH$_3$ | CH$_2$CH(OCH$_3$)$_2$ |
| IA-1214 | A$^1$.2 | CH$_2$C(=O)CH$_3$ | CH$_2$CH(OCH$_3$)$_2$ |
| IA-1215 | A$^1$.2 | CH$_2$C(=O)CH$_2$CH$_3$ | CH$_2$CH(OCH$_3$)$_2$ |
| IA-1216 | A$^1$.2 | CH$_2$COOH | CH$_2$CH(OCH$_3$)$_2$ |
| IA-1217 | A$^1$.2 | CH$_2$COOCH$_3$ | CH$_2$CH(OCH$_3$)$_2$ |
| IA-1218 | A$^1$.2 | CH$_2$COOCH$_2$CH$_3$ | CH$_2$CH(OCH$_3$)$_2$ |
| IA-1219 | A$^1$.2 | cyclo-C$_3$H$_5$ | CH$_2$CH(OCH$_3$)$_2$ |
| IA-1220 | A$^1$.2 | cyclo-C$_4$H$_7$ | CH$_2$CH(OCH$_3$)$_2$ |
| IA-1221 | A$^1$.2 | cyclo-C$_5$H$_9$ | CH$_2$CH(OCH$_3$)$_2$ |
| IA-1222 | A$^1$.2 | cyclo-C$_6$H$_{11}$ | CH$_2$CH(OCH$_3$)$_2$ |
| IA-1223 | A$^1$.2 | C$_6$H$_5$ | CH$_2$CH(OCH$_3$)$_2$ |
| IA-1224 | A$^1$.2 | CH$_2$SCH$_3$ | CH$_2$SCH$_3$ |
| IA-1225 | A$^1$.2 | (CH$_2$)$_3$SCH$_3$ | CH$_2$SCH$_3$ |
| IA-1226 | A$^1$.2 | CH$_2$S(=O)CH$_3$ | CH$_2$SCH$_3$ |
| IA-1227 | A$^1$.2 | CH$_2$S(=O)$_2$CH$_3$ | CH$_2$SCH$_3$ |
| IA-1228 | A$^1$.2 | CH$_2$C(=O)CH$_3$ | CH$_2$SCH$_3$ |
| IA-1229 | A$^1$.2 | CH$_2$C(=O)CH$_2$CH$_3$ | CH$_2$SCH$_3$ |
| IA-1230 | A$^1$.2 | CH$_2$COOH | CH$_2$SCH$_3$ |
| IA-1231 | A$^1$.2 | CH$_2$COOCH$_3$ | CH$_2$SCH$_3$ |
| IA-1232 | A$^1$.2 | CH$_2$COOCH$_2$CH$_3$ | CH$_2$SCH$_3$ |
| IA-1233 | A$^1$.2 | cyclo-C$_3$H$_5$ | CH$_2$SCH$_3$ |
| IA-1234 | A$^1$.2 | cyclo-C$_4$H$_7$ | CH$_2$SCH$_3$ |
| IA-1235 | A$^1$.2 | cyclo-C$_5$H$_9$ | CH$_2$SCH$_3$ |
| IA-1236 | A$^1$.2 | cyclo-C$_6$H$_{11}$ | CH$_2$SCH$_3$ |
| IA-1237 | A$^1$.2 | C$_6$H$_5$ | CH$_2$SCH$_3$ |
| IA-1238 | A$^1$.2 | (CH$_2$)$_3$SCH$_3$ | (CH$_2$)$_3$SCH$_3$ |
| IA-1239 | A$^1$.2 | CH$_2$S(=O)CH$_3$ | (CH$_2$)$_3$SCH$_3$ |
| IA-1240 | A$^1$.2 | CH$_2$S(=O)$_2$CH$_3$ | (CH$_2$)$_3$SCH$_3$ |
| IA-1241 | A$^1$.2 | CH$_2$C(=O)CH$_3$ | (CH$_2$)$_3$SCH$_3$ |
| IA-1242 | A$^1$.2 | CH$_2$C(=O)CH$_2$CH$_3$ | (CH$_2$)$_3$SCH$_3$ |
| IA-1243 | A$^1$.2 | CH$_2$COOH | (CH$_2$)$_3$SCH$_3$ |
| IA-1244 | A$^1$.2 | CH$_2$COOCH$_3$ | (CH$_2$)$_3$SCH$_3$ |
| IA-1245 | A$^1$.2 | CH$_2$COOCH$_2$CH$_3$ | (CH$_2$)$_3$SCH$_3$ |
| IA-1246 | A$^1$.2 | cyclo-C$_3$H$_5$ | (CH$_2$)$_3$SCH$_3$ |
| IA-1247 | A$^1$.2 | cyclo-C$_4$H$_7$ | (CH$_2$)$_3$SCH$_3$ |
| IA-1248 | A$^1$.2 | cyclo-C$_5$H$_9$ | (CH$_2$)$_3$SCH$_3$ |
| IA-1249 | A$^1$.2 | cyclo-C$_6$H$_{11}$ | (CH$_2$)$_3$SCH$_3$ |
| IA-1250 | A$^1$.2 | C$_6$H$_5$ | (CH$_2$)$_3$SCH$_3$ |
| IA-1251 | A$^1$.2 | CH$_2$S(=O)CH$_3$ | CH$_2$S(=O)CH$_3$ |
| IA-1252 | A$^1$.2 | CH$_2$S(=O)$_2$CH$_3$ | CH$_2$S(=O)CH$_3$ |
| IA-1253 | A$^1$.2 | CH$_2$C(=O)CH$_3$ | CH$_2$S(=O)CH$_3$ |
| IA-1254 | A$^1$.2 | CH$_2$C(=O)CH$_2$CH$_3$ | CH$_2$S(=O)CH$_3$ |
| IA-1255 | A$^1$.2 | CH$_2$COOH | CH$_2$S(=O)CH$_3$ |
| IA-1256 | A$^1$.2 | CH$_2$COOCH$_3$ | CH$_2$S(=O)CH$_3$ |
| IA-1257 | A$^1$.2 | CH$_2$COOCH$_2$CH$_3$ | CH$_2$S(=O)CH$_3$ |
| IA-1258 | A$^1$.2 | cyclo-C$_3$H$_5$ | CH$_2$S(=O)CH$_3$ |
| IA-1259 | A$^1$.2 | cyclo-C$_4$H$_7$ | CH$_2$S(=O)CH$_3$ |
| IA-1260 | A$^1$.2 | cyclo-C$_5$H$_9$ | CH$_2$S(=O)CH$_3$ |
| IA-1261 | A$^1$.2 | cyclo-C$_6$H$_{11}$ | CH$_2$S(=O)CH$_3$ |
| IA-1262 | A$^1$.2 | C$_6$H$_5$ | CH$_2$S(=O)CH$_3$ |
| IA-1263 | A$^1$.2 | CH$_2$S(=O)$_2$CH$_3$ | CH$_2$S(=O)$_2$CH$_3$ |
| IA-1264 | A$^1$.2 | CH$_2$C(=O)CH$_3$ | CH$_2$S(=O)$_2$CH$_3$ |
| IA-1265 | A$^1$.2 | CH$_2$C(=O)CH$_2$CH$_3$ | CH$_2$S(=O)$_2$CH$_3$ |
| IA-1266 | A$^1$.2 | CH$_2$COOH | CH$_2$S(=O)$_2$CH$_3$ |
| IA-1267 | A$^1$.2 | CH$_2$COOCH$_3$ | CH$_2$S(=O)$_2$CH$_3$ |
| IA-1268 | A$^1$.2 | CH$_2$COOCH$_2$CH$_3$ | CH$_2$S(=O)$_2$CH$_3$ |
| IA-1269 | A$^1$.2 | cyclo-C$_3$H$_5$ | CH$_2$S(=O)$_2$CH$_3$ |
| IA-1270 | A$^1$.2 | cyclo-C$_4$H$_7$ | CH$_2$S(=O)$_2$CH$_3$ |
| IA-1271 | A$^1$.2 | cyclo-C$_5$H$_9$ | CH$_2$S(=O)$_2$CH$_3$ |
| IA-1272 | A$^1$.2 | cyclo-C$_6$H$_{11}$ | CH$_2$S(=O)$_2$CH$_3$ |
| IA-1273 | A$^1$.2 | C$_6$H$_5$ | CH$_2$S(=O)$_2$CH$_3$ |
| IA-1274 | A$^1$.2 | CH$_2$C(=O)CH$_3$ | CH$_2$C(=O)CH$_3$ |
| IA-1275 | A$^1$.2 | CH$_2$C(=O)CH$_2$CH$_3$ | CH$_2$C(=O)CH$_3$ |
| IA-1276 | A$^1$.2 | CH$_2$COOH | CH$_2$C(=O)CH$_3$ |
| IA-1277 | A$^1$.2 | CH$_2$COOCH$_3$ | CH$_2$C(=O)CH$_3$ |
| IA-1278 | A$^1$.2 | CH$_2$COOCH$_2$CH$_3$ | CH$_2$C(=O)CH$_3$ |
| IA-1279 | A$^1$.2 | cyclo-C$_3$H$_5$ | CH$_2$C(=O)CH$_3$ |
| IA-1280 | A$^1$.2 | cyclo-C$_4$H$_7$ | CH$_2$C(=O)CH$_3$ |
| IA-1281 | A$^1$.2 | cyclo-C$_5$H$_9$ | CH$_2$C(=O)CH$_3$ |
| IA-1282 | A$^1$.2 | cyclo-C$_6$H$_{11}$ | CH$_2$C(=O)CH$_3$ |
| IA-1283 | A$^1$.2 | C$_6$H$_5$ | CH$_2$C(=O)CH$_3$ |
| IA-1284 | A$^1$.2 | CH$_2$C(=O)CH$_2$CH$_3$ | CH$_2$C(=O)CH$_2$CH$_3$ |
| IA-1285 | A$^1$.2 | CH$_2$COOH | CH$_2$C(=O)CH$_2$CH$_3$ |
| IA-1286 | A$^1$.2 | CH$_2$COOCH$_3$ | CH$_2$C(=O)CH$_2$CH$_3$ |
| IA-1287 | A$^1$.2 | CH$_2$COOCH$_2$CH$_3$ | CH$_2$C(=O)CH$_2$CH$_3$ |
| IA-1288 | A$^1$.2 | cyclo-C$_3$H$_5$ | CH$_2$C(=O)CH$_2$CH$_3$ |
| IA-1289 | A$^1$.2 | cyclo-C$_4$H$_7$ | CH$_2$C(=O)CH$_2$CH$_3$ |
| IA-1290 | A$^1$.2 | cyclo-C$_5$H$_9$ | CH$_2$C(=O)CH$_2$CH$_3$ |
| IA-1291 | A$^1$.2 | cyclo-C$_6$H$_{11}$ | CH$_2$C(=O)CH$_2$CH$_3$ |
| IA-1292 | A$^1$.2 | C$_6$H$_5$ | CH$_2$C(=O)CH$_2$CH$_3$ |
| IA-1293 | A$^1$.2 | CH$_2$COOH | CH$_2$COOH |
| IA-1294 | A$^1$.2 | CH$_2$COOCH$_3$ | CH$_2$COOH |
| IA-1295 | A$^1$.2 | CH$_2$COOCH$_2$CH$_3$ | CH$_2$COOH |
| IA-1296 | A$^1$.2 | cyclo-C$_3$H$_5$ | CH$_2$COOH |
| IA-1297 | A$^1$.2 | cyclo-C$_4$H$_7$ | CH$_2$COOH |
| IA-1298 | A$^1$.2 | cyclo-C$_5$H$_9$ | CH$_2$COOH |
| IA-1299 | A$^1$.2 | cyclo-C$_6$H$_{11}$ | CH$_2$COOH |
| IA-1300 | A$^1$.2 | C$_6$H$_5$ | CH$_2$COOH |
| IA-1301 | A$^1$.2 | CH$_2$COOCH$_3$ | CH$_2$COOCH$_3$ |
| IA-1302 | A$^1$.2 | CH$_2$COOCH$_2$CH$_3$ | CH$_2$COOCH$_3$ |
| IA-1303 | A$^1$.2 | cyclo-C$_3$H$_5$ | CH$_2$COOCH$_3$ |
| IA-1304 | A$^1$.2 | cyclo-C$_4$H$_7$ | CH$_2$COOCH$_3$ |
| IA-1305 | A$^1$.2 | cyclo-C$_5$H$_9$ | CH$_2$COOCH$_3$ |
| IA-1306 | A$^1$.2 | cyclo-C$_6$H$_{11}$ | CH$_2$COOCH$_3$ |
| IA-1307 | A$^1$.2 | C$_6$H$_5$ | CH$_2$COOCH$_3$ |
| IA-1308 | A$^1$.2 | CH$_2$COOCH$_2$CH$_3$ | CH$_2$COOCH$_2$CH$_3$ |
| IA-1309 | A$^1$.2 | cyclo-C$_3$H$_5$ | CH$_2$COOCH$_2$CH$_3$ |
| IA-1310 | A$^1$.2 | cyclo-C$_4$H$_7$ | CH$_2$COOCH$_2$CH$_3$ |
| IA-1311 | A$^1$.2 | cyclo-C$_5$H$_9$ | CH$_2$COOCH$_2$CH$_3$ |
| IA-1312 | A$^1$.2 | cyclo-C$_6$H$_{11}$ | CH$_2$COOCH$_2$CH$_3$ |
| IA-1313 | A$^1$.2 | C$_6$H$_5$ | CH$_2$COOCH$_2$CH$_3$ |
| IA-1314 | A$^1$.2 | cyclo-C$_3$H$_5$ | cyclo-C$_3$H$_5$ |
| IA-1315 | A$^1$.2 | cyclo-C$_4$H$_7$ | cyclo-C$_3$H$_5$ |
| IA-1316 | A$^1$.2 | cyclo-C$_5$H$_9$ | cyclo-C$_3$H$_5$ |
| IA-1317 | A$^1$.2 | cyclo-C$_6$H$_{11}$ | cyclo-C$_3$H$_5$ |
| IA-1318 | A$^1$.2 | C$_6$H$_5$ | cyclo-C$_3$H$_5$ |
| IA-1319 | A$^1$.2 | cyclo-C$_4$H$_7$ | cyclo-C$_4$H$_7$ |
| IA-1320 | A$^1$.2 | cyclo-C$_5$H$_9$ | cyclo-C$_4$H$_7$ |
| IA-1321 | A$^1$.2 | cyclo-C$_6$H$_{11}$ | cyclo-C$_4$H$_7$ |
| IA-1322 | A$^1$.2 | C$_6$H$_5$ | cyclo-C$_4$H$_7$ |
| IA-1323 | A$^1$.2 | cyclo-C$_5$H$_9$ | cyclo-C$_5$H$_9$ |
| IA-1324 | A$^1$.2 | cyclo-C$_6$H$_{11}$ | cyclo-C$_5$H$_9$ |
| IA-1325 | A$^1$.2 | C$_6$H$_5$ | cyclo-C$_5$H$_9$ |
| IA-1326 | A$^1$.2 | cyclo-C$_6$H$_{11}$ | cyclo-C$_6$H$_{11}$ |
| IA-1327 | A$^1$.2 | C$_6$H$_5$ | cyclo-C$_6$H$_{11}$ |
| IA-1328 | A$^1$.2 | C$_6$H$_5$ | C$_6$H$_5$ |

Table 883

Compounds of the formula IA (as defined above) wherein Q$^1$ denotes hydrogen, Q$^3$ denotes CF$_3$, and A in each case corresponds to a radical of Table D.

Table 884

Compounds of the formula IA wherein Q$^1$ denotes hydrogen, Q$^3$ denotes bromine, and A in each case corresponds to a radical of Table D.

Table 885

Compounds of the formula IA wherein Q$^1$ denotes hydrogen, Q$^3$ denotes chlorine, and A in each case corresponds to a radical of Table D.

Table 886

Compounds of the formula IA wherein Q$^1$ denotes hydrogen, Q$^3$ denotes CH$_3$, and A in each case corresponds to a radical of Table D.

Table 887

Compounds of the formula IA wherein Q$^1$ denotes hydrogen, Q$^3$ denotes OCH$_3$, and A in each case corresponds to a radical of Table D.

Table 888

Compounds of the formula IA wherein Q$^1$ denotes hydrogen, Q$^3$ denotes OCHCH$_2$, and A in each case corresponds to a radical of Table D.

Table 889

Compounds of the formula IA wherein Q$^1$ denotes hydrogen, Q$^3$ denotes ethoxy, and A in each case corresponds to a radical of Table D.

Table 890
Compounds of the formula IA wherein $Q^1$ denotes hydrogen, $Q^3$ denotes $OCH_2CHFOCH_3$, and A in each case corresponds to a radical of Table D.

Table 891
Compounds of the formula IA wherein $Q^1$ denotes hydrogen, $Q^3$ denotes $OCH_2CH=CH_2$, and A in each case corresponds to a radical of Table D.

Table 892
Compounds of the formula IA wherein $Q^1$ denotes hydrogen, $Q^3$ denotes $OCH_2CCH$, and A in each case corresponds to a radical of Table D.

Table 893
Compounds of the formula IA wherein $Q^1$ denotes hydrogen, $Q^3$ denotes $CH_2OCH_3$, and A in each case corresponds to a radical of Table D.

Table 894
Compounds of the formula IA wherein $Q^1$ denotes hydrogen, $Q^3$ denotes $CH_2OCH_2CH_3$, and A in each case corresponds to a radical of Table D.

Table 895
Compounds of the formula IA wherein $Q^1$ denotes hydrogen, $Q^3$ denotes $CH_2SCH_3$, and A in each case corresponds to a radical of Table D.

Table 896
Compounds of the formula IA wherein $Q^1$ denotes hydrogen, $Q^3$ denotes $CH_2SCH_2CH_3$, and A in each case corresponds to a radical of Table D.

Table 897
Compounds of the formula IA wherein $Q^1$ denotes hydrogen, $Q^3$ denotes $CH_2S(=O)CH_3$, and A in each case corresponds to a radical of Table D.

Table 898
Compounds of the formula IA wherein $Q^1$ denotes hydrogen, $Q^3$ denotes $CH_2S(=O)CH_2CH_3$, and A in each case corresponds to a radical of Table D.

Table 899
Compounds of the formula IA wherein $Q^1$ denotes hydrogen, $Q^3$ denotes $CH_2S(=O)_2CH_3$, and A in each case corresponds to a radical of Table D.

Table 900
Compounds of the formula IA wherein $Q^1$ denotes hydrogen, $Q^3$ denotes $CH_2S(=O)_2CH_2CH_3$, and A in each case corresponds to a radical of Table D.

Table 901
Compounds of the formula IA wherein $Q^1$ denotes hydrogen, $Q^3$ denotes $-OS(=O)_2CH_3$, and A in each case corresponds to a radical of Table D.

Table 902
Compounds of the formula IA wherein $Q^1$ denotes hydrogen, $Q^3$ notes $-OS(=O)_2CH_2CH_3$, and A in each case corresponds to a radical of Table D.

Table 903
Compounds of the formula IA wherein $Q^1$ denotes hydrogen, $Q^3$ notes $-OS(=O)_2CH_2CF_3$, and A in each case corresponds to a radical of Table D.

Table 904
Compounds of the formula IA wherein $Q^1$ denotes hydrogen, $Q^3$ notes $-OS(=O)_2CClF_2$, and A in each case corresponds to a radical of Table D.

Table 905
Compounds of the formula IA wherein $Q^1$ denotes hydrogen, $Q^3$ denotes $OC(=O)CF_3$, and A in each case corresponds to a radical of Table D.

Table 906
Compounds of the formula IA wherein $Q^1$ denotes hydrogen, $Q^3$ denotes $NHCH_2CF_3$, and A in each case corresponds to a radical of Table D.

Table 907
Compounds of the formula IA wherein $Q^1$ denotes hydrogen, $Q^3$ denotes $OCH_2$-cyclopropyl, and A in each case corresponds to a radical of Table D.

Table 908
Compounds of the formula IA wherein $Q^1$ denotes hydrogen, $Q^3$ denotes $OCH_2C(Cl)=CH_2$, and A in each case corresponds to a radical of Table D.

Table 909
Compounds of the formula IA wherein $Q^1$ denotes hydrogen, $Q^3$ denotes $OCH_2CH=CF_2$, and A in each case corresponds to a radical of Table D.

Table 910
Compounds of the formula IA wherein $Q^1$ denotes hydrogen, $Q^3$ denotes $NHS(=O)_2CF_3$, and A in each case corresponds to a radical of Table D.

Table 911
Compounds of the formula IA wherein $Q^1$ denotes hydrogen, $Q^3$ denotes $NHC(=O)CF_3$, and A in each case corresponds to a radical of Table D.

Table 912
Compounds of the formula IA wherein $Q^1$ denotes hydrogen, $Q^3$ denotes $OCH_2CN$, and A in each case corresponds to a radical of Table D.

Table 913
Compounds of the formula IA wherein $Q^1$ denotes hydrogen, $Q^3$ denotes $OCH_2NO_2$, and A in each case corresponds to a radical of Table D.

Table 914
Compounds of the formula IA wherein $Q^1$ denotes hydrogen, $Q^3$ denotes cyclopropyloxy, and A in each case corresponds to a radical of Table D.

Table 915
Compounds of the formula IA wherein $Q^1$ denotes hydrogen, $Q^3$ denotes $CH_2OCHF_2$, and A in each case corresponds to a radical of Table D.

Table 916
Compounds of the formula IA wherein $Q^1$ denotes hydrogen, $Q^3$ denotes $CH_2S(=O)_2CHF_2$, and A in each case corresponds to a radical of Table D.

Table 917
Compounds of the formula IA wherein $Q^1$ denotes hydrogen, $Q^3$ denotes $CH=NOCH_3$, and A in each case corresponds to a radical of Table D.

Table 918
Compounds of the formula IA wherein $Q^1$ denotes hydrogen, $Q^3$ denotes $CH=NOCH_2CH_3$, and A in each case corresponds to a radical of Table D.

Table 919
Compounds of the formula IA wherein $Q^1$ denotes hydrogen, $Q^3$ denotes $CH=NOCH(CH_3)_2$ and A in each case corresponds to a radical of Table D.

Table 920
Compounds of the formula IA wherein $Q^1$ denotes hydrogen, $Q^3$ denotes $CH=NOC(CH_3)_3$, and A in each case corresponds to a radical of Table D.

Table 921
Compounds of the formula IA wherein $Q^1$ denotes hydrogen, $Q^3$ denotes $C(CH_3)=NOCH_3$, and A in each case corresponds to a radical of Table D.

Table 922
Compounds of the formula IA wherein $Q^1$ denotes hydrogen, $Q^3$ denotes $C(CH_3)=NOCH_2CH_3$, and A in each case corresponds to a radical of Table D.

Table 923
Compounds of the formula IA wherein $Q^1$ denotes hydrogen, $Q^3$ denotes $C(CH_3)=NOCH(CH_3)_2$, and A in each case corresponds to a radical of Table D.

Table 924
Compounds of the formula IA wherein $Q^1$ denotes hydrogen, $Q^3$ denotes $C(CH_3)=NOC(CH_3)_3$, and A in each case corresponds to a radical of Table D.

Table 925
Compounds of the formula IA wherein $Q^1$ denotes chlorine, $Q^3$ denotes $CF_3$, and A in each case corresponds to a radical of Table D.

Table 926
Compounds of the formula IA wherein $Q^1$ denotes chlorine, $Q^3$ denotes bromine, and A in each case corresponds to a radical of Table D.

Table 927
Compounds of the formula IA wherein $Q^1$ denotes chlorine, $Q^3$ denotes chlorine, and A in each case corresponds to a radical of Table D.

Table 928
Compounds of the formula IA wherein $Q^1$ denotes chlorine, $Q^3$ denotes $CH_3$, and A in each case corresponds to a radical of Table D.

Table 929
Compounds of the formula IA wherein $Q^1$ denotes chlorine, $Q^3$ denotes $OCH_3$, and A in each case corresponds to a radical of Table D.

Table 930
Compounds of the formula IA wherein $Q^1$ denotes chlorine, $Q^3$ denotes $OCHCH_2$, and A in each case corresponds to a radical of Table D.

Table 931
Compounds of the formula IA wherein $Q^1$ denotes chlorine, $Q^3$ denotes ethoxy, and A in each case corresponds to a radical of Table D.

Table 932
Compounds of the formula IA wherein $Q^1$ denotes chlorine, $Q^3$ denotes $OCH_2CHFOCH_3$, and A in each case corresponds to a radical of Table D.

Table 933
Compounds of the formula IA wherein $Q^1$ denotes chlorine, $Q^3$ denotes $OCH_2CH=CH_2$, and A in each case corresponds to a radical of Table D.

Table 934
Compounds of the formula IA wherein $Q^1$ denotes chlorine, $Q^3$ denotes $OCH_2CCH$, and A in each case corresponds to a radical of Table D.

Table 935
Compounds of the formula IA wherein $Q^1$ denotes chlorine, $Q^3$ denotes $CH_2OCH_3$, and A in each case corresponds to a radical of Table D.

Table 936
Compounds of the formula IA wherein $Q^1$ denotes chlorine, $Q^3$ denotes $CH_2OCH_2CH_3$, and A in each case corresponds to a radical of Table D.

Table 937
Compounds of the formula IA wherein $Q^1$ denotes chlorine, $Q^3$ denotes $CH_2SCH_3$, and A in each case corresponds to a radical of Table D.

Table 938
Compounds of the formula IA wherein $Q^1$ denotes chlorine, $Q^3$ denotes $CH_2SCH_2CH_3$, and A in each case corresponds to a radical of Table D.

Table 939
Compounds of the formula IA wherein $Q^1$ denotes chlorine, $Q^3$ denotes $CH_2S(=O)CH_3$, and A in each case corresponds to a radical of Table D.

Table 940
Compounds of the formula IA wherein $Q^1$ denotes chlorine, $Q^3$ denotes $CH_2S(=O)CH_2CH_3$, and A in each case corresponds to a radical of Table D.

Table 941
Compounds of the formula IA wherein $Q^1$ denotes chlorine, $Q^3$ denotes $CH_2S(=O)_2CH_3$, and A in each case corresponds to a radical of Table D.

Table 942
Compounds of the formula IA wherein $Q^1$ denotes chlorine, $Q^3$ denotes $CH_2S(=O)_2CH_2CH_3$, and A in each case corresponds to a radical of Table D.

Table 943
Compounds of the formula IA wherein $Q^1$ denotes chlorine, $Q^3$ denotes $—OS(=O)_2CH_3$, and A in each case corresponds to a radical of Table D.

Table 944
Compounds of the formula IA wherein $Q^1$ denotes chlorine, $Q^3$ notes $—OS(=O)_2CH_2CH_3$, and A in each case corresponds to a radical of Table D.

Table 945
Compounds of the formula IA wherein $Q^1$ denotes chlorine, $Q^3$ notes $—OS(=O)_2CH_2CF_3$, and A in each case corresponds to a radical of Table D.

Table 946
Compounds of the formula IA wherein $Q^1$ denotes chlorine, $Q^3$ notes $—OS(=O)_2CClF_2$, and A in each case corresponds to a radical of Table D.

Table 947
Compounds of the formula IA wherein $Q^1$ denotes chlorine, $Q^3$ denotes $OC(=O)CF_3$, and A in each case corresponds to a radical of Table D.

Table 948
Compounds of the formula IA wherein $Q^1$ denotes chlorine, $Q^3$ denotes $NHCH_2CF_3$, and A in each case corresponds to a radical of Table D.

Table 949
Compounds of the formula IA wherein $Q^1$ denotes chlorine, $Q^3$ denotes $OCH_2$-cyclopropyl, and A in each case corresponds to a radical of Table D.

Table 950
Compounds of the formula IA wherein $Q^1$ denotes chlorine, $Q^3$ denotes $OCH_2C(Cl)=CH_2$, and A in each case corresponds to a radical of Table D.

Table 951
Compounds of the formula IA wherein $Q^1$ denotes chlorine, $Q^3$ denotes $OCH_2CH=CF_2$, and A in each case corresponds to a radical of Table D.

Table 952
Compounds of the formula IA wherein $Q^1$ denotes chlorine, $Q^3$ denotes $NHS(=O)_2CF_3$, and A in each case corresponds to a radical of Table D.

Table 953
Compounds of the formula IA wherein $Q^1$ denotes chlorine, $Q^3$ denotes $NHC(=O)CF_3$, and A in each case corresponds to a radical of Table D.

Table 954
Compounds of the formula IA wherein $Q^1$ denotes chlorine, $Q^3$ denotes $OCH_2CN$, and A in each case corresponds to a radical of Table D.

Table 955
Compounds of the formula IA wherein $Q^1$ denotes chlorine, $Q^3$ denotes $OCH_2NO_2$, and A in each case corresponds to a radical of Table D.

Table 956
Compounds of the formula IA wherein $Q^1$ denotes chlorine, $Q^3$ denotes cyclopropyloxy, and A in each case corresponds to a radical of Table D.

Table 957
Compounds of the formula IA wherein $Q^1$ denotes chlorine, $Q^3$ denotes $CH_2OCHF_2$, and A in each case corresponds to a radical of Table D.

Table 958
Compounds of the formula IA wherein $Q^1$ denotes chlorine, $Q^3$ denotes $CH_2S(=O)_2CHF_2$, and A in each case corresponds to a radical of Table D.

Table 959
Compounds of the formula IA wherein $Q^1$ denotes chlorine, $Q^3$ denotes $CH=NOCH_3$, and A in each case corresponds to a radical of Table D.

Table 960
Compounds of the formula IA wherein $Q^1$ denotes chlorine, $Q^3$ denotes $CH=NOCH_2CH_3$, and A in each case corresponds to a radical of Table D.

Table 961
Compounds of the formula IA wherein $Q^1$ denotes chlorine, $Q^3$ denotes $CH=NOCH(CH_3)_2$, and A in each case corresponds to a radical of Table D.

Table 962
Compounds of the formula IA wherein $Q^1$ denotes chlorine, $Q^3$ denotes $CH=NOC(CH_3)_3$, and A in each case corresponds to a radical of Table D.

Table 963
Compounds of the formula IA wherein $Q^1$ denotes chlorine, $Q^3$ denotes $C(CH_3)=NOCH_3$, and A in each case corresponds to a radical of Table D.

Table 964
Compounds of the formula IA wherein $Q^1$ denotes chlorine, $Q^3$ denotes $C(CH_3)=NOCH_2CH_3$, and A in each case corresponds to a radical of Table D.

Table 965
Compounds of the formula IA wherein $Q^1$ denotes chlorine, $Q^3$ denotes $C(CH_3)=NOCH(CH_3)_2$, and A in each case corresponds to a radical of Table D.

Table 966
Compounds of the formula IA wherein $Q^1$ denotes chlorine, $Q^3$ denotes $C(CH_3)=NOC(CH_3)_3$, and A in each case corresponds to a radical of Table D.

Table 967
Compounds of the formula IA wherein $Q^1$ denotes bromine, $Q^3$ denotes $CF_3$, and A in each case corresponds to a radical of Table D.

Table 968
Compounds of the formula IA wherein $Q^1$ denotes bromine, $Q^3$ denotes bromine, and A in each case corresponds to a radical of Table D.

Table 969
Compounds of the formula IA wherein $Q^1$ denotes bromine, $Q^3$ denotes chlorine, and A in each case corresponds to a radical of Table D.

Table 970
Compounds of the formula IA wherein $Q^1$ denotes bromine, $Q^3$ denotes $CH_3$, and A in each case corresponds to a radical of Table D.

Table 971
Compounds of the formula IA wherein $Q^1$ denotes bromine, $Q^3$ denotes $OCH_3$, and A in each case corresponds to a radical of Table D.

Table 972
Compounds of the formula IA wherein $Q^1$ denotes bromine, $Q^3$ denotes $OCHCH_2$, and A in each case corresponds to a radical of Table D.

Table 973
Compounds of the formula IA wherein $Q^1$ denotes bromine, $Q^3$ denotes ethoxy, and A in each case corresponds to a radical of Table D.

Table 974
Compounds of the formula IA wherein $Q^1$ denotes bromine, $Q^3$ denotes $OCH_2CHFOCH_3$, and A in each case corresponds to a radical of Table D.

Table 975
Compounds of the formula IA wherein $Q^1$ denotes bromine, $Q^3$ denotes $OCH_2CH=CH_2$, and A in each case corresponds to a radical of Table D.

Table 976
Compounds of the formula IA wherein $Q^1$ denotes bromine, $Q^3$ denotes $OCH_2CCH$, and A in each case corresponds to a radical of Table D.

Table 977
Compounds of the formula IA wherein $Q^1$ denotes bromine, $Q^3$ denotes $CH_2OCH_3$, and A in each case corresponds to a radical of Table D.

Table 978
Compounds of the formula IA wherein $Q^1$ denotes bromine, $Q^3$ denotes $CH_2OCH_2CH_3$, and A in each case corresponds to a radical of Table D.

Table 979
Compounds of the formula IA wherein $Q^1$ denotes bromine, $Q^3$ denotes $CH_2SCH_3$, and A in each case corresponds to a radical of Table D.

Table 980
Compounds of the formula IA wherein $Q^1$ denotes bromine, $Q^3$ denotes $CH_2SCH_2CH_3$, and A in each case corresponds to a radical of Table D.

Table 981
Compounds of the formula IA wherein $Q^1$ denotes bromine, $Q^3$ denotes $CH_2S(=O)CH_3$, and A in each case corresponds to a radical of Table D.

Table 982
Compounds of the formula IA wherein $Q^1$ denotes bromine, $Q^3$ denotes $CH_2S(=O)CH_2CH_3$, and A in each case corresponds to a radical of Table D.

Table 983
Compounds of the formula IA wherein $Q^1$ denotes bromine, $Q^3$ denotes $CH_2S(=O)_2CH_3$, and A in each case corresponds to a radical of Table D.

Table 984
Compounds of the formula IA wherein $Q^1$ denotes bromine, $Q^3$ denotes $CH_2S(=O)_2CH_2CH_3$, and A in each case corresponds to a radical of Table D.

Table 985
Compounds of the formula IA wherein $Q^1$ denotes bromine, $Q^3$ denotes $—OS(=O)_2CH_3$, and A in each case corresponds to a radical of Table D.

Table 986
Compounds of the formula IA wherein $Q^1$ denotes bromine, $Q^3$ notes $—OS(=O)_2CH_2CH_3$, and A in each case corresponds to a radical of Table D.

Table 987
Compounds of the formula IA wherein $Q^1$ denotes bromine, $Q^3$ notes $—OS(=O)_2CH_2CF_3$, and A in each case corresponds to a radical of Table D.

Table 988
Compounds of the formula IA wherein $Q^1$ denotes bromine, $Q^3$ notes $—OS(=O)_2CClF_2$, and A in each case corresponds to a radical of Table D.

Table 989
Compounds of the formula IA wherein $Q^1$ denotes bromine, $Q^3$ denotes $OC(=O)CF_3$, and A in each case corresponds to a radical of Table D.

Table 990
Compounds of the formula IA wherein $Q^1$ denotes bromine, $Q^3$ denotes $NHCH_2CF_3$, and A in each case corresponds to a radical of Table D.

Table 991
Compounds of the formula IA wherein $Q^1$ denotes bromine, $Q^3$ denotes $OCH_2$-cyclopropyl, and A in each case corresponds to a radical of Table D.

Table 992
Compounds of the formula IA wherein $Q^1$ denotes bromine, $Q^3$ denotes $OCH_2C(Cl)=CH_2$, and A in each case corresponds to a radical of Table D.

Table 993
Compounds of the formula IA wherein $Q^1$ denotes bromine, $Q^3$ denotes $OCH_2CH=CF_2$, and A in each case corresponds to a radical of Table D.

Table 994
Compounds of the formula IA wherein $Q^1$ denotes bromine, $Q^3$ denotes $NHS(=O)_2CF_3$, and A in each case corresponds to a radical of Table D.

Table 995
Compounds of the formula IA wherein $Q^1$ denotes bromine, $Q^3$ denotes $NHC(=O)CF_3$, and A in each case corresponds to a radical of Table D.

Table 996
Compounds of the formula IA wherein $Q^1$ denotes bromine, $Q^3$ denotes $OCH_2CN$, and A in each case corresponds to a radical of Table D.

Table 997
Compounds of the formula IA wherein $Q^1$ denotes bromine, $Q^3$ denotes $OCH_2NO_2$, and A in each case corresponds to a radical of Table D.

Table 998
Compounds of the formula IA wherein $Q^1$ denotes bromine, $Q^3$ denotes cyclopropyloxy, and A in each case corresponds to a radical of Table D.

Table 999
Compounds of the formula IA wherein $Q^1$ denotes bromine, $Q^3$ denotes $CH_2OCHF_2$, and A in each case corresponds to a radical of Table D.

Table 1000
Compounds of the formula IA wherein $Q^1$ denotes bromine, $Q^3$ denotes $CH_2S(=O)_2CHF_2$, and A in each case corresponds to a radical of Table D.

Table 1001
Compounds of the formula IA wherein $Q^1$ denotes bromine, $Q^3$ denotes $CH=NOCH_3$, and A in each case corresponds to a radical of Table D.

Table 1002
Compounds of the formula IA wherein $Q^1$ denotes bromine, $Q^3$ denotes $CH=NOCH_2CH_3$, and A in each case corresponds to a radical of Table D.

Table 1003
Compounds of the formula IA wherein $Q^1$ denotes bromine, $Q^3$ denotes $CH=NOCH(CH_3)_2$ and A in each case corresponds to a radical of Table D.

Table 1004
Compounds of the formula IA wherein $Q^1$ denotes bromine, $Q^3$ denotes $CH=NOC(CH_3)_3$, and A in each case corresponds to a radical of Table D.

Table 1005
Compounds of the formula IA wherein $Q^1$ denotes bromine, $Q^3$ denotes $C(CH_3)=NOCH_3$, and A in each case corresponds to a radical of Table D.

Table 1006
Compounds of the formula IA wherein $Q^1$ denotes bromine, $Q^3$ denotes $C(CH_3)=NOCH_2CH_3$, and A in each case corresponds to a radical of Table D.

Table 1007
Compounds of the formula IA wherein $Q^1$ denotes bromine, $Q^3$ denotes $C(CH_3)=NOCH(CH_3)_2$, and A in each case corresponds to a radical of Table D.

Table 1008
Compounds of the formula IA wherein $Q^1$ denotes bromine, $Q^3$ denotes $C(CH_3)=NOC(CH_3)_3$, and A in each case corresponds to a radical of Table D.

Table 1009
Compounds of the formula IA wherein $Q^1$ denotes fluorine, $Q^3$ denotes $CF_3$, and A in each case corresponds to a radical of Table D.

Table 1010
Compounds of the formula IA wherein $Q^1$ denotes fluorine, $Q^3$ denotes bromine, and A in each case corresponds to a radical of Table D.

Table 1011
Compounds of the formula IA wherein $Q^1$ denotes fluorine, $Q^3$ denotes chlorine, and A in each case corresponds to a radical of Table D.

Table 1012
Compounds of the formula IA wherein $Q^1$ denotes fluorine, $Q^3$ denotes $CH_3$, and A in each case corresponds to a radical of Table D.

Table 1013
Compounds of the formula IA wherein $Q^1$ denotes fluorine, $Q^3$ denotes $OCH_3$, and A in each case corresponds to a radical of Table D.

Table 1014
Compounds of the formula IA wherein $Q^1$ denotes fluorine, $Q^3$ denotes $OCHCH_2$, and A in each case corresponds to a radical of Table D.

Table 1015
Compounds of the formula IA wherein $Q^1$ denotes fluorine, $Q^3$ denotes ethoxy, and A in each case corresponds to a radical of Table D.

Table 1016
Compounds of the formula IA wherein $Q^1$ denotes fluorine, $Q^3$ denotes $OCH_2CHFOCH_3$, and A in each case corresponds to a radical of Table D.

Table 1017
Compounds of the formula IA wherein $Q^1$ denotes fluorine, $Q^3$ denotes $OCH_2CH=CH_2$, and A in each case corresponds to a radical of Table D.

Table 1018
Compounds of the formula IA wherein $Q^1$ denotes fluorine, $Q^3$ denotes $OCH_2CCH$, and A in each case corresponds to a radical of Table D.

Table 1019
Compounds of the formula IA wherein $Q^1$ denotes fluorine, $Q^3$ denotes $CH_2OCH_3$, and A in each case corresponds to a radical of Table D.

Table 1020
Compounds of the formula IA wherein $Q^1$ denotes fluorine, $Q^3$ denotes $CH_2OCH_2CH_3$, and A in each case corresponds to a radical of Table D.

Table 1021
Compounds of the formula IA wherein $Q^1$ denotes fluorine, $Q^3$ denotes $CH_2SCH_3$, and A in each case corresponds to a radical of Table D.

Table 1022
Compounds of the formula IA wherein $Q^1$ denotes fluorine, $Q^3$ denotes $CH_2SCH_2CH_3$, and A in each case corresponds to a radical of Table D.

Table 1023
Compounds of the formula IA wherein $Q^1$ denotes fluorine, $Q^3$ denotes $CH_2S(=O)CH_3$, and A in each case corresponds to a radical of Table D.

Table 1024
Compounds of the formula IA wherein $Q^1$ denotes fluorine, $Q^3$ denotes $CH_2S(=O)CH_2CH_3$, and A in each case corresponds to a radical of Table D.

Table 1025
Compounds of the formula IA wherein $Q^1$ denotes fluorine, $Q^3$ denotes $CH_2S(=O)_2CH_3$, and A in each case corresponds to a radical of Table D.

Table 1026
Compounds of the formula IA wherein $Q^1$ denotes fluorine, $Q^3$ denotes $CH_2S(=O)_2CH_2CH_3$, and A in each case corresponds to a radical of Table D.

Table 1027
Compounds of the formula IA wherein $Q^1$ denotes fluorine, $Q^3$ denotes —$OS(=O)_2CH_3$, and A in each case corresponds to a radical of Table D.

Table 1028
Compounds of the formula IA wherein $Q^1$ denotes fluorine, $Q^3$ notes —$OS(=O)_2CH_2CH_3$, and A in each case corresponds to a radical of Table D.

Table 1029
Compounds of the formula IA wherein $Q^1$ denotes fluorine, $Q^3$ notes —$OS(=O)_2CH_2CF_3$, and A in each case corresponds to a radical of Table D.

Table 1030
Compounds of the formula IA wherein $Q^1$ denotes fluorine, $Q^3$ denotes —$OS(=O)_2CClF_2$, and A in each case corresponds to a radical of Table D.

Table 1031
Compounds of the formula IA wherein $Q^1$ denotes fluorine, $Q^3$ denotes $OC(=O)CF_3$, and A in each case corresponds to a radical of Table D.

Table 1032
Compounds of the formula IA wherein $Q^1$ denotes fluorine, $Q^3$ denotes $NHCH_2CF_3$, and A in each case corresponds to a radical of Table D.

Table 1033
Compounds of the formula IA wherein $Q^1$ denotes fluorine, $Q^3$ denotes $OCH_2$-cyclopropyl, and A in each case corresponds to a radical of Table D.

Table 1034
Compounds of the formula IA wherein $Q^1$ denotes fluorine, $Q^3$ denotes $OCH_2C(Cl)=CH_2$, and A in each case corresponds to a radical of Table D.

Table 1035
Compounds of the formula IA wherein $Q^1$ denotes fluorine, $Q^3$ denotes $OCH_2CH=CF_2$, and A in each case corresponds to a radical of Table D.

Table 1036
Compounds of the formula IA wherein $Q^1$ denotes fluorine, $Q^3$ denotes $NHS(=O)_2CF_3$, and A in each case corresponds to a radical of Table D.

Table 1037
Compounds of the formula IA wherein $Q^1$ denotes fluorine, $Q^3$ denotes $NHC(=O)CF_3$, and A in each case corresponds to a radical of Table D.

Table 1038
Compounds of the formula IA wherein $Q^1$ denotes fluorine, $Q^3$ denotes $OCH_2CN$, and A in each case corresponds to a radical of Table D.

Table 1039
Compounds of the formula IA wherein $Q^1$ denotes fluorine, $Q^3$ denotes $OCH_2NO_2$, and A in each case corresponds to a radical of Table D.

Table 1040
Compounds of the formula IA wherein $Q^1$ denotes fluorine, $Q^3$ denotes cyclopropyloxy, and A in each case corresponds to a radical of Table D.

Table 1041
Compounds of the formula IA wherein $Q^1$ denotes fluorine, $Q^3$ denotes $CH_2OCHF_2$, and A in each case corresponds to a radical of Table D.

Table 1042
Compounds of the formula IA wherein $Q^1$ denotes fluorine, $Q^3$ denotes $CH_2S(=O)_2CHF_2$, and A in each case corresponds to a radical of Table D.

Table 1043
Compounds of the formula IA wherein $Q^1$ denotes fluorine, $Q^3$ denotes $CH=NOCH_3$, and A in each case corresponds to a radical of Table D.

Table 1044
Compounds of the formula IA wherein $Q^1$ denotes fluorine, $Q^3$ denotes $CH=NOCH_2CH_3$, and A in each case corresponds to a radical of Table D.

Table 1045
Compounds of the formula IA wherein $Q^1$ denotes fluorine, $Q^3$ denotes $CH=NOCH(CH_3)_2$ and A in each case corresponds to a radical of Table D.

Table 1046
Compounds of the formula IA wherein $Q^1$ denotes fluorine, $Q^3$ denotes $CH=NOC(CH_3)_3$, and A in each case corresponds to a radical of Table D.

Table 1047
Compounds of the formula IA wherein $Q^1$ denotes fluorine, $Q^3$ denotes $C(CH_3)=NOCH_3$, and A in each case corresponds to a radical of Table D.

Table 1048
Compounds of the formula IA wherein $Q^1$ denotes fluorine, $Q^3$ denotes $C(CH_3)=NOCH_2CH_3$, and A in each case corresponds to a radical of Table D.

Table 1049
Compounds of the formula IA wherein $Q^1$ denotes fluorine, $Q^3$ denotes $C(CH_3)=NOCH(CH_3)_2$, and A in each case corresponds to a radical of Table D.

Table 1050
Compounds of the formula IA wherein $Q^1$ denotes fluorine, $Q^3$ denotes $C(CH_3)=NOC(CH_3)_3$, and A in each case corresponds to a radical of Table D.

Table 1051
Compounds of the formula IA wherein $Q^1$ denotes iodine, $Q^3$ denotes $CF_3$, and A in each case corresponds to a radical of Table D.

Table 1052
Compounds of the formula IA wherein $Q^1$ denotes iodine, $Q^3$ denotes bromine, and A in each case corresponds to a radical of Table D.

Table 1053
Compounds of the formula IA wherein $Q^1$ denotes iodine, $Q^3$ denotes chlorine, and A in each case corresponds to a radical of Table D.

Table 1054
Compounds of the formula IA wherein $Q^1$ denotes iodine, $Q^3$ denotes $CH_3$, and A in each case corresponds to a radical of Table D.

Table 1055
Compounds of the formula IA wherein $Q^1$ denotes iodine, $Q^3$ denotes $OCH_3$, and A in each case corresponds to a radical of Table D.

Table 1056
Compounds of the formula IA wherein $Q^1$ denotes iodine, $Q^3$ denotes $OCHCH_2$, and A in each case corresponds to a radical of Table D.

Table 1057
Compounds of the formula IA wherein $Q^1$ denotes iodine, $Q^3$ denotes ethoxy, and A in each case corresponds to a radical of Table D.

Table 1058
Compounds of the formula IA wherein $Q^1$ denotes iodine, $Q^3$ denotes $OCH_2CHFOCH_3$, and A in each case corresponds to a radical of Table D.

Table 1059
Compounds of the formula IA wherein $Q^1$ denotes iodine, $Q^3$ denotes $OCH_2CH=CH_2$, and A in each case corresponds to a radical of Table D.

Table 1060
Compounds of the formula IA wherein $Q^1$ denotes iodine, $Q^3$ denotes $OCH_2CCH$, and A in each case corresponds to a radical of Table D.

Table 1061
Compounds of the formula IA wherein $Q^1$ denotes iodine, $Q^3$ denotes $CH_2OCH_3$, and A in each case corresponds to a radical of Table D.

Table 1062
Compounds of the formula IA wherein $Q^1$ denotes iodine, $Q^3$ denotes $CH_2OCH_2CH_3$, and A in each case corresponds to a radical of Table D.

Table 1063
Compounds of the formula IA wherein $Q^1$ denotes iodine, $Q^3$ denotes $CH_2SCH_3$, and A in each case corresponds to a radical of Table D.

Table 1064
Compounds of the formula IA wherein $Q^1$ denotes iodine, $Q^3$ denotes $CH_2SCH_2CH_3$, and A in each case corresponds to a radical of Table D.

Table 1065
Compounds of the formula IA wherein $Q^1$ denotes iodine, $Q^3$ denotes $CH_2S(=O)CH_3$, and A in each case corresponds to a radical of Table D.

Table 1066
Compounds of the formula IA wherein $Q^1$ denotes iodine, $Q^3$ denotes $CH_2S(=O)CH_2CH_3$, and A in each case corresponds to a radical of Table D.

Table 1067
Compounds of the formula IA wherein $Q^1$ denotes iodine, $Q^3$ denotes $CH_2S(=O)_2CH_3$, and A in each case corresponds to a radical of Table D.

Table 1068
Compounds of the formula IA wherein $Q^1$ denotes iodine, $Q^3$ denotes $CH_2S(=O)_2CH_2CH_3$, and A in each case corresponds to a radical of Table D.

Table 1069
Compounds of the formula IA wherein $Q^1$ denotes iodine, $Q^3$ denotes $—OS(=O)_2CH_3$, and A in each case corresponds to a radical of Table D.

Table 1070
Compounds of the formula IA wherein $Q^1$ denotes iodine, $Q^3$ notes $—OS(=O)_2CH_2CH_3$, and A in each case corresponds to a radical of Table D.

Table 1071
Compounds of the formula IA wherein $Q^1$ denotes iodine, $Q^3$ notes $—OS(=O)_2CH_2CF_3$, and A in each case corresponds to a radical of Table D.

Table 1072
Compounds of the formula IA wherein $Q^1$ denotes iodine, $Q^3$ denotes $—OS(=O)_2CClF_2$, and A in each case corresponds to a radical of Table D.

Table 1073
Compounds of the formula IA wherein $Q^1$ denotes iodine, $Q^3$ denotes $OC(=O)CF_3$, and A in each case corresponds to a radical of Table D.

Table 1074
Compounds of the formula IA wherein $Q^1$ denotes iodine, $Q^3$ denotes $NHCH_2CF_3$, and A in each case corresponds to a radical of Table D.

Table 1075
Compounds of the formula IA wherein $Q^1$ denotes iodine, $Q^3$ denotes $OCH_2$-cyclopropyl, and A in each case corresponds to a radical of Table D.

Table 1076
Compounds of the formula IA wherein $Q^1$ denotes iodine, $Q^3$ denotes $OCH_2C(Cl)=CH_2$, and A in each case corresponds to a radical of Table D.

Table 1077
Compounds of the formula IA wherein $Q^1$ denotes iodine, $Q^3$ denotes $OCH_2CH=CF_2$, and A in each case corresponds to a radical of Table D.

Table 1078
Compounds of the formula IA wherein $Q^1$ denotes iodine, $Q^3$ denotes $NHS(=O)_2CF_3$, and A in each case corresponds to a radical of Table D.

Table 1079
Compounds of the formula IA wherein $Q^1$ denotes iodine, $Q^3$ denotes $NHC(=O)CF_3$, and A in each case corresponds to a radical of Table D.

Table 1080
Compounds of the formula IA wherein $Q^1$ denotes iodine, $Q^3$ denotes $OCH_2CN$, and A in each case corresponds to a radical of Table D.

Table 1081
Compounds of the formula IA wherein $Q^1$ denotes iodine, $Q^3$ denotes $OCH_2NO_2$, and A in each case corresponds to a radical of Table D.

Table 1082
Compounds of the formula IA wherein $Q^1$ denotes iodine, $Q^3$ denotes cyclopropyloxy, and A in each case corresponds to a radical of Table D.

Table 1083
Compounds of the formula IA wherein $Q^1$ denotes iodine, $Q^3$ denotes $CH_2OCHF_2$, and A in each case corresponds to a radical of Table D.

Table 1084
Compounds of the formula IA wherein $Q^1$ denotes iodine, $Q^3$ denotes $CH_2S(=O)_2CHF_2$, and A in each case corresponds to a radical of Table D.

Table 1085
Compounds of the formula IA wherein $Q^1$ denotes iodine, $Q^3$ denotes $CH=NOCH_3$, and A in each case corresponds to a radical of Table D.

Table 1086
Compounds of the formula IA wherein $Q^1$ denotes iodine, $Q^3$ denotes $CH=NOCH_2CH_3$, and A in each case corresponds to a radical of Table D.

Table 1087
Compounds of the formula IA wherein $Q^1$ denotes iodine, $Q^3$ denotes $CH=NOCH(CH_3)_2$ and A in each case corresponds to a radical of Table D.

Table 1088
Compounds of the formula IA wherein $Q^1$ denotes iodine, $Q^3$ denotes CH=NOC(CH$_3$)$_3$, and A in each case corresponds to a radical of Table D.

Table 1089
Compounds of the formula IA wherein $Q^1$ denotes iodine, $Q^3$ denotes C(CH$_3$)=NOCH$_3$, and A in each case corresponds to a radical of Table D.

Table 1090
Compounds of the formula IA wherein $Q^1$ denotes iodine, $Q^3$ denotes C(CH$_3$)=NOCH$_2$CH$_3$, and A in each case corresponds to a radical of Table D.

Table 1091
Compounds of the formula IA wherein $Q^1$ denotes iodine, $Q^3$ denotes C(CH$_3$)=NOCH(CH$_3$)$_2$, and A in each case corresponds to a radical of Table D.

Table 1092
Compounds of the formula IA wherein $Q^1$ denotes iodine, $Q^3$ denotes C(CH$_3$)=NOC(CH$_3$)$_3$, and A in each case corresponds to a radical of Table D.

Table 1093
Compounds of the formula IA wherein $Q^1$ denotes cyano, $Q^3$ denotes CF$_3$, and A in each case corresponds to a radical of Table D.

Table 1094
Compounds of the formula IA wherein $Q^1$ denotes cyano, $Q^3$ denotes bromine, and A in each case corresponds to a radical of Table D.

Table 1095
Compounds of the formula IA wherein $Q^1$ denotes cyano, $Q^3$ denotes chlorine, and A in each case corresponds to a radical of Table D.

Table 1096
Compounds of the formula IA wherein $Q^1$ denotes cyano, $Q^3$ denotes CH$_3$, and A in each case corresponds to a radical of Table D.

Table 1097
Compounds of the formula IA wherein $Q^1$ denotes cyano, $Q^3$ denotes OCH$_3$, and A in each case corresponds to a radical of Table D.

Table 1098
Compounds of the formula IA wherein $Q^1$ denotes cyano, $Q^3$ denotes OCHCH$_2$, and A in each case corresponds to a radical of Table D.

Table 1099
Compounds of the formula IA wherein $Q^1$ denotes cyano, $Q^3$ denotes ethoxy, and A in each case corresponds to a radical of Table D.

Table 1100
Compounds of the formula IA wherein $Q^1$ denotes cyano, $Q^3$ denotes OCH$_2$CHFOCH$_3$, and A in each case corresponds to a radical of Table D.

Table 1101
Compounds of the formula IA wherein $Q^1$ denotes cyano, $Q^3$ denotes OCH$_2$CH=CH$_2$, and A in each case corresponds to a radical of Table D.

Table 1102
Compounds of the formula IA wherein $Q^1$ denotes cyano, $Q^3$ denotes OCH$_2$CCH, and A in each case corresponds to a radical of Table D.

Table 1103
Compounds of the formula IA wherein $Q^1$ denotes cyano, $Q^3$ denotes CH$_2$OCH$_3$, and A in each case corresponds to a radical of Table D.

Table 1104
Compounds of the formula IA wherein $Q^1$ denotes cyano, $Q^3$ denotes CH$_2$OCH$_2$CH$_3$, and A in each case corresponds to a radical of Table D.

Table 1105
Compounds of the formula IA wherein $Q^1$ denotes cyano, $Q^3$ denotes CH$_2$SCH$_3$, and A in each case corresponds to a radical of Table D.

Table 1106
Compounds of the formula IA wherein $Q^1$ denotes cyano, $Q^3$ denotes CH$_2$SCH$_2$CH$_3$, and A in each case corresponds to a radical of Table D.

Table 1107
Compounds of the formula IA wherein $Q^1$ denotes cyano, $Q^3$ denotes CH$_2$S(=O)CH$_3$, and A in each case corresponds to a radical of Table D.

Table 1108
Compounds of the formula IA wherein $Q^1$ denotes cyano, $Q^3$ denotes CH$_2$S(=O)CH$_2$CH$_3$, and A in each case corresponds to a radical of Table D.

Table 1109
Compounds of the formula IA wherein $Q^1$ denotes cyano, $Q^3$ denotes CH$_2$S(=O)$_2$CH$_3$, and A in each case corresponds to a radical of Table D.

Table 1110
Compounds of the formula IA wherein $Q^1$ denotes cyano, $Q^3$ denotes CH$_2$S(=O)$_2$CH$_2$CH$_3$, and A in each case corresponds to a radical of Table D.

Table 1111
Compounds of the formula IA wherein $Q^1$ denotes cyano, $Q^3$ denotes —OS(=O)$_2$CH$_3$, and A in each case corresponds to a radical of Table D.

Table 1112
Compounds of the formula IA wherein $Q^1$ denotes cyano, $Q^3$ notes —OS(=O)$_2$CH$_2$CH$_3$, and A in each case corresponds to a radical of Table D.

Table 1113
Compounds of the formula IA wherein $Q^1$ denotes cyano, $Q^3$ notes —OS(=O)$_2$CH$_2$CF$_3$, and A in each case corresponds to a radical of Table D.

Table 1114
Compounds of the formula IA wherein $Q^1$ denotes cyano, $Q^3$ denotes —OS(=O)$_2$CClF$_2$, and A in each case corresponds to a radical of Table D.

Table 1115
Compounds of the formula IA wherein $Q^1$ denotes cyano, $Q^3$ denotes OC(=O)CF$_3$, and A in each case corresponds to a radical of Table D.

Table 1116
Compounds of the formula IA wherein $Q^1$ denotes cyano, $Q^3$ denotes NHCH$_2$CF$_3$, and A in each case corresponds to a radical of Table D.

Table 1117
Compounds of the formula IA wherein $Q^1$ denotes cyano, $Q^3$ denotes OCH$_2$-cyclopropyl, and A in each case corresponds to a radical of Table D.

Table 1118
Compounds of the formula IA wherein $Q^1$ denotes cyano, $Q^3$ denotes OCH$_2$C(Cl)=CH$_2$, and A in each case corresponds to a radical of Table D.

Table 1119
Compounds of the formula IA wherein $Q^1$ denotes cyano, $Q^3$ denotes OCH$_2$CH=CF$_2$, and A in each case corresponds to a radical of Table D.

Table 1120
Compounds of the formula IA wherein $Q^1$ denotes cyano, $Q^3$ denotes NHS(=O)$_2$CF$_3$, and A in each case corresponds to a radical of Table D.

Table 1121
Compounds of the formula IA wherein $Q^1$ denotes cyano, $Q^3$ denotes NHC(=O)CF$_3$, and A in each case corresponds to a radical of Table D.

Table 1122
Compounds of the formula IA wherein $Q^1$ denotes cyano, $Q^3$ denotes OCH$_2$CN, and A in each case corresponds to a radical of Table D.

Table 1123
Compounds of the formula IA wherein $Q^1$ denotes cyano, $Q^3$ denotes OCH$_2$NO$_2$, and A in each case corresponds to a radical of Table D.

Table 1124
Compounds of the formula IA wherein $Q^1$ denotes cyano, $Q^3$ denotes cyclopropyloxy, and A in each case corresponds to a radical of Table D.

Table 1125
Compounds of the formula IA wherein $Q^1$ denotes cyano, $Q^3$ denotes CH$_2$OCHF$_2$, and A in each case corresponds to a radical of Table D.

Table 1126
Compounds of the formula IA wherein $Q^1$ denotes cyano, $Q^3$ denotes CH$_2$S(=O)$_2$CHF$_2$, and A in each case corresponds to a radical of Table D.

Table 1127
Compounds of the formula IA wherein $Q^1$ denotes cyano, $Q^3$ denotes CH=NOCH$_3$, and A in each case corresponds to a radical of Table D.

Table 1128
Compounds of the formula IA wherein $Q^1$ denotes cyano, $Q^3$ denotes CH=NOCH$_2$CH$_3$, and A in each case corresponds to a radical of Table D.

Table 1129
Compounds of the formula IA wherein $Q^1$ denotes cyano, $Q^3$ denotes CH=NOCH(CH$_3$)$_2$ and A in each case corresponds to a radical of Table D.

Table 1130
Compounds of the formula IA wherein $Q^1$ denotes cyano, $Q^3$ denotes CH=NOC(CH$_3$)$_3$, and A in each case corresponds to a radical of Table D.

Table 1131
Compounds of the formula IA wherein $Q^1$ denotes cyano, $Q^3$ denotes C(CH$_3$)=NOCH$_3$, and A in each case corresponds to a radical of Table D.

Table 1132
Compounds of the formula IA wherein $Q^1$ denotes cyano, $Q^3$ denotes C(CH$_3$)=NOCH$_2$CH$_3$, and A in each case corresponds to a radical of Table D.

Table 1133
Compounds of the formula IA wherein $Q^1$ denotes cyano, $Q^3$ denotes C(CH$_3$)=NOCH(CH$_3$)$_2$, and A in each case corresponds to a radical of Table D.

Table 1134
Compounds of the formula IA wherein $Q^1$ denotes cyano, $Q^3$ denotes C(CH$_3$)=NOC(CH$_3$)$_3$, and A in each case corresponds to a radical of Table D.

Table 1135
Compounds of the formula IA wherein $Q^1$ denotes methyl, $Q^3$ denotes CF$_3$, and A in each case corresponds to a radical of Table D.

Table 1136
Compounds of the formula IA wherein $Q^1$ denotes methyl, $Q^3$ denotes bromine, and A in each case corresponds to a radical of Table D.

Table 1137
Compounds of the formula IA wherein $Q^1$ denotes methyl, $Q^3$ denotes chlorine, and A in each case corresponds to a radical of Table D.

Table 1138
Compounds of the formula IA wherein $Q^1$ denotes methyl, $Q^3$ denotes CH$_3$, and A in each case corresponds to a radical of Table D.

Table 1139
Compounds of the formula IA wherein $Q^1$ denotes methyl, $Q^3$ denotes OCH$_3$, and A in each case corresponds to a radical of Table D.

Table 1140
Compounds of the formula IA wherein $Q^1$ denotes methyl, $Q^3$ denotes OCHCH$_2$, and A in each case corresponds to a radical of Table D.

Table 1141
Compounds of the formula IA wherein $Q^1$ denotes methyl, $Q^3$ denotes ethoxy, and A in each case corresponds to a radical of Table D.

Table 1142
Compounds of the formula IA wherein $Q^1$ denotes methyl, $Q^3$ denotes OCH$_2$CHFOCH$_3$, and A in each case corresponds to a radical of Table D.

Table 1143
Compounds of the formula IA wherein $Q^1$ denotes methyl, $Q^3$ denotes OCH$_2$CH=CH$_2$, and A in each case corresponds to a radical of Table D.

Table 1144
Compounds of the formula IA wherein $Q^1$ denotes methyl, $Q^3$ denotes OCH$_2$CCH, and A in each case corresponds to a radical of Table D.

Table 1145
Compounds of the formula IA wherein $Q^1$ denotes methyl, $Q^3$ denotes CH$_2$OCH$_3$, and A in each case corresponds to a radical of Table D.

Table 1146
Compounds of the formula IA wherein $Q^1$ denotes methyl, $Q^3$ denotes CH$_2$OCH$_2$CH$_3$, and A in each case corresponds to a radical of Table D.

Table 1147
Compounds of the formula IA wherein $Q^1$ denotes methyl, $Q^3$ denotes CH$_2$SCH$_3$, and A in each case corresponds to a radical of Table D.

Table 1148
Compounds of the formula IA wherein $Q^1$ denotes methyl, $Q^3$ denotes CH$_2$SCH$_2$CH$_3$, and A in each case corresponds to a radical of Table D.

Table 1149
Compounds of the formula IA wherein $Q^1$ denotes methyl, $Q^3$ denotes CH$_2$S(=O)CH$_3$, and A in each case corresponds to a radical of Table D.

Table 1150
Compounds of the formula IA wherein $Q^1$ denotes methyl, $Q^3$ denotes CH$_2$S(=O)CH$_2$CH$_3$, and A in each case corresponds to a radical of Table D.

Table 1151
Compounds of the formula IA wherein $Q^1$ denotes methyl, $Q^3$ denotes CH$_2$S(=O)$_2$CH$_3$, and A in each case corresponds to a radical of Table D.

Table 1152
Compounds of the formula IA wherein $Q^1$ denotes methyl, $Q^3$ denotes CH$_2$S(=O)$_2$CH$_2$CH$_3$, and A in each case corresponds to a radical of Table D.

Table 1153
Compounds of the formula IA wherein $Q^1$ denotes methyl, $Q^3$ denotes —OS(=O)$_2$CH$_3$, and A in each case corresponds to a radical of Table D.

Table 1154
Compounds of the formula IA wherein $Q^1$ denotes methyl, $Q^3$ notes —OS(=O)$_2$CH$_2$CH$_3$, and A in each case corresponds to a radical of Table D.

Table 1155
Compounds of the formula IA wherein $Q^1$ denotes methyl, $Q^3$ notes —OS(=O)$_2$CH$_2$CF$_3$, and A in each case corresponds to a radical of Table D.

Table 1156
Compounds of the formula IA wherein $Q^1$ denotes methyl, $Q^3$ denotes —OS(=O)$_2$CClF$_2$, and A in each case corresponds to a radical of Table D.

Table 1157
Compounds of the formula IA wherein $Q^1$ denotes methyl, $Q^3$ denotes OC(=O)CF$_3$, and A in each case corresponds to a radical of Table D.

Table 1158
Compounds of the formula IA wherein $Q^1$ denotes methyl, $Q^3$ denotes NHCH$_2$CF$_3$, and A in each case corresponds to a radical of Table D.

Table 1159
Compounds of the formula IA wherein $Q^1$ denotes methyl, $Q^3$ denotes OCH$_2$-cyclopropyl, and A in each case corresponds to a radical of Table D.

Table 1160
Compounds of the formula IA wherein $Q^1$ denotes methyl, $Q^3$ denotes OCH$_2$C(Cl)=CH$_2$, and A in each case corresponds to a radical of Table D.

Table 1161
Compounds of the formula IA wherein $Q^1$ denotes methyl, $Q^3$ denotes OCH$_2$CH=CF$_2$, and A in each case corresponds to a radical of Table D.

Table 1162
Compounds of the formula IA wherein $Q^1$ denotes methyl, $Q^3$ denotes NHS(=O)$_2$CF$_3$, and A in each case corresponds to a radical of Table D.

Table 1163
Compounds of the formula IA wherein $Q^1$ denotes methyl, $Q^3$ denotes NHC(=O)CF$_3$, and A in each case corresponds to a radical of Table D.

Table 1164
Compounds of the formula IA wherein $Q^1$ denotes methyl, $Q^3$ denotes OCH$_2$CN, and A in each case corresponds to a radical of Table D.

Table 1165
Compounds of the formula IA wherein $Q^1$ denotes methyl, $Q^3$ denotes OCH$_2$NO$_2$, and A in each case corresponds to a radical of Table D.

Table 1166
Compounds of the formula IA wherein $Q^1$ denotes methyl, $Q^3$ denotes cyclopropyloxy, and A in each case corresponds to a radical of Table D.

Table 1167
Compounds of the formula IA wherein $Q^1$ denotes methyl, $Q^3$ denotes CH$_2$OCHF$_2$, and A in each case corresponds to a radical of Table D.

Table 1168
Compounds of the formula IA wherein $Q^1$ denotes methyl, $Q^3$ denotes CH$_2$S(=O)$_2$CHF$_2$, and A in each case corresponds to a radical of Table D.

Table 1169
Compounds of the formula IA wherein $Q^1$ denotes methyl, $Q^3$ denotes CH=NOCH$_3$, and A in each case corresponds to a radical of Table D.

Table 1170
Compounds of the formula IA wherein $Q^1$ denotes methyl, $Q^3$ denotes CH=NOCH$_2$CH$_3$, and A in each case corresponds to a radical of Table D.

Table 1171
Compounds of the formula IA wherein $Q^1$ denotes methyl, $Q^3$ denotes CH=NOCH(CH$_3$)$_2$ and A in each case corresponds to a radical of Table D.

Table 1172
Compounds of the formula IA wherein $Q^1$ denotes methyl, $Q^3$ denotes CH=NOC(CH$_3$)$_3$, and A in each case corresponds to a radical of Table D.

Table 1173
Compounds of the formula IA wherein $Q^1$ denotes methyl, $Q^3$ denotes C(CH$_3$)=NOCH$_3$, and A in each case corresponds to a radical of Table D.

Table 1174
Compounds of the formula IA wherein $Q^1$ denotes methyl, $Q^3$ denotes C(CH$_3$)=NOCH$_2$CH$_3$, and A in each case corresponds to a radical of Table D.

Table 1175
Compounds of the formula IA wherein $Q^1$ denotes methyl, $Q^3$ denotes C(CH$_3$)=NOCH(CH$_3$)$_2$, and A in each case corresponds to a radical of Table D.

Table 1176
Compounds of the formula IA wherein $Q^1$ denotes methyl, $Q^3$ denotes C(CH$_3$)=NOC(CH$_3$)$_3$, and A in each case corresponds to a radical of Table D.

TABLE D

| selected radicals A | |
| --- | --- |
|  | A.11 |
|  | A.12 |
|  | A.13 |
|  | A.14 |
| 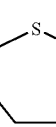 | A.15 |
| 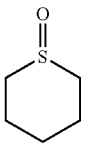 | A.14 |
| 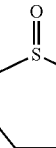 | A.15 |

TABLE D-continued selected radicals A

| | | | | |
|---|---|---|---|---|
| 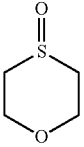 | A.16 | | 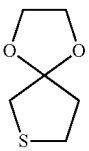 | A.12 |
|  | A.11 | |  | A.13 |
|  | A.12 | | 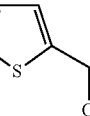 | A.14 |
| 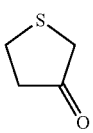 | A.13 | | 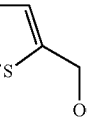 | A.15 |
|  | A.14 | | 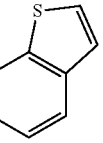 | A.15 |
|  | A.15 | | 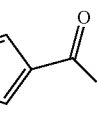 | A.12 |
|  | A.11 | | 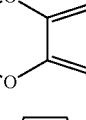 | A.13 |
| 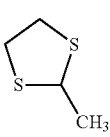 | A.12 | | 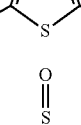 | A.14 |
|  | A.13 | | 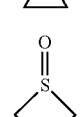 | A.11 |
|  | A.14 | | 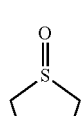 | A.12 |
|  | A.15 | | 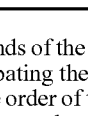 | A.13 |
| 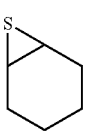 | A.11 | | | |

The compounds of the formula I are especially suitable for efficiently combating the following pests:

insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta,*

*Cydia pomonella, Dendrolimus pini, Diaphania nitidalis, Diatraea grandiosella, Earias insulana, Elasmopalpus lignosellus, Eupoecilia ambiguella, Evetna bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantna cunea, Hyponomeuta malinellus, Keiferia lycopersicella, Lambdina fiscellana, Laphygma exigua, Leucoptera coffeella, Leucoptera scitella, Lithocolletis blancardella, Lobesia botrana, Loxostege sticticalis, Lymantna dispar, Lymantna monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis,* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera* ssp., *Diabrotica longicornis, Diabrotica semipunctata, Diabrotica* 12-*punctata Diabrotica speciosa, Diabrotica virgifera, Epilachna varivestis, Epitrix hirtipennis, Eutinobothrus braslliensis, Hylobius abietis, Hypera brunneipennis, Hypera postica, Ips typographus, Lema bilineata, Lema melanopus, Leptinotarsa decemlineata, Limonius californicus, Lissorhoptrus olyzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllobius pyri, Phyllotreta chrysocephala, Phyllophaga* sp., *Phyllopertha horticola, Phyllotreta nemorum, Phyllotreta striolata, Popillia japonica, Sitona lineatus* and *Sitophllus granaria,* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprin, Lucilia cuprina, Lucilia sericata, Lycoria pectoralis, Mansonia titillanus, Mayetiola destructor, Musca domestica, Muscina stabulans, Oestrus ovis, Opomyza forum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosirnulium mixtum, Rhagoletis cerasi, Rhagoletis pomonella, Sarcophaga haemorrhoidalis, Sarcophaga* sp., *Simulium vittatum, Stomoxys calcitrans, Tabanus bovinus, Tabanus atratus, Tabanus lineola,* and *Tabanus similis, Tipula oleracea,* and *Tipula paludosa* trips (Thysanoptera), e.g. *Dichromothrips corbetti, Dichromothrips* ssp, *Frankliniella fusca, Frankliniella occidentalis, Frankliniella tritici, Scirtothrips citri, Thrips oryzae, Thrips palmi* and *Thrips tabaci,* termites (Isoptera), e.g. *Calotermes flavicollis, Leucotermes flavipes, Heterotermes aureus, Reticulitermes flavipes, Reticulitermes virginicus, Reticulitermes lucifugus, Termes natalensis,* and *Coptotermes formosanus,* cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis,* true bugs (Hemiptera), e.g. *Acrosternum hilare, Blissus leucopterus, Cyrtopeltis notatus, Dysdercus angulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onobrychis, Adelges laricis, Aphidula nasturtii, Aphis fabae, Aphis forbesi, Aphis pomi, Aphis gossypii, Aphis grossulanae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horn, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus vanans, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, Viteus vitifolii, Cimex lectularius, Cimex hemipterus, Reduvius senilis, Triatoma* spp., and *Arilus critatus.* ants, bees, wasps, sawflies (Hymenoptera), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus* spp. *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile,* crickets, grasshoppers, locusts (Orthoptera), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus varie-* gatus, *Hieroglyphus daganensis, Kraussaria angulifera, Calliptamus italicus, Chortoicetes terminifera*, and *Locustana pardalina*, Arachnoidea, such as arachnids (Acarina), e.g. of the families Argasidae, Ixodidae and Sarcoptidae, such as *Amblyomma americanum, Amblyomma variegatum, Amblyomma maculatum, Argas persicus, Boophilus annulatus, Boophilus decoloratus, Boophilus microplus, Dermacentor silvarum, Dermacentor andersoni, Dermacentor variabilis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi, Sarcoptes scabiei*, and Eriophyidae spp. such as *Aculus schlechtendali, Phyllocoptrata oleivora* and *Eriophyes sheldoni*, Tarsonemidae spp. such as *Phytonemus pallidus* and *Polyphagotarsonemus latus*, Tenuipalpidae spp. such as *Brevipalpus phoenicis*; Tetranychidae spp. such as *Tetranychus cinnabarinus, Tetranychus kanzawai, Tetranychus pacificus, Tetranychus telarius* and T*etranychus urticae, Panonychus ulmi, Panonychus citri*, and *Oligonychus pratensis; Araneida*, e.g. *Latrodectus mactans*, and *Loxosceles reclusa*, fleas (Siphonaptera), e.g. *Ctenocephalides felis, Ctenocephalides canis, Xenopsylla cheopis, Pulex irritans, Tunga penetrans*, and *Nosopsyllus fasciatus*, silverfish, firebrat (Thysanura), e.g. *Lepisma saccharin* and *Thermobia domestica*, centipedes (Chilopoda), e.g. *Scutigera coleoptrata*, millipedes (Diplopoda), e.g. *Narceus* spp., Earwigs (Dermaptera), e.g. *forficula auricularia*, lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus*, Plant parasitic nematodes such as root-knot nematodes, *Meloidogyne arenaria, Meloidogyne chitwoodi, Meloidogyne exigua, Meloidogyne hapla, Meloidogyne incognita, Meloidogyne javanica* and other *Meloidogyne* species; cyst nematodes, *Globodera rostochiensis, Globodera pallida, Globodera tabacum* and other *Globodera* species; *Heterodera avenae, Heterodera glycines, Heterodera schachtii, Heterodera trifolii*, and other *Heterodera* species; seed gall nematodes, *Anguina funesta, Anguina tritici* and other *Anguina* species; stem and foliar nematodes, *Aphelenchoides besseyi, Aphelenchoides fragariae, Aphelenchoides ritzemabosi* and other *Aphelenchoides* species; sting nematodes, *Belonolaimus longicaudatus* and other *Belonolaimus* species; pine nematodes, *Bursaphelenchus xylophilus* and other *Bursaphelenchus* species; ring nematodes, *Criconema* species, *Criconemella* species, *Criconemoides* species, and *Mesocriconema* species; stem and bulb nematodes, *Ditylenchus destructor, Ditylenchus dipsaci, Ditylenchus myceliophagus* and other *Ditylenchus* species; awl nematodes, *Dolichodorus* species; spiral nematodes, *Helicotylenchus dihystera, Helicotylenchus multicinctus* and other *Helicotylenchus* species, *Rotylenchus robustus* and other *Rotylenchus* species; sheath nematodes, *Hemicycliophora* species and *Hemicriconemoides* species; *Hirshmanniella* species; lance nematodes, *Hoplolaimus columbus, Hoplolaimus galeatus* and other *Hoplolaimus* species, false root-knot nematodes, *Nacobbus aberrans* and other *Nacobbus* species; needle nematodes, *Longidorus elongates* and other *Longidorus* species; pin nematodes, *Paratylenchus* species; lesion nematodes, *Pratylenchus brachyurus, Pratylenchus coffeae, Pratylenchus curvitatus, Pratylenchus goodeyi, Pratylencus neglectus, Pratylenchus penetrans, Pratylenchus scribneri, Pratylenchus vulnus, Pratylenchus zeae* and other *Pratylenchus* species; *Radinaphelenchus cocophilus* and other *Radinaphelenchus* species; burrowing nematodes, *Radopholus similis* and other *Radopholus* species; reniform nematodes, *Rotylenchulus reniformis* and other *Rotylenchulus* species; *Scutellonema* species; stubby root nematodes, *Trichodorus primitivus* and other *Trichodorus* species; *Paratrichodorus minor* and other *Paratrichodorus* species; stunt nematodes, *Tylenchorhynchus claytoni, Tylenchorhynchus dubius* and other *Tylenchorhynchus* species and *Merlinius* species; citrus nematodes, *Tylenchulus semipenetrans* and other *Tylenchulus* species; dagger nematodes, *Xiphinema americanum, Xiphinema index, Xiphinema diversicaudatum* and other *Xiphinema* species; and other plant parasitic nematode species.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and binders.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used.

Examples of suitable carriers are ground natural minerals (for example kaolins, clays, talc, chalk) and ground synthetic minerals (for example highly disperse silica, silicates).

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides such as can be added to the formulation.

Suitable antifoaming agents are for example antifoaming agents based on silicon or magnesium stearate.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound(s). In this case, the active compound(s) are employed in a purity of from 90% to 100% by weight, preferably 95% to 100% by weight (according to NMR spectrum).

The compounds of formula I can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compound(s) according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% per weight.

The active compound(s) may also be used successfully in the ultra-low-volume process (ULV), it being possible to apply formulations comprising over 95% by weight of active compound, or even to apply the active compound without additives.

The following are examples of formulations: 1. Products for dilution with water for foliar applications. For seed treatment purposes, such products may be applied to the seed diluted or undiluted.

A) Water-Soluble Concentrates (SL, LS)

10 parts by weight of the active compound(s) are dissolved in 90 parts by weight of water or a water-soluble solvent. As an alternative, wetters or other auxiliaries are added. The active compound(s) dissolves upon dilution with water, whereby a formulation with 10% (w/w) of active compound(s) is obtained.

B) Dispersible Concentrates (DC)

20 parts by weight of the active compound(s) are dissolved in 75 parts by weight of cyclohexanone with addition of 10 parts by weight of a dispersant, for example polyvinylpyrrolidone. Dilution with water gives a dispersion, whereby a formulation with 20% (w/w) of active compound(s) is obtained.

C) Emulsifiable Concentrates (EC)

15 parts by weight of the active compound(s) are dissolved in 75 parts by weight of xylene with addition of calcium dodecylbenzenesulfonate and castor oil ethoxylate (in each case 5 parts by weight). Dilution with water gives an emulsion, whereby a formulation with 15% (w/w) of active compound(s) is obtained.

D) Emulsions (EW, EO, ES)

40 parts by weight of the active compound(s) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound(s) is obtained.

E) Suspensions (SC, OD, FS)

In an agitated ball mill, 20 parts by weight of the active compound(s) are comminuted with addition of 10 parts by weight of dispersants, wetters and 70 parts by weight of water or of an organic solvent to give a fine active compound(s) suspension. Dilution with water gives a stable suspension of the active compound(s), whereby a formulation with 20% (w/w) of active compound(s) is obtained.

F) Water-Dispersible Granules and Water-Soluble Granules (WG, SG)

50 parts by weight of the active compound(s) are ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound(s), whereby a formulation with 50% (w/w) of active compound(s) is obtained.

G) Water-Dispersible Powders and Water-Soluble Powders (WP, SP, SS, WS)

75 parts by weight of the active compound(s) are ground in a rotor-stator mill with addition of 25 parts by weight of dispersants, wetters and silica gel. Dilution with water gives a stable dispersion or solution of the active compound(s), whereby a formulation with 75% (w/w) of active compound(s) is obtained.

2. Products to be applied undiluted for foliar applications. For seed treatment purposes, such products may be applied to the seed diluted or undiluted.

H) Dustable Powders (DP, DS)

5 parts by weight of the active compound(s) are ground finely and mixed intimately with 95 parts by weight of finely divided kaolin. This gives a dustable product having 5% (w/w) of active compound(s)

I) Granules (GR, FG, GG, MG)

0.5 part by weight of the active compound(s) is ground finely and associated with 95.5 parts by weight of carriers, whereby a formulation with 0.5% (w/w) of active compound(s) is obtained. Current methods are extrusion, spray-drying or the fluidized bed. This gives granules to be applied undiluted for foliar use.

J) ULV Solutions (UL, LS)

10 parts by weight of the active compound(s) are dissolved in 90 parts by weight of an organic solvent, for example xylene. This gives a product having 10% (w/w) of active compound(s), which is applied undiluted for foliar use.

Various types of oils, wetters, adjuvants, herbicides, fungicides, other pesticides, or bactericides may be added to the active ingredients, if appropriate just immediately prior to use (tank mix). These agents usually are admixed with the agents according to the invention in a weight ratio of 1:10 to 10:1.

The compounds of formula I are effective through both contact and ingestion.

The compounds of formula I are also suitable for the protection of the seed, plant propagules and the seedlings' roots and shoots, preferably the seeds, against soil pests and also for the treatment plant seeds which tolerate the action of herbicides or fungicides or insecticides owing to breeding, including genetic engineering methods.

Conventional seed treatment formulations include for example flowable concentrates FS, solutions LS, powders for dry treatment DS, water dispersible powders WS or granules for slurry treatment, water soluble powders SS and emulsion ES. Application to the seeds is carried out before sowing, either directly on the seeds.

The seed treatment application of the compounds of formula I or formulations containing them is carried out by spraying or dusting the seeds before sowing of the plants and before emergence of the plants.

The invention also relates to the propagation product of plants, and especially the treated seed comprising, that is, coated with and/or containing, a compound of formula I or a composition comprising it. The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient. The seed comprises the inventive compounds or compositions comprising them in an amount of from 0.1 g to 10 kg per 100 kg of seed.

Compositions of this invention may also contain other active ingredients, for example other pesticides, insecticides, herbicides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

The following list of pesticides together with which the compounds according to the invention can be used, is intended to illustrate the possible combinations, but not to impose any limitation:

A.1. Organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

A.2. Carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

A.3. Pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin;

A.4. Growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, a tetronic acid derivative of formula Γ¹,

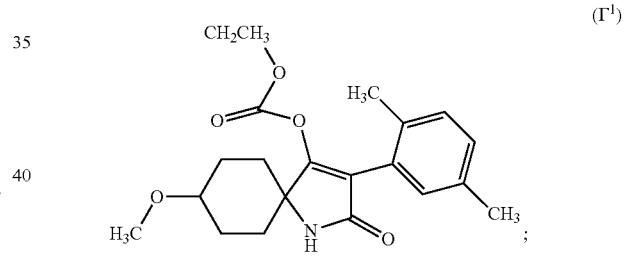

(Γ¹)

A.5. Nicotinic receptor agonists/antagonists compounds: clothianidin, dinotefuran, imidacloprid, thiamethoxam, nitenpyram, acetamiprid, thiacloprid;

A.6. GABA antagonist compounds: acetoprole, endosulfan, ethiprole, fipronil, vaniliprole;

A.7. Macrocyclic lactone insecticides: abamectin, emamectin, milbemectin, lepimectin, spinosad;

A.8. METI I acaricides: fenazaquin, pyridaben, tebufenpyrad, tolfenpyrad;

A.9. METI II and III compounds: acequinocyl, fluacyprim, hydramethylnon;

A.10. Uncoupler compounds: chlorfenapyr;

A.11. Oxidative phosphorylation inhibitor compounds: cyhexatin, diafenthiuron, fenbutatin oxide, propargite;

A.12. Moulting disruptor compounds: cryomazine;

A.13. Mixed Function Oxidase inhibitor compounds: piperonyl butoxide;

A.14. Sodium channel blocker compounds: indoxacarb, metaflumizone;

A.15. Various: benclothiaz, bifenazate, cartap, flonicamid, pyridalyl, pymetrozine, sulfur, thiocyclam, N—R'-2,2-dihalo-1-R"cyclo-propanecarboxamide-2-(2,6-dichloro-α,α,α-trifluoro-p-tolyl)phydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R'" is methyl or ethyl, and the aminoisothiazole compounds of formula I'²,

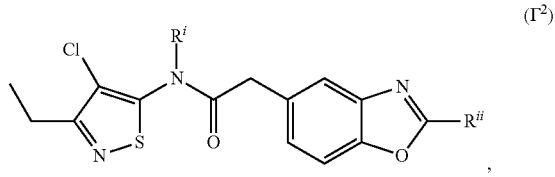

wherein $R^i$ is —$CH_2OCH_2CH_3$ or H and $R^{ii}$ is $CF_2CF_2CF_3$ or $CH_2CH(CH_3)_3$, anthranilamide compounds of formula I'³

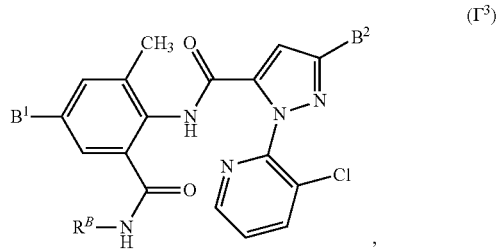

wherein $B^1$ is hydrogen or a chlorine atom, $B^2$ is a bromine atom or $CF_3$, and $R^B$ is $CH_3$ or $CH(CH_3)_2$, and malononitrile compounds as described in JP 2002 284608, WO 02/89579, WO 02/90320, WO 02/90321, WO 04/06677, WO 04/20399, or JP 2004 99597.

The insects may be controlled by contacting the target parasite/pest, its food supply, habitat, breeding ground or its locus with a pesticidally effective amount of compounds of or compositions of formula I.

"Locus" means a habitat, breeding ground, plant, seed, soil, area, material or environment in which a pest or parasite is growing or may grow.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

The compounds or compositions of the invention can also be applied preventively to places at which occurrence of the pests is expected.

The compounds of formula I may also be used to protect growing plants from attack or infestation by pests by contacting the plant with a pesticidally effective amount of compounds of formula I. As such, "contacting" includes both direct contact (applying the compounds/compositions directly on the pest and/or plant—typically to the foliage, stem or roots of the plant) and indirect contact (applying the compounds/compositions to the locus of the pest and/or plant).

In the case of soil treatment or of application to the pests dwelling place or nest, the quantity of active ingredient ranges from 0.0001 to 500 g per 100 m², preferably from 0.001 to 20 g per 100 m².

For use in treating crop plants, the rate of application of the active ingredients of this invention may be in the range of 0.1 g to 4000 g per hectare, desirably from 25 g to 600 g per hectare, more desirably from 50 g to 500 g per hectare.

Compounds of formula I and compositions comprising them can also be used for controlling and preventing infestations and infections in animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formula I and compositions comprising them are suitable for systemic and/or non-systemic control of ecto- and/or endoparasites. They are active against all or some stages of development.

Administration can be carried out both prophylactically and therapeutically. Administration of the active compounds is carried out directly or in the form of suitable preparations, orally, topically/dermally or parenterally.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:
Solutions such as oral solutions, concentrates for oral administration after dilution, solutions for use on the skin or in body cavities, pouring-on formulations, gels;
Emulsions and suspensions for oral or dermal administration; semi-solid preparations;
Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Generally it is favorable to apply solid formulations which release compounds of formula I in total amounts of 10 mg/kg to 300 mg/kg, preferably 20 mg/kg to 200 mg/kg. The active compounds can also be used as a mixture with synergists or with other active compounds which act against pathogenic endo- and ectoparasites.

In general, the compounds of formula I are applied in parasiticidally effective amount meaning the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

SYNTHESIS EXAMPLES

With due modification of the starting compounds, the protocols shown in the synthesis examples below were used for obtaining further compounds I. The resulting compounds, together with physical data, are listed in the Tables 1 to 3 which follow.

2-[5-Bromo-2-(3-chloro-pyridin-2-yl)-2H-pyrazol-3-yl]-8-methyl-benzo[d][1,3]oxazin-4-one is known from WO 04/011447.

Example 1

Methyl-phenyl-sulfamoyl-N-(5-bromo-2-(3-chloro-pyridin-2-yl)-2H-pyrazole-3-carboxylic acid (2-carbamoyl-6-methyl-phenyl))-amide, compound I.1-33

0.089 g Methyl-phenyl-sulfamoyl-amine was dissolved in 5 ml methylene chloride. 0.017 g sodium hydride was added at 20-25° C. and the solution was stirred for 1 hour. 0.20 g 2-[5-Bromo-2-(3-chloro-pyridin-2-yl)-2H-pyrazol-3-yl]-8-methyl-benzo[d][1,3]oxazin-4-one were added and the resulting mixture was refluxed for 24 h. The solvent was removed and the residue was purified by column chromatography (cyclo hexane/ethyl acetate 1:2) to yield 0.18 g methyl-phenyl-sulfamoyl-N-(5-bromo-2-(3-chloro-pyridin-2-yl)-2H-pyrazole-3-carboxylic acid (2-carbamoyl-6-methyl-phenyl))-amide

Example 2

Step A: Preparation of 5-bromo-2-(3-chloro-pyridin-2-yl)-2H-pyrazole-3-carboxylic acid (2-carbamoyl-6-methyl-phenyl)-amide 1.00 g 2-[5-Bromo-2-(3-chloro-pyridin-2-yl)-2H-pyrazol-3-yl]-8-methyl-benzo[d][1,3]oxazin-4-one was taken up in 10 ml of a 25% ammonia solution in water and stirred for 72 h. The solids were filtered and washed with cold water to yield 0.80 g of the amide.

Step B: S,S-Dimethyl-N-(5-bromo-2-(3-chloro-pyridin-2-yl)-2H-pyrazole-3-carboxylic acid (2-carbamoyl-6-methyl-phenyl))-sulfimide, compound I.3-2

0.071 ml DMSO were dissolved under a nitrogen atmosphere in 0.5 ml methylene chloride and cooled to −60° C. 0.14 ml trifluoroacetic acid anhydride were slowly added at this temperature followed by the addition of 0.20 g 5-bromo-2-(3-chloro-pyridin-2-yl)-2H-pyrazole-3-carboxylic acid (2-carbamoyl-6-methyl-phenyl)-amide. The resulting solution was stirred at −35° C. for 1 h. After diluting with 5 ml methylene chloride, the reaction mixture was extracted with aqueous sodium hydroxide once and two times with water. The organic solvent was dried and the solvent removed. The residue was diluted with diethyl ether and the solid residue was filtered off and dried to yield 0.08 g of the desired sulfimide.

Example 3

S,S Dimethyl-S-Aminosulfonium mesitylenesulfonate was prepared according to Y. Tamura et al, Tetrahedron, 1975, 31, 3035-3040.

S,S-Dimethyl-N-(5-bromo-2-(3-chloro-pyridin-2-yl)-2H-pyrazole-3-carboxylic acid (2-carbamoyl-6-methyl-phenyl)-sulfimide, compound I.3-2

0.2 g S,S Dimethyl-S-Aminosulfonium mesitylenesulfonate were dissolved in 20 ml methylene chloride. 0.26 g potassium t-butylate, 0.54 g 2-[5-Bromo-2-(3-chloro-pyridin-2-yl)-2H-pyrazol-3-yl]-8-methyl-benzo[d][1,3]oxazin-4-one were added and the resulting mixture was stirred at 20-25° C. for additional 3.5 h. The reaction mixture was extracted with aqueous sodium hydroxide once and two times with water. The organic solvent was dried and the solvent removed. Column chromatography yielded 0.3 g of the desired product.

Example 4

2-{2-[5-Bromo-2-(2-chloro-phenyl)-2H-pyrazol-3-yl]-2-oxo-ethyl}-5-chloro-3-methyl-N-(1-oxo-hexahydro-1lambda*6*-thiopyran-1-ylidene)-benzamide 0.2 g 2-{2-[5-Bromo-2-(2-chloro-phenyl)-2H-pyrazol-3-yl]-2-oxo-ethyl}-5-chloro-3-methyl-N-(tetrahydro-1lambda*4*-thiopyran-1-ylidene)-benzamide (0.35 mmol) were dissolved in 10 ml acetic acid. 4 mg Sodium wolframate dihydrate were added. 45 mg of a 30% solution of hydrogen-peroxide was added dropwise and the resulting solution was stirred for 18 h. The reaction mixture was poured into a saturated aqueous sodium carbonate solution, methylene chloride was added and the organic pase was subsequently washed with water and saturated aqueous sodium carbonate. The organic solvent was dried and the solvent removed. Column chromatography yielded 0.07 g of the desired product, compound I.4-22.

The products were characterized by coupled High Performance Liquid Chromatography/mass spectrometry (HPLC/MS), by NMR or by their melting points.

TABLE I

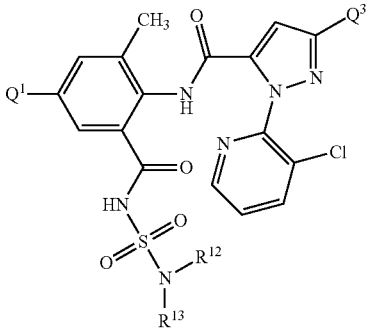

(I.1)

| No. | $Q^1$ | $Q^3$ | $R^{12}$ | $R^{13}$ | Physical Data: Meltingpoint [° C.] $^1$H-NMR, δ [ppm] |
|---|---|---|---|---|---|
| I.1-1 | Cl | Br | CH$_2$CH$_3$ | i-C$_3$H$_7$ | >210 |
| I.1-2 | Cl | Br | CH$_2$CH$_3$ | c-C$_6$H$_{11}$ | 191 |
| I.1-3 | Cl | Br | i-C$_3$H$_7$ | i-C$_3$H$_7$ | 150-151 |
| I.1-4 | Cl | Br | i-C$_3$H$_7$ | CH$_2$CHCH$_2$ | >210 |
| I.1-5 | Cl | Br | CH$_3$ | CH$_2$CCH | 162-163 |
| I.1-6 | Cl | Br | CH$_3$ | CH$_2$CHCH$_2$ | 123 |
| I.1-7 | Cl | Br | CH$_3$ | CH$_2$CH$_3$ | 102.20 |
| I.1-8 | Cl | Br | CH$_3$ | i-C$_3$H$_7$ | 200 |
| I.1-9 | Cl | Br | CH$_3$ | CH$_3$ | 203 |
| I.1-10 | Cl | Br | CH$_3$ | c-C$_6$H$_{11}$ | 176-177 |
| I.1-11 | Cl | Br | CH$_3$ | CH$_2$C$_6$H$_5$ | 154-155 |
| I.1-12 | Cl | Br | CH$_3$ | C$_6$H$_5$ | 155-156 |
| I.1-13 | Cl | Br | CH$_3$ | i-C$_4$H$_9$ | 148-149 |
| I.1-14 | Cl | Br | CH$_3$ | CH$_2$CH$_2$C$_6$H$_5$ | 167-168 |
| I.1-15 | Cl | Br | n-C$_3$H$_7$ | i-C$_3$H$_7$ | >210 |
| I.1-16 | Cl | Br | n-C$_3$H$_7$ | CH$_2$CH$_2$OMe | 150-151 |
| I.1-17 | H | Br | CH$_2$CH$_3$ | c-C$_6$H$_{11}$ | 191 |
| I.1-18 | H | Br | CH$_2$CH$_3$ | CH$_2$CH$_3$ | 191 |
| I.1-19 | H | Br | CH$_2$CH$_3$ | i-C$_3$H$_7$ | 209 |
| I.1-20 | H | Br | i-C$_3$H$_7$ | CH$_2$CHCH$_2$ | 185 |
| I.1-21 | H | Br | i-C$_3$H$_7$ | n-C$_3$H$_7$ | 204 |
| I.1-22 | H | Br | i-C$_3$H$_7$ | i-C$_3$H$_7$ | 151 |
| I.1-23 | H | Br | CH$_3$ | CH$_2$CHCH$_2$ | 153 |
| I.1-24 | H | Br | CH$_3$ | CH$_2$C$_6$H$_5$ | 2.3 (s), 2.6 (s), 4.2 (s), 7.2-7.7 (m), 8.1 (d), 8.4 (d), 10.3 (s), 11.9 (s) [d$_6$-DMSO] |
| I.1-25 | H | Br | CH$_3$ | CH$_2$CCH | 172 |
| I.1-26 | H | Br | CH$_3$ | CH$_2$CH$_2$C$_6$H$_5$ | 178 |
| I.1-27 | H | Br | CH$_3$ | CH$_2$CH$_3$ | 202 |
| I.1-28 | H | Br | CH$_3$ | i-C$_4$H$_9$ | 0.8 (d), 1.8 (m), 2.2 (s), 2.6 (s), 2.8 (s), 7.2-7.6 (m), 8.1 (d), 8.5 (d), 10.2 (s), 11.7 (s) [d$_6$-DMSO] |
| I.1-29 | H | Br | CH$_3$ | i-C$_3$H$_7$ | 1.0 (d), 2.2 (s), 2.8 (s), 4.3 (m), 7.2-7.4 (m), 7.8 (d), 8.4 (d), 8.6 (s), 9.6 (s) [CDCl$_3$] |
| I.1-30 | H | Br | CH$_3$ | CH$_3$ | 205 |
| I.1-31 | H | Br | CH$_3$ | n-C$_3$H$_7$ | 203 |
| I.1-32 | H | Br | CH$_3$ | C$_6$H$_5$ | 1.0 (d), 2.1 (s), 7.2-7.7 (m), 8.1 (d), 8.4 (d), 10.3 (s), 11.9 (s) [d$_6$-DMSO] |
| I.1-33 | H | Br | CH$_3$ | C$_6$H$_5$ | 199 |
| I.1-34 | Cl | CF$_3$ | CH$_2$CH$_2$OMe | CH$_2$CH$_2$CH$_3$ | 150 |
| I.1-35 | Cl | CF$_3$ | CH$_2$CHCH$_2$ | i-C$_3$H$_7$ | 190 |
| I.1-36 | Cl | CF$_3$ | CH$_2$CH$_3$ | c-C$_6$H$_{11}$ | 185 |
| I.1-37 | Cl | CF$_3$ | CH$_2$CH$_3$ | CH$_2$CH$_3$ | >240 |
| I.1-38 | Cl | CF$_3$ | CH$_2$CH$_3$ | i-C$_3$H$_7$ | 155 |
| I.1-39 | Cl | CF$_3$ | i-C$_3$H$_7$ | i-C$_3$H$_7$ | 180 |
| I.1-40 | Cl | CF$_3$ | i-C$_3$H$_7$ | n-C$_3$H$_7$ | 175 |
| I.1-41 | Cl | CF$_3$ | CH$_3$ | CH$_2$CCH | 155 |
| I.1-42 | Cl | CF$_3$ | CH$_3$ | CH$_2$CH$_2$Ph | 160 |
| I.1-43 | Cl | CF$_3$ | CH$_3$ | CH$_2$CHCH$_2$ | 90 |
| I.1-44 | Cl | CF$_3$ | CH$_3$ | c-C$_6$H$_{11}$ | 102 |
| I.1-45 | Cl | CF$_3$ | CH$_3$ | CH$_2$CH$_3$ | 110 |
| I.1-46 | Cl | CF$_3$ | CH$_3$ | i-C$_3$H$_5$ | 160 |

TABLE I-continued

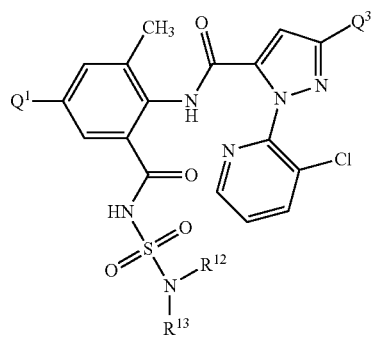

(I.1)

| No. | Q¹ | Q³ | R¹² | R¹³ | Physical Data: Meltingpoint [° C.] ¹H-NMR, δ [ppm] |
|---|---|---|---|---|---|
| I.1-47 | Cl | CF₃ | CH₃ | CH₃ | 198 |
| I.1-48 | Cl | CF₃ | CH₃ | CH₂C₆H₅ | 120 |
| I.1-49 | Cl | CF₃ | CH₃ | C₆H₅ | 130 |
| I.1-50 | H | CF₃ | CH₂CH₂OMe | n-C₃H₇ | 180 |
| I.1-51 | H | CF₃ | CH₂CHCH₂ | i-C₃H₇ | 177 |
| I.1-52 | H | CF₃ | CH₂CH₃ | c-C₆H₁₁ | 200 |
| I.1-53 | H | CF₃ | CH₂CH₃ | CH₂CH₃ | 180 |
| I.1-54 | H | CF₃ | i-C₃H₇ | i-C₃H₇ | 190 |
| I.1-55 | H | CF₃ | i-C₃H₇ | n-C₃H₇ | 185 |
| I.1-56 | H | CF₃ | CH₃ | CH₂C₆H₅ | 165 |
| I.1-57 | H | CF₃ | CH₃ | CH₂CCH | 165 |
| I.1-58 | H | CF₃ | CH₃ | CH₂CH₂C₆H₅ | 165 |
| I.1-59 | H | CF₃ | CH₃ | CH₂CHCH₂ | 160 |
| I.1-60 | H | CF₃ | CH₃ | c-C₆H₁₁ | 205 |
| I.1-61 | H | CF₃ | CH₃ | CH₂CH₃ | 195 |
| I.1-62 | H | CF₃ | CH₃ | i-C₄H₉ | 175 |
| I.1-63 | H | CF₃ | CH₃ | i-C₃H₇ | 1.1 (d),2.2 (s), 2.8 (s), 4.3 (m), 7.2-7.5 (m), 7.9 (d), 8.5 (d), 8.6 (s), 9.7 (s) [CDCl₃] |
| I.1-64 | H | CF₃ | CH₃ | CH₃ | 183 |
| I.1-65 | H | CF₃ | CH₃ | C₆H₅ | 115 |
| I.1-66 | Cl | CF₃ | n-C₃H₇ | CH₂=C(Cl)CH₂ | 140 |
| I.1-67 | H | CF₃ | n-C₃H₇ | CH₂=C(Cl)CH₂ | 195 |
| I.1-68 | H | Br | n-C₃H₇ | CH₂=C(Cl)CH₂ | 199 |
| I.1-69 | Cl | Br | n-C₃H₇ | CH₂=C(Cl)CH₂ | 159-160 |

TABLE II
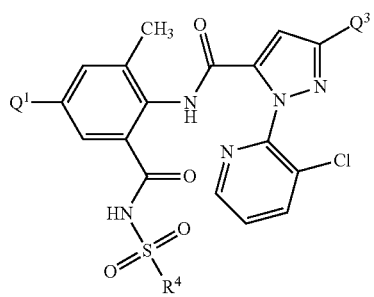
(I.2)
| No. | Q¹ | Q³ | R⁴ | Physical Data Melting Point [° C.] ¹H-NMR, δ [ppm] |
|---|---|---|---|---|
| I.2-1 | Cl | CF₃ | 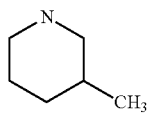 | 115 |
| I.2-2 | Cl | CF₃ | 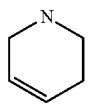 | 160 |
| I.2-3 | Cl | CF₃ | 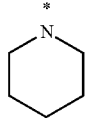 | 145 |
| I.2-4 | Cl | CF₃ | 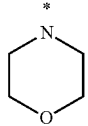 | 115 |
| I.2-5 | Cl | Br | 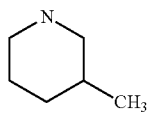 | 105-106 |
| I.2-6 | Cl | Br | 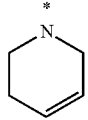 | 138-139 |
| I.2-7 | H | CF₃ | 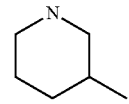 | 175 |
| I.2-8 | H | CF₃ | 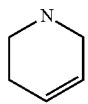 | 182 |
TABLE II-continued
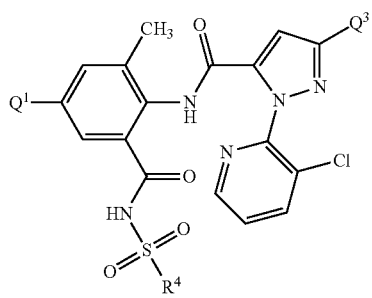
(I.2)
| No. | Q¹ | Q³ | R⁴ | Physical Data Melting Point [° C.] ¹H-NMR, δ [ppm] |
|---|---|---|---|---|
| I.2-9 | H | CF₃ | 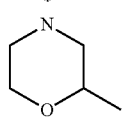 | 150 |
| I.2-10 | Cl | Br | 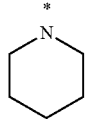 | oil |
| I.2-11 | Cl | Br | 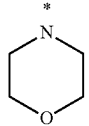 | 135 |
| I.2-12 | H | Br | 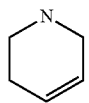 | 162 |
| I.2-13 | H | Br | 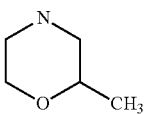 | 151 |
| I.2-14 | H | Br | 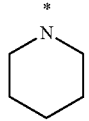 | 162 |
| I.2-15 | H | Br | 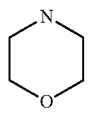 | 150 |
| I.2-16 | Cl | CF₃ | 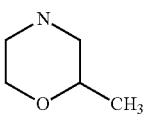 | 198 |

TABLE II-continued

(I.2)

| No. | Q¹ | Q³ | R⁴ | Physical Data Melting Point [° C.] $^1$H-NMR, δ [ppm] |
|---|---|---|---|---|
| I.2-17 | H | CF₃ | * (piperidine) | 190 |
| I.2-18 | H | CF₃ | * (morpholine) | 165 |

* denotes the binding site

TABLE III

(I.3)

| No. | Q¹ | Q³ | R² | R³ | Melting Point [° C.] |
|---|---|---|---|---|---|
| 1.3-1 | Cl | CF₃ | i-C₃H₇ | i-C₃H₇ | 163 |
| 1.3-2 | H | Br | CH₃ | CH₃ | 165 |
| 1.3-3 | Cl | Br | CH₂CH₃ | CH₂CH₃ | oil |
| 1.3-4 | Cl | Br | CH₃ | CH₃ | 185 |
| 1.3-5 | Cl | Br | i-C₃H7 | i-C₃H₇ | 165 decomp. |
| 1.3-6 | Cl | CF₃ | i-C₃H₇ | i-C₃H₇ | 142 |
| 1.3-7 | H | Br | CH₃ | CH₃ | 200 |
| 1.3-8 | Cl | CF₃ | CH₃ | CH₃ | 182 |
| 1.3-9 | H | Br | n-C₃H₇ | CH₃ | 150 |
| 1.3-10 | H | CF₃ | n-C₃H₇ | CH₃ | 143 |
| 1.3-11 | Cl | Br | n-C₃H₇ | CH₃ | 179 |
| 1.3-12 | Cl | Br | n-C₅H₁₁ | CH₂CH₂OH | 160 |
| 1.3-13 | H | Br | n-C₅H₁₁ | CH₂CH₂OH | 70 decomp. |
| 1.3-14 | Cl | CF₃ | CH₃ | n-C₃H₇ | 60 decomp. |
| 1.3-15 | I | CF₃ | CH₃ | n-C₃H₇ | 85 |
| 1.3-16 | I | Br | CH₃ | n-C₃H₇ | 180 decomp. |
| 1.3-17 | H | CF₃ | n-C₅H₁₁ | CH₂CH₂OH | 106 |
| 1.3-18 | I | Br | n-C₅H₁₁ | CH₂CH₂OH | 150 decomp. |
| 1.3-19 | I | Br | i-C₃H₇ | i-C₃H₇ | 75 |
| 1.3-20 | I | CF₃ | i-C₃H₇ | i-C₃H₇ | 75 |
| 1.3-21 | H | Br | i-C₃H₇ | i-C₃H₇ | 180 |
| 1.3-22 | I | Br | CH₃ | CH₃ | 115 |
| 1.3-23 | I | CF₃ | CH₃ | CH₃ | 165 |
| 1.3-24 | H | CF₃ | CH₃ | CH₃ | 206 |
| 1.3-25 | Cl | Br | CH₂CH₃ | CH₃ | 192 |
| 1.3-26 | H | Br | CH₂CH₃ | CH₃ | 161 |
| 1.3-27 | I | Br | CH₂CH₃ | CH₃ | 124 |
| 1.3-28 | Cl | CF₃ | CH₂CH₃ | CH₃ | 181 |
| 1.3-29 | H | CF₃ | CH₃ | CH₂CH₃ | 181 |
| 1.3-30 | I | CF₃ | CH₂CH₃ | CH₃ | 181 |
| 1.3-31 | H | CF₃ | i-C₃H₇ | i-C₃H₇ | 192 |
| 1.3-32 | Cl | CF₃ | n-C₅H₁₁ | CH₂CH₂OH | 133 |
| 1.3-33 | I | CF₃ | n-C₅H₁₁ | CH₂CH₂OH | 135 |
| 1.3-34 | Cl | CF₃ | CH₃ | p-F-C₆H₄ | 185 |
| 1.3-35 | Cl | Br | CH₃ | p-F-C₆H₄ | 195 |
| 1.3-36 | H | Br | CH₃ | p-F-C₆H₄ | 120 |
| 1.3-37 | H | CF₃ | CH₃ | p-F-C₆H₄ | 180 |
| 1.3-38 | I | CF₃ | CH₃ | p-F-C₆H₄ | 182 |
| 1.3-39 | I | Br | CH₃ | p-F-C₆H₄ | 201 |
| 1.3-40 | Cl | Br | CH₂CH₂Cl | CH₂CH₃ | 158 |
| 1.3-41 | Cl | Br | CH₂CH₃ | CHCH₂ | 75 |
| 1.3-42 | H | Br | CH₂CH₃ | CHCH₂ | 60 |
| 1.3-43 | I | Br | CH₂CH₃ | CHCH₂ | 80 |
| 1.3-44 | I | Br | CH₂CH₂Cl | CH₂CH₃ | 80 |
| 1.3-45 | Cl | OCH₂CCH | i-C₃H₇ | i-C₃H₇ | oil |
| 1.3-46 | I | OCH₂CCH | i-C₃H₇ | i-C₃H₇ | oil |
| 1.3-47 | Cl | OCH₂CCH | CH₃ | p-F-C₆H₄ | oil |
| 1.3-48 | I | OCH₂CCH | CH₃ | p-F-C₆H₄ | oil |
| 1.3-49 | Cl | OCH₂CCH | CH₂CH₂OH | n-C₅H₁₁ | oil |
| 1.3-50 | I | OCH₂CCH | CH₂CH₂OH | n-C₅H₁₁ | oil |
| 1.3-51 | H | CF₃ | CH₂CH₃ | CH₂CH₂Cl | 171 |
| 1.3-52 | I | CF₃ | CH₂CH₂Cl | CH₂CH₃ | 164 |
| 1.3-53 | CN | CF₃ | n-C₃H₇ | CH₃ | 70 |
| 1.3-54 | CN | CF₃ | p-F-C₆H₄ | CH₃ | 72 |
| 1.3-55 | CN | CF₃ | CH₃ | CH₃ | 225 |
| 1.3-56 | CN | Br | n-C₃H₇ | CH₃ | 70 |
| 1.3-57 | CN | Br | p-F-C₆H₄ | CH₃ | 180 |
| 1.3-58 | CN | Br | n-C₅H₁₁ | CH₂CH₂OH | 50 |
| 1.3-59 | CN | Br | i-C₃H₇ | i-C₃H₇ | 185 |
| 1.3-60 | CN | Br | CH₃ | CH₃ | 205 |
| 1.3-61 | CN | Br | CH₂CH₃ | CH₃ | 80 |
| 1.3-62 | CN | Br | CH₂CH₃ | CHCH₂ | 60 |
| 1.3-63 | CN | Br | CH₃ | s-C₄H₉ | 71 |
| 1.3-64 | CN | CF₃ | CH₂CH₃ | CHCH₂ | 60 |
| 1.3-65 | CN | CF₃ | CH₃ | CH₂CH₃ | 65 |
| 1.3-66 | CN | CF₃ | CH₂CH₂OH | n-C₅H₁₁ | 47 |
| 1.3-67 | CN | CF₃ | s-C₄H₉ | CH₃ | 66 |
| 1.3-68 | CN | CF₃ | i-C₃H₇ | i-C₃H₇ | 131 |

"decomp." denotes the onset temperature of the decomposition.

TABLE IV (I.4)

| No. | Q¹ | Q³ | [O]ₙ=S*(R²)(R³) | Physical Data: Meltingpoint [° C.] |
|---|---|---|---|---|
| 1.4-1 | Cl | Br | tetrahydrothiophene (S*) | 203 |
| 1.4-2 | I | Br | tetrahydrothiophene (S*) | 195 |
| 1.4-3 | I | CF₃ | tetrahydrothiophene (S*) | 185 |
| 1.4-4 | H | CF₃ | tetrahydrothiophene (S*) | 208 |
| 1.4-5 | Cl | CF₃ | 1,3-dithiolane (S*) | 182 |
| 1.4-6 | Cl | Br | 1,3-dithiolane (S*) | 165 |
| 1.4-7 | I | Br | 1,3-dithiolane (S*) | 120 |
| 1.4-8 | H | CF₃ | 1,3-dithiolane (S*) | 188 |
| 1.4-9 | H | Br | 1,3-dithiolane (S*) | 169 |
| 1.4-10 | I | CF₃ | 1,3-dithiolane (S*) | 148 |
| 1.4-11 | I | CF₃ | tetrahydrothiopyran (S*) | 215 |
| 1.4-12 | Cl | Br | tetrahydrothiopyran (S*) | 223 |
| 1.4-13 | I | Br | tetrahydrothiopyran (S*) | 213 |
| 1.4-14 | Cl | OCH₂CCH | tetrahydrothiopyran (S*) | Oil |
| 1.4-15 | Cl | OCH₂CCH | 1,3-dithiolane (S*) | Oil |
| 1.4-16 | CN | CF₃ | tetrahydrothiopyran (S*) | 85 |
| 1.4-17 | CN | Br | 1,3-dithiolane (S*) | 92 |
| 1.4-18 | CN | Br | 1,3-dithiolane (S*) | 85 |
| 1.4-19 | CN | Br | tetrahydrothiopyran (S*) | 85 |
| 1.4-20 | CN | CF₃ | 1,3-dithiolane (S*) | 88 |
| 1.4-21 | CN | CF₃ | tetrahydrothiophene (S*) | 194 |
| 1.4-22 | Cl | Br | tetrahydrothiopyran-1-oxide (S*=O) | Oil |
| 1.4-23 | Cl | CF₃ | [CH₂CH₂OH] [(CH₂)₄CH₃]S(=O)— | oil |

Examples for the Action Against Harmful Pests

1. Activity Against Boll Weevil (*Anthonomus grandis*)

The active compounds were formulated in 1:3 DMSO: water. 10 to 15 eggs were placed into microtiterplates filled with 2% agar-agar in water and 300 ppm formaline. The eggs were sprayed with 20 μl of the test solution, the plates were sealed with pierced foils and kept at 24-26° C. and 75-85% humidity with a day/night cycle for 3 to 5 days. Mortality was assessed on the basis of the remaining unhatched eggs or larvae on the agar surface and/or quantity and depth of the digging channels caused by the hatched larvae. Tests were replicated 2 times.

In this test, compounds I.1-3, I.1-11, I.1-15, I.1-32, I.1-35, I.1-48, I.1-69, I.2-2, I.3-1, I.3-3, I.3-4, I.3-5, I.3-6, I.3-7, I.3-8, I.3-9, I.3-10, I.3-11, I.3-12, I.3-13, I.3-14, I.3-19, I.3-20, I.3-21, I.3-22, I.3-23, I.3-24, I.3-25, I.3-26, I.3-27, I.3-28, I.3-29, I.3-30, I.3-31, I.3-32, I.3-33, I.3-34, I.3-35, I.3-36, I.3-37, I.3-38, I.3-39, I.3-40, I.3-41, I.3-42, I.3-43, I.3-44, I.3-45, I.3-46, I.3-47, I.3-48, I.3-49, I.3-51, I.3-52, I.3-53, I.3-54, I.3-55, I.3-56, I.3-57, I.3-58, I.4-1, I.4-2, I.4-3, I.4-4, I.4-5, I.4-6, I.4-7, I.4-8, I.4-9, I.4-10, I.4-11, I.4-12, I.4-13, I.4-14, I.4-15, I.4-16, I.4-17, I.4-22, and I.4-23 at 2500 ppm showed over 75% mortality.

2. Activity Against Mediterranean Fruitfly (*Ceratitis capitata*)

The active compounds were formulated in 1:3 DMSO: water. 50 to 80 eggs were placed into microtiterplates filled with 0.5% agar-agar and 14% diet in water. The eggs were sprayed with 5 μl of the test solution, the plates were sealed with pierced foils and kept at 27-29° C. and 75-85% humidity under fluorescent light for 6 days. Mortality was assessed on the basis of the agility of the hatched larvae. Tests were replicated 2 times.

In this test, compounds I.1-12, I.1-38, I.1-43, I.1-44, I.1-49, I.3-1, I.3-8, I.3-9, I.3-10, I.3-11, I.3-12, I.3-13, I.3-14, I.3-19, I.3-20, I.3-22, I.3-23, I.3-24, I.3-25, I.3-26, I.3-27, I.3-28, I.3-29, I.3-30, I.3-32, I.3-33, I.3-34, I.3-35, I.3-37, I.3-38, I.3-39, I.3-40, I.3-41, I.3-42, I.3-43, I.3-44, I.3-45, I.3-46, I.3-47, I.3-48, I.3-49, I.3-51, I.3-52, I.3-53, I.3-54, I.3-55, I.3-56, I.3-57, I.3-58, I.4-1, I.4-2, I.4-3, I.4-4, I.4-5, I.4-6, I.4-7, I.4-8, I.4-9, I.4-10, I.4-11, I.4-12, I.4-13, I.4-15, I.4-16, I.4-17, I.4-22 and I.4-23 at 2500 ppm showed over 75% mortality.

3. Activity Against Tobacco Budworm (*Heliothis virescens*)

The active compounds were formulated in 1:3 DMSO: water. 15 to 25 eggs were placed into microtiterplates filled with diet. The eggs were sprayed with 10 μl of the test solution, the plates were sealed with pierced foils and kept at 27-29° C. and 75-85% humidity under fluorescent light for 6 days. Mortality was assessed on the basis of the agility and of comparative feeding of the hatched larvae. Tests were replicated 2 times.

4. In this test, compounds I.1-1, I.1-3, I.1-10, I.1-11, I.1-12, I.1-13, I.1-14, I.1-15, I.1-16, I.1-19, I.1-21, I.1-24, I.1-28, I.1-31, I.1-32, I.1-34, I.1-35, I.1-36, I.1-38, I.1-39, I.1-40, I.1-41, I.1-42, I.1-43, I.1-44, I.1-46, I.1-48, I.1-49, I.1-53, I.1-54, I.1-62, I.1-66, I.1-67, I.1-69, I.2-1, I.2-2, I.2-3, I.2-4, I.2-5, I.2-6, I.3-1, I.3-3, I.3-4, I.3-5, I.3-6, I.3-7, I.3-8, I.3-9, I.3-10, I.3-11, I.3-12, I.3-13, I.3-14, I.3-19, I.3-20, I.3-21, I.3-22, I.3-23, I.3-24, I.3-25, I.3-26, I.3-27, I.3-28, I.3-29, I.3-30, I.3-31, I.3-32, I.3-33, I.3-34, I.3-35, I.3-36, I.3-37, I.3-38, I.3-39, I.3-40, I.3-41, I.3-42, I.3-43, I.3-44, I.3-45, I.3-46, I.3-47, I.3-48, I.3-49, I.3-51, I.3-52, I.3-53, I.3-54, I.3-55, I.3-56, I.3-57, I.3-58, I.4-1, I.4-2, I.4-3, I.4-4, I.4-5, I.4-6, I.4-7, I.4-8, I.4-9, I.4-10, I.4-11, I.4-12, I.4-13, I.4-14, I.4-15, I.4-16, I.4-17, I.4-22 and I.4-23 at 2500 ppm showed over 75% mortality.

4. Activity Against Vetch Aphid (*Megoura viciae*)

The active compounds were formulated in 1:3 DMSO: water. Bean leaf disks were placed into microtiterplates filled with 0.8% agar-agar and 2.5 ppm OPUS™. The leaf disks were sprayed with 2.5 μl of the test solution and 5 to 8 adult aphids were placed into the microtiterplates which were then closed and kept at 22-24° C. and 35-45% under fluorescent light for 6 days. Mortality was assessed on the basis of vital, reproduced aphids. Tests were replicated 2 times.

In this test, compounds I.1-12, I.1-19, I.1-32, I.1-49, I.1-50, I.1-53, I.2-9, I.3-1, I.3-3, I.3-4, I.3-5, I.3-6, I.3-7, I.3-8, I.3-9, I.3-10, I.3-11, I.3-12, I.3-13, I.3-14, I.3-19, I.3-20, I.3-21, I.3-22, I.3-23, I.3-24, I.3-25, I.3-26, I.3-27, I.3-28, I.3-29, I.3-30, I.3-32, I.3-33, I.3-34, I.3-35, I.3-36, I.3-37, I.3-38, I.3-39, I.3-40, I.3-41, I.3-42, I.3-43, I.3-44, I.3-45, I.3-47, I.3-49, I.3-51, I.3-52, I.3-53, I.3-54, I.3-55, I.3-56, I.3-57, I.3-58, I.4-1, I.4-2, I.4-3, I.4-4, I.4-5, I.4-6, I.4-7, I.4-8, I.4-9, I.4-10, I.4-11, I.4-12, I.4-13, I.4-14, I.4-15, I.4-16, I.4-17, I.4-22 and I.4-23 at 2500 ppm showed over 75% mortality compared to 0% mortality of untreated controls.

5. Activity Against Oat Aphid (*Rhopalosiphum padi*)

The active compounds were formulated in 1:3 DMSO: water. Barlay leaf disk were placed into microtiterplates filled with 0.8% agar-agar and 2.5 ppm OPUS™. The leaf disks were sprayed with 2.5 μl of the test solution and 3 to 8 adult aphids were placed into the microtiterplates which were then closed and kept at 22-24° C. and 35-45% humidity under fluorescent light for 5 days. Mortality was assessed on the basis of vital aphids. Tests were replicated 2 times.

In this test, compound I.3-1 at 2500 ppm showed over 75% mortality compared to 0% mortality of untreated controls.

6. Activity Against Cotton Aphid (*Aphis gossypii*)

The active compounds were formulated in 50:50 acetone: water and 100 ppm Kinetic™ surfactant.

Cotton plants at the cotyledon stage (one plant per pot) were infested by placing a heavily infested leaf from the main colony on top of each cotyledon. The aphids were allowed to transfer to the host plant overnight, and the leaf used to transfer the aphids was removed. The cotyledons were dipped in the test solution and allowed to dry. After 5 days, mortality counts were made.

In this test, compound I.3-1, I.3-3, I.3-4, I.3-5, I.3-6, I.3-7, I.3-8, I.3-9, I.3-10, I.3-11, I.3-12, I.3-13, I.3-14, I.3-15, I.3-16, I.3-17, I.3-18, I.3-19, I.3-20, I.3-21, I.3-22, I.3-23, I.3-24, I.3-25, I.3-26, I.3-27, I.3-28, I.3-29, I.3-30, I.3-32, I.3-33, I.3-34, I.3-35, I.3-36, I.3-38, I.3-39, I.3-40, I.3-41, I.3-42, I.3-43, I.3-44, I.3-51, I.3-52, I.3-53, I.3-54, I.4-1, I.4-2, I.4-3, I.4-4, I.4-5, I.4-6, I.4-7, I.4-8, I.4-9, I.4-10, I.4-11, I.4-12, I.4-13 and I.4-16 at 300 ppm showed over 50% mortality.

7. Activity Against Southern Armyworm (*Spodoptera eridania*), 2nd Instar Larvae The active compounds were formulated for testing the activity against insects and arachnids as a 10.000 ppm solution in a mixture of 35% acetone and water, which was diluted with water, if needed.

A Sieva lima bean leaf was dipped in the test solution and allowed to dry. The leaf was then placed in a petri dish containing a filter paper on the bottom and ten 2nd instar caterpillars. At 5 days, observations are made of mortality and reduced feeding.

In this test, compounds I.1-1, I.1-3, I.1-7, I.1-9, I.1-10, I.1-11, I.1-12, I.1-13, I.1-14, I.1-15, I.1-16, I.1-19, I.1-21, I.1-24, I.1-27, I.1-28, I.1-30, I.1-31, I.1-32, I.1-34, I.1-35, I.1-36, I.1-38, I.1-39, I.1-40, I.1-41, I.1-42, I.1-43, I.1-44, I.1-45, I.1-46, I.1-47, I.1-49, I.1-53, I.1-54, I.1-57, I.1-61, I.1-63, I.1-66, I.1-69, I.2-1, I.2-2, I.2-3, I.2-4, I.2-5, I.2-6, I.2-8, I.2-9, I.3-3, I.3-4, I.3-5, I.3-6, I.3-7, I.3-8, I.3-9, I.3-10, I.3-11, I.3-12, I.3-13, I.3-14, I.3-15, I.3-16, I.3-17, I.3-18, I.3-19, I.3-20, I.3-21, I.3-22, I.3-23, I.3-24, I.3-25, I.3-26, I.3-27, I.3-28, I.3-29, I.3-30, I.3-32, I.3-33, I.3-34, I.3-35, I.3-37, I.3-38, I.3-39, I.3-40, I.3-41, I.3-42, I.3-43, I.3-44, I.3-51, I.3-52, I.3-53, I.3-54, I.4-1, I.4-2, I.4-3, I.4-4, I.4-5, I.4-6, I.4-7, I.4-8, I.4-9, I.4-11, I.4-12, I.4-13, I.4-16, I.4-22 and I.4-23 at 300 ppm showed over 75% mortality.

8. Activity Against Silverleaf Whitefly (*Bemisia argentifolii*)

The active compounds were formulated in 50:50 acetone:water and 100 ppm Kinetic™ surfactant.

Selected cotton plants were grown to the cotyledon state (one plant per pot). The cotyledons were dipped into the test solution to provide complete coverage of the foliage and placed in a well-vented area to dry. Each pot with treated seedling was placed in a plastic cup and 10 to 12 whitefly adults (approximately 3-5 day old) were introduced. The insects were collected using an aspirator and an 0.6 cm, non-toxic Tygon™ tubing (R-3603) connected to a barrier pipette tip. The tip, containing the collected insects, was then gently inserted into the soil containing the treated plant, allowing insects to crawl out of the tip to reach the foliage for feeding. The cups were covered with a reusable screened lid (150 micron mesh polyester screen PeCap from Tetko Inc). Test plants were maintained in the holding room at about 25° C. and 20-40% relative humidity for 3 days avoiding direct exposure to the fluorescent light (24 hour photoperiod) to prevent trapping of heat inside the cup. Mortality was assessed 3 days after treatment of the plants.

In this test, compound I.3-1, I.3-3, I.3-4, I.3-5, I.3-6, I.3-8, I.3-9, I.3-10, I.3-11, I.3-12, I.3-13, I.3-14, I.3-15, I.3-16, I.3-17, I.3-19, I.3-20, I.3-22, I.3-23, I.3-25, I.3-26, I.3-27, I.3-28, I.3-30, I.4-1, I.4-2 and I.4-3 at 300 ppm showed over 90% mortality.

9. Activity Against Diamond Back Moth (*Plutella xylostella*)

The active compounds were formulated in 50:50 acetone:water and 0.1% (vol/vol) Alkamuls EL 620 surfactant. A 6 cm leaf disk of cabbage leaves was dipped in the test solution for 3 seconds and allowed to air dry in a Petri plate lined with moist filter paper. The leaf disk was inoculated with 10 third instar larvae and kept at 25-27° C. and 50-60% humidity for 3 days. Mortality was assessed after 72 h of treatment.

In this test, compounds I.1-1, I.1-7, I.1-9, I.1-15, I.1-19, I.1-21, I.1-24, I.1-27, I.1-28, I.1-29, I.1-31, I.1-32, I.1-45, I.1-47, I.1-61, I.1-63, I.3-5, I.3-6, I.3-7, I.3-8, I.3-9, I.3-10, I.3-11, I.3-12, I.3-13, I.3-14, I.3-15, I.3-16, I.3-17, I.3-18, I.3-19, I.3-20, I.3-21, I.3-22, I.3-23, I.3-24, I.3-25, I.3-26, I.3-27, I.3-28, I.3-29, I.3-30, I.3-31, I.3-32, I.3-33, I.3-34, I.3-35, I.3-36, I.3-37, I.3-38, I.3-39, I.3-40, I.3-41, I.4-42, I.3-43, I.3-44, I.3-45, I.3-46, I.3-47, I.3-48, I.3-49, I.3-51, I.3-52, I.3-53, I.3-54, I.3-55, I.3-56, I.3-57, I.3-58, I.3-59, I.3-60, I.3-61, I.3-62, I.3-63, I.4-1, I.4-2, I.4-3, I.4-4, I.4-5, I.4-6, I.4-7, I.4-8, I.4-9, I.4-10, I.4-11, I.4-12, I.4-13, I.4-16, I.4-17, I.4-18, I.4-19, and I.4-22 at 300 ppm showed over 75% mortality.

10. Activity Against Argentine Ant (*Linepithema humile*), Harvester Ant (*Pogonomyrmex californicus*), Acrobat Ant (*Crematogaster* spp.), Carpenter Ant (*Camponotus floridanus*), Fire Ant (*Solenopsis invicta*), House Fly (*Musca domestica*), Stable Fly (*Stomoxys calcitrans*), Flesh Fly (*Sarcophaga* sp.), Yellowfever Mosquito (*Aedes aegyptii*), House Mosquito (*Culex quinquefasciatus*), Malaria Mosquito (*Anopheles albimanus*), German Cockroach (*Blattella Germanica*), Cat Flea (*Ctenocephalides felis*), and Brown Dog Tick (*Rhipicephalus sanguineus*) Via Glass Contact Glass vials were treated with 0.5 ml of a solution of active ingredient in acetone and allowed to dry. Insects or ticks were placed into each vial together with some food and moisture supply. The vials were kept at 22° C. and were observed for treatment effects at various time intervals.

In this test, compounds I.3-4, I.3-5 and I.3-6 at 10 ppm showed over 70% mortality of yellowfever mosquito.

11. Activity Against Yellowfever Mosquito (*Aedes aegyptii*), House Mosquito (*Culex quinquefasciatus*) and Malaria Mosquito (*Anopheles albimanus*) Larvae Via Water Treatment Well plates were used as test arenas. The active ingredient was dissolved in acetone and diluted with water to obtain the concentrations needed. The final solutions containing appr. 1% acetone were placed into each well. Approximately 10 mosquito larvae ($4^{th}$-instars) in 1 ml water were added to each well. Larvae were fed one drop of liver powder each day. The dishes were covered and maintained at 22° C. Mortality was recorded daily and dead larvae and live or dead pupae were removed daily. At the end of the test remaining live larvae were recorded and percent mortality was calculated.

In this test, compounds I.1-37, I.1-38, I.1-49, I.1-69, I.3-4, I.3-5, I.3-6 and I.3-7 at 10 ppm showed over 70% mortality of yellowfever mosquito.

12. Activity Against Root-Knot Nematode (*Meloidogyne incognita*):

Test compounds are prepared and formulated into aqueous formulations using acetone. Tomato plants (var. Bonny Best) are grown in the greenhouse in plastic tubs (4 to 6 plants per tub). The plants and soil (a 50:50 mixture of sand and "New Egypt" sandy loam) are infested with *M. incognita* J2 (to establish the "in-house" colony, *M. incognita* J2 were initially acquired from Auburn University). The plants are kept pruned and are used on an "as needed" basis. The tomato plants are kept in the cylinder containing hydroponic solution and aerated until the nematodes are no longer present in the solution (usually about 60 days). The cultures are checked daily by eluting a small volume (approximately 20 ml) from the bottom of a funnel attached to the cylinder into a small crystallizing dish and observed using a binocular dissecting scope. If needed for testing, the nematodes are cleaned and concentrated by pouring the culture solution through a sieve for cleaning and a sieve for concentrating. The nematodes are then resuspended in water to a concentration of approximately 20 to 50 nematodes per 50 µl. These are counted by putting 25 µl of the nematode solution into a well of an unused well of an assay plate. The total is then multiplied by 2 for a final total of nematodes per 50 µl of solution. To microtiter plates containing about 1.0 mg of compound, 80:20 acetone is added to each well and the solution is mixed to obtain the desired compound concentration. The nematode solution is added to each plate. The plates are then sealed and they are placed in an incubator at 27° C. and 50% (+/−2%) relative humidity. After 72 hours, the population mortality is read, whereby immobility of nematodes is regarded as mortality.

We claim:

1. A compound of formula I having the following structure,

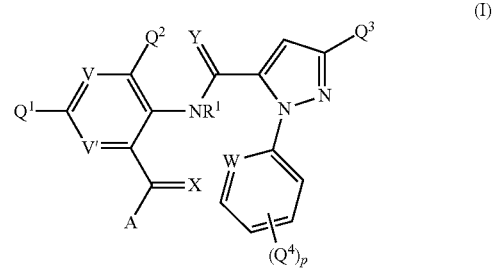

wherein A is $A^1$

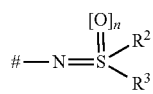
(A¹)

wherein
R¹ is hydrogen;
R² and R³ each independently are phenyl, $C_1$-$C_6$-alkyl, $C_2$-$C_6$-alkenyl, or $C_2$-$C_6$-alkynyl, which are unsubstituted or substituted with any combination of 1 to 6 groups selected from halogen and cyano;
W is N;
Q¹ is hydrogen, halogen, cyano, SCN, nitro, hydroxy, $C_1$-$C_{10}$-alkyl, $C_1$-$C_{10}$-haloalkyl, $C_3$-$C_8$-cycloalkyl, $C_1$-$C_{10}$-alkoxy, $C_1$-$C_{10}$-haloalkoxy, $C_1$-$C_{10}$-alkylthio, $C_1$-$C_{10}$-haloalkylthio, $C_1$-$C_{10}$-alkylsulfonyl, $C_1$-$C_{10}$-alkylsulfonyloxy, $C_1$-$C_{10}$-alkylamino or di($C_1$-$C_{10}$-alkyl)amino;
Q² is halogen, cyano, SCN, nitro, hydroxy, $C_1$-$C_{10}$-alkyl, $C_1$-$C_{10}$-haloalkyl, $C_3$-$C_8$-cycloalkyl, $C_1$-$C_{10}$-alkoxy, $C_1$-$C_{10}$-haloalkoxy, $C_1$-$C_{10}$-alkylthio, $C_1$-$C_{10}$-haloalkylthio, $C_1$-$C_{10}$-alkylsulfonyl, $C_1$-$C_{10}$-alkylsulfonyloxy, $C_1$-$C_{10}$-alkylamino or di($C_1$-$C_{10}$-alkyl)amino;
Q³ is halogen, $C_1$-$C_{10}$-alkyl, $C_1$-$C_{10}$-haloalkyl, $C_2$-$C_{10}$-alkynyl, $C_3$-$C_8$-cycloalkyl, or $C_3$-$C_8$-halocycloalkyl, each unsubstituted or independently substituted with 1 to 2 groups selected from cyano, $C_1$-$C_{10}$-alkoxy, $C_1$-$C_{10}$-haloalkoxy or $C_1$-$C_1$-alkylthio;
Q⁴ is halogen, cyano, nitro, $C_1$-$C_{10}$-alkyl, $C_1$-$C_{10}$-haloalkyl, $C_1$-$C_{10}$-alkoxy, $C_1$-$C_{10}$-haloalkoxy, $C_1$-$C_{10}$-alkylthio, $C_1$-$C_{10}$-haloalkylthio, $C_1$-$C_{10}$-alkylsulfinyl, $C_1$-$C_{10}$-haloalkylsulfinyl, $C_1$-$C_{10}$-alkylsulfonyl, $C_1$-$C_{10}$-haloalkylsulfonyl, or $C_1$-$C_{10}$-alkoxycarbonyl;
each of V and V' is CH;
p is 0, 1, 2, 3, or 4;
n is 0 or 1;
X and Y are oxygen;
or an enantiomer, a salt or an N-oxide thereof.

2. The compound of claim 1, wherein Q¹ is hydrogen, halogen, cyano, $C_1$-$C_4$-alkyl, or $C_1$-$C_4$-haloalkyl.

3. The compound of claim 2, wherein Q¹ is halogen or cyano.

4. The compound of claim 1, wherein Q² is halogen, cyano, $C_1$-$C_4$-alkyl, or $C_1$-$C_4$-haloalkyl.

5. The compound of claim 1, wherein Q³ is halogen, $C_1$-$C_4$-haloalkyl, or $C_1$-$C_4$-haloalkoxy.

6. The compound of claim 5, wherein Q³ is $C_1$-$C_4$-haloalkyl.

7. The compound of claim 1, wherein Q⁴ is halogen or $C_1$-$C_4$-haloalkyl and is in the ortho-position.

8. The compound of claim 1, wherein Q⁴ is halogen.

9. A method for controlling insects, acarids or nematodes comprising, contacting said insect, acarid or nematode or their food supply, habitat, breeding ground or their locus with a pesticidally effective amount of one or more compounds of claim 1.

10. The method of claim 9, wherein Q¹ is hydrogen, halogen, cyano, $C_1$-$C_4$-alkyl, or $C_1$-$C_4$-haloalkyl.

11. The method of claim 10, wherein Q¹ is halogen or cyano.

12. The method of claim 9, wherein Q² is halogen, cyano, $C_1$-$C_4$-alkyl, or $C_1$-$C_4$-haloalkyl.

13. The method of claim 9, wherein Q³ is halogen, $C_1$-$C_4$-haloalkyl, or $C_1$-$C_4$-haloalkoxy.

14. The method of claim 13, wherein Q³ is $C_1$-$C_4$-haloalkyl.

15. The method of claim 9, wherein Q⁴ is halogen or $C_1$-$C_4$-haloalkyl and is in the ortho-position.

16. The method of claim 9, wherein Q⁴ is halogen.

17. A method of protecting growing plants from attack or infestation by insects, acarids or nematodes comprising, applying to the foliage of the plants, or to the soil or water in which said plants are growing a pesticidally effective amount of one or more compounds of claim 1.

18. The method of claim 17, wherein Q¹ is hydrogen, halogen, cyano, $C_1$-$C_4$-alkyl, or $C_1$-$C_4$-haloalkyl.

19. The method of claim 18, wherein Q¹ is halogen or cyano.

20. The method of claim 17, wherein Q² is halogen, cyano, $C_1$-$C_4$-alkyl, or $C_1$-$C_4$-haloalkyl.

21. The method of claim 17, wherein Q³ is halogen, $C_1$-$C_4$-haloalkyl, or $C_1$-$C_4$-haloalkoxy.

22. The method of claim 21, wherein Q³ is $C_1$-$C_4$-haloalkyl.

23. The method of claim 17, wherein Q⁴ is halogen or $C_1$-$C_4$-haloalkyl and is in the ortho-position.

24. The method of claim 17, wherein Q⁴ is halogen.

25. A method for treating an animal infected by parasites or controlling, preventing or protecting the animal against infestation or infection by parasites comprising, administering orally, topically or parenterally, or applying to said animal a parasiticidally effective amount of one or more compounds of claim 1.

* * * * *